United States Patent
Urano et al.

(10) Patent No.: US 8,232,089 B2
(45) Date of Patent: Jul. 31, 2012

(54) CYTOSOLIC ISOBUTANOL PATHWAY LOCALIZATION FOR THE PRODUCTION OF ISOBUTANOL

(75) Inventors: Jun Urano, Englewood, CO (US); Catherine Asleson Dundon, Englewood, CO (US)

(73) Assignee: Gevo, Inc., Englewood, CO (US)

( * ) Notice: Subject to any disclaimer, the term of this patent is extended or adjusted under 35 U.S.C. 154(b) by 0 days.

(21) Appl. No.: 12/855,276

(22) Filed: Aug. 12, 2010

(65) Prior Publication Data
US 2011/0076733 A1    Mar. 31, 2011

Related U.S. Application Data

(60) Provisional application No. 61/272,058, filed on Aug. 12, 2009, provisional application No. 61/272,059, filed on Aug. 12, 2009.

(51) Int. Cl.
  C12N 1/00    (2006.01)
  C07H 21/02    (2006.01)
  C12P 7/16    (2006.01)

(52) U.S. Cl. ............... 435/254.2; 536/23.1; 435/160

(58) Field of Classification Search .................. None
See application file for complete search history.

(56) References Cited

U.S. PATENT DOCUMENTS

| | | |
|---|---|---|
| 2003/0228567 A1 | 12/2003 | Famili et al. |
| 2007/0092957 A1 | 4/2007 | Donaldson et al. |
| 2008/0138870 A1 | 6/2008 | Bramucci et al. |
| 2008/0261230 A1 | 10/2008 | Liao et al. |
| 2008/0274522 A1 | 11/2008 | Bramucci et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2009/0081746 A1 | 3/2009 | Liao et al. |
| 2009/0139134 A1 | 6/2009 | Yoshikuni et al. |
| 2009/0151018 A1 | 6/2009 | Hammer et al. |
| 2009/0155873 A1 | 6/2009 | Kashiyama et al. |
| 2009/0163376 A1 | 6/2009 | Li et al. |
| 2009/0215137 A1 | 8/2009 | Hawkins et al. |
| 2009/0226990 A1 | 9/2009 | Hawkins et al. |
| 2009/0226991 A1 | 9/2009 | Feldman et al. |
| 2009/0269823 A1 | 10/2009 | Bramucci et al. |
| 2009/0305363 A1 | 12/2009 | Anthony et al. |
| 2009/0305369 A1 | 12/2009 | Donaldson et al. |
| 2010/0048964 A1 | 2/2010 | Calabria et al. |
| 2010/0081154 A1 | 4/2010 | Flint et al. |
| 2010/0081179 A1 | 4/2010 | Anthony et al. |
| 2010/0081182 A1 | 4/2010 | Paul et al. |
| 2010/0081183 A1 | 4/2010 | Paul et al. |
| 2010/0120105 A1 | 5/2010 | Anthony et al. |
| 2010/0129886 A1 | 5/2010 | Anthony et al. |
| 2010/0129887 A1 | 5/2010 | Anthony et al. |
| 2010/0143997 A1 | 6/2010 | Buelter et al. |
| 2010/0151545 A1 | 6/2010 | Roessler et al. |
| 2010/0167363 A1 | 7/2010 | Bramucci et al. |
| 2010/0167364 A1 | 7/2010 | Bramucci et al. |
| 2010/0167365 A1 | 7/2010 | Bramucci et al. |
| 2010/0167371 A1 | 7/2010 | Chotani et al. |
| 2010/0197519 A1 | 8/2010 | Li et al. |
| 2011/0053235 A1 | 3/2011 | Festel et al. |
| 2011/0081348 A1 | 4/2011 | Brogdon et al. |
| 2011/0201083 A1 | 8/2011 | Liao et al. |

FOREIGN PATENT DOCUMENTS

| | | |
|---|---|---|
| WO | WO 94/08020 A1 | 4/1994 |
| WO | WO 2009/143455 A2 | 11/2009 |
| WO | WO 2010/017230 A2 | 2/2010 |
| WO | WO 2010/071851 A2 | 6/2010 |
| WO | WO 2010/075504 A2 | 7/2010 |

OTHER PUBLICATIONS

Armburst et al., "The genome of the diatom *Thalassiosira pseudonana*: ecology, evolution, and metabolism." Science (2004), 306, 79-86.

Atsumi et al., "Acetolactate synthase from *Bacillus subtilis* serves as a 2-ketoisovalerate decarboxylase for isobutanol biosynthesis in *Escherichia coli*," Applied and Environmental Microbiology (2009), 75(19), 6306-6311.

Atsumi et al., "Engineering synthetic pathways for production of higher alcohols as biofuels," Abstracts of Papers, 236th ACS National Meeting, Philadelphia, PA, United States, Aug. 17-21, 2008, BIOT-241.

Atsumi et al., "Engineering the isobutanol biosynthetic pathway in *Escherichia coli* by comparison of three aldehyde reductase/alcohol dehydrogenase genes," Applied Microbiology and Biotechnology (2010), 85(3), 651-657.

Atsumi et al., "Non-fermentative pathways for synthesis of branched-chain higher alcohols as biofuels," Nature (London, United Kingdom) (2008), 451(7174), 86-89.

Bolotin et al., "The complete genome sequence of the lactic acid bacterium *Lactococcus lactis* ssp. Lactis IL1403," Genome Research (2001), 11, 731-753.

Brynildsen et al., "An integrated network approach identifies the isobutanol response network of *Escherichia coli*," Molecular Systems Biology (2009), 5, 277, 13 pages.

(Continued)

*Primary Examiner* — Tekchand Saidha
*Assistant Examiner* — MD. Younus Meah
(74) *Attorney, Agent, or Firm* — Cooley LLP

(57) ABSTRACT

The present invention provides recombinant microorganisms comprising isobutanol producing metabolic pathway with at least one isobutanol pathway enzyme localized in the cytosol, wherein said recombinant microorganism is selected to produce isobutanol from a carbon source. Methods of using said recombinant microorganisms to produce isobutanol are also provided. In various aspects of the invention, the recombinant microorganisms may comprise a cytosolically active isobutanol pathway enzymes. In some embodiments, the invention provides mutated, modified, and/or chimeric isobutanol pathway enzymes with cytosolic activity. In various embodiments described herein, the recombinant microorganisms may be microorganisms of the *Saccharomyces* clade, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

20 Claims, 5 Drawing Sheets

OTHER PUBLICATIONS

Connor et al., "Microbial production of advanced transportation fuels in non-natural hosts," Current Opinion in Biotechnology (2009), 20(3), 307-315.

Hanai et al., "Production of next generation bio-alcohol by genetically engineered *E. coli*," Baiosaiensu to Indasutori (2008), 66(10), 553-556.

Kim et al., "OptORF: Optimal metabolic and regulatory perturbations for metabolic engineering of microbial strains," BMC Systems Biology (2010), 4, 53, 19 pages.

Shen et al., "Metabolic engineering of *Escherichia coli* for 1-butanol and 1-propanol production via the keto-acid pathways," Metabolic Engineering (2008), 10(6), 312-320.

Smith et al., "Engineering *Corynebacterium glutamicum* for isobutanol production," Applied Microbiology and Biotechnology (2010), 87(3), 1045-1055.

Smith et al., "Evolutionary strategy for improving isobutanol production in *Escherichia coli*," Abstracts of Papers, 239th ACS National Meeting, San Francisco, CA, United States, Mar. 21-25, 2010, BIOT-2.

International Search Report and Written Opinion mailed Nov. 8, 2010 in the International (PCT) Application No. PCT/US10/45295, 9 pages.

J. W. Myers, 1961, "Dihydroxy Acid Dehydratase: an Enzyme Involved in the Biosynthesis of Isoleucine and Valine," Journal of Biological Chemistry 236(5): 1414-8.

Boulton et at., 2001, Brewing Yeast & Fermentation, Chapter 3, first ed., Blackwell Science Ltd, Oxford, United Kingdom, pp. 69-142.

CYTOSOLIC ISOBUTANOL PATHWAY LOCALIZATION FOR THE PRODUCTION OF ISOBUTANOL

CROSS-REFERENCE TO RELATED APPLICATIONS

This application claims priority to U.S. Provisional Application Ser. No. 61/272,058, filed Aug. 12, 2009, and U.S. Provisional Application Ser. No. 61/272,059, filed Aug. 12, 2009, both of which are herein incorporated by reference in their entireties for all purposes.

ACKNOWLEDGMENT OF GOVERNMENTAL SUPPORT

This invention was made with government support under Contract No. IIP-0823122, awarded by the National Science Foundation, and under Contract No. EP-D-09-023, awarded by the Environmental Protection Agency. The government has certain rights in the invention.

TECHNICAL FIELD

Recombinant microorganisms and methods of producing such organisms are provided. Also provided are methods of producing metabolites that are biofuels by contacting a suitable substrate with recombinant microorganisms and enzymatic preparations therefrom.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_041_08US_SeqList_ST25.txt, date recorded: Aug. 10, 2010, file size: 337 kilobytes).

BACKGROUND

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s coupled to the decrease in US oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivations for developing biofuels are of economical, political, and environmental nature.

One is the threat of 'peak oil', the point at which the consumption rate of crude oil exceeds the supply rate, thus leading to significantly increased fuel cost results in an increased demand for alternative fuels. In addition, instability in the Middle East and other oil-rich regions has increased the demand for domestically produced biofuels. Also, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

Ethanol is the most abundant fermentatively produced fuel today but has several drawbacks when compared to gasoline. Butanol, in comparison, has several advantages over ethanol as a fuel: it can be made from the same feedstocks as ethanol but, unlike ethanol, it is compatible with gasoline at any ratio and can also be used as a pure fuel in existing combustion engines without modifications. Unlike ethanol, butanol does not absorb water and can thus be stored and distributed in the existing petrochemical infrastructure. Due to its higher energy content which is close to that of gasoline, the fuel economy (miles per gallon) is better than that of ethanol. Also, butanol-gasoline blends have lower vapor pressure than ethanol-gasoline blends, which is important in reducing evaporative hydrocarbon emissions.

Isobutanol has the same advantages as butanol with the additional advantage of having a higher octane number due to its branched carbon chain. Isobutanol is also useful as a commodity chemical and is also a precursor to MTBE.

Isobutanol has been produced in recombinant microorganisms expressing a heterologous, five-step metabolic pathway (See, e.g., WO/2007/050671 to Donaldson et al., WO/2008/098227 to Liao et al., and WO/2009/103533 to Festel et al.). However, the microorganisms produced have fallen short of commercial relevance due to their low performance characteristics, including, for example low productivity, low titer, low yield, and the requirement for oxygen during the fermentation process. Thus, recombinant microorganisms exhibiting increased isobutanol productivity, titer, and/or yield are desirable.

SUMMARY OF THE INVENTION

The present invention provides cytosolically active dihydroxyacid dehydratase (DHAD) enzymes and recombinant microorganisms comprising said cytosolically active DHAD enzymes. In some embodiments, said recombinant microorganisms may further comprise one or more additional enzymes catalyzing a reaction in an isobutanol producing metabolic pathway. As described herein, the recombinant microorganisms of the present invention are useful for the production of several beneficial metabolites, including, but not limited to isobutanol.

In a first aspect, the invention provides cytosolically active dihydroxyacid dehydratase (DHAD) enzymes. These cytosolically active DHAD enzymes generally exhibit the ability to convert 2,3-dihydroxyisovalerate to ketoisovalerate in the cytosol. The cytosolically active DHAD enzymes of the present invention, as described herein, can include native (i.e. parental) DHAD enzymes that exhibit cytosolic activity, as well DHAD enzymes that have been modified or mutated to increase their cytosolic localization and/or activity as compared to native (i.e. parental) DHAD enzymes.

In various embodiments described herein, the DHAD enzymes may be derived from a prokaryotic organism. In one embodiment, the prokaryotic organism is a bacterial organism. In another embodiment, the bacterial organism is *Lactococcus lactis*. In a specific embodiment, the DHAD enzyme from *L. lactis* comprises the amino acid sequence of SEQ ID NO: 18. In another embodiment, the bacterial organism is *Francisella tularensis*. In a specific embodiment, the DHAD enzyme from *F. tularensis* comprises the amino acid sequence of SEQ ID NO: 14. In another embodiment, the bacterial organism is *Gramella forsetii*. In a specific embodiment, the DHAD enzyme from *G. forsetii* comprises the amino acid sequence of SEQ ID NO: 17.

In alternative embodiments described herein, the DHAD enzyme may be derived from a eukaryotic organism. In one embodiment, the eukaryotic organism is a fungal organism. In an exemplary embodiment, the fungal organism is *Neurospora crassa*. In a specific embodiment, the DHAD enzyme from *N. crassa* comprises the amino acid sequence of SEQ ID NO: 165.

In some embodiments, the invention provides modified or mutated DHAD enzymes, wherein said DHAD enzymes exhibit increased cytosolic activity as compared to their parental DHAD enzymes. In another embodiment, the invention provides modified or mutated DHAD enzymes, wherein said DHAD enzymes exhibit increased cytosolic activity as compared to the DHAD enzyme comprised by the amino acid sequence of SEQ ID NO: 11.

In further embodiments, the invention provides DHAD enzymes comprising the amino acid sequence P(I/L)XXXGX(I/L)XIL (SEQ ID NO: 27), wherein X is any natural or non-natural amino acid, and wherein said DHAD enzymes exhibit the ability to convert 2,3-dihydroxyisovalerate to ketoisovalerate in the cytosol.

In some embodiments, the DHAD enzymes of the present invention exhibit a properly folded iron-sulfur cluster domain and/or redox active domain in the cytosol. In one embodiment, the DHAD enzymes comprise a mutated or modified iron-sulfur cluster domain and/or redox active domain.

In another aspect, the present invention provides recombinant microorganisms comprising a cytosolically active DHAD enzyme. In one embodiment, the invention provides recombinant microorganisms comprising a DHAD enzyme derived from a prokaryotic organism, wherein said DHAD enzyme exhibits activity in the cytosol. In one embodiment, the DHAD enzyme is derived from a bacterial organism. In a specific embodiment, the DHAD enzyme is derived from *L. lactis* and comprises the amino acid sequence of SEQ ID NO: 18. In another embodiment, the invention provides recombinant microorganisms comprising a DHAD enzyme derived from a eukaryotic organism, wherein said DHAD enzyme exhibits activity in the cytosol. In one embodiment, the DHAD enzyme is derived from a fungal organism. In an alternative embodiment, the DHAD enzyme is derived from a yeast organism.

In one embodiment, the invention provides recombinant microorganisms comprising a modified or mutated DHAD enzyme, wherein said DHAD enzyme exhibits increased cytosolic activity as compared to the parental DHAD enzyme. In another embodiment, the invention provides recombinant microorganisms comprising a modified or mutated DHAD enzyme, wherein said DHAD enzyme exhibits increased cytosolic activity as compared to the DHAD enzyme comprised by the amino acid sequence of SEQ ID NO: 11.

In another embodiment, the invention provides recombinant microorganisms comprising a DHAD enzyme comprising the amino acid sequence P(I/L)XXXGX(I/L)XIL (SEQ ID NO: 27), wherein X is any natural or non-natural amino acid, and wherein said DHAD enzymes exhibit the ability to convert 2,3-dihydroxyisovalerate to ketoisovalerate in the cytosol.

In some embodiments, the invention provides recombinant microorganisms comprising a DHAD enzyme fused to a peptide tag, whereby said DHAD enzyme exhibits increased cytosolic localization and/or cytosolic DHAD activity as compared to the parental microorganism. In one embodiment, the peptide tag is non-cleavable. In another embodiment, the peptide tag is fused at the N-terminus of the DHAD enzyme. In another embodiment, the peptide tag is fused at the C-terminus of the DHAD enzyme. In certain embodiments, the peptide tag may be selected from the group consisting of ubiquitin, ubiquitin-like (UBL) proteins, myc, HA-tag, green fluorescent protein (GFP), and the maltose binding protein (MBP).

In certain embodiments described herein, it may be desirable to further overexpress an additional enzyme that converts 2,3-dihydroxyisovalerate (DHIV) to ketoisovalerate (KIV) in the cytosol. In a specific embodiment, the enzyme may be selected from the group consisting of 3-isopropylmalate isomerase (Leu1p) and imidazoleglycerol-phosphate dehydrogenase (His3p).

In various embodiments described herein, the recombinant microorganisms may be further engineered to express an isobutanol producing metabolic pathway comprising at least one exogenous gene that catalyzes a step in the conversion of pyruvate to isobutanol. In one embodiment, the recombinant microorganism may be engineered to express an isobutanol producing metabolic pathway comprising at least two exogenous genes. In another embodiment, the recombinant microorganism may be engineered to express an isobutanol producing metabolic pathway comprising at least three exogenous genes. In another embodiment, the recombinant microorganism may be engineered to express an isobutanol producing metabolic pathway comprising at least four exogenous genes. In another embodiment, the recombinant microorganism may be engineered to express an isobutanol producing metabolic pathway comprising five exogenous genes. Thus, the present invention further provides recombinant microorganisms that comprise an isobutanol producing metabolic pathway and methods of using said recombinant microorganisms to produce isobutanol.

In one embodiment, the recombinant microorganisms comprise an isobutanol producing metabolic pathway with at least one isobutanol pathway enzyme localized in the cytosol. In another embodiment, the recombinant microorganisms comprise an isobutanol producing metabolic pathway with at least two isobutanol pathway enzymes localized in the cytosol. In another embodiment, the recombinant microorganisms comprise an isobutanol producing metabolic pathway with at least three isobutanol pathway enzymes localized in the cytosol. In another embodiment, the recombinant microorganisms comprise an isobutanol producing metabolic pathway with at least four isobutanol pathway enzymes localized in the cytosol. In an exemplary embodiment, the recombinant microorganisms comprise an isobutanol producing metabolic pathway with five isobutanol pathway enzymes localized in the cytosol. In a further exemplary embodiment, at least one of the pathway enzymes localized to the cytosol is a cytosolically active DHAD enzyme as disclosed herein.

In various embodiments described herein, the isobutanol pathway enzyme(s) is/are selected from the group consisting of acetolactate synthase (ALS), ketol-acid reductoisomerase (KARI), dihydroxyacid dehydratase (DHAD), 2-keto-acid decarboxylase (KIVD), and alcohol dehydrogenase (ADH).

As described herein, the cytosolically active isobutanol pathway enzymes of the present invention can include native (i.e., parental) enzymes that exhibit cytosolic activity, as well isobutanol pathway enzymes that have been modified or mutated to increase their cytosolic localization and/or activity as compared to native (i.e. parental) pathway enzymes.

In various embodiments described herein, the isobutanol pathway enzymes may be derived from a prokaryotic organism. In alternative embodiments described herein, the isobutanol pathway enzymes may be derived from a eukaryotic organism.

In some embodiments, the invention provides modified or mutated isobutanol pathway enzymes, wherein said isobutanol pathway enzymes exhibit increased cytosolic activity as compared to their parental isobutanol pathway enzymes. In another embodiment, the invention provides modified or mutated isobutanol pathway enzymes, wherein said isobutanol pathway enzymes exhibit increased cytosolic activity as compared to the homologous isobutanol pathway enzyme from *S. cerevisiae*.

In various embodiments described herein, at least one of the isobutanol pathway enzymes exhibiting cytosolic activity is ALS. In one embodiment, the ALS is derived from a prokaryotic organism, including, but not limited to *Bacillus subtilis* or *L. lactis*. In another embodiment, the ALS is derived from a eukaryotic organism, including, but not limited to *Magnaporthe grisea, Phaeosphaeria nodorum, Talaromyces stipitatus*, and *Trichoderma atroviride*.

In additional embodiments, at least one of the isobutanol pathway enzymes exhibiting cytosolic activity is KARI. In one embodiment, the KARI is derived from a prokaryotic organism, including, but not limited to *Escherichia coli, B. subtilis* or *L. lactis*. In another embodiment, the KARI is derived from a eukaryotic organism, including, but not limited to *Piromyces* sp. E2, *S. cerevisiae*, and *Arabidopsis*. In certain specific embodiments, the KARI comprises an amino acid sequence selected from an organism selected from the group consisting of *E. coli, S. cerevisiae, B. subtilis Piromyces* sp. E2, *Buchnera aphidicola, Spinacia oleracea, Oryza sativa, Chlamydomonas reinhardtii, N. crassa, Schizosaccharomyces pombe, Laccaria bicolor, Ignicoccus hospitalis, Picrophilus torridus, Acidiphilium cryptum, Cyanobacteria/Synechococcus* sp., *Zymomonas mobilis, Bacteroides thetaiotaomicron, Methanococcus maripaludis, Vibrio fischeri, Shewanella* sp, *G. forsetii, Psychromonas ingrhamaii*, and *Cytophaga hutchinsonii*. In additional embodiments, the KARI may be an NADH-dependent KARI.

In various embodiments described herein, the isobutanol pathway enzyme may be mutated or modified to remove an N-terminal mitochondrial targeting sequence (MTS). Removal of the MTS can increase cytosolic localization of the isobutanol pathway enzyme and/or increase the cytosolic activity of the isobutanol pathway enzyme as compared to the parental isobutanol pathway enzyme.

In some embodiments, the MTS may be modified or mutated to reduce or eliminate its, ability to target the isobutanol pathway enzyme to the mitochondria. Selected modification of the MTS can increase cytosolic localization of the isobutanol pathway enzyme and/or increase the cytosolic activity of the isobutanol pathway enzyme as compared to the parental isobutanol pathway enzyme.

In additional embodiments, the invention provides recombinant microorganisms comprising an isobutanol pathway enzyme fused to a peptide tag, whereby said isobutanol pathway enzyme exhibits increased cytosolic localization and/or cytosolic activity as compared to the parental enzyme. As a result, the recombinant microorganism comprising the tagged isobutanol pathway enzyme will generally exhibit an increased ability to perform a step involved in the conversion of pyruvate to isobutanol in the cytosol. In one embodiment, the peptide tag is non-cleavable. In another embodiment, the peptide tag is fused at the N-terminus of the isobutanol pathway enzyme. In another embodiment, the peptide tag is fused at the C-terminus of the isobutanol pathway enzyme. In certain embodiments, the peptide tag may be selected from the group consisting of ubiquitin, ubiquitin-like (UBL) proteins, myc, HA-tag, green fluorescent protein (GFP), and the maltose binding protein (MBP).

In various embodiments described herein, the recombinant microorganisms may further comprise a nucleic acid encoding a chaperone protein, wherein said chaperone protein assists the folding of a protein exhibiting cytosolic activity. In a preferred embodiment, the protein exhibiting cytosolic activity is an isobutanol pathway enzyme. In one embodiment, the chaperone may be a native protein. In another embodiment, the chaperone protein may be an exogenous protein. In some embodiments, the chaperone protein may be selected from the group consisting of: endoplasmic reticulum oxidoreductin 1 (Ero1) including variants of Ero1 that have been suitably altered to reduce or prevent its normal localization to the endoplasmic reticulum; thioredoxins (including, but not limited to, Trx1 and Trx2), thioredoxin reductase (Trr1), glutaredoxins (including, but not limited to, Grx1, Grx2, Grx3, Grx4, Grx5, Grx6, Grx7, and Grx8), glutathione reductase (Glr1), and Jac1, including variants of Jac1 that have been suitably altered to reduce or prevent its normal mitochondrial localization; and homologs or variants thereof.

In some embodiments, the recombinant microorganisms may further comprise one or more genes encoding an iron-sulfur cluster assembly protein. In one embodiment, the iron-sulfur cluster assembly protein encoding genes may be derived from prokaryotic organisms. In one embodiment, the iron-sulfur cluster assembly protein encoding genes are derived from a bacterial organism, including, but not limited to *E. coli, L. lactis, Helicobacter pylori*, and *Entamoeba histolytica*. In specific embodiments, the bacterially derived iron-sulfur cluster assembly protein encoding genes are selected from the group consisting of cyaY, iscS, iscU, iscA, hscB, hscA, fdx, isuX, sufA, sufB, sufC, sufD, sufS, sufE, apbC, and homologs or variants thereof.

In another embodiment, the iron-sulfur cluster assembly protein encoding genes may be derived from eukaryotic organisms, including, but not limited to yeasts and plants. In one embodiment, the iron-sulfur cluster protein encoding genes are derived from a yeast organism, including, but not limited to *S. cerevisiae*. In specific embodiments, the yeast derived genes encoding iron-sulfur cluster assembly proteins are selected from the group consisting of Cfd1, Nbp35, Nar1, Cia1, and homologs or variants thereof. In a further embodiment, the iron-sulfur cluster assembly protein encoding genes may be derived from plant nuclear genes which encode proteins translocated to chloroplast or plant genes found in the chloroplast genome itself.

In some embodiments, one or more genes encoding an iron-sulfur cluster assembly protein may be mutated or modified to remove a signal peptide, whereby localization of the product of said one or more genes to the mitochondria or other subcellular compartment is prevented. In certain embodiments, it may be preferable to overexpress one or more genes encoding an iron-sulfur cluster assembly protein.

In certain embodiments described herein, it may be desirable to reduce or eliminate the activity and/or proteins levels of one or more iron-sulfur cluster containing cytosolic proteins. In a specific embodiment, the iron-sulfur cluster containing cytosolic protein is 3-isopropylmalate dehydratase (Leu1p). In one embodiment, the recombinant microorganism comprises a mutation in the LEU1 gene resulting in the reduction of Leu1p protein levels. In another embodiment, the recombinant microorganism comprises a partial deletion in the LEU1 gene resulting in the reduction of Leu1p protein levels. In another embodiment, the recombinant microorganism comprises a complete deletion in the LEU1 gene resulting in the reduction of Leu1p protein levels. In another embodiment, the recombinant microorganism comprises a modification of the regulatory region associated with the LEU1 gene resulting in the reduction of Leu1p protein levels. In yet another embodiment, the recombinant microorganism comprises a modification of a transcriptional regulator for the LEU1 gene resulting in the reduction of Leu1p protein levels.

In additional embodiments, the present invention provides recombinant microorganisms comprising chimeric proteins consisting of isobutanol pathway enzymes. In one embodiment, the chimeric proteins consist of ALS and at least one additional protein. In a specific embodiment, the additional protein is KARI. In a preferred embodiment, the chimeric protein exhibits the biocatalytic properties of both ALS and KARI. Such a chimeric protein allows for an increase in the concentration of 2-acetolactate at the active site of KARI as compared to the parental microorganism, giving the recombinant microorganism an enhanced ability to convert 2-acetolactate to 2,3-dihydroxyisovalerate. In another embodiment, the chimeric proteins consist of KARI and at least one additional protein. In a specific embodiment, the additional protein is DHAD. In a preferred embodiment, the chimeric protein exhibits the biocatalytic properties of both KARI and DHAD. In each of the various embodiments described herein, the proteins may be connected via a flexible linker.

In various embodiments described herein, the recombinant microorganisms may be engineered to express native genes that catalyze a step in the conversion of pyruvate to isobutanol. In one embodiment, the recombinant microorganism is engineered to increase the activity of a native metabolic pathway gene for conversion of pyruvate to isobutanol. In another embodiment, the recombinant microorganism is further engineered to include at least one enzyme encoded by an exogenous gene and at least one enzyme encoded by a native gene. In yet another embodiment, the recombinant microorganism comprises a reduction in the activity of a native metabolic pathway as compared to a parental microorganism.

In another embodiment, the present invention provides recombinant microorganisms comprising a scaffold system tethered to one or more isobutanol pathway enzymes. In a specific embodiment, the scaffold system is the MAP kinase scaffold (Ste5) system. In a further embodiment, one or more of the isobutanol pathway enzymes may be modified or mutated to comprise a protein domain allowing for binding to the scaffold system.

In various embodiments described herein, the recombinant microorganisms may be microorganisms of the *Saccharomyces* clade, *Saccharomyces sensu stricto* microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces sensu stricto* microorganisms. In one embodiment, the *Saccharomyces sensu stricto* is selected from the group consisting of *S. cerevisiae, S. kudriavzevii, S. mikatae, S. bayanus, S. uvarum. S. carocanis* and hybrids thereof.

In some embodiments, the recombinant microorganisms may be Crabtree-negative recombinant yeast microorganisms. In one embodiment, the Crabtree-negative yeast microorganism is classified into a genera selected from the group consisting of *Kluyveromyces, Pichia, Hansenula, Issatchenkia*, or *Candida*. In additional embodiments, the Crabtree-negative yeast microorganism is selected from *Kluyveromyces lactis, Kluyveromyces marxianus, Pichia anomala, Pichia stipitis, Hansenula anomala, Issatchenkia orientalis, Candida utilis* and *Kluyveromyces waltii*.

In some embodiments, the recombinant microorganisms may be Crabtree-positive recombinant yeast microorganisms. In one embodiment, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces*. In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. bailli, Z. rouxii, Debaryomyces hansenii, Pichia pastorius, Schizosaccharomyces pombe*, and *Saccharomyces uvarum*.

In some embodiments, the recombinant microorganisms may be post-WGD (whole genome duplication) yeast recombinant microorganisms. In one embodiment, the post-WGD yeast recombinant microorganism is classified into a genera selected from the group consisting of *Saccharomyces* or *Candida*. In additional embodiments, the post-WGD yeast is selected from the group consisting of *Saccharomyces cerevisiae, Saccharomyces uvarum, Saccharomyces bayanus, Saccharomyces paradoxus, Saccharomyces castelli*, and *Candida glabrata*.

In some embodiments, the recombinant microorganisms may be pre-WGD (whole genome duplication) yeast recombinant microorganisms. In one embodiment, the pre-WGD yeast recombinant microorganism is classified into a genera selected from the group consisting of *Saccharomyces, Kluyveromyces, Candida, Pichia, Debaryomyces, Hansenula, Pachysolen, Yarrowia, Issatchenkia*, and *Schizosaccharomyces*. In additional embodiments, the pre-WGD yeast is selected from the group consisting of *Saccharomyces kluyveri, Kluyveromyces thermotolerans, Kluyveromyces marxianus, Kluyveromyces well, Kluyveromyces lactis, Candida tropicalis, Pichia pastoris, Pichia anomala, Pichia stipitis, Debaryomyces hansenii, Hansenula anomala, Pachysolen tannophilis, Yarrowia lipolytica, Issatchenkia orientalis*, and *Schizosaccharomyces pombe*.

In some embodiments, the recombinant microorganisms may be microorganisms that are non-fermenting yeast microorganisms, including, but not limited to those, classified into a genera selected from the group consisting of *Tricosporon, Rhodotorula*, or *Myxozyma*.

In another aspect, the present invention provides methods of producing isobutanol using one or more recombinant microorganisms of the invention. In one embodiment, the method includes cultivating one or more recombinant microorganisms in a culture medium containing a feedstock providing the carbon source until a recoverable quantity of the isobutanol is produced and optionally, recovering the isobutanol. In one embodiment, the microorganism is selected to produce isobutanol from a carbon source at a yield of at least about 5 percent theoretical. In another embodiment, the microorganism is selected to produce isobutanol at a yield of at least about 10 percent, at least about 15 percent, about least about 20 percent, at least about 25 percent, at least about 30 percent, at least about 35 percent, at least about 40 percent, at least about 45 percent at least about 50 percent, at least about 55 percent, at least about 60 percent, at least about 65 percent, at least about 70 percent, at least about 75 percent, at least about 80 percent theoretical, at least about 85 percent theoretical, or at least about 90 percent theoretical.

In one embodiment, the microorganism produces isobutanol from a carbon source at a specific productivity of at least about 0.7 mg/L/hr per OD. In another embodiment, the microorganism produces isobutanol from a carbon source at a specific productivity of at least about 1 mg/L/hr per OD, at least about 10 mg/L/hr per OD, at least about 50 mg/L/hr. per OD, at least about 100 mg/L/hr per OD, at least about 250 mg/L/hr per OD, or at least about 500 g/L/hr per OD.

BRIEF DESCRIPTION OF DRAWINGS

Illustrative embodiments of the invention are illustrated in the drawings, in which.

DETAILED DESCRIPTION

Figure 1:
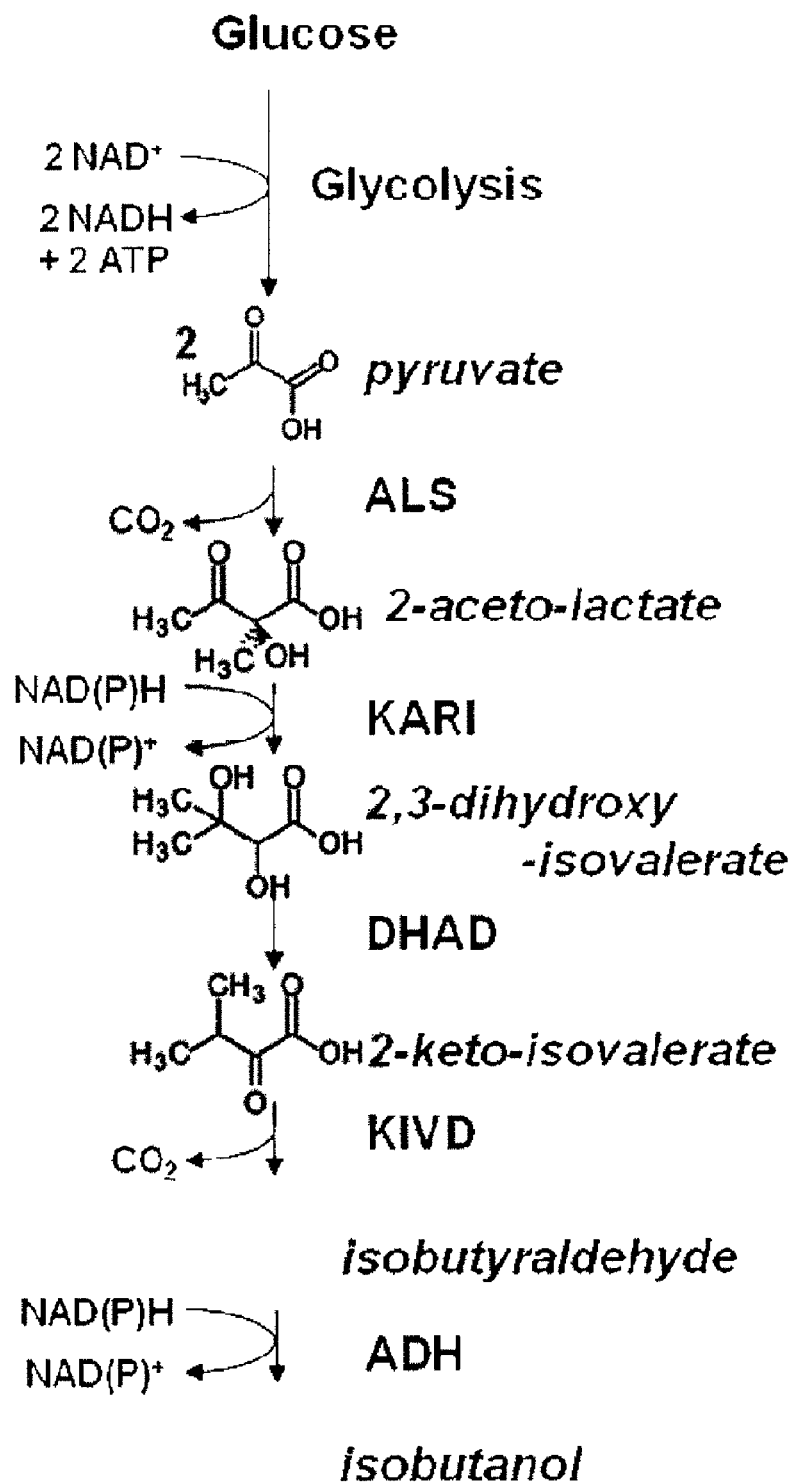
FIG. 1 illustrates an exemplary embodiment of an isobutanol pathway.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "genus" is defined as a taxonomic group of related species according to the Taxonomic Outline of Bacteria and Archaea (Garrity et al., 2007, TOBA Release 7.7, Michigan State University Board of Trustees).

The term "species" is defined as a collection of closely related organisms with greater than 97% 16S ribosomal RNA sequence homology and greater than 70% genomic hybridization and sufficiently different from all other organisms so as to be recognized as a distinct unit.

The terms "recombinant microorganism," "modified microorganism" and "recombinant host cell" are used interchangeably herein and refer to microorganisms that have been genetically modified to express or over-express endogenous polynucleotides, or to express heterologous polynucleotides, such as those included in a vector, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism.

The term "engineer" refers to any manipulation of a microorganism that results in a detectable change in the microorganism, wherein the manipulation includes but is not limited to inserting a polynucleotide and/or polypeptide heterologous to the microorganism and mutating a polynucleotide and/or polypeptide native to the microorganism.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial selection pressure. In still other embodiments, the mutations in the microorganism genome are the result of genetic engineering.

The term "biosynthetic pathway", also referred to as "metabolic pathway", refers to a set of anabolic or catabolic, biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "heterologous" as used herein with reference to molecules and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a recombinant microorganism as described herein.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate The term "fermentation" or "fermentation process" is defined as a process in which a microorganism is cultivated in a culture medium containing raw materials, such as feedstock and nutrients, wherein the microorganism converts raw materials, such as a feedstock, into products.

The term "volumetric productivity" or "production rate" is defined as the amount of product formed per volume of medium per unit of time. Volumetric productivity is reported in gram per liter per hour (g/L/h).

The term "specific productivity" or "specific production rate" is defined as the amount of product formed per volume of medium per unit of time per amount of cells. Volumetric productivity is reported in gram or milligram per liter per hour per OD (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

"Aerobic conditions" are defined as conditions under which the oxygen concentration in the fermentation medium is sufficiently high for an aerobic or facultative anaerobic microorganism to use as a terminal electron acceptor.

In contrast, "anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to pyruvate, yielding ethanol. Fermentative pathways are usually active under anaerobic conditions but may also occur under aerobic conditions, under conditions where NADH is not fully oxidized via the respiratory chain. For example, above certain glucose concentrations, Crabtree positive yeasts produce large amounts of ethanol under aerobic conditions.

The term "byproduct" means an undesired product related to the production of a biofuel or biofuel precursor. Byproducts are generally disposed as waste, adding cost to a production process.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. $3^{rd}$ edition. p. 28-29. Cambridge University Press, Cambridge, UK) or by monitoring the production of fermentation productions such as ethanol and $CO_2$.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different, molecule including polynucleotides.

The term "protein", "peptide" or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

Cytosolically Localized Isobutanol Pathway Enzymes and Recombinant Microorganisms Comprising the Same Biosynthetic pathways for the production of isobutanol and 2-methyl-1-butanol by recombinant microorganisms are described by Atsumi et al. (Atsumi et al., 2008, *Nature* 451: 86-89). One strategy described herein for improving isobutanol production by recombinant microorganisms is the localization of the enzymes catalyzing the biosynthetic isobutanol pathway to the yeast cytosol. Cytosolic localization of the isobutanol pathway enzymes activity is desirable, especially for the production of isobutanol since the ideal biocatalyst (e.g. recombinant microorganism) will have the entire isobutanol pathway functionally expressed in the same compartment (e.g. preferably in the cytosol). In addition, this localization allows the pathway to utilize pyruvate and NAD(P)H that is generated in the cytosol by glycolysis and/or the pentose phosphate pathway without the need for transfer of these metabolites to an alternative compartment (i.e. the mitochondria). However, such a strategy of compartmental localization in yeast is not feasible unless the pathway enzymes exhibit cytosolic activity in that compartment. Thus, if one or more of the cytosolically localized pathway enzymes lacks catalytic activity in the cytosol, high level isobutanol production will not occur. As the present application shows in the Examples below, inefficient cytosolic activity of one or more isobutanol pathway enzymes (e.g. DHAD or ALS) can limit isobutanol production.

The present inventors describe herein cytosolically active isobutanol pathway enzymes and their use in the production of various beneficial metabolites, such as isobutanol and 2-methyl-1-butanol. Using a combination of genetic selection and biochemical analyses, the present inventors have identified a number of isobutanol pathway enzymes, including DHAD enzymes, that have activity in the cytosol. Accordingly, in one aspect, the present application describes the discovery of DHADs with enhanced cytosolic activity and shows that these newly identified, cytosolically active DHADs facilitate improved isobutanol production when co-expressed in the cytosol with the remaining four isobutanol pathway enzymes.

As shown in Example 3 below, the native DHAD of yeast is localized to the mitochondria. Therefore, for economically viable production of isobutanol to occur in the yeast cytosol, the identification of heterologous DHAD enzymes that are "cytosolically active" in yeast (i.e. "active in the cytosol" of the yeast) is important. In addition, the present application shows that in the absence of ALS, KARI, KIVD, and ADH which are "cytosolically active" or "active in the cytosol" in the cytosol of yeast, economically viable isobutanol production will not occur, thus making identification of native and/or heterologous ALS, KARI, KIVD, and ADH enzymes additionally and/or independently important to cytosolic isobutanol production.

As used herein, the term "cytosolically active" or "active in the cytosol" means the enzyme exhibits enzymatic activity in the cytosol of a eukaryotic organism. Cytosolically active enzymes may further be additionally and/or independently characterized as enzymes that generally exhibit a specific cytosolic activity which is greater than the specific mitochondrial activity. In certain respects, a "cytosolically active" enzymes of the present invention exhibit a ratio of the specific activity of the mitochondrial fraction over the specific activity of the whole cell fraction of less than 1, as determined by the method disclosed in Example 3 herein. Cytosolically active enzymes may further be additionally and/or independently characterized as enzymes that, when overexpressed, result in increased activity in the whole cell fraction and do not result in increased activity in the mitochondrial fraction, as determined by the method disclosed in Example 20. Cytosolically active enzymes may further be additionally and/or independently characterized as enzymes that, when overexpressed as one of the five enzymes that together comprise the fivestep biosynthetic pathway for the conversion of pyruvate isobutanol, result in increased isobutanol production compared to enzymes that are not cytosolically active or that are less cytosolically active.

As used herein, the term "cytosolically localized" or "cytosolic localization" means the enzyme is localized in the cytosol of a eukaryotic organism. Cytosolically localized enzymes may further be additionally and/or independently characterized as enzymes that exhibit a cytosolic protein level which is greater than the mitochondrial protein level.

Identification of Cytosolically Active Isobutanol Pathway Enzymes

In one aspect, the present invention encompasses a number of strategies for identifying cytosolically active and/or localized isobutanol pathway enzymes that exhibit cytosolic activity and/or cytosolic localization, as well as methods for modifying said isobutanol pathway enzymes to increase their ability to exhibit cytosolic activity and/or cytosolic localization.

In various embodiments described herein, the isobutanol pathway enzymes may be derived from a prokaryotic organism. In alternative embodiments described herein, the isobutanol pathway enzyme may be derived from a eukaryotic organism. In one embodiment, the eukaryotic organism is a fungal organism. As described herein, the present inventors have found that in general, an enzyme from a fungal source is more likely to show activity in yeast than a bacterial enzyme expressed in yeast. In addition, homologs that are normally expressed in the cytosol are desired, as a normally cytoplasmic enzyme is likely to show higher activity in the cytosol as compared to an enzyme that is relocalized to the cytosol from other organelles, such as the mitochondria. Fungal homologs of various isobutanol pathway enzymes are often localized to the mitochondria. The present inventors have found that fungal homologs of isobutanol pathway enzymes that are cytosolically localized will generally be expected to exhibit higher activity in the cytosol of yeast than those of wild-type yeast strains. Thus, in one embodiment, the present invention provides fungal isobutanol pathway enzyme homologs that are cytosolically active and/or cytosolically localized.

Dihydroxyacid Dehydratase (DHAD)

In additional embodiments, at least one of the isobutanol pathway enzymes exhibiting cytosolic activity is a dihydroxyacid dehydratase (DHAD). In accordance with this embodiment, the present invention provides cytosolically active dihydroxyacid dehydratases (DHADs) and further describes methods for their use in the production of various beneficial metabolites, such as isobutanol and 2-methyl-1- butanol. As noted above, biosynthetic pathways for the production of isobutanol and 2-methyl-1-butanol have been described (Atsumi et al., 2008, Nature 451: 86-89). In these biosynthetic pathways, DHAD catalyzes the conversion of 2,3-dihydroxyisovalerate to 2-ketoisovalerate, and 2,3-dihydroxy-3-methylvalerate to 2-keto-3-methylvarate, respectively. Using a combination of genetic selection and biochemical analyses, the present inventors have identified a number of DHAD homologs that have activity in the cytosol.

Among the many strategies for identifying cytosolically active DHADs, the present inventors performed multiway-protein alignments between several DHAD homologs. Using this analysis, the present inventors identified a protein motif that was surprisingly unique to a subset of DHAD homologs exhibiting cytosolical activity. This protein motif, P(I/L)XXXGX(I/L)XIL (SEQ ID NO: 27) was found in DHAD homologs demonstrating cytosolic activity in yeast. Therefore, in one embodiment, the present invention provides DHAD enzymes comprising the amino acid sequence P(I/L)XXXGX(I/L)XIL (SEQ ID NO: 27), wherein X is any natural or non-natural amino acid, and wherein said DHAD enzyme exhibits the ability to convert 2,3-dihydroxyisovalerate to ketoisovalerate in the cytosol. DHAD enzymes harboring this sequence include those derived from *L. lactis* (SEQ ID NO: 18), *G. forsetii* (SEQ ID NO: 17), *Acidobacteria bacterium* Ellin345 (SEQ ID NO: 16), *Saccharopolyspora erythraea* (SEQ ID NO: 19), *Yarrowia lipolytica* (SEQ ID NO: 13), *Francisella tularensis* (SEQ ID NO: 14), *Arabidopsis thaliana* (SEQ ID NO: 15), *Thermotoga petrophila* (SEQ ID NO: 10), and *Victivallis vadensis* (SEQ ID NO: 11). Also encompassed herein are DHAD enzymes that comprise a motif that is at least about 70% similar, at least about 80% similar, or at least about 90% similar to the motif shown in SEQ ID NO: 27.

As described herein, an even more specific version of this motif has been identified by the present inventors. Thus, in a further embodiment, the present invention provides DHAD enzymes comprising the amino acid sequence PIKXXGX(I/L)XIL (SEQ ID NO: 28), wherein X is any natural or non-natural amino acid, and wherein said DHAD enzyme exhibits the ability to convert 2,3-dihydroxyisovalerate to ketoisovalerate in the cytosol. DHAD enzymes harboring this sequence include those derived from *L. lactis* (SEQ ID NO: 18), *G. forsetii* (SEQ ID NO: 17), *Acidobacteria bacterium* Ellin345 (SEQ ID NO: 16), *Y. lipolytica* (SEQ ID NO: 13), *F. tularensis* (SEQ ID NO: 14), *A. thaliana* (SEQ ID NO: 15), *T. petrophila* (SEQ ID NO: 10), and *V. vadensis* (SEQ ID NO: 11). Also encompassed herein are DHAD enzymes that comprise a motif that is at least about 70% similar, at least about 80% similar, or at least about 90% similar to the motif shown in SEQ ID NO: 28.

As noted above, one such cytosolically active DHAD identified herein is exemplified by the *L. lactis* DHAD amino acid sequence of SEQ ID NO: 18, which is encoded by the *L. lactis* ilvD gene. As described herein, the present inventors have discovered that yeast strains expressing the cytosolically active *L. lactis* ilvD (DHAD) exhibit higher isobutanol production than yeast strains expressing the *S. cerevisiae* ILV3 (DHAD), even when the ILV3 from *S. cerevisiae* is truncated at its N-terminus to remove a putative mitochondrial targeting sequence. In addition to the use and identification of the cytosolically active DHAD homolog from *L. lactis*, the present invention encompasses a number of different strategies for identifying DHAD enzymes that exhibit cytosolic activity and/or cytosolic localization, as well as methods for modifying DHADs to increase their ability to exhibit cytosolic activity and/or cytosolic localization.

In various embodiments described herein, the DHAD enzymes may be derived from a prokaryotic organism. In one embodiment, the prokaryotic organism is a bacterial organism. In another embodiment, the bacterial organism is *L. lactis*. In a specific embodiment, the DHAD enzyme from *L. lactis* comprises the amino acid sequence of SEQ ID NO: 18. In other embodiments, the bacterial organisms are of the genus *Lactococcus, Gramella, Acidobacteria, Francisella, Thermotoga* and *Victivallis*.

In alternative embodiments, the DHAD enzyme may be derived from a eukaryotic organism. In one embodiment, the eukaryotic organism is a fungal organism. In an exemplary embodiment, the fungal organism is *Neurospora crassa*. In a specific embodiment, the DHAD enzyme from *N. crassa* comprises the amino acid sequence of SEQ ID NO: 165.

As described herein, the present inventors have found that in general, an enzyme from a fungal source is more likely to show activity in yeast than a bacterial enzyme expressed in yeast. In addition, homologs that are normally expressed in the cytosol are desired, as a normally cytoplasmic enzyme is likely to show higher activity in the cytosol as compared to an enzyme that is relocalized to the cytosol from other organelles, such as the mitochondria. Fungal homologs of various isobutanol pathway enzymes, including DHAD, are often localized to the mitochondria. The present inventors have found that fungal homologs of DHAD that are cytosolically localized will generally be expected to exhibit higher activity in the cytosol of yeast than those of wild-type yeast strains. Thus, in one embodiment, the present invention provides fungal DHAD homologs that are cytosolically active and/or cytosolically localized.

In another embodiment, the eukaryotic organism is a yeast organism. In another embodiment, the eukaryotic organism is selected from the group consisting of the genera *Enamoeba* and *Giardia*.

In various embodiments described herein, the recombinant microorganism may exhibit at least about 5 percent greater dihydroxyacid dehydratase (DHAD) activity in the cytosol as compared to the parental microorganism. In another embodiment, the recombinant microorganism may exhibit at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 100 percent, at least about 200 percent, or at least about 500 percent greater dihydroxyacid dehydratase (DHAD) activity in the cytosol as compared to the parental microorganism.

In another embodiment, the present invention provides DHAD enzymes that, when overexpressed in yeast, result in increased activity in the whole cell fraction and do not result in increased activity in the mitochondrial fraction. In one embodiment, the DHAD activity in the whole cell fraction is increased by at least about 2-fold. In another embodiment, DHAD activity in the whole cell fraction is increased by at least about 5-fold. In yet another embodiment, DHAD activity in the whole cell fraction is increased by at least about 7-fold. In yet another embodiment, DHAD activity in the whole cell fraction is increased by at least about 10-fold. In yet another embodiment, DHAD activity in the whole cell fraction is increased by at least about 50-fold. In yet another embodiment, DHAD activity in the whole cell fraction is increased by at least about 100-fold.

Acetolactate Synthase (ALS)

As described herein, the isobutanol pathway enzymes in addition to DHAD should preferably be active in the cytosol. These cytosolically active isobutanol pathway enzymes will generally exhibit enzymatic activity in the cytosol. For instance, a cytosolically active ALS should generally exhibit the ability to convert 2 pyruvate to acetolactate in the cytosol. Thus, in various embodiments described herein, at least one of the isobutanol pathway enzymes exhibiting cytosolic activity is acetolactate synthase (ALS). In yeasts such as *S. cerevisiae*, the native acetolactate synthase, encoded in *S. cerevisiae* by the ILV2 gene, is naturally expressed in the yeast mitochondria. Unlike the endogenous acetolactate synthase of yeast, expression of heterologous, acetolactate synthases such as the *B. subtilis* alsS and the *L. lactis* alsS in yeast occurs in the yeast cytosol (i.e. cytosolically-localized). Thus, cytosolic expression of acetolactate synthase is achieved by transforming a yeast with a gene encoding an acetolactate synthase protein (EC 2.2.1.6).

ALS homologs that could be cytosolically expressed and localized in yeast are predicted to lack a mitochondrial targeting sequence as analyzed using mitoprot (Claros at, 1996, *Eur. J. Biochem* 241: 779-86). Such cytosolically localized ALS proteins can be used as the first step in the isobutanol pathway. ALS homologs include, but are not limited to, the following: the *Serratia marcescens* ALS (GenBank Accession No. ADH43113.1) (probability of mitochondrial localization 0.07), the *Enterococcus faecalis* ALS (GenBank Accession No. NP_814940) (probability of mitochondrial localization 0.21), the *Leuconostoc mesenteroides* (GenBank Accession No. YP_818010.1) (probability of mitochondrial localization 0.21), the *Staphylococcus aureus* ALS (GenBank Accession No. YP 417545) (probability of mitochondrial localization 0.13), the *Burkholderia cenocepacia* ALS (GenBank Accession No. YP_624435) (probability of mitochondrial localization 0.15), the *T. atroviride* ALS (SEQ ID NO: 71) (probability of mitochondrial localization 0.19), the *T. stipitatus* ALS (SEQ ID NO: 72) (probability of mitochondrial localization 0.19), and the *Magnaporthe grisea* ALS (GenBank Accession No. EDJ99221) (probability of mitochondrial localization 0.02), a homolog or variant of any of the foregoing, and a polypeptide having at least 60% identity to anyone of the foregoing and exhibiting cytosolic ALS activity.

In one embodiment, the cytosolically active ALS is derived from a prokaryotic organism, including, but not limited to *B. subtilis* or *L. lactis*, which exhibit cytosolic activity. In another embodiment, the ALS may be derived from an eukaryotic organism, including, but not limited to *M. grisea, P. nodorum, T. stipitatus*, and *T. atroviride*.

In some embodiments, an ALS enzyme that is predicted to be mitochondrially localized may be mutated or modified to remove or modify an N-terminal mitochondrial targeting sequence (MTS) to remove or eliminate its ability to target the ALS enzyme to the mitochondria. Removal of the MTS can increase cytosolic localization of the ALS and/or increase the cytosolic activity of the ALS as compared to the parental ALS.

The conversion of two pyruvate molecules to acetolactate can be carried out by either an acetohydroxyacid synthase (AHAS) or an acetolactate synthase (ALS). AHASs are involved in biosynthesis of branched chain amino acids in the mitochondria of yeasts. They are FAD-dependent and are feedback inhibited by branched chain amino acids. ALSs are catabolic and are involved in the conversion of pyruvate to acetoin. ALS are FAD-independent and not feedback inhibited by branched chain amino acids. In addition, ALSs are specific for the conversion of two pyruvates to acetolactate. Therefore, ALSs are favored over AHASs. In addition, in the case of yeast, AHASs are normally mitochondrial, therefore a fungal ALS that is cytoplasmic is favored. Sequence analysis has shown that there is a conserved sequence 'RFDDR' found in AHASs that is not conserved among ALSs (Le et al., 2005, *Bull. Korean Chem Soc* 26: 916-20). This sequence is likely involved in FAD-binding by AHASs and thus could be used to distinguish between the FAD-dependent AHASs and the FAD-independent ALSs. Using this region to distinguish between AHASs and ALSs BLAST searches of fungal sequence databases were performed and resulted in the identification of ALS homologs from several fungal species (*M. grisea, P. nodorum, T. atroviride, T. stipitatus, P. marneffei*, and *Glomerella graminicola*). Of these sequences, the ALS homologs from *M. grisea, P. nodorum, T. stipitatus*, and *T. atroviride* will generally be expected to be cytosolically localized.

In one embodiment, the recombinant microorganism may exhibit at least about 5 percent greater acetolactate synthase (ALS) activity in the cytosol as compared to the parental microorganism. In another embodiment, the recombinant microorganism may exhibit at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 100 percent, at least about 200 percent, or at least about 500 percent greater acetolactate synthase (ALS) activity in the cytosol as compared to the parental microorganism.

Ketol-Acid Reductoisomerase (KARI)

In additional embodiments, at least one of the isobutanol pathway enzymes exhibiting cytosolic activity is a ketol-acid reductoisomerase (KARI). A cytosolically active KARI should generally exhibit the ability to convert acetolactate to 2,3-dihydroxyisovalerate in the cytosol.

In one embodiment, the KARI is derived from a prokaryotic organism, including, but not limited to *Escherichia coli, B. subtilis* or *L. lactis*.

in another embodiment, the KARI is derived from a eukaryotic organism, including, but not limited to *Piromyces* sp. E2, *S. cerevisiae*, and *Arabidopsis*. Fungal homologs of KARI are generally mitochondrially localized. The present inventors have identified a fungal homolog from the anaerobic rumenal fungi, *Piromyces* sp. E2, that is cytosolically localized.

In certain specific embodiments, the KARI comprises an amino acid sequence selected from the group consisting of *E. coli* (GenBank No: NP_418222, SEQ ID NO: 1), *S. cerevisiae* (GenBank No: NP_013459, SEQ ID NO: 2), and *B. subtilis* (GenBank No: CAB14789) and the KARI enzymes from *Piromyces* sp E2 (GenBank No: CAA76356), *B. aphidicola* (GenBank No: AAF13807), *S. oleracea* (GenBank No: CAA40356), *O. sativa* (GenBank No: NP_001056384, SEQ ID NO: 3), *C. reinhardtii* (GenBank No: XP_001702649, SEQ ID NO: 6), *N. crassa* (GenBank No: XP_961335), *S. pombe* (GenBank No: NP_001018845), *L. bicolor* (GenBank No: XP_001880867), *I. hospitalis* (GenBank No: YP_001435197), *P. torridus* (GenBank No: YP_023851, SEQ ID NO: 7), *A. cryptum* (GenBank No: YP_001235669, SEQ ID NO: 5), *Cyanobacteria/Synechococcus* sp. (GenBank No: YP_473733), *Z. mobilis* (GenBank No: YP_162876: SEQ ID NO. 8), *B. thetaiotaomicron* (GenBank No: NP 810987), *M. maripaludis* (GenBank No: YP_001097443, SEQ ID NO: 4), *V. fischeri* (GenBank No:

YP_205911), *Shewanella* sp (GenBank No: YP_732498.1), *G. forsetti* (GenBank No: YP 862142), *P. ingrhamaii* (GenBank No: YP_942294), and *C. hutchinsonii* (GenBank No: YP_677763), a homolog or variant of any of the foregoing, and a polypeptide having at least 60% identity to anyone of the foregoing and exhibiting cytosolic KARI activity.

In additional embodiments, the KARI may be an NADH-dependent KARI. Thus, in one embodiment, the present invention provides recombinant microorganisms in which the NADPH-dependent enzymes KARI is replaced with an enzyme that preferentially depends on NADH (i.e. a KARI that is NADH-dependent). In one embodiment, such enzymes may be identified in nature. In an alternative embodiment, such enzymes may be generated by protein engineering techniques including but not limited to directed evolution or site-directed mutagenesis. NADH-dependent KARIs useful in various methods of the present invention are described in commonly owned and co-pending applications U.S. Ser. No. 12/610,784 and PCT/US09/62952 (published as WO/2010/051527), which are herein incorporated by reference in their entireties for all purposes.

In one embodiment, a microorganism is, provided in which cofactor usage is balanced during the production of a fermentation product and the microorganism produces the fermentation product at a higher yield compared to a modified microorganism in which the cofactor usage in not balanced. In another embodiment of the present invention, a microorganism is provided in which the cofactor usage is balanced during the production of isobutanol and the microorganism produces isobutanol at a higher yield compared to a modified microorganism in which the cofactor usage in not balanced. Methods for achieving co-factor balance are described in commonly owned and co-pending applications U.S. Ser. No. 12/610,784 and PCT/US09/62952 (published as WO/2010/051527), which are herein incorporated by reference in their entireties for all purposes.

In one embodiment, the recombinant microorganism may exhibit at least about 5 percent greater ketol-acid reductoisomerase (KARI) activity in the cytosol as compared to the parental microorganism. In another embodiment, the recombinant microorganism may exhibit at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 100 percent, at least about 200 percent, or at least about 500 percent greater ketol-acid reductoisomerase (KARI) activity in the cytosol as compared to the parental microorganism.

Keto-Acid Decarboxylase (KIVD)

A cytosolically active KIVD should generally exhibit the ability to convert ketoisovalerate to isobutyraldehyde in the cytosol. In one embodiment, the cytosolically active KIVD is derived from a prokaryotic organism, including, but not limited to *L. lactis*, which exhibits cytosolic activity. In a specific embodiment, the KIVD enzyme from *L. lactis* comprises the amino acid sequence of SEQ ID NO: 173. In additional embodiments, the cytosolically active KIVD is derived from, for example, *Enterobacter cloacae* (Accession No. P23234.1), *Mycobacterium smegmatis* (Accession No. A0R480.1), *Mycobacterium tuberculosis* (Accession No. O53865.1), *Mycobacterium avium* (Accession No. Q742Q2.1), *Azospirillum brasilense* (Accession No. P51852.1), *B. subtilis* (see Oku et al., 1988, *J. Biol. Chem.* 263: 18386-96), a homolog or variant of any of the foregoing, and a polypeptide having at least 60% identity to anyone of the foregoing and exhibiting cytosolic KIVD activity.

In an alternative embodiment, the KIVD may be derived from an eukaryotic organism.

In one embodiment, the recombinant microorganism may exhibit at least about 5 percent greater 2-keto-acid decarboxylase (KIVD) activity in the cytosol as compared to the parental microorganism. In another embodiment, the recombinant microorganism may exhibit at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 100 percent, at least about 200 percent, or at least about 500 percent greater 2-keto-acid decarboxylase (KIVD) activity in the cytosol as compared to the parental microorganism.

Alcohol Dehydrogenase (ADH)

A cytosolically active ADH (used interchangeably herein with isobutanol dehydrogenase, "IDH") should generally exhibit the ability to convert isobutyraldehyde to isobutanol in the cytosol. In one embodiment, the cytosolically active ADH is derived from a prokaryotic organism, including, but not limited to *L. lactis*. In a specific embodiment, the ADH enzyme from *L. lactis* comprises the amino acid sequence of SEQ ID NO: 175. In additional embodiments, the ADH is derived from, for example, *Lactobacillus brevis* (Accession No. YP_794451.1), *Pediococcus acidilactici* (Accession No. ZP_06197454.1), *Bacillus cereus* (Accession No. YP_001374103.1), *Bacillus thuringiensis* (Accession No. ZP_04101989.1), *Leptotrichia goodfellowii* (Accession No. ZP_06011170.1), *Actinobacillus pleuropneumoniae* (Accession No. ZP_00134308.2), *Streptococcus sanguinis* (Accession No. YP_001035842.1), *Eikenella corrodens* (Accession No. ZP_03713785.1), *Exiguobacterium* sp. (Accession No. YP_002886170.1), *Neisseria elongate* (Accession No. ZP_06736067.1), *E. coli* (Accession No. ZP_06937530.1), *Neisseria meningitidis* (Accession No. CBA03965.1), *Erwinia pyrifoliae* (Accession No. CAY75147.1), and *Colwellia psychrerythraea* (Accession No. YP_270515.1), a homolog or variant of any of the foregoing, and a polypeptide having at least 60% identity to anyone of the foregoing and having cytosolic ADH activity.

In an alternative embodiment, the ADH may be derived from an eukaryotic organism, including, but not limited to *S. cerevisiae* and *D. melanogaster*. In a specific embodiment, the ADH enzyme from *S. cerevisiae* is Adh7. In another specific embodiment, the ADH enzyme from *D. melanogaster* comprises the amino acid sequence of SEQ ID NO: 176.

In one embodiment, the recombinant microorganism may exhibit at least about 5 percent greater alcohol dehydrogenase (ADH) activity in the cytosol as compared to the parental microorganism. In another embodiment, the recombinant microorganism may exhibit at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 100 percent, at least about 200 percent, or at least about 500 percent greater alcohol dehydrogenase (ADH) activity in the cytosol as compared to the parental microorganism.

Chimeric Isobutanol Pathway Enzymes

In another aspect, the present invention provides recombinant microorganisms comprising chimeric proteins consisting of isobutanol pathway enzymes. In one embodiment, the chimeric proteins consist of ALS and at least one additional protein. In a specific embodiment, the additional protein is KARI. In a preferred embodiment, the chimeric protein exhibits the biocatalytic properties of both ALS and KARI. By creating a chimeric protein that incorporates the activities of both ALS and KARI, this will generally be expected to reduce the effect of diffusion and decreasing the time for spontaneous decomposition to occur. By using a flexible linker and/or structural and sequence information to create a protein with the biocatalytic properties of both ALS and KARI, this will generally increase the concentration of 2-acetolactate at the active site of KARI, causing 2-acetolactate to be converted to 2,3-dihydroxyisovalerate near its theoretical maximum (very little effect of diffusion), and thus, the total concentration of 2-acetolactate should remain low correspondingly decreasing its spontaneous decomposition. This will generally have the effect of increasing the rate of conversion of 2-acetolactate to 2,3-dihydroxyisovalerate.

In another embodiment, the chimeric proteins consist of KARI and at least one additional protein. In a specific embodiment, the additional protein is DHAD. In a preferred embodiment, the chimeric protein exhibits the biocatalytic properties of both KARI and DHAD. In each of the various embodiments described herein, the proteins may be connected via a flexible linker.

Isobutanol Pathway Enzymes Attached to a Protein Scaffold

In another aspect, the present invention provides recombinant microorganisms comprising a scaffold system tethered to one or more isobutanol pathway enzymes. In a specific embodiment, the scaffold system is the MAP kinase scaffold (Ste5) system. In a further embodiment, one or more of the isobutanol pathway enzymes may be modified or mutated to comprise a protein domain allowing for binding to the scaffold system.

The present inventors have found that via the use of a protein scaffold, the isobutanol pathway enzymes that act in concert as part of a single pathway can be co-localized. In some embodiments, the scaffold systems are adapted for binding to the isobutanol pathway enzymes. By tethering the enzymes that work together in the pathway to a scaffold protein, they are brought into close physical proximity with each other, thus increasing the efficiency of the isobutanol production.

There are several advantages to keeping pathway enzymes together on a scaffold system. One is that proteins that normally would localize to an intracellular compartment, like the mitochondria, are partitioned onto the scaffold, thus keeping a sizeable portion of the protein population in the cytosol. Another is that the chemical products of each enzyme is physically close to the next enzyme in the pathway, which speeds reaction time and decreases the possibility that the product would be used in a competing pathway. Finally, unstable products of the enzymes would be used more quickly, since the next enzyme in the pathway would be adjacent to use it as a substrate, thus decreasing nonproductive degradation of the product.

In a preferred embodiment, the isobutanol pathway enzymes are arranged in the sequence in which they are needed to function (i.e. ALS followed by KARI followed by DHAD followed by KIVD followed by ADH). In another embodiment, the scaffolded protein complex is targeted to the cytosol by adding localization signals to the scaffold. In yet another embodiment, the scaffolded protein complex is targeted to the cell wall by adding localization signals to the scaffold. As would be understood by one of skill in the art, the scaffold system allows for co-localization of proteins or enzymes in addition to the isobutanol pathway enzymes. Such proteins may include chaperone proteins, proteins for the conversion of xylose to xylulose-5P, cellulases, etc.

Removal and/or Modification of N-Terminal Mitochondrial Targeting Sequences

The localization of the enzymes involved in production of isobutanol is desired to be cytosolic. Cytosolic localization allows for the pathway to utilize pyruvate and NAD(P)H that is generated in the cytosol by glycolysis and/or the pentose phosphate pathway without the need for the transfer of these metabolites to an alternative compartment (i.e. mitochondria). However, the yeast enzymes acetohydroxyacid synthase (AHAS; Ilv2+Ilv6), ketol-acid reductoisomerase (KARI; Ilv5), and dihydroxyacid dehydratase (DHAD; Ilv3) that carry out the first three steps of isobutanol production are physiologically localized to the mitochondria. Mitochondrial matrix proteins are typically targeted to the mitochondria by a N-terminal mitochondrial targeting sequence (MTS), which is then cleaved off in the mitochondria resulting in the 'mature' form of the enzyme (Paschen et al., 2001, *IUBMB Life* 52: 101-112). Indeed, the N-terminal targeting sequences for Ilv6 has been defined (Pang et al., 1999 *Biochemistry* 38: 5222-31). N-terminal deletions of Ilv5 has also been shown to re-localize this enzyme to the cytosol (Omura, 2008, *Appl. Microbiol. Biotechnol.* 78: 503-513; See also Omura, WO/2009/078108 A1, hereby incorporated by reference in its entirety).

One mechanism identified by the present inventors for the cytosolic localization of isobutanol pathway enzymes involves the removal and/or modification of N-terminal mitochondrial targeting sequences (MTS). Nuclear genome-encoded proteins destined to reside in the mitochondria often contain an N-terminal Mitochondrial Targeting Sequence (MTS) that is recognized by a set of proteins collectively known as mitochondrial import machinery. Following recognition and import, the MTS is then physically cleaved off of the imported protein. In eukaryotes, homologs of two of the isobutanol pathway enzymes, ketol-acid reductoisomerase (KARI, e.g. *S. cerevisiae* Ilv5) and dihydroxy acid dehydratase (DHAD, e.g. *S. cerevisiae* Ilv3), are predicted to be mitochondrial, based upon the presence of an N-terminal MTS as well as several in vivo functional and mutational studies (See e.g., Omura, F., 2008, *Appl Gen & Mol Biot* 78: 503-513). As described herein, the present inventors have designed isobutanol pathway enzymes, whereby the predicted MTS is removed or modified. In some instances, there exists experimental evidence for the length of the MTS. Specifically, the MTS of Ilv6 has been experimentally defined to be the N-terminal 61 amino acids (Pang et al., 1999, *Biochemistry* 38: 5222-31). The MTS of Ilv5 has been reported to be the N-terminal 47 residues (Kassow. A., 1992, "Metabolic effects of deleting the region encoding the transit peptide in *Saccharomyces cerevisiae* ILV5" PhD thesis, University of Copenhagen). In addition, the deletion of the N-terminal 46 amino acids of Ilv5 has been shown to result in an active enzyme that is localized in the cytosol (Omura, F., 2008, *Appl Gen & Mol Biot* 78: 503-513).

As described herein, the present inventors utilize deletions and/or modifications of the N-terminal MTS to localize the enzymes of the isobutanol pathway to the cytosol. In various embodiments, the MTS can be entirely or partly deleted or its sequence can be modified to eliminate its ability to target the protein to the mitochondria. A benefit of removing the entire MTS is that the resulting protein would essentially be the 'mature' form of the enzyme. The use of deletion of the N-terminal MTS can also be expanded to all enzymes/homologs to be used for isobutanol production. This is especially true for homologs from eukaryotic organisms other than *S. cerevisiae* where the enzymes are localized to the mitochondria. In addition, some bacterial homologs may have a putative MTS. As bacterial enzymes do not undergo an N-terminal cleavage, N-terminal deletions may be deleterious to these enzymes. In such cases, modifications of the sequence to block the MTS function of the N-terminal sequence may be preferable as such alterations would likely be less deleterious to the enzyme's activity. N-terminal MTS can be predicted by MitoProt II (See, e.g., Claros et al., 1996, *Eur. J. Biochem.* 241: 779-786). Using this program, the lengths of the MTS for Ilv2 and Ilv3 were predicted to be the N-terminal 55 and 20 amino acids, respectively. Modification of the MTS as contemplated herein includes the introduction of one or multiple mutations to inhibit MTS function. It is thought that the mitochondrial import machinery recognizes the aliphatic alpha helix that is formed by the MTS. Thus modifications that may inhibit MTS functions would be amino acid changes that would alter the aliphatic amino acids such as mutating the charged residues. Such modification(s) prevent its recognition by the mitochondrial import machinery and subsequent cleavage of the MTS and import into the mitochondria.

Peptide Tags to Augment Cytosolic Localization of Isobutanol Pathway Enzymes

In additional embodiments, the mitochondrially imported isobutanol pathway enzymes can be expressed as a chimeric fusion protein to augment cytosolic localization. In one embodiment, the isobutanol pathway enzyme is fused to a peptide tag, whereby said isobutanol pathway enzyme exhibits increased cytosolic localization and/or cytosolic activity in yeast as compared to the parental isobutanol pathway enzyme. In one embodiment, the Isobutanol pathway enzyme is fused to, a peptide tag following removal of the N-terminal Mitochondrial Targeting Sequence (MTS). In one embodiment, the peptide tag is non-cleavable. In a preferred embodiment, the peptide tag is fused at the N-terminus of the isobutanol pathway enzyme. Peptide tags useful in the present invention preferably have the following properties: (1) they do not significantly hinder the normal enzymatic function of the isobutanol pathway enzyme; (2) it folds in such as a way as to block recognition of an N-terminal MTS by the normal mitochondrial import machinery; (3) it promotes the stable expression and/or folding of the isobutanol pathway enzyme it precedes; (4) it can be detected, for example, by Western blotting or SDS-PAGE plus Coomassie staining to facilitate analysis of the overexpressed chimeric protein.

Suitable peptide tags for use in the present invention include, but are not limited to, ubiquitin, ubiquitin-like (UBL) proteins, myc, HA-tag, green fluorescent protein (GFP), and the maltose binding protein (MBP). Ubiquitin, and the Ubiquitin-like protein (Ubl's) offer several advantages. For instance, the use of Ubiquitin or similar Ubl's (e.g., SUMO) as a solubility- and expression-enhancing fusion partner has been well documented (Ecker et al., 1989, *J Biol Chem* 264: 7715-9; Marblestone et al., 2006, *Protein Science* 15: 182-9). In fact, in *S. cerevisiae*, several ribosomal proteins are expressed as C-terminal fusions to ubiquitin. Following translation and protein folding, ubiquitin is cleaved from its co-expressed partner by a highly specific ubiquitin hydrolase, which recognizes and requires the extreme C-terminal Gly-Gly motif present in ubiquitin and cleaves immediately following this sequence; a similar pathway removes Ubl proteins from their fusion partners.

The invention described here describes a method to re-localize a normally mitochondrial protein or enzyme by expressing it as fusion with an N-terminal, non-cleavable ubiquitin or ubiquitin-like molecule. In doing so, the re-targeted enzyme enjoys enhanced expression, solubility, and function in the cytosol. In another embodiment, the sequence encoding the MTS can be replaced with a sequence encoding one or more copies of the c-myc epitope tag (amino acids EQKLISEEDL, SEQ ID NO: 9), which will generally not target a protein into the mitochondria and can easily be detected by commercially available antibodies.

Altering the Iron-Sulfur Cluster Domain and/or Redox Active Domain

In general, the yeast cytosol demonstrates a different redox potential than a bacterial cell, as well as the yeast mitochondria. As a result, isobutanol pathway enzymes which exhibit an iron sulfur (FeS) domain and/or redox active domain, may require the redox potential of the native environments to be folded or expressed in a functional form. Expressing some isobutanol pathway enzymes in the yeast cytosol, which can harbor unfavorable redox potential, has the propensity to result in inactive proteins, even if the proteins are expressed. The present inventors have identified a number of different strategies to overcome this problem, which can arise when an isobutanol pathway enzyme which is suited to a particular environment with a specific redox potential is expressed in the yeast cytosol.

In one embodiment, the present invention provides isobutanol pathway enzymes that exhibit a properly folded iron-sulfur cluster domain and/or redox active domain in the cytosol. Such isobutanol pathway enzymes will generally comprise a mutated or modified iron-sulfur cluster domain and/or redox active domain, allowing for a non-native isobutanol pathway enzyme to be expressed in the yeast cytosol in a functional form.

In various embodiments described herein, the recombinant microorganisms may further comprise a nucleic acid encoding a chaperone protein, wherein said chaperone protein assists the folding of a protein exhibiting cytosolic activity. In a preferred embodiment, the protein exhibiting cytosolic activity is DHAD. In one embodiment, the chaperone may be a native protein. In another embodiment, the chaperone protein may be an exogenous protein. In some embodiments, the chaperone protein may be selected from the group consisting of: endoplasmic reticulum oxidoreductin 1 (Ero1, Accession No. NP_013576.1), including variants of Ero1 that have been suitably altered to reduce or prevent its normal localization to the endoplasmic reticulum; thioredoxins (which includes Trx1, Accession No. NP_013144.1; and Trx2, Accession No. NP_011725.1), thioredoxin reductase (Trr1, Accession No. NP_010640.1); glutaredoxins (which includes Grx1, Accession No. NP_009895.1; Grx2, Accession No. NP_010801.1; Grx3, Accession No. NP_010383.1; Grx4, Accession No. NP_01101.1; Grx5, Accession No. NP_015266.1; Grx6, Accession No. NP_010274.1; Grx7, Accession No. NP_009570.1; Grx8, Accession No. NP_013468.1); glutathione reductase Girl (Accession No. NP_015234.1); and Jac1 (Accession No. NP_011497.1), including variants of Jac1 that have been suitably altered to reduce or prevent its normal mitochondrial localization; and homologs or variants thereof.

As described herein, iron-sulfur cluster assembly for insertion into yeast apo-iron-sulfur proteins begins in yeast mitochondria. To assemble in yeast the active iron-sulfur proteins containing the cluster, either the apo-iron-sulfur protein is imported into the mitochondria from the cytosol and the iron-sulfur cluster is inserted into the protein and the active protein remains localized in the mitochondria; or the iron-sulfur clusters or precursors thereof are exported from the mitochondria to the cytosol and the active protein is assembled in the cytosol or other cellular compartments.

Targeting of yeast mitochondrial iron-sulfur proteins or non-yeast iron-sulfur proteins to the yeast cytosol can result in such proteins not being properly assembled with their iron-sulfur clusters. This present invention overcomes this problem by co-expression and cytosolic targeting in yeast of proteins for iron-sulfur cluster assembly and cluster insertion into apo-iron-sulfur proteins, including iron-sulfur cluster assembly and insertion proteins from organisms other than yeast, together with the apo-iron-sulfur protein to provide assembly of active iron-sulfur proteins in the yeast cytosol.

Therefore, in one embodiment of this invention, the apo-iron-sulfur protein DHAD enzyme encoded by the *E. coli* ilvD gene is expressed in yeast together with *E. coli* iron-sulfur cluster assembly and insertion genes comprising either the cyaY, iscS, iscU, iscA, hscB, hscA, fdx and isuX genes or the sufA, sufB, sufC, sufD, sufS and sufE genes. This strategy allows for both the apo-iron-sulfur protein (DHAD) and the iron-sulfur cluster assembly and insertion components (the products of the isc or suf genes) to come from the same organism, causing assembly of the active DHAD iron-sulfur protein in the yeast cytosol. As a modification of this embodiment, for those *E. coli* iron-sulfur cluster assembly and insertion components that localize to or are predicted to localize to the yeast mitochondria upon expression in yeast, the genes for these components are engineered to eliminate such targeting signals to ensure localization of the components in the yeast cytoplasm. Thus, in some embodiments, one or more genes encoding an iron-sulfur cluster assembly protein may be mutated or modified to remove a signal peptide, whereby localization of the product of said one or more genes to the mitochondria is prevented. In certain embodiments, it may be preferable to overexpress one or more genes encoding an iron-sulfur cluster assembly protein.

In additional embodiments, iron-sulfur cluster assembly and insertion components from other than *E. coli* can be co-expressed with the *E. coli* DHAD protein to provide assembly of the active DHAD iron-sulfur cluster protein. Such iron-sulfur cluster assembly and insertion components from other organisms can consist of the products of the *Helicobacter pylori* nifS and nifU genes or the *Entamoeba histolytica* nifS and nifU genes. As a modification of this embodiment, for those non-*E. coli* iron-sulfur cluster assembly and insertion components that localize to or are predicted to localize to the yeast mitochondria upon expression in yeast, the genes for these components can be engineered to eliminate such targeting signals to ensure localization of the components in the yeast cytoplasm.

As a further modification of this embodiment, in addition to co-expression of these proteins in aerobically-grown yeast, these proteins may be co-expressed in anaerobically-grown yeast to lower the redox state of the yeast cytoplasm to improve assembly of the active iron-sulfur protein.

In another embodiment, the above iron-sulfur cluster assembly and insertion components can be co-expressed with DHAD apo-iron-sulfur enzymes other than the *E. coli* IlvD gene product to generate active DHAD enzymes in the yeast cytoplasm. As a modification of this embodiment, for those DHAD enzymes that localize to or are predicted to localize to the yeast mitochondria upon expression in yeast, then the genes for these enzymes can be engineered to eliminate such targeting signals to ensure localization of the enzymes in the yeast cytoplasm.

In additional embodiments, the above methods used to generate active DHAD enzymes localized to yeast cytoplasm may be combined with methods to generate active acetolactate synthase, KARI, KIVD and ADH enzymes in the same yeast for the production of isobutanol by yeast.

In another embodiment, production of active iron-sulfur proteins other than DHAD enzymes in yeast cytoplasm can be accomplished by co-expression with iron-sulfur cluster assembly and insertion proteins from organisms other than yeast, with proper targeting of the proteins to the yeast cytoplasm if necessary and expression in anaerobically growing yeast if needed to improve assembly of the active proteins.

In another embodiment, the iron-sulfur cluster assembly protein encoding genes may be derived from eukaryotic organisms, including, but not limited to yeasts and plants. In one embodiment, the iron-sulfur cluster protein encoding genes are derived from a yeast organism, including, but not limited to *S. cerevisiae*. In specific embodiments, the yeast derived genes encoding iron-sulfur cluster assembly proteins are selected from the group consisting of Cfd1 (Accession No. NP_012263.1), Nbp35 (Accession No. NP_011424.1), Nar1 (Accession No. NP_014159.1), Cia1 (Accession No. NP_010553.1), and, homologs or variants thereof. In a further embodiment, the iron-sulfur cluster assembly protein encoding genes may be derived from plant nuclear genes which encode proteins translocated to chloroplast or plant genes found in the chloroplast genome itself.

As noted above, the iron-sulfur cluster assembly genes may be derived from eukaryotic organisms, including, but not limited to yeasts and plants. In one embodiment, the iron-sulfur cluster genes are derived from a yeast organism, including, but not limited to *S. cerevisiae*. In specific embodiments, the yeast derived iron-sulfur cluster assembly genes are selected from the group consisting of CFD1, NBP35, NAR1, CIA1, and homologs or variants thereof. In a further embodiment, the iron-sulfur cluster assembly genes may be derived from a plant chloroplast.

In certain embodiments described herein, it may be desirable to reduce or eliminate the activity and/or proteins levels of one or more iron-sulfur cluster containing cytosolic proteins. This modification increases the capacity of a yeast to incorporate [Fe—S] clusters into cytosolically expressed proteins wherein said proteins can be native proteins that are expressed in a non-native compartment or heterologous proteins. This is achieved by deletion of a highly expressed native cytoplasmic [Fe—S]-dependent protein. More specifically, the gene LEU1 is deleted coding for the 3-isopropylmalate dehydratase which catalyses the conversion of 3-isopropyl-malate into 2-isopropylmalate as part of the leucine biosynthetic pathway in yeast. Leu1p contains an 4Fe-4S cluster which takes part in the catalysis of the dehydratase. DHAD also contains a 4Fe-4S cluster involved in its dehydratase activity. Therefore, although the two enzymes have different substrate preferences the process of incorporation of the Fe—S cluster is generally similar for the two proteins. Given that Leu1p is present in yeast at 10000 molecules per cell (Ghaemmaghami et al., 2003, *Nature* 425: 737), deletion of LEU1 therefore ensures that the cell has enough spare capacity to incorporate [Fe—S] clusters into at least 10000 molecules of cytosolically expressed DHAD. Taking into account the specific activity of DHAD (*E. coli* DHAD is reported to have a specific activity of 63 U/mg) (Flint et al., 1993, *J Biological Chem* 268: 14732), the LEU1 deletion yeast strain would generally exhibit an increased capacity for DHAD activity in the cytosol as measured in cell lysate.

In alternative embodiments, it may be desirable to further overexpress an additional enzyme that converts 2,3-dihydroxyisovalerate to ketoisovalerate in the cytosol. In a specific embodiment, the enzyme may be selected from the group consisting of 3-isopropylmalate dehydratase (Leu1p) and imidazoleglycerol phosphate dehydrogenase (His3p). Because DHAD activity is limited in the cytosol, alternative dehydratases that convert dihydroxyisovalerate (DHIV) to 2-ketoisovalerate (KIV) and are physiologically localized to the yeast cytosol may be utilized. Leu1p and His3p are dehydratases that potentially may exhibit affinity for DHIV. Leu1p is an Fe—S binding protein that is involved in leucine biosynthesis and is also normally localized to the cytosol. His3p is involved in histidine biosynthesis and is similar to Leu1p, it is generally localized to the cytosol or predicted to be localized to the cytosol. This modification overcomes the problem of a DHAD that is limiting isobutanol production in the cytosol of yeast. The use of an alternative dehydratase that has activity in the cytosol with a low activity towards DHIV may thus be used in place of the DHAD in the isobutanol pathway. As described herein, such enzyme may be further engineered to increase activity with DHIV.

The Microorganism in General

Native producers of 1-butanol, such as *Clostridium acetobutylicum*, are known, but these organisms also generate byproducts such as acetone, ethanol, and butyrate during fermentations. Furthermore, these microorganisms are relatively difficult to manipulate, with significantly fewer tools available than in more commonly used production hosts such as *S. cerevisiae* or *E. coli*. Additionally, the physiology and metabolic regulation of these native producers are much less well understood, impeding rapid progress towards high-efficiency production. Furthermore, no native microorganisms have been identified that can metabolize glucose into isobutanol in industrially relevant quantities.

The production of isobutanol and other fusel alcohols by various yeast species, including *Saccharomyces cerevisiae* is of special interest to the distillers of alcoholic beverages, for whom fusel alcohols constitute often undesirable off-notes. Production of isobutanol in wild-type yeasts has been documented on various growth media, ranging from grape must from winemaking (Romano et al., 2003, *World J. of Microbiol Blot.* 19: 311-5), in which 12-219 mg/L isobutanol were produced, to supplemented minimal media (Oliviera et al., 2005, *World J. of Microbiol Blot.* 21: 1569-76), producing 16-34 mg/L isobutanol. Work from Dickinson et al. (*J Biol Chem.* 272: 26871-8, 1997) has identified the enzymatic steps utilized in an endogenous *S. cerevisiae* pathway converting branch-chain amino acids (e.g., valine or leucine) to isobutanol.

Recombinant microorganisms provided herein can express a plurality of heterologous and/or native target enzymes involved in pathways for the production of isobutanol from a suitable carbon source.

Accordingly, "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material into and/or the modification of the expression of native genes in a parental microorganism results in a new or modified ability to produce isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

In addition to the introduction of a genetic material into a host or parental microorganism, an engineered or modified microorganism can also include alteration, disruption, deletion or knocking-out of a gene or polynucleotide to alter the cellular physiology and biochemistry of the microorganism. Through the alteration, disruption, deletion or knocking-out of a gene or polynucleotide the microorganism acquires new or improved properties (e.g., the ability to produce a new metabolite or greater quantities of an intracellular metabolite, improve the flux of a metabolite down a desired pathway, and/or reduce the production of byproducts).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, and isobutanol. The metabolite isobutanol can be produced by a recombinant microorganism which expresses or over-expresses a metabolic pathway that converts pyruvate to isobutanol. An exemplary metabolic pathway that converts pyruvate to isobutanol may be comprised of an acetohydroxy acid synthase (ALS), a ketolacid reductoisomerase (KARI), a dihydroxy-acid dehydratase (DHAD), a 2-keto-acid decarboxylase (KIVD), and an alcohol dehydrogenase (ADH).

Accordingly, provided herein are recombinant microorganisms that produce isobutanol and in some aspects may include the elevated expression of target enzymes such as ALS, KARI, DHAD, KIVD, and ADH The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89.

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See commonly owned and co-pending application US 2009/0226991. A typical algorithm used comparing a molecule sequence to a database containing a large number of sequences from different organisms is the computer program BLAST. When searching a database containing sequences from a large number of different organisms, it is typical to compare amino acid sequences. Database searching using amino acid sequences can be measured by algorithms described in commonly owned and co-pending application US 2009/0226991.

The disclosure provides recombinant microorganisms comprising a biochemical pathway for the production of isobutanol from a suitable substrate at a high yield. A recombinant microorganism of the disclosure comprises one or more recombinant polynucleotides within the genome of the organism or external to the genome within the organism. The microorganism can comprise a reduction in expression, disruption or knockout of a gene found in the wild-type organism and/or introduction of a heterologous polynucleotide and/or expression or overexpression of an endogenous polynucleotide.

In one aspect, the disclosure provides a recombinant microorganism comprising elevated expression of at least one target enzyme as compared to a parental microorganism or encodes an enzyme not found in the parental organism. In another or further aspect, the microorganism comprises a reduction in expression, disruption or knockout of at least one gene encoding an enzyme that competes with a metabolite necessary for the production of isobutanol. The recombinant microorganism produces at least one metabolite involved in a biosynthetic pathway for the production of isobutanol. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of isobutanol. The target enzyme is encoded by, and expressed from, a polynucleotide derived from a suitable biological source. In some embodiments, the polynucleotide comprises a gene derived from a prokaryotic or eukaryotic source and recombinantly engineered into the microorganism of the disclosure. In other embodiments, the polynucleotide comprises a gene that is native to the host organism.

It is understood that a range of microorganisms can be modified to include a recombinant metabolic pathway suitable for the production of isobutanol. In various embodiments, microorganisms may be selected from yeast microorganisms. Yeast microorganisms for the production of isobutanol may be selected based on certain characteristics:

One characteristic may include the property that the microorganism is selected to convert various carbon sources into isobutanol. The term "carbon source" generally refers to a substance suitable to be used as a source of carbon for prokaryotic or eukaryotic cell growth. Examples of suitable carbon sources are described in commonly owned and co-pending application US 2009/0226991. Accordingly, in one embodiment, the recombinant microorganism herein disclosed can convert a variety of carbon sources to products, including but not limited to glucose, galactose, mannose, xylose, arabinose, lactose, sucrose, and mixtures thereof.

The recombinant microorganism may thus further include a pathway for the fermentation of isobutanol from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via a xylulokinase (XK) enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugar. Accordingly, a yeast species that can efficiently ferment xylose and other pentose sugars into a desired fermentation product is therefore very desirable.

Thus, in one aspect, the recombinant is engineered to express a functional exogenous xylose isomerase. Exogenous xylose isomerases functional in yeast are known in the art. See, e.g., Rajgarhia et al, US20060234364, which is herein incorporated by reference in its entirety. In an embodiment according to this aspect, the exogenous xylose isomerase gene is operatively linked to promoter and terminator sequences that are functional in the yeast cell. In a preferred embodiment, the recombinant microorganism further has a deletion or disruption of a native gene that encodes for an enzyme (e.g. XR and/or XDH) that catalyzes the conversion of xylose to xylitol. In a further preferred embodiment, the recombinant microorganism also contains a functional, exogenous xylulokinase (XK) gene operatively linked to promoter and terminator sequences that are functional in the yeast cell. In one embodiment, the xylulokinase (XK) gene is overexpressed.

In one embodiment, the microorganism has reduced or no pyruvate decarboxylase (PDC) activity. PDC catalyzes the decarboxylation of pyruvate to acetaldehyde, which is then reduced to ethanol by ADH via an oxidation of NADH to NADH+. Ethanol production is the main pathway to oxidize the NADH from glycolysis. Deletion of this pathway increases the pyruvate and the reducing equivalents (NADH) available for the isobutanol pathway. Accordingly, deletion of PDC genes can further increase the yield of isobutanol.

In another embodiment, the microorganism has reduced or no glycerol-3-phosphate dehydrogenase (GPD) activity. GPD catalyzes the reduction of dihydroxyacetone phosphate (DHAP) to glycerol-3-phosphate (G3P) via the oxidation of NADH to NAD+. Glycerol is then produced from G3P by Glycerol-3-phosphatase (GPP). Glycerol production is a secondary pathway to oxidize excess NADH from glycolysis. Reduction or elimination of this pathway would increase the pyruvate and reducing equivalents (NADH) available for the isobutanol pathway. Thus, deletion of GPD genes can further increase the yield of isobutanol.

In yet another embodiment, the microorganism has reduced or no PDC activity and reduced or no GPD activity.

In one embodiment, the yeast microorganisms may be selected from the "*Saccharomyces* Yeast Glade", as described in commonly owned and co-pending application US 2009/0226991.

The term "*Saccharomyces sensu stricto*" taxonomy group is a cluster of yeast species that are highly related to *S. cerevisiae* (Rainieri et al., 2003, *J. Biosci Bioengin* 96: 1-9). *Saccharomyces sensu stricto* yeast species include but are not limited to *S. cerevisiae*, *S. cerevisiae*, *S. kudriavzevii*, *S. mikatae*, *S. bayanus*, *S. uvarum*, *S. carocanis* and hybrids derived from these species (Masneuf et al., 1998, *Yeast* 7: 61-72).

An ancient whole genome duplication (WGD) event occurred during the evolution of the hemiascomycete yeast and was discovered using comparative genomic tools (Kellis et al., 2004, *Nature* 428: 617-24; Dujon et al., 2004, *Nature* 430:35-44; Langkjaer et al., 2003, *Nature* 428: 848-52; Wolfe et al., 1997, *Nature* 387: 708-13). Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae*, *S. uvarum*, *S. bayanus*, *S. paradoxus*, *S. castelli*, and *C. glabrata*.

In another embodiment, the yeast microorganism may be selected from a pre-whole genome duplication (pre-WGD) yeast genus including but not limited to *Saccharomyces*, *Kluyveromyces*, *Candida*, *Pichia*, *Issatchenkia*, *Debaryomyces*, *Hansenula*, *Yarrowia* and, *Schizosaccharomyces*. Representative pre-WGD yeast species include: *S. kluyveri*, *K. thermotolerans*, *K. marxianus*, *K. waltii*, *K. lactis*, *C. tropicalis*, *P. pastoris*, *P. anomala*, *P. stipitis*, *I. orientalis*, *I. occidentalis*, *I. scutulata*, *D. hansenii*, *H. anomala*, *Y. lipolytica*, and *S. pombe*.

A yeast microorganism may be either Crabtree-negative or Crabtree-positive as described in described in commonly owned and co-pending application US 2009/0226991. In one embodiment the yeast microorganism may be selected from yeast with a Crabtree-negative phenotype including but not limited to the following genera: *Kluyveromyces*, *Pichia*, *Issatchenkia*, *Hansenula*, and *Candida*. Crabtree-negative species include but are not limited to: *K. lactis*, *K. marxianus*, *P. anomala*, *P. stipitis*, *I. orientalis*, *I. occidentalis*, *I. scutulata*, *H. anomala*, and *C. utilis*. In another embodiment, the yeast microorganism may be selected from a yeast with a Crabtree-positive phenotype, including but not limited to *Saccharomyces*, *Kluyveromyces*, *Zygosaccharomyces*, *Debaryomyces*, *Pichia* and *Schizosaccharomyces*. Crabtree-positive yeast species include but are not limited to: *S. cerevisiae*, *S. uvarum*, *S. bayanus*, *S. paradoxus*, *S. castelli*, *S. kluyveri*, *K. thermotolerans*, *C. glabrata*, *Z. bailli*, *Z. rouxii*, *D. hansenii*, *P. pastorius*, and *S. pombe*.

Another characteristic may include the property that the microorganism is that it is non-fermenting. In other words, it cannot metabolize a carbon source anaerobically while the yeast is able to metabolize a carbon source in the presence of oxygen. Nonfermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). In one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the isobutanol pathway. Fermentative pathways contribute to low yield and low productivity of isobutanol. Accordingly, deletion of PDC may increase yield and productivity of isobutanol.

In some embodiments, the recombinant microorganisms may be microorganisms that are non-fermenting yeast microorganisms, including, but not limited to those, classified into a genera selected from the group consisting of *Tricosporon, Rhodotorula,* or *Myxozyma.*

In one embodiment, a yeast microorganism is engineered to convert a carbon source, such as glucose, to pyruvate by glycolysis and the pyruvate is converted to isobutanol via an engineered isobutanol pathway (See, e.g., WO/2007/050671, WO/2008/098227, and Atsumi et al., 2008, *Nature* 45: 86-9). Alternative pathways for the production of isobutanol have been described in WO/2007/050671 and in Dickinson et al., 1998, *J Biol Chem* 273:25751-6.

Accordingly, the engineered isobutanol pathway to convert pyruvate to isobutanol can be comprised of the following reactions:
1. 2 pyruvate→acetolactate+$CO_2$
2. acetolactate+NAD(P)H→2,3-dihydroxyisovalerate+NAD(P)$^+$
3. 2,3-dihydroxyisovalerate→alpha-ketoisovalerate
4. alpha-ketoisovalerate→4 isobutyraldehyde+$CO_2$
5. isobutyraldehyde+NAD(P)H isobutanol+NAD(P)

These reactions are carried out by the enzymes 1) Acetolactate Synthase (ALS), 2) Keto-acid Recucto-Isomerase (KARI), 3) Dihydroxy-acid dehydratase (DHAD), 4) Keto-isovalerate decarboxylase (KIVD), and 5) an Alcohol dehydrogenase (ADH) (FIG. 1). In another embodiment, the yeast microorganism is engineered to overexpress these enzymes. For example, these enzymes can be encoded by native genes. Alternatively, these enzymes can be encoded by heterologous genes. For example, ALS can be encoded by the alsS gene of *B. subtilis*, alsS of *L. lactis*, or the ilvK gene of *K. pneumonia*. For example, KARI can be encoded by the ilvC genes of *E. coli, C. glutamicum, M. maripaludis,* or *Piromyces* sp E2. For example, DHAD can be encoded by the ilvD genes of *E. coli, C. glutamicum,* or *L. lactis*. For example, KIVD can be encoded by the kivD gene of *L. lactis*. ADH can be encoded by ADH2, ADH6, or ADH7 of *S. cerevisiae*.

In one embodiment, pathway steps 2 and 5 may be carried out by KARI and ADH enzymes that utilize NADH (rather than NADPH) as a co-factor. Such enzymes are described in commonly owned and co-pending applications U.S. Ser. No. 12/610,784 and PCT/US09/62952 (published as WO/2010/051527), which are herein incorporated by reference in their entireties for all purposes. The present inventors have found that utilization of NADH-dependent KARI and ADH enzymes to catalyze pathway steps 2 and 5, respectively, surprisingly enables production of isobutanol under anaerobic conditions. Thus, in one embodiment, the recombinant microorganisms of the present invention may use an NADH-dependent KARI to catalyze the conversion of acetolactate (+NADH) to produce 2,3-dihydroxyisovalerate. In another embodiment, the recombinant microorganisms of the present invention may use an NADH dependent ADH to catalyze the conversion of isobutyraldehyde (+NADH) to produce isobutanol. In yet another embodiment, the recombinant microorganisms of the present invention may use both an NADH-dependent KARI to catalyze the conversion of acetolactate (+NADH) to produce 2,3-dihydroxyisovalerate, and an NADH-dependent ADH to catalyze the conversion of isobutyraldehyde (+NADH) to produce isobutanol.

The yeast microorganism of the invention may be engineered to have increased ability to convert pyruvate to isobutanol. In one embodiment, the yeast microorganism may be engineered to have increased ability to convert pyruvate to isobutyraldehyde. In another embodiment, the yeast microorganism may be engineered to have increased ability to convert pyruvate to keto-isovalerate. In another embodiment, the yeast microorganism may be engineered to have increased ability to convert pyruvate to 2,3-dihydroxyisovalerate. In another embodiment, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans, K. lactis,* and *K. marxianus, Pichia* spp., *Hansenula* spp., including *H. polymorpha, Candida* spp., *Trichosporon* spp., *Yamadazyma* spp., including *Y.* spp. *stipitis, Torulaspora pretoriensis, Schizosaccharomyces* spp., including *S. pombe, Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Methods in General

Identification of PDC and GPD in a Yeast Microorganism

Any method can be used to identify genes that encode for enzymes with, pyruvate decarboxylase (PDC) activity or glycerol-3-phosphate dehydrogenase (GPD) activity. Suitable methods for the identification of PDC and GPD are described in co-pending applications U.S. Ser. No. 12/343,375 (published as US 2009/0226991), U.S. Ser. No. 12/696,645, and U.S. Ser. No. 12/820,505, which claim priority to U.S. Provisional Application 61/016,483, all of which are herein incorporated by reference in their entireties for all purposes.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., 1992, *Nuc Acids Res.* 27: 69-74; Ito et al., 1983, *J. Bacteriol.* 153: 163-8; and Becker et al., 1991, *Methods in Enzymology* 194: 182-7.

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., 1981, *PNAS USA* 78: 6354-58).

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the yeast microorganism may occur via random integration (Kooistra et al., 2004, *Yeast* 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke et al., 1984, *Mol. Gen. Genet* 197: 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced glycerol-3-phosphate dehydrogenase activity. The term "reduced" as used herein with respect to a particular enzymatic activity refers to a lower level of enzymatic activity than that measured in a comparable yeast cell of the same species. The term reduced also refers to the elimination of enzymatic activity than that measured in a comparable yeast cell of the same species. Thus, yeast cells lacking glycerol-3-phosphate dehydrogenase activity are considered to have reduced glycerol-3-phosphate dehydrogenase activity since most, if not all, comparable yeast strains have at least some glycerol-3-phosphate dehydrogenase activity. Such reduced enzymatic activities can be the result of lower enzyme concentration, lower specific activity of an enzyme, or a combination thereof. Many different methods can be used to make yeast having reduced enzymatic activity. For example, a yeast cell can be engineered to have a disrupted enzyme-encoding locus using common mutagenesis or knock-out technology. In addition, certain point-mutation(s) can be introduced which results in an enzyme with reduced activity.

Alternatively, antisense technology can be used to reduce enzymatic activity. For example, yeast can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Yeast having a reduced enzymatic activity can be identified using many methods. For example, yeast having reduced glycerol-3-phosphate dehydrogenase activity can be easily identified using common methods, which may include, for example, measuring glycerol formation via liquid chromatography.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any yeast within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical, techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, 1992, *Appl. Micro. Biot.* 38:17-22.

Increase of Enzymatic Activity

Yeast microorganisms of the invention may be further engineered to have increased activity of enzymes. The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the Km for the substrate, or by directed evolution. See, e.g., Methods in Molecular Biology (vol. 231), ed. Arnold and Georgiou, Humana Press (2003).

Microorganism Characterized by Producing Isobutanol at High Yield

For a biocatalyst to produce isobutanol most economically, it is desired to produce a high yield. Preferably, the only product produced is isobutanol. Extra products lead to a reduction in product yield and an increase in capital and operating costs, particularly if the extra products have little or no value. Extra products also require additional capital and operating costs to separate these products from isobutanol.

The microorganism may convert one or more carbon sources derived from biomass into isobutanol with a yield of greater than 5% of theoretical. In one embodiment, the yield is greater than 10%. In one embodiment, the yield is greater than 50% of theoretical. In one embodiment, the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment, the yield is greater than 90% of theoretical. In yet another embodiment, the yield is greater than 95% of theoretical. In still another embodiment, the yield is greater than 97.5% of theoretical.

More specifically, the microorganism converts glucose, which can be derived from biomass into isobutanol with a yield of greater than 5% of theoretical. In one embodiment, the yield is greater than 10% of theoretical. In one embodiment, the yield is greater than 50% of theoretical. In one embodiment the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment the yield is greater than 90% of theoretical. In yet another embodiment, the yield is greater than 95% of theoretical. In still another embodiment, the yield is greater than 97.5% of theoretical Microorganism Characterized by Production of Isobutanol from Pyruvate Via an Overexpressed Isobutanol Pathway and a Pdc-Minus and Gpd-Minus Phenotype In yeast, the conversion of pyruvate to acetaldehyde is a major drain on the pyruvate pool, and, hence, a major source of competition with the isobutanol pathway. This reaction is catalyzed by the pyruvate decarboxylase (PDC) enzyme. Reduction of this enzymatic activity in the yeast microorganism results in an increased availability of pyruvate and reducing equivalents to the isobutanol pathway and may improve isobutanol production and yield in a yeast microorganism that expresses a pyruvate-dependent isobutanol pathway.

Reduction of PDC activity can be accomplished by 1) mutation or deletion of a positive transcriptional regulator for the structural genes encoding for PDC or 2) mutation or deletion of all PDC genes in a given organism. The term "transcriptional regulator" can specify a protein or nucleic acid that works in trans to increase or to decrease the transcription of a different locus in the genome. For example, in *S. cerevisiae*, the PDC2 gene, which encodes for a positive transcriptional regulator of PDC1,5,6 genes can be deleted; a *S. cerevisiae* in which the PDC2 gene is deleted is reported to have only ~10% of wildtype PDC activity (Hohmann, 1993, *Mol Gen Genet* 241:657-66). Alternatively, for example, all structural genes for PDC (e.g. in *S. cerevisiae*, PDC1, PDC5, and PDC6, or in *K. lactis*, PDC1) are deleted.

Crabtree-positive yeast strains such as *S. cerevisiae* strain that contains disruptions in all three of the PDC alleles no longer produce ethanol by fermentation. However, a downstream product of the reaction catalyzed by PDC, acetyl-CoA, is needed for anabolic production of necessary molecules. Therefore, the Pdc− mutant is unable to grow solely on glucose, and requires a two-carbon carbon source, either ethanol or acetate, to synthesize acetyl-CoA (Flikweert et al., 1999, *FEMS Microbiol Lett.* 174: 73-9; and van Maris et al., 2004, *Appl. Environ Microbiol.* 70: 159-66).

Thus, in an embodiment, such a Crabtree-positive yeast strain may be evolved to generate variants of the PDC mutant yeast that do not have the requirement for a two-carbon molecule and has a growth rate similar to wild type on glucose. Any method, including chemostat evolution or serial dilution may be utilized to generate variants of strains with deletion of three PDC alleles that can grow on glucose as the sole carbon source at a rate similar to wild type (van Maris et al., 2004, *Appl Envir Micro* 70: 159-66).

Another byproduct that would decrease yield of isobutanol is glycerol. Glycerol is produced by 1) the reduction of the glycolysis intermediate, dihydroxyacetone phosphate (DHAP), to glycerol-3-phosphate (G3P) via the oxidation of NADH to NAD$^+$ by Glycerol-3-phosphate dehydrogenase (GPD) followed by 2) the dephosphorylation of glycerol-3-phosphate to glycerol by glycerol-3-phosphatase (GPP). Production of glycerol results in loss of carbons as well as reducing equivalents. Reduction of GPD activity would increase yield of isobutanol. Reduction of GPD activity in addition to PDC activity would further increase yield of isobutanol.

Reduction of glycerol production has been reported to increase yield of ethanol production (Nissen et al., 2000, *Yeast* 16, 463-74; Nevoigt et al., Method of modifying a yeast cell for the production of ethanol, WO/2009/056984). Disruption of this pathway has also been reported to increase yield of lactate in a yeast engineered to produce lactate instead of ethanol (Dundon et al., Yeast cells having disrupted pathway from dihydroxyacetone phosphate to glycerol, US 2009/0053782).

In one embodiment, the microorganism is a Crabtree-positive yeast with reduced or no GPD activity. In another embodiment, the microorganism is a crabtree positive yeast with reduced or no GPD activity, and expresses an isobutanol biosynthetic pathway and produces isobutanol. In yet another embodiment, the microorganism is a Crabtree-positive yeast with reduced or no GPD activity and with reduced or no PDC activity. In another embodiment, the microorganism is a crabtree positive yeast with reduced or no GPD activity, with reduced or no PDC activity, and expresses an isobutanol biosynthetic pathway and produces isobutanol.

In another embodiment, the microorganism is a Crabtree-negative yeast with reduced or no GPD activity. In another embodiment, the microorganism is a Crabtree-negative yeast with reduced or no GPD activity, expresses the isobutanol biosynthetic pathway and produces isobutanol. In yet another embodiment, the microorganism is a Crabtree-negative yeast with reduced or no GPD activity and with reduced or no PDC activity. In another embodiment, the microorganism is a Crabtree-negative yeast with reduced or no GPD activity, with reduced or no PDC activity, expresses an isobutanol biosynthetic pathway and produces isobutanol.

PDC-minus/GPD-minus yeast production strains are described in co-pending applications U.S. Ser. No. 12/343,375 (published as US 2009/0226991), U.S. Ser. No. 12/696,645, and U.S. Ser. No. 12/820,505, which claim priority to U.S. Provisional Application 61/016,483, all of which are herein incorporated by reference in their entireties for all purposes.

Method of Using Microorganism for High-Yield Isobutanol Fermentation

In a method to produce isobutanol from a carbon source at high yield, the yeast microorganism is cultured in an appropriate culture medium containing a carbon source.

Another exemplary embodiment provides a method for producing isobutanol comprising a recombinant yeast microorganism of the invention in a suitable culture medium containing a carbon source that can be converted to isobutanol by the yeast microorganism of the invention.

In certain embodiments, the method further includes isolating isobutanol from the culture medium. For example, isobutanol may be isolated from the culture medium by any method known to those skilled in the art, such as distillation, pervaporation, or liquid-liquid extraction, including methods disclosed in co-pending applications U.S. Ser. No. 12/342,992 (published as US 2009/0171129) and PCT/US08/88187 (published as WO/2009/086391), which are herein incorporated by reference in their entireties for all purposes.

This invention is further illustrated by the following examples that should not be construed as limiting. The contents of all references, patents, and published patent applications cited throughout this application, as well as the Figure and the Sequence Listing, are incorporated herein by reference for all purposes.

EXAMPLES

General Methods

TABLE 1

Amino acid sequences disclosed herein.

| SEQ ID NO | Protein, Accession No. |
|---|---|
| 1 | *E. coli* IlvC, NP_418222 |
| 2 | *S. cerevisiae* Ilv5, NP_013459 |
| 3 | *Oryza sativa* KARI, NP_001056384 |
| 4 | *Methanococcus maripaludis* KARI, YP_001097443 |
| 5 | *Acidiphilium cryptum* KARI, YP_001235669 |
| 6 | *Chlamydomonas reinhardtii* KARI, XP_001702649 |
| 7 | *Picrophilus torridus* KARI, YP_023851 |
| 8 | *Zymomonas mobilis* KARI, YP_162876 |
| 9 | c-myc epitope tag |
| 10 | *Thermotoga petrophila* RKU-1 dihydroxyacid dehydratase (DHAD), YP_001243973.1 |
| 11 | *Victivailis vadensis* ATCC BAA-548 dihydroxyacid dehydratase (DHAD), ZP_01924101.1 |
| 12 | Termite group 1 bacterium phylotype Rs-D17 dihydroxyacid dehydratase (DHAD), YP_001956631.1 |
| 13 | *Yarrowia lipolytica* dihydroxyacid dehydratase (DHAD), XP_502180.2 |
| 14 | *Francisella tularensis* subsp. *tularensis* WY96-3418 dihydroxyacid dehydratase (DHAD), YP_001122023.1 |
| 15 | *Arabidopsis thaliana* dihydroxyacid dehydratase (DHAD), AAK64025.1 |
| 16 | Candidatus Koribacter versatilis Ellin345 dihydroxyacid dehydratase (DHAD), YP_592184.1 (Acidobacter) |
| 17 | *Gramella forsetii* KT0803 dihydroxyacid dehydratase (DHAD), YP_862145.1 |
| 18 | *Lactococcus lactis* subsp. *lactis* Il1403 dihydroxyacid dehydratase (DHAD), NP_267379.1 |
| 19 | *Saccharopolyspora erythraea* NRRL 2338 dihydroxyacid dehydratase (DHAD), YP_001103528.2 |
| 20 | *Saccharomyces cerevisiae* Ilv3, NP_012550.1 |
| 21 | *Piromyces* sp E2 ilvD |
| 22 | *Ralstonia eutropha* JMP134 ilvD, YP_298150.1 |
| 23 | *Chromohalobacter salexigens* ilvD, YP_573197.1 |
| 24 | *Picrophilus torridus* DSM9790 ilvD, YP_024215.1 |
| 25 | *Sulfolobus tokodaii* str. 7 dihydroxyacid dehydratase (DHAD), NP_378168.1 |
| 26 | *Saccharomyces cerevisiae* Ilv3ΔN |

TABLE 1-continued

Amino acid sequences disclosed herein.

SEQ ID NO   Protein, Accession No.

| | |
|---|---|
| 27 | P(I/L))XXXGX(I/L)XIL (conserved motif described in Example 17) |
| 28 | PIKXXGX(I/L)XIL (conserved motif described in Example 17) |

TABLE 2

Nucleic acid sequences disclosed herein.

SEQ ID NO   Gene, Accession No.

| | |
|---|---|
| 87 | *Lactococcus lactis* subsp. *lactis* Il1403 (Ll_ilvD) |
| 88 | *Saccharomyces cerevisiae* ILV3 (ScILV3(FL)) |
| 89 | *Saccharomyces cerevisiae* ILV3ΔN (ScILV3ΔN) |
| 90 | GramsIla forsetii KT0803 (Gf_ilvD) |
| 91 | *Saccharopolyspora erythraea* NRRL 2338 (Se_ilvD) |
| 92 | Candidatus Koribacter versatilis Ellin345 ilvD (Acidobacter) |
| 93 | *Piromcyes* sp E2 ilvD (*Piromyces* ilvD) |
| 94 | *Ralstonia eutropha* JMP134 ilvD, (Re_ilvD) |
| 95 | *Chromohalobacter salexigens* ilvD, (Cs_ilvD) |
| 96 | *Picrophilus torridus* DSM9790 ilvD, (Pt_ilvD) |
| 97 | *Sulfolobus* tokodaii str. 7 ilvD, (St_ilvD) |
| 98 | *E. coli* ilvC$^{Q110V}$, ( Ec_itvC(Q110V)) |
| 99 | *Lactococcus lactic* kivD, (Ll_kivD) |
| 100 | *S. cerevisiae* ILV5, (ScILV5) |

Determination of optical density. The optical density of the yeast cultures is determined at 600 nm using a DU 800 spectrophotometer (Beckman-Coulter, Fullerton, Calif., USA). Samples are diluted as necessary to yield an optical density of between 0.1 and 0.8.

Gas Chromatography. Analysis of volatile organic compounds, including ethanol and isobutanol was performed on a HP 5890 gas chromatograph fitted with an HP 7673 Autosampler, a DB-FFAP column (J&W; 30 m length, 0.32 mm ID, 0.25 μM film thickness) or equivalent connected to a flame ionization detector (FID). The temperature program was as follows: 200° C. for the injector, 300° C. for the detector, 50° C. oven for 1 minute, 31° C./minute gradient to 140° C., and then hold for 2.5 min. Analysis was performed using authentic standards (>99%, obtained from Sigma-Aldrich), and a 5-point calibration curve with 1-pentanol as the internal standard.

High Performance Liquid Chromatography for quantitative analysis of glucose and organic acids. Analysis of glucose and organic acids was performed on a HP-1100 High Performance Liquid Chromatography system equipped with an Aminex HPX-87H Ion Exclusion column (Bio-Rad, 300×7.8 mm) or equivalent and an H$^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was Isocratic with 0.008 N sulfuric acid in water as the mobile phase. Flow was set at 1 mL/min. Injection volume was 20 μL and the run time was 30 minutes.

High Performance Liquid Chromatography for quantitative analysis of ketoisovalerate and isobutyraldehyde. Analysis of the DNPH derivatives of ketoisovalerate and isobutyraldehyde was performed on a HP-1100 High Performance Liquid Chromatography system equipped with a Hewlett Packard 1200 HPLC stack column (Agilent Eclipse XDB-18, 150×4.0 mm; 5 μm particles [P/N #993967-902] and C18 Guard cartridge). The analytes were detected using an HP-1100 UV detector at 360 nm The column temperature was 50° C. This method was isocratic with 0.1% H$_3$PO$_4$ and 70% acetonitrile in water as mobile phase. Flow was set at 3 mL/min. Injection size was 10 μL and the run time was 2 minutes.

Molecular biology and bacterial cell culture. Standard molecular biology methods for cloning and plasmid construction are generally used, unless otherwise noted (Sambrook, J., Russel, D. W. *Molecular Cloning, A Laboratory Manual*. 3 ed. 2001, Cold Spring Harbor, N.Y.: Cold Spring Harbor Laboratory Press).

Standard recombinant DNA and molecular biology techniques used in the Examples are well known in the art and are described by Sambrook, J., Russel, D. W. *Molecular Cloning, A Laboratory Manual*. 3 ed. 2001, Cold Spring Harbor, N.Y.: Cold Spring Harbor Laboratory Press; and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

General materials and methods suitable for the routine maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

Yeast transformations—*S. cerevisiae*. *S. cerevisiae* strains were transformed by the Lithium Acetate method (Gietz et al., *Nucleic Acids Res.* 27:69-74 (1992): Cells from 50 mL YPD cultures (YPGal for valine auxotrophs) were collected by centrifugation (2700 rcf, 2 minutes, 25° C.) once the cultures reached an OD$_{600}$ of 1.0. The cells were washed cells with 50 mL sterile water and collected by centrifugation at 2700 rcf for 2 minutes at 25° C. The cells were washed again with 25 mL sterile water and collected cells by centrifugation at 2700 rcf for 2 minutes at 25° C. The cells were resuspended in 1 mL of 100 mM lithium acetate and transferred to a 1.5 mL eppendorf tube. The cells were collected cells by centrifugation for 20 sec at 18,000 rcf, 25° C. The cells were resuspended cells in a volume of 100 mM lithium acetate that was approximately 4× the volume of the cell pellet. A mixture of DNA (final volume of 15 μl with sterile water), 72 μl 50% PEG, 10 μl 1 M lithium acetate, and 3 μl denatured salmon sperm DNA was prepared for each transformation. In a 1.5 mL tube, 15 μl of the cell suspension was added to the DNA mixture (85 μl), and the transformation suspension was vortexed with 5 short pulses. The transformation was incubated at 30 minutes at 30° C., followed by incubation for 22 minutes at 42° C. The cells were collected by centrifugation for 20 sec at 18,000 rcf, 25° C. The cells were resuspended in 100 μl SOS (1 M sorbitol, 34% (v/v) YP (1% yeast extract, 2% peptone), 6.5 mM CaCl$_2$) or 100 μl YP (1% yeast extract, 2% peptone) and spread over an appropriate selective plate.

Yeast transformations—*K. lactis. K. lactis* cells were transformed according to a slightly modified version of the protocol as described by Kooistra et al., *Yeast* 21: 781-792 (2004). Saturated overnight-grown cultures of *K. lactis* cells were diluted 1:50 into 100 mL YPD and were placed in 30° C. shaker (250 rpm) and grown for 4-5 hours until the culture reached an $OD_{600}$ of 0.3-0.5. Cells were collected by centrifugation (2 min, 3000×g) and washed with 50 ml cold sterile EB (electroporation buffer; 10 mM Tris-HCl, pH 7.5, 270 mM sucrose, 1 mM $MgCl_2$) at 4° C. Cells were resuspended in 50 mL YPD that contained 25 mM DTT and 20 mM HEPES, pH 8.0 Cells were transferred back into flasks used to grow cells and incubated in 30° C. incubator (without shaking) for 30 minutes. Cells were then collected by centrifugation (2 minutes, 3000×g) and washed with 10 mL ice-cold sterile EB, as above. Cells were then resuspended using one cell pellet volume of ice-cold sterile EB. Sixty microliters of cells were mixed with plasmid DNA and incubated on ice for 15 minutes. For targeted integrations, or transformation of linear DNA, approximately 200-400 ng of non-specific, short (50-500 bp) linear DNA fragments were added to 300-400 ng of the linearized integrating DNA construct. This DNA was either provided by gel-purified AluI-digested salmon sperm DNA, or a mixture of annealed primers 35+36 (yielding a ~85 bp linear duplex fragment). Cells were transferred cells to a chilled electroporation (2 mm) cuvette and pulsed using a BioRad Gene Pulser at 1 kV, 400Ω, and 25 uF. The cell suspension was immediately transferred to a 14 mL round-bottom Falcon tube with 1 mL room temperature YPD and allowed to incubate vertically at 30° C., 225 RPM for at 6-18 h. Cells were collected in an 1.7 mL by centrifugation for 10 seconds at maximum speed, and resuspended with 150 µL YPD before being spread onto appropriate selection plates.

Yeast colony PCR with FailSafe® PCR System (EPICENTRE® Biotechnologies, Madison, Wis.; Catalog #FS99250): Cells from each colony were added to 20 µl of colony PCR mix (per reaction mix contains 6.8 µl water, 1.5 µl of each primer, 0.2 µl of FailSafe PCR Enzyme Mix and 10 µl 2× FailSafe Master Mix). Unless otherwise noted, 2× FailSafe Master Mix E was used. The PCR reactions were incubated in a thermocycler using the following touchdown PCR conditions: 1 cycle of 94° C.×2 min, 10 cycles of 94° C.×20 s, 63°-54° C.×20 s (decrease 1° C. per cycle), 72° C.×60 s, 40 cycles of 94° C.×20 s, 53° C.×20 s, 72° C.×60 s and 1 cycle of 72° C.×5 min.

Zymoclean Gel DNA Recovery Kit (Zymo Research, Orange, Calif.; Catalog #D4002) Protocol: DNA fragments were recovered from agarose gels according to manufacturer's protocol.

Zymo Research DNA Clean and Concentrator Kit (Zymo Research, Orange, Calif.; Catalog #D4004) Protocol: DNA fragments were purified according to manufacturer's protocol.

Preparation of cell lysates for in vitro enzyme assays. To grow cultures for cell lysates, triplicate independent cultures of the desired strain were grown overnight in 3 mL of the appropriate medium at 30° C., 250 rpm. The following day, the overnight cultures were diluted into 50 mL fresh medium in 250 mL baffle-bottomed Erlenmeyer flasks and incubated at 30° C. at 250 rpm. Cells were grown for at least 4 generations and the cultures were harvested in mid log phase ($OD_{600}$ of 1-3) The cells of each culture were collected by centrifugation (2700×g, 5 min, 4° C.). The cell pellets were washed by resuspending in 20 mL of ice cold water. The cells were centrifuged at 2700×g, 4° C. for 5 min, All supernatant was removed from each tube and the tubes were frozen at −80° C. until use.

Lysates were prepared by thawing each cell pellet on ice and preparing a 20% (w/v) cell suspension in lysis buffer. The lysis buffer was varied for each enzyme assay and consisted of: 0.1 M Tris-HCl pH 8.0, 5 mM $MgSO_4$, for DHAD assays, 50 mM potassium phosphate buffer pH 6.0, 1 mM $MgSO_4$ for ALS assays, 250 mM $KPO_4$ pH 7.5, 10 mM $MgCl_2$ for KARI assays, 50 mM $NaHPO_4$, 5 mM $MgCl_2$, for KIVD assays. 10 µL of Yeast/Fungal. Protease Arrest solution (G Biosciences, catalog #788-333) per 1 mL of lysis buffer was used. 800 microliters of cell suspension were added to 1 mL of 0.5 mm glass beads that had been placed in a chilled 1.5 mL tube. Cells were lysed by bead beating (6 rounds, 1 minute per round, 30 beats per second) with 2 minutes chilling on ice in between rounds. The tubes were then centrifuged (20,000×g, 15 min) to pellet debris and the supernatants (cell lysates) were retained in fresh tubes on ice. The protein concentration of each lysate was measured using the BioRad Bradford protein assay reagent (BioRad, Hercules, Calif.) according to manufacturer's instructions.

Preparation of fractionated lysates from *S. cerevisiae* strains for in vitro enzyme assays. To grow cultures for cell fractionated cell lysates, triplicate independent cultures of the desired strain were grown overnight in 3 mL of the appropriate medium at 30° C., 250 rpm. The following day, the overnight cultures were used to inoculate 1 L cultures of each strain which were grown in the appropriate medium at 30° C. at 250 rpm until they reached an $OD_{600}$ of approximately 2. The cells were collected by centrifugation (1600×g, 2 min) and the culture medium was decanted. The cell pellets were resuspended in 50 mL sterile deionized water, collected by centrifugation (1600×g, 2 min), and the supernatant was discarded.

To obtain spheroplasts, the cell pellets were resuspended in 0.1M Tris-$SO_4$, pH 9.3, to a final concentration of 0.1 g/mL, and DTT was added to a final concentration of 10 mM. Cells were incubated with gentle (60 rev/min) agitation on an orbital shaker for 20 min at 30° C., and the cells were then collect by centrifugation (1600×g, 2 min) and the supernatant discarded. Each cell pellet was resuspended in spheroplasting buffer, which consists of (final concentrations): 1.2M sorbitol (Amresco, catalog #0691), 20 mM potassium phosphate pH 7.4) and then collected by centrifugation (1600×g, 10 min). Each cell pellet was resuspended in spheroplasting buffer to a final concentration of 01 g cells/mL in a 500 mL centrifuge bottle, and 50 mg of Zymolyase 20T (Seikagaku Biobusiness, Code#120491) was added to each cell suspension. The suspensions were incubated overnight (approximately 16 hrs) at 30° C. with gentle agitation (60 rev/min) on an orbital shaker. The efficacy of spheroplasting was ascertained by diluting an aliquot of each cell suspension 1:10 in either sterile water or in spheroplasting buffer, and comparing the aliquots microscopically (under 40× magnification). In all cases, >90% of the water-diluted cells lysed, indicating efficient spheroplasting. The spheroplasts were centrifuged (3000×g, 10 min, 20° C.), and the supernatant was discarded. Each cell pellet was resuspended in 50 mL spheroplast buffer without Zymolyase, and cells were collected by centrifugation (3000×g, 10 min, 20° C.).

To fractionate spheroplasts, the cells were resuspended to a final concentration of 0.5 g/mL in ice cold mitochondrial isolation buffer (MIB), consisting of (final concentration): 0.6M D-mannitol (BD Difco Cat#217020), 20 mM HEPES-KOH, pH 7.4. For each 1 mL of resulting cell suspension, 0.01 mL of Yeast/Fungal Protease Arrest solution (G Biosciences, catalog #788-333) was added. The cell suspension was subjected to 35 strokes of a Dounce homogenizer with the B (tight) pestle, and the resulting cell suspension was centrifuged (2500×g, 10 min, 4° C.) to collect cell debris and unbroken cells and spheroplasts. Following centrifugation, 2 mL of each sample (1 mL of the pGV1900 transformed cells) were saved in a 2 mL centrifuge tube on ice and designated the "W" (for Whole cell extract) fraction, while the remaining supernatant was transferred to a clean, ice-cold 35 mL Oakridge screw-cap tube and centrifuged (12,000×g, 20 min, 4° C.) to pellet mitochondria and other organellar structures. Following centrifugation, 5 mL of each resulting supernatant was transferred to a clean tube on ice, being careful to avoid the small, loose pellet, and labelled the "S" (soluble cytosol) fraction. The resulting pellets were resuspended in MIB containing Protease Arrest solution, and were labelled the "P" ("pellet") fractions. The BioRad Protein Assay reagent (Bio-Rad, Hercules, Calif.) was used according to manufacturer's instructions to determine the protein concentration of each fraction.

Preparation of fractionated lysates from *K. lactis* strains for in vitro enzyme assays Cultures (20 mL YPD) were inoculated with yeast cells (GEVO1742 and GEVO1829) and incubated at 30° C. while shaking at 250 RPM until they reached late-log to stationary phase ($OD_{600}$ of approximately 10). Cells from the 20 mL cultures were used to inoculate a 250 mL YPD culture at an $OD_{800}$ of approximately 0.2. The cultures were incubated at 30° C. while shaking at 250 RPM until they reached mid-log($OD_{600}$~2).

To prepare spheroplasts, the cells were collected in 500 mL bottles at 5000×g for 5 minutes at room temperature. The pellets were resuspended with 8 mL Spheroplasting Buffer A (25 mM potassium phosphate (pH 7.5), 1 mM $MgCl_2$, 1 mM EDTA, 1.25 mM TPP, 1 mM DTT) without sorbitol and transferred to pre-weighed 50 mL tubes. The cells were collected at 1600×g for 5 minutes at room temperature. The cells were resuspended with 8 mL of Spheroplasting Buffer A with 2.5 M Sorbitol (Amresco Code#0691) and protease inhibitor (G Biosciences Yeast/Fungal ProteaseArrest™ (Catalog #788-333)). Approximately 5 mg of Zymolyase 20T Zymolyase 20T (Seikagaku Biobusiness Code#120491) was added to each cell suspension. The suspensions were incubated at 30° C. with gentle agitation (e.g. 50 RPM), with the tube on its side for good mixing, for 1-2 hours. The efficiency of formation of spheroplasts was verified by dilution of the spheroplast suspension 1:10 into Spheroplasting Buffer A with 2.5 M sorbitol and 1:10 in water. Spheroplasts should remain intact when diluted into the buffer but appear fuzzy or completely disappear when diluted into water. The spheroplasts were collected at 1600×g for 7 minutes at 4° C. The spheroplasts were gently washed with 2 mL of Spheroplasting Buffer A with 2.5 M sorbitol and protease inhibitor, and collected at 1600×g for 7 minutes at 4° C. The spheroplasts were resuspended in 2 mL of Spheroplasting Buffer A with 2.5 M sorbitol and protease inhibitor.

To fractionate the spheroplasts, 8 mL of Spheroplasting Buffer A with 0.2 M sorbitol and protease inhibitor was slowly added to the cell suspension, bringing the final concentration of Sorbitol to 0.66 M. The spheroplasts were broken with 10 strokes using a B (tight fitting) pestle in a 15 mL Dounce homogenizer (Bellco Glass, Inc. Cat#1984-10015) on ice. The homogenate was transferred to a 50 mL tube, and the cell debris was collected by centrifugation at 4° C. for 10 minutes at 1600×g. The supernatant was transferred to a 15 mL tube with a pipette. This supernatant is the "W" fraction. 5 mL of this "W" fraction was transferred to a 35 mL Oakridge tube and centrifuged at 48,000×g for 20 minutes at 4° C. The resulting supernatant was transferred to a 15 mL tube and labeled "S." The pellet was resuspended in 5 mL of Spheroplasting Buffer A with 0.66 M Sorbitol and protease inhibitor and labeled "P." All fractions were stored on ice at 4° C. while in use. The BioRad Protein Assay reagent (BioRad, Hercules, Calif.) was used according to manufacturer's instructions to determine the protein concentration of each fraction.

ALS Assay. Cell lysates were prepared and protein concentrations were determined as described above. The colorimetric ALS Assay (FAD-independent) performed here was based on the assay described in Hugenholtz, J. and Starrenburg, J. C., Appl. Microbiol. Biotechnol. (1992) 38:17-22. Reaction buffer was prepared by mixing 900 µl 1M potassium phosphate buffer pH 6.0, 180 µl 100 mM $MgSO_4$, 180 µl 100 mM TPP, 3.96 ml 500 mM pyruvate and 12.78 ml water. For the no substrate control, the volume of pyruvate was replaced with water. Lysates were prepared at a final protein concentration of 2 µg/µl in Spheroplasting Buffer A with 0.66 M sorbitol. To 900 µL ALS Buffer, 100 µL of lysate was added and incubated at 30° C. for 30 min. Acetoin standards were also prepared at concentrations of 2 mM, 1 mM, 0.5 mM, and 0 mM. From each sample and standard, 175 µL was transferred to a fresh 1.5 mL tube. To each sample and standard was added 25 µL 35% (v/v) $H_2SO_4$, and all were incubated at 37° C. for 30 mins. After the incubation, the following were added in order, to each standard and sample, with the solutions being mixed by vortexing in between each addition: 50 µL 50% (w/v) NaOH, 50 µL 0.5% creatine, and 50 µL 5% 1-naphthol (in 2.5N NaOH). The samples and standards were incubated at room temperature for 1 hour, being mixed by vortexing every 15 minutes. To a 96 well, half-area, UV-Star, transparent, flat-bottom plate (Catalog #675801, Greiner Bio One, Frickenhausen, Germany), 100 uL of each sample or standard was transferred, and the samples were analyzed by a plate reader by measuring absorbance at 530 nm.

KARI Assay. Cell lysates were prepared and protein concentrations were determined as described above. Acetolactate substrate was made by mixing 50 µl of ethyl-2 acetoxy-2-methyl-acetoacetate with 990 µl of water. Then 10 µl of 2 N NaOH was sequentially added, with vortex mixing between additions, until 260 µl of NaOH was added. The acetolactate was agitated at room temperature for 20 min and then held on ice. NADPH was prepared in 0.01N NaOH (to improve stability) to a concentration of 50 mM. The concentration was determined by reading the OD of a diluted sample at 340 nm in a spectrophotometer and using the molar extinction coefficient of 6.22 $M^{-1}$ $cm^{-1}$ to calculate the actual concentration (the $OD_{340}$ of a 100 µM solution of NAD(P)H should be 0.622). Three buffers were prepared and held on ice. Reaction buffer contained 250 mM $KPO_4$ pH 7.5, 10 mM $MgCl_2$, 1 mM DTT, 10 mM acetolactate, and 0.2 mM NADPH. No substrate buffer contained everything except the acetolactate. No NAD(P)H buffer contained everything except the NADPH. Reactions were performed in triplicate using 10 µl of cell extract with 90 µl of reaction buffer in a 96-well plate in a SpectraMax 340PC multi-plate reader (Molecular Devices, Sunnyvale, Calif.). The reaction was followed at 340 nm by measuring a kinetic curve for 5 minutes, with OD readings taken every 10 seconds. The reactions were performed at 30° C. The reactions were performed in complete, no substrate, and no NAD(P)H buffers. The $V_{max}$ for each extract was determined after subtracting the background reading of the no substrate control from the reading in complete buffer.

DHAD Assay. Cell lysates were prepared and protein concentrations were determined as described above. The DHAD activity of each lysate was ascertained as follows. In a fresh 1.5 mL centrifuge tube, 50 µL of each lysate was mixed with 50 µL of 0.1M 2,3-dihydroxyisovalerate (DHIV), 25 µL of 0.1M $MgSO_4$, and 375 µL of 0.05M Tris-HCl pH 8.0, and the mixture was incubated for 30 min at 35° C. Each tube was then heated to 95° C. for 5 min to inactivate any enzymatic activity, and the solution was centrifuged (16,000×g for 5 min) to pellet insoluble debris. To prepare samples for analysis, 100 µL of each reaction were mixed with 100 µL of a solution consisting of 4 parts 15 mM dinitrophenyl hydrazine (DNPH) in acetonitrile with 1 part 50 mM citric acid, pH 3.0, and the mixture was heated to 70° C. for 30 min in a thermocycler. The solution was then analyzed by HPLC as described above in General Methods to quantitate the concentration of ketoisovalerate (KIV) present in the sample.

KIVD Assay. Cell lysates were prepared and protein concentrations were determined as described above. KIVD Assay buffer, containing 1 Roche Protease Inhibitor tablet per 5 mL buffer, was added to each cell pellet to create a 20% (w/v) cell suspension. The KIVD assay buffer was prepared at a final concentration of 0.05 M $NaHPO_4*H_2O$, 5 mM $MgCl_2*8H_2O$, and 1.5 mM Thiamin pyrophosphate chloride. The reaction substrate, α-keto-isovalerate (3-methyl-2-oxobutanoic acid, Acros Organics), was added where appropriate at 30 mM. Lysates were diluted in reaction buffer at a final protein concentration of 0.1 µg/µL. To 1.5 mL tubes, 50 µL of lysate (5 µg of protein) was mixed with: 200 µL of reaction buffer with or without substrate. The reactions were incubated at 37° C. for 20 minutes, and the reactions were immediately filtered through a 2 µm filter plate. The filtered samples were diluted 1:10 in water, and 100 µL of the 1:10 dilution was mixed with 100 µL of derivatization reagent in a 0.2 ml thin-wall PCR tubes. Derivatization reagent was prepared by mixing 4 ml of 2,4-Dinitrophenyl Hydrazine (DNPH) in 15 mM in HPLC-grade Acetonitrile with 1 ml 50 mM Citric Acid Buffer, pH 3. The samples were incubated at 70° C. for 30 minutes. The samples were analyzed by HPLC.

ADH Assay. Cell lysates were prepared and protein concentrations were determined as described above. Assays (set up in triplicate for each lysate) contained 10 µL of each lysate (or an appropriate dilution of each lysate) plus 90 µl of reaction buffer, which consisted of (final concentrations present in 1× reaction buffer): 0.1M Tris-HCl pH 7.5, 10 mM $MgCl_2$, 1 mM DTT, 0.2 mM NADH (or NADPH, where indicated; each diluted from a 4.4 mM spectrophotometrically-confirmed stock), and 11 mM isobutyraldehyde. Where indicated, as controls a parallel set of assay reactions were set up using reaction buffer lacking isobutyraldehyde and/or NAD(P)H, as indicated. For experiments measuring the acetaldehyde-dependent oxidation of NAD(P)H, reaction buffer was prepared in which acetaldehyde was substituted for isobutyraldehyde. In these cases, the reaction buffer contained at least 11 mM acetaldehyde, although the exact amount present is an estimate due to the inherent difficulties of pipetting acetaldehyde solution. Finally, in some cases a parallel set of reactions lacking yeast cell lysate was included as a negative control. After being added (using a multi-channel pipet) to the wells of a 96-well plate, the reactions were immediately placed into a plate reader that had been pre-warmed to 30° C., and the absorbance at 340 nm was measured every 12 seconds over a period of 300 seconds. Kinetic parameters were computed from assays with linear slopes (where necessary, assays were repeated with appropriate dilutions to obtain linear NAD(P)H consumption curves).

Composition of Culture Media

Drugs: When indicated, G418 (Calbiochem, Gibbstown, N.J.) was added at 0.2 g/L, Phleomycin (InvivoGen, San Diego, Calif.) was added at 7.5 mg/L, Hygromycin (InvivoGen, San Diego, Calif.) was added at 0.2 g/L, and 5-fluoro-orotic acid (FOA; Toronto Research Chemicals, North York, Ontario, Canada) was added at 1 g/L.

YP: 1% (w/v) yeast extract, 2% (w/v) peptone.

YPD: YP containing 2% (w/v) glucose unless otherwise noted,

YPGal: YP containing 2% (w/v) galactose

YPE: YP containing 2% (w/v) Ethanol.

SC media: 6.7 g/L Difco™ Yeast Nitrogen Base, 14 g/L Sigma™ Synthetic Dropout Media supplement (includes amino acids and nutrients excluding histidine, tryptophan, uracil, and leucine; Sigma-Aldrich, St. Louis, Mo.), 0.076 g/L histidine, 0.076 g/L tryptophan, 0.380 g/L leucine, and 0.076 g/L uracil. Drop-out versions of SC media is made by omitting one or more of histidine (H), tryptophan (W), leucine (L), or uracil (U or Ura). When indicated, SC media are supplemented with additional isoleucine (9xI; 0.684 g/L), valine (9xV; 0.684 g/L) or both isoleucine and valine (9xIV). SCD is SC containing 2% (w/v) glucose unless otherwise noted, SCGal is SC containing 2% (w/v) galactose and SCE is SC containing 2% (w/v) ethanol. For example, SCD-Ura+9xIV would be composed of 6.7 g/L Difco™ Yeast Nitrogen Base, 14 g/L Sigma™ Synthetic Dropout Media supplement (includes amino acids and nutrients excluding histidine, tryptophan, uracil, and leucine), 0.076 g/L histidine, 0.076 g/L tryptophan, 0.380 g/L leucine, 0.684 g/L isoleucine, 0.684 g/L valine, and 20 g/L glucose.

SCD-V+9xI: 6.7 g/L Difco™ Yeast Nitrogen Base, 0.076 g/L Adenine hemisulfate, 0.076 g/L Alanine 0.076 g/L, Arginine hydrochloride, 0.076 g/L Asparagine monohydrate, 0.076 g/L Aspartic acid, 0.076 g/L Cysteine hydrochloride monohydrate, 0.076 g/L Glutamic acid monosodium salt, 0.076 g/L Glutamine, 0.076 g/L Glycine, 0.076 g/L myo-Inositol, 0.76 g/L Isoleucine, 0.076 g/L Lysine monohydrochloride, 0.076 g/L Methionine, 0.008 g/L p-Aminobenzoic acid potassium salt, 0.076 g/L Phenylalanine, 0.076 g/L Proline, 0.076 g/L Serine, 0.076 g/L Threonine, 0.076 g/L Tyrosine disodium salt, and 20 g/L glucose.

YNB: 6.7 g/L Difco™ Yeast Nitrogen Base supplemented with indicated nutrients as follows: histidine (H; 0.076 g/L), tryptophan (W; 0.076 g/L), leucine (L; 0.380 g/L), uracil (U or Ura; 0.076 g/L), isoleucine (I; 0.076 g/L), valine (V; 0.076 g/L), and casamino acids (CM; 10 g/L). When indicated, YNB media are supplemented with higher amounts of isoleucine (10xI=0.76 g/L), valine (10xV=0.76 g/L) or both isoleucine and valine (10xIV). YNBD is YNB containing 2% (w/v) glucose unless otherwise noted, YNBGal is YNB containing 2% (w/v) galactose and YNBE is YNB containing 2% (w/v) ethanol. For example, YNBGal+HWLU+10xI+G418 would be composed of 6.7 g/L Difco™ Yeast Nitrogen Base, 0.076 g/L histidine, 0.076 g/L tryptophan, 0.380 g/L leucine, 0.076 g/L uracil, 0.76 g/L isoleucine, 0.2 g/L G418, and 20 g/L galactose.

Plates: Solid versions of the above described media contain 2% (w/v) agar.

Example 1

Isobutanol Pathway is Partially Cytosolic when Expressed in Yeast

The purpose of this example is to illustrate that three enzymes in the isobutanol biosynthetic pathway (acetolactate synthase, ketoisovalerate decarboxylase, and isobutanol dehydrogenase) are localized to the cytosol when expressed in yeast.

TABLE 3

Genotype of strains disclosed in Example 1.

| GEVO No. | Genotype/Source |
|---|---|
| 1287 | K. lactis ATCC 200826 MAT α uraA1 trp1 leu2 lysA1 ade1 lac4-8 [pKD1] |
| 1742 | K. lactis ATCC 200826 MAT α uraA1 trp1 leu2 lysA1 ade1 lac4-8 [pKD1] pdc1::Kan$^R$ |
| 1829 | K. lactis ATCC 200826 MAT α uraA1 trp1 leu2 lysA1 ade1 lac4-8 [pKD1] pdc1::kan$^R$ {P$_{TDH3}$:Ec__ilvC-ΔN; P$_{TEF1}$:Ec_ilvD-ΔN(codon optimized for K. lactis): ScLEU2 integrated} {P$_{TEF1}$:Ll__kivD; P$_{TDH3}$ScADH7: KmURA3 integrated} {P$_{CUP1-1}$:Bs__alsS, TRP1 random integrated} |

TABLE 4

Plasmids disclosed in Example 1.

| pGV No. | Genotype |
|---|---|
| pGV1503 | ScTEF1promoter-kanR bla, pUC ori (GEVO) |
| pGV1537 | KlPDC1 promoter region + Klpdc1 3'UTR sequence, ScTEF1promoter-kanR bla, pUC ori (GEVO) |
| pGV1590 | TEF1 promoter:Ll-kivd (codon optimized for E. coli): TDH3 promoter:ADH7:CYC1 terminator, Km-URA3, 1.6 micron ori, bla, pUC ori (GEVO) |
| pGV1726 | CUP1 promoter:Bs-alsS:CYC1 terminator, TRP1, bla, pUC-ori |
| pGV1727 | TEF1 promoter:Ec-ilvDΔN (codon optimized for K. lactis):TDH3 promoter:Ec-ilvCΔN:CYC1 terminator, LEU2, bla, pUC ori (GEVO) |

Plasmids pGV1503 contains an S. cerevisiae TEF1 promoter region driving a G418-resistance gene (kan$^R$).

pGV1537 was constructed by inserting an (AatII plus MfeI)-digested PCR product containing approximately 500 bp each of KlPDC1 5' and 3' untranslated regions, into (AatII plus EcoRI)-digested pGV1503. The insert was generated by SOE-PCR. First, the KlPDC1 5' and 3' untranslated regions were amplified from K. lactis genomic DNA by primer pairs 1006+1016 and 1017+1009, respectively. Primers 1016 and 1017 were designed to have overlapping sequences. The two fragments were then joined by PCR using primers 1006+1009.

pGV1590 is a K. lactis plasmid for expression of the L. lactis kivD and the S. cerevisiae ADH7. Expression of the L. lactis kivD is driven by the S. cerevisiae TEF1 promoter and expression of the S. cerevisiae ADH7 is driven by the S. cerevisiae TDH3 promoter. pGV1590 was generated by cloning a SalI-NotI fragment carrying the S. cerevisiae ADH7 gene into the XhoI-NotI sites of pGV1585. The S. cerevisiae ADH7 gene fragment originated as a PCR product from S. cerevisiae genomic DNA using primers 410 and 411.

pGV1726 is a yeast integration plasmid (utilizing the S. cerevisiae TRP1 gene as selection marker) for random integration (i.e. for K. lactis). This plasmid does not carry a yeast replication origin, thus is unable to replicate episomally. This plasmid also carries the B. subtilis alsS gene, whose expression is under the control of the S. cerevisiae CUP1 promoter. pGV1726 was generated by cloning a SacI-NgoMIV fragment carrying the S. cerevisiae CUP1 promoter, Bs-alsS ORF and the CYC1 terminator into the same sites of pGV1645. The vector, pGV1645, is a K. lactis expression plasmid that was used for expression of the B. subtilis alsS under the control of the K. lactis PDC1 promoter. This plasmid also carries the S. cerevisiae TRP1 gene as a selection marker and the 1.6 micron replication origin. Digestion of pGV1645 with SacI and NgoMIV removes the K. lactis PDC1 promoter, B. subtilis alsS, CYC1 terminator and the 1.6 micron origin of replication. The insert fragment carrying the S. cerevisiae CUP1 promoter, B. subtilis alsS ORF and the CYC1 terminator was obtained from pGV1649 via digestion with SacI and NgoMIV. The CUP1 promoter originated as a PCR product from S. cerevisiae genomic DNA using primers 637 and 638. The B. subtilis alsS originated as a PCR product from B. subtilis genomic DNA using primers 767 and 697.

pGV1727 is a yeast integration plasmid (utilizing the S. cerevisiae LEU2 gene as selection marker) for random integration (i.e. for K. lactis). This plasmid does not carry a yeast replication origin, thus is unable to replicate episomally. This plasmid carries the E. coli ilvCΔN and ilvCΔN genes, whose expressions are under the control of the S. cerevisiae TEF1 and TDH3 promoters respectively. The E. coli ilvDΔN is a shortened version of E. coli ilvD where the sequence coding for the first 24 amino acids, which encodes for a putative mitochondrial targeting sequence, was removed. Likewise, the E. coli ilvCΔN is a shortened version of E. coli ilvC where the sequence coding for the first 22 amino acids, which is predicted to function as a mitochondrial targeting sequence was removed. pGV1727 was generated by cloning a XhoI-NgoMIV fragment carrying the E. coli ilvCΔN gene and the CYC1 terminator into the same sites of pGV1635. The vector, pGV1635, is a K. lactis expression plasmid that was used for expression of the E. coli ilvDΔN gene under the control of the S. cerevisiae TEF1 promoter. The ilvDΔN gene is followed by the TDH3 promoter, a short MCS (includes an XhoI site), the CYC1 terminator and the 1.6 micron replication origin. This plasmid carries the S. cerevisiae LEU2 gene as a selection marker. Digestion of pGV1635 with XhoI and NgoMIV removes the CYC1 terminator and the 1.6 micron replication origin. This sequence was replaced by the insert fragment carrying the E. coli ilvCΔN and the CYC1 terminator which was obtained from pGV1677 digested with XhoI and NgoMIV. The E. coli ilvDΔN originated as a PCR product from pGV1578 (plasmid carrying E. coli ilvD codon optimized for K. lactis from DNA2.0, Menlo Park, Calif.) using primers 1151 and 1152. The E. coli ilvCΔN originated as a PCR product from pGV1160 (plasmid carrying the full length E. coli ilvC gene) using primers 1149 and 1150. The E. coli ilvC in pGV1160 originated as a PCR product from E. coli genomic DNA using primers 387 and 388.

GEVO1287 was transformed with PmlI-digested pGV1537, yielding GEVO1742. GEVO1829 was constructed by sequentially transforming GEVO1742 with gene fragments from pGV1590, pGV1727, and pGV1726 following the standard lithium acetate protocol. First, a 7.8 kb fragment of pGV1590 generated by digestion with NgoMIV and MfeI was transformed into GEVO1742. Next, this transformant strain was transformed with pGV1727 (FIG. 4) that had been linearized by digestion with BcgI. Finally, this transformant strains was transformed with pGV1726 that had been linearized by digestion with AhdI. The final transformant was GEVO1829.

Cellular fractions were prepared from GEVO1742 and GEVO1829 as described above. The protein concentration used to calculate specific activities from all three fractions ("W," "S," and "P") was measured for the "W" fraction. Below are the results for the assays measuring isobutanol dehydrogenase, acetolactate synthase, and ketoisovalerate decarboxylase activities.

Alcohol Dehydrogenase (ADH) Assay

The results from the assay are summarized in Table 5. The "W" fraction and the "S" fraction of the pathway carrying strain (GEVO1829) contained at least three times the NADPH dependent alcohol dehydrogenase activity found in the same fractions of GEVO1742. The "W" and "S" fractions of GEVO1829 contained more than four times the activity present in the "P" fraction. These data indicated that *S. cerevisiae* Adh7 activity was predominantly localized to the cytosol.

TABLE 5

Alcohol Dehydrogenase Activity.

| Sample | Specific Alcohol Dehydrogenase Activity (U/mg protein) |
|---|---|
| 1742 W | 0.08 ± 0.00 |
| 1742 S | 0.07 ± 0.02 |
| 1742 P | 0.03 ± 0.012 |
| 1829 W | 0.26 ± 0.00 |
| 1829 S | 0.25 ± 0.02 |
| 1829 P | 0.04 ± 0.02 |

Acetolactate Synthase (ALS) Assay

The results from the assay are summarized in Table 6. The "W" and "S" fractions of the isobutanol pathway carrying strain (GEVO1829) contained ALS activity, while no activity was detected in the same fractions of GEVO1742. The "W" and "S" fractions contained three times higher ALS activity than the "P" fraction. These data indicated that *B. subtilis* ALS activity was predominantly localized to the cytosol.

TABLE 6

Acetolactate Synthase Activity.

| Sample | Specific Acetolactate Synthase Activity (U/mg protein) |
|---|---|
| 1742 W | 0.00 ± 0.00 |
| 1742 S | 0.00 ± 0.00 |
| 1742 P | 0.00 ± 0.00 |
| 1829 W | 0.10 ± 0.01 |
| 1829 S | 0.10 ± 0.00 |
| 1829 P | 0.03 ± 0.00 |

Ketoisovalerate Decarboxylase (KIVD) Assay

The results from the assay are summarized in Table 7. The "W" and "S" fractions of the isobutanol pathway carrying strain (GEVO1829) contained 8-10 times greater activity than in the same fractions of GEVO1742. Furthermore, the activity in "S" fraction was 45× higher than what was detected in "P" fraction. These data indicated that *L. lactis* KIVD activity was predominantly localized in the cytosol.

TABLE 7

Ketoisovalerate decarboxylase (KIVD) Assay.

| Sample | Specific Ketoisovalerate Decarboxylase Activity (U/mg protein) |
|---|---|
| 1742 W | 0.05 ± 0.00 |
| 1742 S | 0.05 ± 0.04 |
| 1742 P | 0.03 ± 0.00 |
| 1829 W | 0.38 ± 0.02 |
| 1829 S | 0.45 ± 0.04 |
| 1829 P | 0.01 ± 0.00 |

Example 2

Construction of an ILV3 Deletion Mutant

The purpose of this example is to describe the construction of an ILV3 deletion mutant of *S. cerevisiae*, GEVO2244.

TABLE 8

Genotype of strains disclosed in Example 2.

| GEVO No. | Genotype/Source |
|---|---|
| GEVO1147 | *K. lactis*, NRRL Y-1140, (obtained from USDA) |
| GEVO1188 | *S. cerevisiae*, CEN.PK, (obtained from Euroscarf); MATα ura3 leu2 his3 trp1 |
| GEVO2145 | *S. cerevisiae*, CEN.PK; MATα ura3 leu2 his3 trp1 ilv3::Kl_URA3 |
| GEVO2244 | *S. cerevisiae*, CEN.PK; MATα ura3 leu2 his3 trp1 ilv3Δ |

TABLE 9

Plasmids disclosed in Example 2.

| Plasmid name | Genotype |
|---|---|
| pUC19 | bla, pUC-ori (obtained from Invitrogen) |
| pGV1299 | *K. lactis* URA3, bla, pUC-ori (GEVO) |

Plasmid pGV1299 was constructed by cloning the *K. lactis* URA3 gene into pUC19. The *K. lactis* URA3 was obtained by PCR using primers 575 and 576 from *K. lactis* genomic DNA. The PCR product was digested with EcoRI and BamHI and cloned into pUC19 which was similarly digested. The *K. lactis* URA3 insert was sequenced (Laragen Inc) to confirm correct sequence.

The ilv3::Kl_URA3 integration cassette contained, from 5' to 3', the following: 1) a 80 bp homology to ILV3 (position +158 to 237) that functions as the 5' targeting sequence for the integration, 2) the *K. lactis* URA3 marker gene, 3) a 60 bp homology to a region ILV3 (position −21 to +39) that is further upstream of the 5' targeting sequence to facilitate loop-out of the *K. lactis* URA3 marker, and 4) a 221 bp homology to the 3' region of ILV3 (position +1759 to 1979) that functions as the 3' targeting sequence for the integration. This cassette was generated by SOE-PCR. The *K. lactis* URA3 gene was amplified from pGV1299 using primers 1887 and 1888. Only the 3' region of ILV3 was initially amplified using primers 1623 and 1892 from genomic DNA and this product was used as template to amplify the 3' region of ILV3 using primers 1889 and 1890. The *K. lactis* URA3 and the 3' region of ILV3 were combined by SOE-PCR using primers 1886 and 1890.

GEVO1188 was transformed with the ilv3::Kl_URA3 cassette described above and plated onto YNBD+W+CAA (−Ura) plates. Initially, eight colonies (#1-8) were patched onto YNBD+HUWLIV plates and then replica plated onto YNBD+HUWLI (−V) plates to test for valine auxotrophy. As none of these exhibited valine auxotrophy, an additional eight colonies (#9-16) were streaked out for single colonies and 3 or 4 isolates (A through C or D) from each streak were tested for valine auxotrophy. Isolates A-C from clone #12 exhibited valine auxotrophy.

These isolates were tested for the correct integrations by colony PCR using primer pairs 1916+1920 and 1917+1921 for the 5' and 3' junctions, respectively. Correct sized bands were observed with clones #12A through C with primer pair 1916+1920. Correct sized bands were observed with clone 12A when FailSafe Master Mix A or C was used with primer pair 1917+1921. Clone #12A was designated as GEVO2145. The valine auxotrophies of GEVO2145 were reconfirmed by streaking them onto SCD+9xIV and SCD-V+9xI plates. GEVO2145 exhibited no growth on the medium lacking valine (SCD-V+9xI) while it grew on medium supplemented with valine (SCD+9xIV). The parent strain, GEVO1188, grew on both media.

GEVO2145 was streaked onto YNBE+W+CAA+FOA to isolate strains in which the *K. lactis* URA3 had been excised through homologous recombination, i.e. "looped out". Five FOA resistant clones (A-E) were tested for auxotrophies for valine and uracil. All five clones exhibited auxotrophies to both nutrients. Clone A was designated GEVO2244. Colony PCR using primers 1891 and 1892 with FailSafe Buffer C was performed and the loss of the Kl_URA3 cassette was confirmed.

Example 3

DHAD Activity is Localized to Mitochondria

The purpose of this Example is to demonstrate that the DHAD activity encoded by ScILV3 is localized to the mitochondria.

TABLE 9

Genotype of strains disclosed in Example 3.

| GEVO No. | Genotype/Source |
| --- | --- |
| Gevo2244 | *S. cerevisiae*, CEN.PK; MATα ura3 leu2 his3 trp1 ilv3Δ |

TABLE 10

Plasmids disclosed in Example 3.

| pGV No. | Genotype |
| --- | --- |
| pGV1106 | pUC ori, bla (AmpR), 2 micron ori, URA3, TDH3 promoter-Myc tag-polylinker-CYC1 terminator |
| pGV1900 | pUC ori, bla (AmpR), 2 micron ori, URA3, TEF1 promoter-ScILV3(FL) |

Plasmid pGV1106 is a variant of p426GPD (described, in Mumberg et al, 1995, *Gene* 119-122). To obtain pGV1106, annealed oligos 271 and 272 were ligated into p426GPD that had been digested with SpeI and XhoI, and the inserted DNA was confirmed by sequencing.

Plasmid pGV1900 was generated by amplifying the full-length, native ScILV3 nucleotide sequence from *S. cerevisiae* strain CEN.PK genomic DNA using primers 1617 and 1618. The resulting 1.76 kb fragment, which contained the complete ScILV3 coding sequence (SEQ ID NO: 88) flanked by 5' SalI and 3' BamHI restriction site sequences was digested with SalI and BamHI and ligated into pGV1662 (described in Example 6) which had been digested with SalI and BamHI.

To measure DHAD activities present in fractionated cell extracts, GEVO2244 was transformed singly with either pGV1106, which served as an empty vector control, or with pGV1900, which is an expression plasmid for ScILV3.

An independent clonal transformant of each plasmid was isolated, and a 1 L culture of each strain was grown in SCGal-Ura+9xIV at 30° C. at 250 rpm. The $OD_{600}$ was noted, the cells were collected by centrifugation (1600×g, 2 min) and the culture medium was decanted. The cell pellets were resuspended in 50 mL sterile deionized water, collected by centrifugation (1600×g, 2 min), and the supernatant was discarded. The $OD_{600}$ and total wet cell pellet weight of each culture are listed in Table 11, below:

TABLE 11

$OD_{600}$ and pellet mass (g) of strain GEVO2244 transformed with the indicated plasmids.

| Plasmid | $OD_{600}$ | Pellet mass (g) |
| --- | --- | --- |
| pGV1106 | 2.2 | 7.6 |
| pGV1900 | 1.3 | 3.8 |

To obtain spheroplasts, the cell pellets were resuspended in 0.1M Tris-$SO_4$, pH 9.3, to a final concentration of 0.1 g/mL, and DTT was added to a final concentration of 10 mM. Cells were incubated with gentle (60 rev/min) agitation on an orbital shaker for 20 min at 30° C., and the cells were then collect by centrifugation (1600×g, 2 min) and the supernatant discarded. Each cell pellet was resuspended in spheroplasting buffer, which consists of (final concentrations): 1.2M sorbitol (Amresco, catalog #0691), 20 mM potassium phosphate pH 7.4) and then collected by centrifugation (1600×g, 10 min). Each cell pellet was resuspended in spheroplasting buffer to a final concentration of 0.1 g cells/mL in a 500 mL centrifuge bottle, and 50 mg of Zymolyase 20T (Seikagaku Biobusiness, Code#120491) was added to each cell suspension. The suspensions were incubated overnight (~16 hrs) at 30° C. with gentle agitation (60 rev/min) on an orbital shaker. The efficacy of spheroplasting was ascertained by diluting an aliquot of each cell suspension 1:10 in either sterile water or in spheroplasting buffer, and comparing the aliquots microscopically (under 40× magnification). In all cases, >90% of the water-diluted cells lysed, indicating efficient spheroplasting. The spheroplasts were centrifuged (3000×g, 10 min, 20° C.), and the supernatant was discarded. Each cell pellet was resuspended in 50 mL spheroplast buffer without Zymolyase, and cells were collected by centrifugation (3000×g, 10 min, 20° C.).

To fractionate spheroplasts, the cells were resuspended to a final concentration of 0.5 g/mL in ice cold mitochondrial isolation buffer (MIB), consisting of (final concentration): 0.6M D-mannitol (BD Difco Cat#217020), 20 mM HEPES-KOH, pH 7.4. For each 1 mL of resulting cell suspension, 0.01 mL of Yeast/Fungal Protease Arrest solution (G Biosciences, catalog #788-333) was added. The cell suspension was subjected to 35 strokes of a Dounce homogenizer with the B (tight) pestle, and the resulting cell suspension was centrifuged (2500×g, 10 min, 4° C.) to collect cell debris and unbroken cells and spheroplasts. Following centrifugation, 2 mL of each sample (1 mL of the pGV1900 transformed cells) were saved in a 2 mL centrifuge tube on ice and designated the "W" (for Whole cell extract) fraction, while the remaining supernatant was transferred to a clean, ice-cold 35 mL Oakridge screw-cap tube and centrifuged (12,000×g, 20 min, 4° C.) to pellet mitochondria and other organellar structures. Following centrifugation, 5 mL of each resulting supernatant was transferred to a clean tube on ice, being careful to avoid the small, loose pellet, and labelled the "S" (soluble cytosol) fraction. The resulting pellets were resuspended in MIB containing Protease Arrest solution, and were labelled the "P" ("pellet") fractions. Protein from the "P" fraction was released after dilution 1:5 in DHAD assay buffer (see above) by rapid mixing in a 1.5 mL tube with a Retsch Ball Mill MM301 in the presence of 0.1 mM glass beads. The mixing was performed 4 times for 1 minute.

The BioRad Protein Assay reagant (BioRad, Hercules, Calif.) was used according to manufacturer's instructions to determine the protein concentration of each fraction.

The DHAD activity of each fraction was ascertained as described in the methods above.

TABLE 12

Specific activities (KIV generation) and ratios of specific activities from fractionated lysates of *S. cerevisiae* strain GEVO2244 carrying plasmids to overexpress the indicated DHAD homolog.

| Lysate (pGV# and fraction*) | DHAD | Sp. Activity [U/mg protein in fraction] | Std. Dev. |
| --- | --- | --- | --- |
| 1106 W | — | n.d. | |
| 1106 S | — | n.d. | |
| 1106 P | — | n.d. | |
| 1900 W | ScILV3(FL) | 0.0096 | 0.0018 |
| 1900 S | ScILV3(FL) | 0.0052 | 0.0004 |
| 1900 P | ScILV3(FL) | 0.0340 | 0.0029 |

Each data point is the result of triplicate samples.

Cells overexpressing the full-length, native *S. cerevisiae* Ilv3 contained in a greater proportion of the specific DHAD activity in the mitochondrial fraction (P) versus the cytosolic fraction (S).

Example 4

Replacing Current Mitochondrially Targeted Isobutanol Pathway Enzymes with Fungal Homologs or Functional Analogs that are Targeted to the Cytosol The purpose of this example is to illustrate that fungal homologs of isobutanol a pathway enzymes exhibit cytosolic activity.

TABLE 13

Genotype of strains disclosed in Example 4.

| GEVO No. | Genotype/Source |
| --- | --- |
| 1187 | MATa ura3-52 leu2-3_112 his3Δ1 trp1-289 ADE2 CEN.PK2-1C |
| 2280 | MATa ura3-52 leu2-3_112 his3Δ1 trp1-289 ADE2 CEN.PK2-1C integrated pGV1730 at PDC1 locus |
| 2618 | MATa ura3-52 leu2-3_112 his3Δ1 trp1-289 ADE2 CEN.PK2-1C integrated pGV2114 at PDC1 locus |
| 2621 | MATa ura3-52 leu2-3_112 his3Δ1 trp1-289 ADE2 CEN.PK2-1C integrated pGV2117 at PDC1 locus |
| 2622 | MATa ura3-52 leu2-3_112 his3Δ1 trp1-289 ADE2 CEN.PK2-1C integrated pGV2118 at PDC1 locus |

TABLE 14

Plasmids disclosed in Example 4.

| pGV No. | Genotype |
| --- | --- |
| 1730 | $P_{Cup1-1}$:Bs_alsS, pUC ORI, $Amp^R$, TRP1, PDC1 3'-fragment-NruI-PDC1 5'-fragment. |
| 2114 | $P_{Cup1-1}$:Bs_alsScoSc, pUC ORI, $Amp^R$, TRP1, PDC1 3'-fragment-NruI-PDC1 5'-fragment. |
| 2117 | $P_{Cup1-1}$:Ta_alsS, pUC ORI, $Amp^R$, TRP1, PDC1 3'-fragment-NruI-PDC1 5'-fragment. |
| 2118 | $P_{Cup1-1}$:Ts_alsS, pUC ORI, $Amp^R$, TRP1, PDC1 3'-fragment-NruI-PDC1 5'-fragment. |

Yeast AHASs are normally mitochondrial, thus favoring fungal ALS enzymes for as cytosolically functional isobutanol pathway enzymes. Sequence analysis by Le and Choi (*Bull. Korean Chem. Soc.* (2005) 26:916-920) showed that there is a conserved sequence 'RFDDR' found in AHASs that is not conserved among ALSs. This sequence is likely involved in FAD-binding by AHASs and thus could be used to distinguish between the FAD-dependent AHASs and the FAD-independent ALSs. Using this region to distinguish between AHASs and ALSs BLAST searches of fungal sequence databases were performed and resulted in the identification of ALS homologs from several fungal species (*Magnaporthe grisea, Phaeosphaeria nodorum, Trichoderma atroviride* (SEQ ID NO: 71), *Talaromyces stipitatus* (SEQ ID NO: 72), *Penicillium marneffei*, and *Glomerella graminicola*). Of these sequences, the ALS homologs from *M. grisea, P. nodorum, T. atroviride* and *T. stipitatus* are predicted to be cytoplasmic by Mitoprot II v.1.101 as described in the paper M. G. Claros, P. Vincens. Computational method to predict mitochondrially imported proteins and their targeting sequences. Eur. J. Biochem. 241, 779-786 (1996).

Fungal ALS genes were synthesized by DNA 2.0 with codon optimization biased for *S. cerevisiae*. The following ALS constructs were made and tested for ALS activity by assaying acetoin in the media during a growth timecourse. All ALS genes were cloned into the integration vector pGV1730 (SEQ ID NO: 69) as described herein.

Plasmid pGV1730 is a yeast integration plasmid used to replace the PDC1 gene in *S. cerevisiae* with the *B. subtilis* alsS gene (SEQ ID NO: 70) (not codon optimized for *S. cerevisiae*) expressed using the *S. cerevisiae* CUP1 promoter. This plasmid carries the *S. cerevisiae* TRP1 gene as a selection marker.

Construction of pGV2114: pGV1730 was treated with BamHI and SalI and the 4932 bp vector fragment was purified by gel electrophoresis as described. The *B. subtilis* AlsS (codon-optimized for expression in *S. cerevisiae*) gene was ligated to the pGV1730 vector fragment as a BamHI and SalI 1722 bp fragment using standard methods with an approximately 5:1 insert:vector molar ratio and transformed into TOP10 chemically competent *E. coli* cells. Plasmid DNA was isolated and correct clones were confirmed using restriction enzyme analysis.

Construction of pGV2117. pGV1730 was treated with BamHI and SalI and the 4932 bp vector fragment was purified by gel electrophoresis as described. The *T. atroviride* ALS gene was ligated to the pGV1730 vector fragment as a BamHI and SalI 1686 bp fragment using standard methods with an approximately 5:1 insert:vector molar ratio and transformed into TOP10 chemically competent *E. coli* cells. Plasmid DNA was isolated and correct clones were confirmed using restriction enzyme analysis.

Construction of pGV2118. pGV1730 was treated with BamHI and SalI and the 4932 bp vector fragment was purified by gel electrophoresis as described. The T. stipitatus ALS gene was ligated to the pGV1730 vector fragment as a BamHI and SalI 1707 bp fragment using standard methods with an approximately 5:1 insert:vector molar ratio and transformed into TOP10 chemically competent *E. coli* cells. Plasmid DNA was isolated and correct clones were confirmed using restriction enzyme analysis.

All yeast strains were constructed by treating the plasmid to be integrated with NruI and then transforming the plasmid according to the standard yeast transformation protocol as described herein. Transformants were selected by plating transformed cells onto SCD-W media and growing at 30° C. for 2 days. Primary transformants were single colony purified and then tested for correct integration using colony PCR.

Colony PCR was performed using the Yeast colony PCR to check for proper integration of the integrative plasmids used the FailSafe™ PCR System (EPICENTRE® Biotechnologies, Madison, Wis.; Catalog #FS99250) according to the manufacturer protocol The PCR reactions were incubated in a thermocycler using the following conditions: 1 cycle of 94° C. for 2 min, 40 cycles of 94° C. for 30 s, 53° C. for 30 s, 72° C. for 60 s and 1 cycle of 72° C. for 10 min. Presence of the positive PCR product was assessed using agarose gel electrophoresis. Primer pairs for the 5'-end and 3'-end integration sites contained one primer on the plasmid and one primer in the genome.

Figure 2:
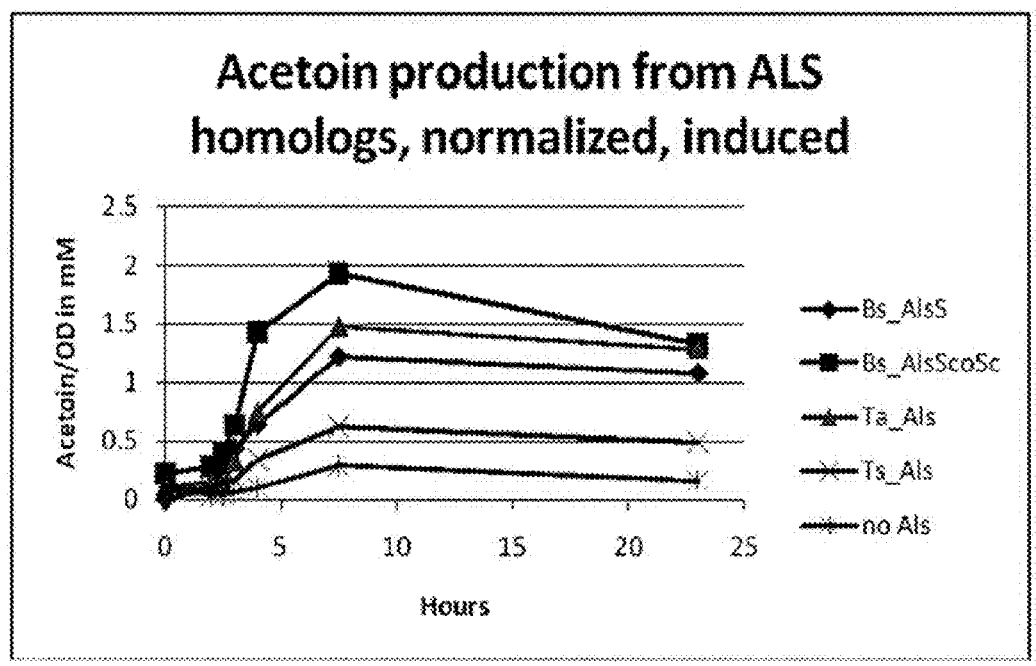
FIG. 2 illustrates acetoin produced from GEVO 1187 (no ALS), 2280 (*B. subtilis* AlsS not codon optimized), GEVO 2618 (*B. subtilis* AlsS), GEVO 2621 (*T. atroviride* ALS) and GEVO 2622 (*T. stipitatus* ALS). All acetoin values are normalized to $OD_{600}$ and reported as mM/OD.

Yeast strains GEVO1187, 2280, 2618, 2621 and 2622 were grown in YPD overnight at 30° C. A 100 mL culture was inoculated to 1 OD/mL and split into 2.50 mL cultures. This was the time zero. One of the 50 mL cultures received 500 μM $CuSO_4$ at time 2 hours and the other did not. Timepoints consisted of removing 1 mL at times 0, 2, 2.5, 3, 4, 7.5, and 23 hours. At each timepoint the $OD_{600}$ was determined and acetoin concentrations were determined using GC as described in the General Methods. Before GC samples were treated with $H_2SO_4$ to convert intermediates to acetoin. The graph shows the acetoin concentrations in the media of the strains in which transcription of the ALS genes was induced by $CuSO_4$. The acetoin values were normalized to cell OD. Both the *T. stipitatus* ALS and the *T. atroviride* ALS showed increased levels of acetoin as compared to the no ALS control (FIG. 2).

ALS activity in whole cell lysates is determined as described in General Methods. Activity in mitochondrial/organellar (P) and cytosolic (S) fractions and whole cell (W) lysates is assayed as described in General Methods Example 5

Replacing Current Mitochondrially Targeted Isobutanol Pathway Enzymes with Homologs or Functional Analogs from Anaerobic Fungi The purpose of this example is to illustrate that homologues of isobutanol a pathway enzymes from anaerobic fungi exhibit cytosolic activity.

TABLE 15

Genotype of strains disclosed in Example 5.

| GEVO No. | Genotype |
|---|---|
| GEVO2244 | *S. cerevisiae*, CEN.PK; MATα ura3 leu2 his3 trp1 ilv3Δ |

TABLE 16

Plasmids disclosed in Example 5.

| Plasmid name | Genotype |
|---|---|
| pGV1106 | pUC ori, bla (AmpR), 2 μm ori, URA3, TDH3 promoter-Myc tag-polylinker-CYC1 terminator |
| pGV1662 | pUC ori, bla (AmpR), 2 μm ori, URA3, TEF1 promoter-(kivD) |
| pGV1855 | pUC ori, bla (AmpR), 2 μm ori, URA3, TEF1 promoter-Ll_ilvD |

Plasmid pGV1106 is described in Example 3, above.

Plasmid pGV1662 (SEQ ID NO: 81) served as the parental plasmid of pGV1855, pGV1900, and pGV2019. The salient features of pGV1662 include the yeast 2 micron origin of replication, the URA3 selectable marker, and the ScTEF1 promoter sequence followed by restriction sites into which an ORF can be cloned to permit its expression under the regulation of the TEF1 promoter.

Plasmid pGV1855 contains the *L. lactis* ilvD. The *L. lactis* ilvD sequence was synthesized (DNA2.0, Menlo Park, Calif.) and included a unique SalI and a NotI site at the 5' and 3' end of the coding sequence, respectively. The synthesized DNA was digested with SalI and NotI and ligated into vector pGV1662 that had been digested with SalI plus NotI, yielding pGV1855.

The DHAD homolog (ilvD) from the anaerobic fungi *Piromyces* sp. E2 has a predicted MTS of 49 amino acids at the N-terminus. Thus, a nucleotide sequence encoding the Piromyces ilvD lacking the N-terminal 49 amino acids and with a start codon placed at the N-terminus was synthesized (SEQ ID NO: 73). In addition, a SalI site and a BamHI site were introduced at the 5' and 3' ends of this ORF. This fragment was cloned into the SalI and BamHI sites of pGV1662. The resulting plasmid was transformed in to GEVO2242. An empty vector, pGV1106, is used as a negative control. Plasmid, pGV1855, expressing *L. lactis* ilvD is used as a positive control.

An independent clonal transformant of each plasmid is isolated, and a 1 L culture of each strain is grown in SCGal-Ura+9xIV at 30° C. at 250 rpm. The $OD_{600}$ is noted, the cells are collected by centrifugation (1600×g, 2 min) and the culture medium is decanted. The cell pellets are resuspended in 50 mL sterile deionized water, collected by centrifugation (1600×g, 2 min), and the supernatant is discarded.

To obtain spheroplasts, the cell pellets are resuspended in 0.1M Tris-$SO_4$, pH 9.3, to a final concentration of 0.1 g/mL, and DTT is added to a final concentration of 10 mM. Cells are incubated with gentle (60 rev/min) agitation on an orbital shaker for 20 min at 30° C., and the cells are then collected by centrifugation (1600×g, 2 min) and the supernatant discarded. Each cell pellet is resuspended in spheroplasting buffer, which consists of (final concentrations): 1.2M sorbitol (Amresco, catalog #0691), 20 mM potassium phosphate pH 7.4) and then collected by centrifugation (1600×g, 10 min). Each cell pellet is resuspended in spheroplasting buffer to a final concentration of 0.1 g cells/mL in a 500 mL centrifuge bottle and 50 mg of Zymolyase 20T (Seikagaku Biobusiness, Code#120491) is added to each cell suspension. The suspensions are incubated overnight (approximately 16 hrs) at 30° C. with gentle agitation (60 rev/min) on an orbital shaker. The efficacy of spheroplasting is ascertained by diluting an aliquot of each cell suspension 1:10 in either sterile water or in spheroplasting buffer, and comparing the aliquots microscopically (under 40× magnification). The spheroplasts are centrifuged (3000×g, 10 min, 20° C.), and the supernatant is discarded. Each cell pellet is resuspended in 50 mL spheroplast buffer without Zymolyase and cells are collected by centrifugation (3000×g, 10 min, 20° C.).

To fractionate spheroplasts, the cells are resuspended to a final concentration of 0.5 g/mL in ice cold mitochondrial isolation buffer (MIB), consisting of (final concentration): 0.6M D-mannitol (BD Difco Cat#217020), 20 mM HEPES-KOH, pH 7.4. For each 1 mL of resulting cell suspension, 0.01 mL of Yeast/Fungal Protease Arrest solution (G Biosciences, catalog #788-333) is added. The cell suspension is subjected to 35 strokes of a Dounce homogenizer with the B (tight) pestle, and the resulting cell suspension is centrifuged (2500×g, 10 min, 4° C.) to collect cell debris and unbroken cells and spheroplasts. Following centrifugation, 2 mL of each sample (1 mL of the pGV1900 transformed cells) are saved in a 2 mL centrifuge tube on ice and designated the "W"

(for Whole cell extract) fraction, while the remaining supernatant is transferred to a clean, ice-cold 35 mL Oakridge screw-cap tube and centrifuged (12,000×g, 20 min, 4° C.) to pellet mitochondria and other organellar structures. Following centrifugation, 5 mL of each resulting supernatant is transferred to a clean tube on ice, being careful to avoid the small, loose pellet, and labelled the "S" (soluble cytosol) fraction. The resulting pellets are resuspended in MIB containing Protease Arrest solution, and are labelled the "P" ("pellet") fractions. The protein concentration of each fraction is determined using the BioRad Protein Assay reagent (BioRad, Hercules, Calif.) according to manufacturer's instructions.

The DHAD activity of each fraction is ascertained using the DHAD assays as described above in the General Methods.

Example 6

Modification of the N-Terminal Mitochondrial Targeting Sequence of an Isobutanol Pathway Enzyme The purpose of this example is to illustrate that removal or modification of N-terminal mitochondrial targeting sequences allows for cytosolic activity of isobutanol pathway enzymes.

TABLE 17

Genotype of strains disclosed in Example 6.

| GEVO No. | Genotype |
| --- | --- |
| 1803 | MATa/alpha ura3/ura3 leu2/leu2 his3/his3 trp1/trp1 pdc1::Bs-alsS, TRP1/PDC1 |

TABLE 18

Plasmids disclosed in Example 6.

| Plasmid name | Relevant Genes/Usage | Genotype |
| --- | --- | --- |
| pGV1354 | Plasmid that contains the Ilv5ΔN47 gene. | P$_{TDH3}$:ILV5ΔN47: CYC1 term, bla, ColE1 ORI, URA3, 2μ ori. |
| pGV1662 | Parent vector that has Ampicillin resistance, the 2μ origin, a URA3 gene, the TEF1 promoter, CYC1 terminator region and an E. coli origin. It also has the L. lactis KivD gene that is removed by cutting the plasmid with SalI and NotI, and then gel purifying the vector portion. SalI and NotI were used for cloning genes to be expressed from the TEF1 promoter. | pTEF1::L. lactis kivD::CYC1 term, bla, ColE1 ORI, URA3, 2μ ori. |
| pGV1810 | Plasmid that contains the full length ILV5 gene. This was used as a PCR template to generate the Δ46-ilv5 mutant. | pTEF1::ILV5::CYC1 term, bla, ColE1 ORI, URA3, 2μ ori. |
| pGV1831 | Plasmid that contains the Ilv5ΔN47 gene under control of the TEF1 promoter. | pTEF1::Sc Ilv5□N47::CYC1 term, bla, ColE1 ORI, URA3, 2μ ori. |
| pGV1833 | Plasmid that contains the full length ILV5 gene under control of the TEF1 promoter. | pTEF1::Sc ILV5:CYC1 term, bla, ColE1 ORI, URA3, 2μ ori |
| pGV1901 | The S. cerevisiae KARI with the N-terminal 46 amino acid deleted (Δ46) cloned into pGV1662 at the SalI-NotI sites of the vector. The S. cerevisiae Δ46 KARI was a SalI-NotI fragment that was PCR amplified from pGV1810 using primers 1809 and 1615. | pTEF1::Δ46ilv5 KARI::CYC1 term, bla, ColE1 ORI, URA3, 2μ ori |
| pGV1824 | The E. coli coSc KARI cloned into pGV1662 at SalI-BamHI sites of the vector. | pTEF1::E. coli coSc KARI:CYC1 term, bla, ColE1 ORI, URA3, 2μ ori |

The yeast enzymes acetohydroxyacid synthase (AHAS; ILV2+ILV6), ketol-acid reductoisomerase (KARI; ILV5), and dihydroxyacid dehydratase (DHAD; ILV3) that carry out the first three steps of isobutanol production are physiologically localized to the mitochondria. Mitochondrial matrix proteins are typically targeted to the mitochondria by an N-terminal mitochondrial targeting sequence (MTS), which is then cleaved off in the mitochondria resulting in the 'mature' form of the enzyme. N-terminal deletions of ILV5 have been shown to re-localize this enzyme to the cytosol (Omura, 2008, *Appl. Microbiol. Biotechnol.* 78: 503-513; Omura, WO12009/078108 A1, hereby incorporated by reference in its entirety).

N-terminal mitochondria targeting sequences (MTS) are predicted by MitoProt II software; Claros et al., 1996, *Eur. J. Biochem.* 241: 779-786. Two N-terminal deletions of the ILV5 gene was constructed, one missing the first 46 amino acids and one missing the first 47 amino acids.

pGV1831 was constructed as follows. pGV1662 was digested with SalI and NotI and the large fragment (6.3 Kb vector backbone) was gel purified by agarose gel electrophoresis. The Ilv5ΔN47 gene was excised from plasmid pGV1354 (SEQ ID NO: 80) using SalI and NotI. The ilv5ΔN47 gene fragment (1.06 Kb) was purified away from the larger vector fragment by agarose gel electrophoresis. The pGV1662 vector and ilv5ΔN47 insert were ligated using standard methods in an approximately 5:1 insert:vector molar ratio and transformed into TOP10 chemically competent *E. coli* cells. Plasmid DNA was isolated and correct clones were confirmed using restriction enzyme analysis, namely generation of the correct insert size by digesting clones with SalI and NotI enzymes. The clones were verified by sequencing with the primers 351, 1625, and 1626. Purified plasmid DNA was transformed into *S. cerevisiae* strain GEVO1803 using a standard yeast transformation protocol.

pGV1833 was constructed as follows. pGV1662 was digested with SalI and NotI and the large fragment (6.3 Kb vector backbone) was gel purified by agarose gel electrophoresis. Primers 1615 and 1616 were used to amplify the *S. cerevisiae ILV5* gene from the plasmid template pGV1810 by PCR. The correct fragment size was verified with DNA gel electrophoresis. (1.2 Kb). The PCR product was purified after PCR using the Qiagen QIAquick PCR Purification Kit. The PCR product was then digested with XhoI and NotI to generate ends compatible with the pGV1662 backbone (the XhoI end of the PCR product is compatible with the SalI end of the vector, although the ligated DNA fragment can't be recut with either enzyme). After digestion, the PCR product was purified with a Qiagen QIAquick PCR Purification Kit. The two fragments were ligated using standard methods in an approximately 5:1 insert:vector molar ratio and transformed into TOP10 chemically competent. *E. coli* cells. Plasmid DNA was isolated and correct clones were confirmed using restriction enzyme analysis. In this case, SacI plus NotI digestion yielded a fragment of the predicted size (1.6 Kb). The clones were verified by sequencing with the primers 351, 1625, and 1626. Purified plasmid DNA was transformed into *S. cerevisiae* strain GEVO1803.

pGV1901 was constructed as follows. pGV1662 was digested with SalI and NotI and the large fragment (6.3 Kb vector backbone) was gel purified by agarose gel electrophoresis. The ILV5 gene was amplified from pGV1810 (SEQ ID NO: 82) using primers 1809 (which removes the first 46 amino acids from the N-terminus while adding a methionine codon) and 1615. The PCR product was digested with SalI and NotI. After digestion, the PCR product was purified on an agarose gel and the proper fragment (1.07 Kb) was recovered using the Zymoclean Gel DNA Recovery Kit. The pGV1662 vector and Ilv5-Δ46 PCR products were ligated using standard methods in an approximately 5:1 insert:vector molar ratio and transformed into TOP10 chemically competent *E. coli* cells. Plasmid DNA was isolated and correct clones were confirmed with PCR screening of colonies using primers 351 and 1577. The predicted correct PCR product was 580 bp. The clones were sequenced using primers 351, 1625, and 1626. Purified plasmid DNA was transformed into *S. cerevisiae* strain GEVO1803 using the standard yeast transformation protocol.

pGV1824 contains the *E. coli* ilvC gene that is codon optimized for *S. cerevisiae* cloned into the SalI and BamHI of pGV1662 as described above. The sequence of the codon optimized *E. coli* ilvC is found as SEQ ID NO: 83.

Figure 3:
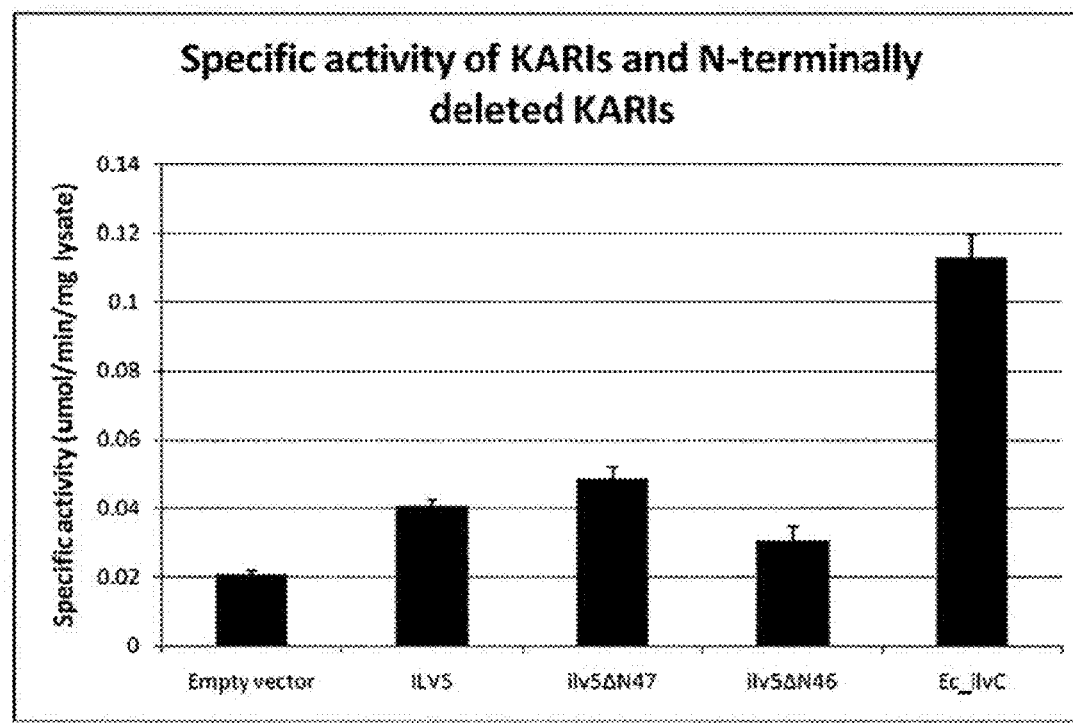
FIG. 3 illustrates the specific activity at pH 7.5 of KARI enzyme in whole cell lysates for GEVO1803 containing empty vector (pGV1102), ilv5ΔN47 (pGV1831), ilv5ΔN46 (pGV1901), Full length ILV5 (pGV1833) and *E. coli* ilvC codon optimized for *S. cerevisiae* (pGV1824).

Plasmids were transformed into the yeast strain GEVO1803 and an individual colony was purified from each transformation. KARI assays of whole cell lysates were performed at pH 7.5 as described in General Methods. Results are shown in FIG. 3.

KARI activity in mitochondrial/organellar (P) and cytosolic (S) fractions and whole cell (W) lysates is assayed as described in General Methods

Example 7

Scaffolding Two or More Isobutanol Pathway Enzymes

The purpose of this example is to illustrate how isobutanol pathway enzymes can be scaffolded in order to localize them to the cytosol.

Cellulolytic microorganisms utilize a scaffolded enzyme complex called a cellulosome. In such a complex, numerous enzymes are docked to a single scaffold protein, called a scaffoldin, which contain multiple binding domains called cohesin domains. Each cohesin domain interacts with a dockerin domain. In a cellulosome complex, each cellulytic enzyme also has a dockerin domain that allows it to bind to the scaffoldin.

The cohesin domains of a scaffoldin protein, for example, CipA from *Clostridium thermocellum*, can be expressed in yeast. The dockerin domains from the cellulolytic enzymes from the same organism, for example Xyn10B, can be fused to the isobutanol enzymes and the fusion proteins expressed in yeast.

The activity of each pathway enzyme in whole cell lysates is determined as described in General Methods. Activity in mitochondrial/organellar (P) and cytosolic (S) fractions and whole cell (W) lysates is assayed as described in General Methods.

Example 8

Adding of Tags, e.g. Ubiquitin Tags, to the N-Terminus of an Isobutanol Pathway Enzyme The purpose of this is example is to demonstrate that isobutanol pathway enzymes can be targeted to the yeast cytosol. For instance, this example illustrates how a DHAD enzyme can be targeted to the yeast cytosol.

TABLE 18

Genotype of strains disclosed in Example 8.

| GEVO No. | Genotype/Source |
|---|---|
| Gevo2242 | *S. cerevisiae*, CEN.PK; MAT-alpha ura3 leu2 his3 trp1 ilv5$^{O255E}$ pdc1::Bs-alsS, TRP1 |
| Gevo2244 | *S. cerevisiae*, CEN.PK; MATα ura3 leu2 his3 trp1 ilv3Δ |

TABLE 19

Plasmids disclosed in Example 8.

| pGV No. | Genotype |
|---|---|
| pGV1106 | pMB1 ori, bla (AmpR), 2 µm ori, URA3, TDH3 promoter-Myc tag-polylinker-CYC1 terminator |
| pGV1662 | pMB1 ori, bla (AmpR), 2 µm ori, URA3, TEF1 promoter-(kivD) |
| pGV1784 | pUC ori, kanR, Mm_ubiquitin coding sequence |
| pGV1855 | pMB1 ori, bla (AmpR), 2 µm ori, URA3, TEF1 promoter-Ll_ilvD |
| pGV1897 | pMB1 ori, bla (AmpR), 2 µm ori, URA3, TEF1 promoter-Mm_ubiquitin(Gly-X) |
| pGV1900 | pMB1 ori, bla (AmpR), 2 µm ori, URA3, TEF1 promoter-ScILV3(FL) |
| pGV2019 | pUC ori, bla (AmpR), 2 µm ori, URA3, TEF1 promoter-ScILV3ΔN |
| pGV2052 | pMB1 ori, bla (AmpR), 2 µm ori, URA3, TEF1 promoter-Mm_ubiquitin(Gly-X)-ScIlv3(FL) |
| pGV2053 | pMB1 ori, bla (AmpR), 2 µm ori, URA3, TEF1 promoter-Mm_ubiquitin(Gly-X)-ScIlv3ΔN |
| pGV2054 | pMB1 ori, bla (AmpR), 2 µm ori, URA3, TEF1 promoter-Mm_ubiquitin(Gly-X)-Ll_ilvD |
| pGV2055 | pMB1 ori, bla (AmpR), 2 µm ori, URA3, TEF1 promoter-Mm_ubiquitin(Gly-X)-Gf_ilvD |
| pGV2056 | pMB1 ori, bla (AmpR), 2 µm ori, URA3, TEF1 promoter-Mm_ubiquitin(Gly-X)-Se_ilvD |

To develop the constructs required to express DHAD as a fusion with an N-terminal ubiquitin, plasmid pGV1784 was synthesized by DNA2.0. This plasmid contained the synthesized sequence for the *Mus musculus* ubiquitin gene, codon-optimized for expression in *S. cerevisiae* (SEQ ID NO: 86). Using this plasmid as the template, the *M. musculus* ubiquitin gene was amplified via PCR using primers 1792 and 1794 to generate a PCR product containing the *M. musculus* ubiquitin gene codon sequence flanked by restriction sites XhoI and NotI at its 5' and 3' ends, respectively, and altered so as to lack the codon for its endogenous C-terminal most glycine residue (denoted as Gly-X). This PCR product was cloned into pGV1662 (described in Example 6), yielding pGV1897.

Plasmid pGV1897 was then used as a recipient cloning vector for sequences encoding *S. cerevisiae* ILV3 (ScIlv3 (FL), SEQ ID NO: 88), *S. cerevisiae* Ilv3ΔN (ScIlv3ΔN, SEQ ID NO: 89), *L. lactis* (Ll_ilvD SEQ ID NO: 87), *G. forsetti* ilvD (Gf_ilvD, SEQ ID NO: 90), and *S. erythraea* ilvD (Se_ilvD, SEQ ID NO: 91), yielding plasmids pGV2052-2056, respectively.

The DHAD activity exhibited by cells transformed with each of the resulting constructs is ascertained by in vitro assay. GEVO2244 is transformed (singly) with pGV2052-2056, pGV1106 (empty control vector), pGV1855 (expressing native, unfused Ll_ilvD) or pGV1900 (expressing native, full-length Sc_ILV3(FL)). Lysates of transformants are prepared and DHAD activity in mitochondrial/organellar (P) and cytosolic (S) fractions and whole cell (W) lysates is assayed as described in Example 3.

In an analogous manner, a desired ALS (e.g., the *B. subtilis* alsS) or KARI gene whose product is known or predicted to be mitochondrial can be re-targeted to the cytosol by means of the methods detailed in this example. The nucleotide sequence encoding for a full-length, or variant, ALS or KARI is amplified by PCR using primers that introduce restriction sites convenient for cloning the final product as an in-frame fusion of the *M. musculus* ubiquitin gene. The resulting construct is transformed into a host *S. cerevisiae* cell suitable for assaying the in vitro activity of the expressed *M. musculus* ubiquitin-gene chimeric fusion protein, using methods described in Example 3.

Example 9

Dihydroxy Acid Dehydratase Limits Isobutanol Production in Yeast

This example illustrates the specific activity of various DHAD homologs in yeast. The example also illustrates that high specific activity of the *Lactococcus lactis* IlvD enzyme (SEQ ID NO: 18) correlates with an increase in isobutanol production.

Plasmid pGV1106 was used as a control and is described in Example 3. Plasmid pGV1662 (described in Example 6) served as the parental plasmid of pGV1855, pGV1900, and pGV2019 (see Example 5). Plasmids pGV1851-1855 and pGV1904-1907 are all variants of pGV1662 (See Table 20), in which the kivD ORF sequence present in pGV1662 was excised and replaced with a sequence encoding a DHAD homolog, as indicated below.

TABLE 20

Plasmids disclosed in Example 9.

| pGV No. | Genotype |
|---|---|
| pGV1851 | pUC ori, bla (AmpR), 2 µm ori, URA3, TEF1 promoter-*Gramella forsetti* ilvD |
| pGV1852 | pUC ori, bla (AmpR), 2 µm ori, URA3, TEF1 promoter-*Chromohalobacter salexigens* ilvD |
| pGV1853 | pUC ori, bla (AmpR), 2 µm ori, URA3, TEF1 promoter-*Ralstonia eutropha* ilvD |
| pGV1854 | pUC ori, bla (AmpR), 2 µm ori, URA3, TEF1 promoter-*Saccharopolyspora erythraea* ilvD |
| pGV1855 | pUC ori, bla (AmpR), 2 µm ori, URA3, TEF1 promoter-Ll_ilvD |
| pGV1900 | pUC ori, bla (AmpR), 2 µm ori, URA3, TEF1 promoter-ScILV3(FL) |
| pGV1904 | pUC ori, bla (AmpR), 2 µm ori, URA3, TEF1 promoter-*Acidobacteria bacterium* Ellin345 ilvD |
| pGV1905 | pUC ori, bla (AmpR), 2 µm ori, URA3, TEF1 promoter-*Picrophilus torridus* DSM 9790 ilvD |
| pGV1906 | pUC ori, bla (AmpR), 2 µm ori, URA3, TEF1 promoter-*Piromyces* species E2 ilvD |
| pGV1907 | pUC ori, bla (AmpR), 2 µm ori, URA3, TEF1 promoter-*Sulfolobus tokodaii* strain 7 ilvD |

Plasmid pGV1851 contains the *G. forsetti* ilvD gene (SEQ ID NO: 90). Plasmid pGV1852 contains the *C. salexigens* gene (SEQ ID NO: 95). Plasmid pGV1853 contains the *R. eutropha* gene (SEQ ID NO: 94). Plasmid pGV1854 contains the *S. erythraea* ilvD (SEQ ID NO: 91). Plasmid pGV1855 contains the *L. lactis* ilvD (SEQ ID NO: 87). Plasmid pGV1900 contains the *S. cerevisiae* ILV3 (SEQ ID NO: 88). Plasmid pGV1904 contains the *A. bacterium* Ellin345 ilvD (SEQ ID NO: 92). Plasmid pGV1905 contains the *P. torridus* DSM 9790 ilvD (SEQ ID NO: 96). Plasmid pGV1906 contains the *Piromyces* sp. E2 ilvD (SEQ ID NO: 93). Plasmid pGV1907 contains the *S. tokodaii* ilvD (SEQ ID NO: 97). All sequences (except that of the *S. cerevisiae* ILV3 (full length)) were synthesized with 5' SalI and 3' NotI sites by DNA2.0 (Menlo Park, Calif.), digested with SalI and NotI, and ligated into pGV1662 which had also been digested with SalI and NotI. For plasmid pGV1900, the sequence containing the open reading frame of the *S. cerevisiae* ILV3 (full length) was amplified from *S. cerevisiae* genomic DNA using primers 1617 and 1618, and the resulting 1.8 kb fragment was digested with SalI plus BamHI and cloned into pGV1662. Various DHADs were tested for in vitro activity using whole cell lysates. In this case, the DHADs were expressed in a yeast deficient for DHAD activity (GEVO2244; ilv3Δ) (see Example 2) to minimize endogenous background activity.

To grow cultures for cell lysates, triplicate independent cultures of each desired strain were grown overnight in 3 mL SCD-Ura+9xIV at 30° C., 250 rpm. The following day, the overnight cultures were diluted 1:50 into 50 mL fresh. SCD-Ura in a 250 mL baffle-bottomed Erlenmeyer flask and incubated at 30° C. at 250 rpm. After approximately 10 hours, the $OD_{600}$ of all cultures were measured, and the cells of each culture were collected by centrifugation (2700×g, 5 min). The cell pellets were washed by resuspending in 1 mL of water, and the suspension was placed in a 1.5 mL tube and the cells were collected by centrifugation (16,000×g, 30 seconds). All supernatant was removed from each tube and the tubes were frozen at −80° C. until use.

Lysates were prepared by resuspending each cell pellet in 0.7 mL of lysis buffer. Lysate lysis buffer consisted of: 0.1M Tris-HCl pH 8.0, 5 mM $MgSO_4$, with 10 µL of Yeast/Fungal Protease Arrest solution (G Biosciences, catalog #788-333) per 1 mL of lysis buffer. Eight hundred microliters of cell suspension were added to 1 mL of 0.5 mm glass beads that had been placed in a chilled 1.5 mL tube. Cells were lysed by bead beating (6 rounds, 1 minute per round, 30 beats per second) with 2 minutes chilling on ice in between rounds. The tubes were then centrifuged (20,000×g, 15 min) to pellet debris and the supernatant (cell lysates) were retained in fresh tubes on ice. The protein concentration of each lysate was measured using the BioRad Bradford protein assay reagent (BioRad, Hercules, Calif.) according to manufacturer's instructions.

The DHAD activity of each lysate was ascertained as follows. In a fresh 1.5 mL centrifuge tube, 50 µL of each lysate was mixed with 50 µL of 0.1M 2,3-dihydroxyisovalerate (DHIV), 25 µL of 0.1M $MgSO_4$, and 375 µL of 0.05M Tris-HCl pH 8.0, and the mixture was incubated for 30 min at 35° C. Each tube was then heated to 95° C. for 5 min to inactivate any enzymatic activity, and the solution was centrifuged (16,000×g for 5 min) to pellet insoluble debris. To prepare samples for analysis, 100 µL of each reaction were mixed with 100 µL of a solution consisting of 4 parts 15 mM dinitrophenyl hydrazine (DNPH) in acetonitrile with 1 part 50 mM citric acid, pH 3.0, and the mixture was heated to 70° C. for 30 min in a thermocycler. The solution was then analyzed by HPLC as described above in General Methods to quantitate the concentration of ketoisovalerate (KIV) present in the sample. The results are shown in Table 21.

TABLE 21

Specific activities (KIV generation) from lysates of S. cerevisiae strain GEVO2244 carrying plasmids to overexpress the indicated DHAD homolog.

| Plasmid | Gene | Specific activity (U/mg total protein) |
|---|---|---|
| pGV1106 | Control (i.e. no DHAD) | n.d. |
| pGV1851 | Gramella forsetti ilvD | 0.012 |
| pGV1852 | Chromohalobacter salexigens (SEQ ID NO: 95) | n.d. |
| pGV1853 | Ralstonia eutropha (SEQ ID NO: 94) | n.d. |
| pGV1854 | Saccharopolyspora erythraea ilvD | 0.002 |
| pGV1855 | Lactococcus lactis ilvD | 0.027 |
| pGV1900 | Saccharomyces cerevisiae ILV3(FL) | 0.148 |
| pGV1904 | Acidobacteria bacterium Ellin345 DHAD | 0.004 |
| pGV1905 | Picrophilus torridus DSM 9790 DHAD | n.d. |
| pGV1906 | Piromyces Sp E2 DHAD | 0.016 |
| pGV1907 | Sulfolobus tokodaii str. 7 DHAD | 0.001 |

Each data point is the result of triplicate samples.
* n.d., not detectable

Example 10

Dihydroxy Acid Dehydratase Limits Isobutanol Production in Yeast

This example illustrates that high specific DHAD activity, and in particular the high specific activity of the L. lactis IlvD enzyme (SEQ ID NO: 18) correlates with an increase in isobutanol production.

TABLE 22

Genotype of strains disclosed in Example 10.

| GEVO No. | Genotype/Source |
|---|---|
| GEVO1186 | S.cerevisiae, CEN.PK; MATa/α ura3/ura3 leu2/leu2 his3/his3 trp1/trp1 |
| GEVO1188 | S.cerevisiae, CEN.PK; MATα ura3 leu2 his3 trp1 |
| GEVO1803 | MATa/α ura3/ura3 leu2/leu2 his3/his3 trp1/trp1 pdc1::Bs-alsS, TRP1/PDC1 |
| GEVO2107 | MATa/α ura3/ura3 leu2/leu2 his3/his3 trp1/trp1 pdc1::Bs-alsS, TRP1/PDC1 pdc6::{ScTEF1p-Ll_kivd ScTDH3p-Dm_ADH URA3}/PDC6 |

TABLE 23

Plasmids disclosed in Example 10.

| pGV No. | Genotype |
|---|---|
| p423GPD | $P_{TDH3}$:MCS:$T_{CYC1}$, HIS3, 2-micron, bla, pUC ori (Mumberg, D. et al. (1995) Gene 156:119-122; obtained from ATCC) |
| pGV1103 | $P_{TDH3}$:myc-tag:MCS:$T_{CYC1}$, HIS3, 2 micron, bla, pUC ori |
| pGV1730 | $P_{CUP1}$:Bs-alsS:$T_{PDC1}$ IPDC1-3' region:PDC1-5' region, TRP1, bla, pUC ori |
| pGV1914 | $P_{TEF1}$:Ll_kivD $P_{TDH3}$:Dm_ADH PDC6 5', 3' targeting homology URA3 pUC ori bla(ampR) |
| pGV1974 | $P_{TEF1}$:Sc_ILV3ΔN:$P_{TDH3}$:Ec_ilvC$^{Q110V}$-coSc:$T_{CYC1}$, HIS3, 2 micron, bla, pUC ori bla(ampR) |
| pGV1981 | $P_{TEF1}$:Lactococcus lactis ilvD-coSc:$P_{TDH3}$: Ec_ilvC$^{Q110V}$-coSc:$T_{CYC1}$, HIS3, 2 micron, bla, pUC ori |
| pGV2001 | $P_{TEF1}$:$P_{TDH3}$:Ec_ilvC$^{Q110V}$-coSc:$T_{CYC1}$, HIS3, 2 micron, bla, pUC ori |

Plasmid pGV1103 was generated by inserting a linker (primers 271 annealed to primer 272) containing a myc-tag and a new MCS (SalI-EcoRI-SmaI-BamHI-NotI) into the SpeI and XhoI sites of p423GPD. The construction of plasmid pGV1730 is described in Example 4.

pGV1914 (SEQ ID NO: 117) is a yeast integrating vector that includes the S. cerevisiae URA3 gene as a selection marker and contains homologous sequence for targeting the HpaI-digested, linearized plasmid for integration at the PDC6 locus of S. cerevisiae. pGV1914 carries the D. melanogaster adh (Dm_ADH) (SEQ ID NO: 116) and L. lactis kivd (Ll_kivD) genes, expressed under the control of the S. cerevisiae TDH3 and TEF1 promoters, respectively. The open reading frame sequence of DmADH was originally amplified by PCR from clone RH54514 (available from the Drosophila Genome Resource Center).

Plasmid pGV1974 is a yeast high copy plasmid with HIS3 as a marker for the expression of E. coli ilvC$^{110V}$ (SEQ ID NO: 98) and S. cerevisiae ILV3ΔN (SEQ ID NO: 89). pGV1974 was generated by cloning a SacI-NotI fragment (4.9 kb, SEQ ID NO: 118) carrying the S. cerevisiae TEF1 promoter: S. cerevisiae ilv3ΔN: S. cerevisiae TDH3 promoter: E. coli ilvC$^{Q110V}$ into the SacI-NotI sites of pGV1103 (5.4 kb), a yeast expression plasmid carrying the HIS3 marker.

Plasmid pGV1981 is a yeast high copy plasmid with HIS3 as a marker for the expression of E. coli ilvC$^{Q110V}$ and L. lactis ilvD. pGV1981 was generated by cloning a SalI-BamHI fragment (1.7 kb) carrying the L. lactis ilvD ORF (SEQ ID NO: 87 with a SalI and BamHI sites introduces at the 5' and 3' ends, respectively) into the SalI-BamHI of pGV1974 (8.5 kb), replacing the S. cerevisiae Ilv34N ORF.

Plasmid pGV2001 is a yeast high copy plasmid with HIS3 as a marker for the expression of E. coli ilvV$^{Q110V}$. pGV2001 was generated by digesting pGV1974 with SalI-BamHI to remove the S. cerevisiae Ilv3ΔN ORF. The digest was treated with Klenow to fill-in the 5' overhangs, the larger 8.5 kb fragment was isolated and self-ligated.

GEVO1803 was made by transforming GEVO1186 with the 6.7 kb pGV1730 (contains S. cerevisiae TRP1 marker and the CUP1 promoter-driven B. subtilis alsS) that had been linearized by digestion with NruI. Completion of the digest was confirmed by running a small sample on a gel. The digested DNA was then purified using Zymo Research DNA Clean and Concentrator and used in the transformation. Trp+ clones were confirmed for the correct integration into the PDC1 locus by colony PCR using primer pairs 1440+1441 and 1442+1443 for the 5' and 3' junctions, respectively. Expression of B. subtilis alsS was confirmed by qRT-PCR using, primer pairs 1323+1324.

GEVO2107 was made by transforming GEVO1803 with linearized, HpaI-digested pGV1914. Correct integration of pGV1914 at the PDC6 locus was confirmed by analyzing candidate Ura+ colonies by colony PCR using primers 1440 plus 1441, or 1443 plus 1633, to detect the 5' and 3' junctions of the integrated construct, respectively. Expression of all transgenes were confirmed by qRT-PCR using primer pairs 1321 plus 1322, 1587 plus 1588, and 1633 plus 1634 to examine Bs_alsS, Ll_kivD, and Dm_ADH transcript levels, respectively.

Figure 4:
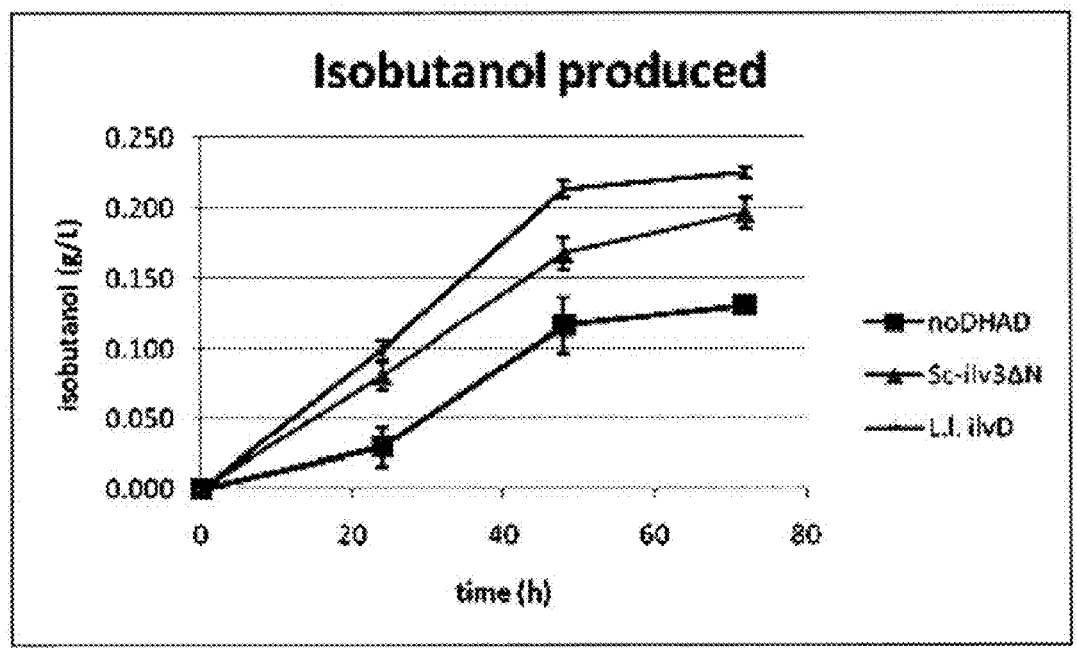
FIG. 4 illustrates the results from fermentations of GEVO2107 transformed with plasmids for expression of KARI and different DHAD homologs (shown in legend).

GEVO 2107 was transformed with plasmids that contained either a KARI alone (pGV2001 with E. coli ilvC$^{Q110V}$) or the same KARI with a DHAD (pGV1974 with the S. cerevisiae Ilv3ΔN or pGV1981 with the L. lactis ilvD). Fermentations were carried out with three independent transformants for each DHAD homolog being tested, as well as the no DHAD control plasmid. Seed cultures were grown in SCD-H medium to mid-log phase. The fermentations were initiated by collecting cells and resuspending in 25 mL of SCD-H (5% glucose) medium to an $OD_{600}$ of 1. Fermentations were performed aerobically in 125 mL unbaffled flasks shaken at 250 rpm at 30° C. At 0, 24, 48 and 72 hours, the $OD_{600}$ was checked and 2 mL samples were taken. These samples were centrifuged at 18,000×g in a microcentrifuge and 1.5 mL of the clarified media was transferred to a 1.5 mL Eppendorf tube. The clarified media was stored at 4° C. until analyzed by GC and HPLC as described in General Methods. At 24 and 48 hours, 2.5 mL of glucose from a 400 g/L stock solution was added to the cultures. FIG. 4 shows the production of isobutanol in these fermentations. All values were adjusted for the dilution caused by the volume change from adding glucose. An increased amount of isobutanol was produced from the cells expressing the *L. lactis* ilvD.

Example 11

Assaying DHAD Activity in Fractionated Cell Extracts

The purpose of this Example is to describe how DHAD activity can be measured in fractionated cellular extracts that are enriched for either mitochondrial or soluble cytosolic components.

Plasmids pGV1106, pGV1662, pGV1855, pGV1900 are described in Example 9 above. To measure the DHAD activities present in fractionated cell extracts, the strain GEVO2244 was transformed singly with either pGV1106, which served as an empty vector control, or with one of: pGV1855, pGV1900, or pGV2019, which are expression plasmids for *L. lactis* IlvD, *S. cerevisiae* ILV3 (full length), and *S. cerevisiae* ILV3ΔN, respectively.

An independent clonal transformant of each plasmid was isolated, and a 1 L culture of each strain was grown in SCGal-Ura+9xIV at 30° C. at 250 rpm. The $OD_{600}$ was noted, the cells were collected by centrifugation (1600×g, 2 min) and the culture medium was decanted. The cell pellets were resuspended in 50 mL sterile deionized water, collected by centrifugation (1600×g, 2 min), and the supernatant was discarded. The $OD_{600}$ and total wet cell pellet weight of each culture are listed in Table 24, below:

TABLE 24

$OD_{600}$ and pellet mass (g) of strain GEVO2244 transformed with the indicated plasmids.

| Plasmid | $OD_{600}$ | Pellet mass (g) |
|---|---|---|
| pGV1106 | 2.2 | 7.6 |
| pGV1855 | 2.3 | 7.7 |
| pGV1900 | 1.3 | 3.8 |
| pGV2019 | 2.6 | 8.4 |

To obtain spheroplasts, the cell pellets were resuspended in 0.1M Tris-$SO_4$, pH 9.3 to a final concentration of 0.1 g/mL, and DTT was added to a final concentration of 10 mM. Cells were incubated with gentle (60 rev/min) agitation on an orbital shaker for 20 min at 30° C., and the cells were then collect by centrifugation (1600×g, 2 min) and the supernatant discarded. Each cell pellet was resuspended in spheroplasting buffer, which consists of (final concentrations): 1.2M sorbitol (Amresco, catalog #0691), 20 mM potassium phosphate pH 7A) and then collected by centrifugation (1600×g, 10 min). Each cell pellet was resuspended in spheroplasting buffer to a final concentration of 0.1 g cells/mL in a 500 mL centrifuge bottle, and 50 mg of Zymolyase 20T (Seikagaku Biobusiness, Code#120491) was added to each cell suspension. The suspensions were incubated overnight (approximately 16 hrs) at 30° C. with gentle agitation (60 rev/min) on an orbital shaker. The efficacy of spheroplasting was ascertained by diluting an aliquot of each cell suspension 1:10 in either sterile water or in spheroplasting buffer, and comparing the aliquots microscopically (under 40× magnification). In all cases, >90% of the water-diluted cells lysed, indicating efficient spheroplasting. The spheroplasts were centrifuged (3000×g, 10 min, 20° C.), and the supernatant was discarded. Each cell pellet was resuspended in 50 mL spheroplast buffer without Zymolyase, and cells were collected by centrifugation (3000×g, 10 min, 20° C.).

To fractionate spheroplasts, the cells were resuspended to a final concentration of 0.5 g/mL in ice cold mitochondrial isolation buffer (MIB), consisting of (final concentration): 0.6M D-mannitol (BD Difco Cat#217020), 20 mM HEPES-KOH, pH 7.4. For each 1 mL of resulting cell suspension, 0.01 mL of Yeast/Fungal Protease Arrest solution (G Biosciences, catalog #788-333) was added. The cell suspension was subjected to 35 strokes of a Dounce homogenizer with the B (tight) pestle, and the resulting cell suspension was centrifuged (2500×g, 10 min, 4° C.) to collect cell debris and unbroken cells and spheroplasts. Following centrifugation, 2 mL of each sample (1 mL of the pGV1900 transformed cells) were saved in a 2 mL centrifuge tube on ice and designated the "W" (for Whole cell extract) fraction, while the remaining supernatant was transferred to a clean, ice-cold 35 mL Oakridge screw-cap tube and centrifuged (12,000×g, 20 min, 4° C.) to pellet mitochondria and other organellar structures. Following centrifugation, 5 mL of each resulting supernatant was transferred to a clean tube on ice, being careful to avoid the small, loose pellet, and labelled the "S" (soluble cytosol) fraction. The resulting pellets were resuspended in MIB containing Protease Arrest solution, and were labelled the "P" ("pellet") fractions. Protein from the "P" fraction was released after dilution 1:5 in DHAD assay buffer (see above) by rapid mixing in a 1.5 mL tube with a Retsch Ball Mill MM301 in the presence of 0.1 mM glass beads. The bead-beating was performed 4 times for 1 minute, 30 beats per second, after which insoluble debris was removed by centrifugation (20,000×g, 10 min, 4° C.) and the soluble portion retained for use.

The BioRad Protein Assay reagant (BioRad, Hercules, Calif.) was used according to manufacturer's instructions to determine the protein concentration of each fraction; the data are summarized in Table 25, below:

TABLE 25

Protein concentrations of mitochondrial/organellar (P) and cytosolic (S) fractions and whole cell (W) lysates, prepared as described in the text.

| plasmid/fraction | protein [µg/µL] |
|---|---|
| 1106 P | 20.3 |
| 1855 P | 17.7 |
| 1900 P | 9.2 |
| 2019 P | 19.7 |
| 1106 S | 12.3 |
| 1855 S | 12.9 |
| 1900 S | 7.9 |
| 2019 S | 12.4 |
| 1106 W | 14.0 |
| 1855 W | 15.0 |

TABLE 25-continued

Protein concentrations of mitochondrial/organellar (P) and cytosolic (S) fractions and whole cell (W) lysates, prepared as described in the text.

| plasmid/fraction | protein [µg/µL] |
|---|---|
| 1900 W | 7.9 |
| 2019 W | 14.7 |

The DHAD activity of each fraction was ascertained as follows. In a fresh 1.5 mL centrifuge tube, 50 µL of each fraction was mixed with 50 µL of 0.1M 2,3-dihydroxyisovalerate (DHIV), 25 µL of 0.1M MgSO$_4$, and 375 µL of 0.05M Tris-HCl pH 8.0, and the mixture was incubated for 30 min at 35° C. Each reaction was carried out in triplicate. Each tube was then heated to 95° C. for 5 min to inactivate any enzymatic activity, and the solution was centrifuged (16,000×g for 5 min) to pellet insoluble debris. To prepare samples for analysis, 100 µL of each reaction were mixed with 100 µL of a solution consisting of 4 parts 15 mM dinitrophenyl hydrazine (DNPH) in acetonitrile with 1 part 50 mM citric acid, pH 3.0, and the mixture was heated to 70° C. for 30 min in a thermocycler. Analysis of ketoisovalerate via HPLC was carried out as described in General Methods. Data from the experiment are summarized below in Table 26.

TABLE 26

Specific activities (KIV generation) and ratios of specific activities from fractionated lysates of *S. cerevisiae* strain GEVO2244 carrying plasmids to overexpress the indicated DHAD homolog.

| Lysate (pGV# and fraction*) | DHAD | Sp. Activity [U/mg protein in fraction] | Std. Dev. | Ratio of Sp. Activities (Cyto or Mito to Whole-Cell) |
|---|---|---|---|---|
| 1106 WCL | — | n.d. | | |
| 1106 cyto | — | n.d. | | |
| 1106 mito | — | n.d. | | |
| 1855 WCL | Ll_ilvD | 0.0006 | 4.7E−05 | |
| 1855 cyto | Ll_ilvD | 0.0011 | 0.0001 | 1.76 |
| 1855 mito | Ll_ilvD | 2E−05 | 3.5E−05 | 0.03 |
| 1900 WCL | ScILV3(FL) | 0.0096 | 0.0018 | |
| 1900 cyto | ScILV3(FL) | 0.0052 | 0.0004 | 0.54 |
| 1900 mito | ScILV3(FL) | 0.0340 | 0.0029 | 3.53 |

Each data point is the result of triplicate samples.
*WCL, whole cell lysate; cyto, cytosolic-enriched fraction; mito, mitochondrial (organellar)-enriched fraction Cells overexpressing the *L. lactis* ilvD generated a significantly greater proportion of DHAD activity in the cytosolic fraction versus the mitochondrial fraction, whereas cells overexpressing the full-length, native (mitochondrial) *S. cerevisiae* ILV3 resulted in a greater proportion of the specific activity residing in the mitochondrial fraction.

Example 12

Alternative, Native Dehydratases with DHAD Activity

This example describes how the overexpression of native dehydratases in *S. cerevisiae* for the conversion of 2,3-dihydroxyisovalerate to ketoisovalerate is measured.

TABLE 27

Plasmids disclosed in Example 12.

| pGV No. | Genotype |
|---|---|
| p426TEF | P$_{TEF1}$:MCS:T$_{CYC1}$, URA3, 2-micron, bla, pUC-ori (Mumberg, D. et al. (1995) Gene 156:119-122; obtained from ATCC) |
| 1102 | P$_{TEF1}$:HA-tag:MCS:T$_{CYC1}$, URA3, 2-micron, bla, pUC-ori |
| 1106 | P$_{TDH3}$:myc-tag:MCS:T$_{CYC1}$, URA3, 2-micron, bla, pUC-ori |
| 1662 | P$_{TEF1}$:Ll_kivd:T$_{CYC1}$, URA3, 2-micron, bla, pUC-ori |
| 1894 | P$_{TEF1}$:Ec_ilvC$^{Q110V}$-coSc:T$_{CYC1}$, URA3, 2-micron, bla, pUC-ori |
| 2000 | P$_{TEF1}$:Sc_ILV3ΔN:P$_{TDH3}$:Ec_ilvC$^{Q110V}$-coSc:T$_{CYC1}$, URA3, 2-micron, bla, pUC-ori |
| 2111 | P$_{TEF1}$:Ll_ilvD:P$_{TDH3}$:Ec_ilvC$^{Q110V}$-coSc:T$_{CYC1}$, URA3, 2-micron, bla, pUC-ori |
| 2112 | P$_{TEF1}$:Sc_LEU1:P$_{TDH3}$:Ec_ilvC$^{Q110V}$-coSc:T$_{CYC1}$, URA3, 2-micron, bla, pUC-ori |
| 2113 | P$_{TEF1}$:Sc_HIS3:P$_{TDH3}$:Ec_ilvC$^{Q110V}$-coSc:T$_{CYC1}$, URA3, 2-micron, bla, pUC-ori |

Plasmid pGV1102 was generated by inserting a linker (primers 269 annealed to primer 270) containing a HA-tag and a new MCS (SalI-EcoRI-SmaI-BamHI-NotI) into the SpeI and XhoI sites of p426TEF. Plasmids pGV1106 and pGV1662 are described in Examples 3 and 5, respectively. Plasmid pGV1894 is a yeast high copy plasmid with URA3 as a marker for the expression of *E. coli* ilvC$^{Q110V}$ and was generated by cloning a XhoI-NotI fragment (1.5 kb) carrying the *E. coli* ilvC$^{Q110V}$ ORF (SEQ ID NO: 98) into the SalI-NotI of pGV1:662 (6.3 kb), replacing the *L. lactis* kivD ORF. Plasmids pGV2000, pGV2111, pGV2112, and pGV2113 are yeast high copy plasmids with URA3 as a marker for the expression of *E. coli* ilvC$^{Q110V}$ and a DHAD. pGV2000 is generated by cloning a SacI-NotI fragment (4.9 kb) from pGV1974 (described in Example 10) carrying the *S. cerevisiae* TEF1 promoter: *S. cerevisiae* Ilv3ΔN: *S. cerevisiae* TDH3 promoter: *E. coli* ilvC$^{Q110V}$ into the SacI-NotI sites of pGV1106 (6.6 kb), a yeast expression plasmid carrying the URA3 marker. pGV2111 is generated by cloning a SalI-BamHI fragment (1.7 kb) carrying the *L. lactis* ilvD ORF (SEQ. ID NO: 97) with SalI and BamHI sites introduced at the 5' and 3' ends, respectively) into the SalI-BamHI of pGV2000 (8.4 kb), replacing the *S. cerevisiae* Ilv3ΔN ORF. pGV2112 is generated by cloning the *S. cerevisiae* LEU1 gene as a SalI-BamHI fragment (2.3 kb), generated by PCR using primers 2163 and 1842 using genomic DNA as template, into the SalI-BamHI of pGV2000 (8.4 kb), replacing the *S. cerevisiae* Ilv3ΔN ORF. pGV2113 is generated by cloning the *S. cerevisiae* HIS3 gene as a SalI-BamHI fragment (0.7 kb), generated by PCR using primers 2183 and 2184 using genomic DNA as template, into the SalI-BamHI of pGV2000 (8.4 kb), replacing the *S. cerevisiae* Ilv3ΔN ORF.

DHADs are tested for in vitro activity using whole cell lysates. The DHADs as well as LEU1 and HIS3 are expressed from pGV2000, pGV2112, and pGV2113 GEVO2244 to minimize endogenous DHAD background activity. A plasmid that does not express DHAD, pGV1894, and a plasmid that expresses the *L. lactis* ilvD, pGV2111, are used as negative and positive controls, respectively To grow cultures for cell lysates, triplicate independent cultures of each desired strain are grown overnight in 3 mL YNBD+HLW+10xIV at 30° C., 250 rpm. The following day, the overnight cultures are diluted 1:50 into 50 mL fresh YNBD+HLW+10xIV in a 250 mL baffle-bottomed Erlenmeyer flask and incubated at 30° C. at 250 rpm. After approximately 10 hours, the $OD_{600}$ of all cultures are measured, and the cells of each culture are collected by centrifugation (2700×g, 5 min). The cell pellets are washed by resuspending in 1 mL of water, and the suspension is placed in a 1.5 mL tube and the cells are collected by centrifugation (16,000×g, 30 seconds). All supernatant is removed from each tube and the tubes are frozen at −80° C. until use.

Lysates are prepared by resuspending each cell pellet in 0.7 ml of lysis buffer. Lysate lysis buffer consisted of: 0.1M Tris-HCl pH 8.0, 5 mM $MgSO_4$, with 10 μL of Yeast/Fungal Protease Arrest solution (G Biosciences, catalog #788-333) per 1 mL of lysis buffer. Eight hundred microliters of cell suspension are added to 1 mL of 0.5 mm glass beads that had been placed in a chilled 1.5 mL tube. Cells are lysed by bead beating (6 rounds, 1 minute per round, 30 beats per second) with 2 minutes chilling on ice in between rounds. The tubes are then centrifuged (20,000×g, 15 min) to pellet debris and the supernatant (cell lysates) are retained in fresh tubes on ice. The protein concentration of each lysate is measured using the BioRad Bradford protein assay reagent (BioRad, Hercules, Calif.) according to manufacturer's instructions.

The DHAD activity of each lysate is ascertained as follows. In a fresh 1.5 mL centrifuge tube, 50 μL of each lysate is mixed with 50 μL of 0.1M 2,3-dihydroxyisovalerate (DHIV), 25 μL of 0.1M $MgSO_4$, and 375 μL of 0.05M Tris-HCl pH 8.0, and the mixture is incubated for 30 min at 35° C. Each tube is then heated to 95° C. for 5 min to inactivate any enzymatic activity, and the solution is centrifuged (16,000×g for 5 min) to pellet insoluble debris. To prepare samples for analysis, 100 μL of each reaction are mixed with 100 μL of a solution consisting of 4 parts 15 mM dinitrophenyl hydrazine (DNPH) in acetonitrile with 1 part 50 mM citric acid, pH 3.0, and the mixture is heated to 70° C. for 30 min in a thermocycler. The solution is then analyzed by HPLC as described above in General Methods to quantitate the concentration of ketoisovalerate (KIV) present in the sample.

DHADs are tested for in vitro activity using whole cell lysates. The DHADs are expressed in a yeast deficient for DHAD activity (GEVO2244; ilv3Δ) to minimize endogenous background activity.

Example 13

Cloning of Low-Abundance, Endogenous Cytosolic Iron-Sulfur Cluster Assembly Machinery for Overexpression in S. Cerevisiae The purpose of this example is to describe how three known components of the S. cerevisiae cytosolic iron-sulfur assembly machinery were cloned to permit their overexpression in S. cerevisiae, to increase cytosolic DHAD activity.

In the yeast S. cerevisiae, at four least genes—CIA1, CFD1, NAR1, and NBP35—encode activities that contribute to the proper assembly and/or transfer of iron-sulfur [Fe—S] clusters of cytosolic proteins. Of these four genes, three—CFD1, NAR1, and NBP35—have been shown to be expressed at very low levels during aerobic growth on glucose (Ghaemmaghami et al., 2003, *Nature*, 425: 737-741). These three genes thus represent attractive candidates for overexpression to increase the cellular capacity for proper cytosolic [Fe—S] cluster protein assembly.

TABLE 27

Plasmids disclosed in Example 13.

| pGV No. | Genotype |
|---|---|
| pGV2074 | pUC ori, bla (AmpR), 2 μm ori, TPI1 promoter-hph (HygroR), PGK1 promoter, TEF1 promoter, TDH3 promoter |
| pGV2127 | pUC ori, bla (AmpR), 2 μm ori, TPI1 promoter-hph (HygroR), PGK1 promoter, TEF1 promoter, TDH3 promoter-CFD1 |
| pGV2138 | pUC ori, bla (AmpR), 2 μm ori, TPI1 promoter-hph (HygroR), PGK1 promoter, TEF1 promoter-NAR1, TDH3 promoter-CFD1 |
| pGV2144 | pUC ori, bla (AmpR), 2 μm ori, TPI1 promoter-hph (HygroR), PGK1 promoter-NBP35, TEF1 promoter, TDH3 promoter |
| pGV2147 | pUC ori, bla (AmpR), 2 μm ori, TPI1 promoter-hph (HygroR), PGK1 promoter-NBP35, TEF1 promoter-NAR1, TDH3 promoter-CFD1 |

To clone the sequences for CFD1, NAR1, and NBP35 into an appropriate S. cerevisiae expression vector, the following steps were carried out: Vector pGV2074 (SEQ ID NO: 133) was used as a parental plasmid for subsequent cloning steps described below. The salient features of pGV2074 include a bacterial origin of replication (pUC) and selectable marker (bla), an S. cerevisiae 2 μm origin of replication and selectable marker (the hph gene, conferring resistance to hygromycin, operably linked to the TPI1 promoter region), and sequences containing the S. cerevisiae promoters for the PGK1, TDH3 and TEF1 genes, each followed by one or more unique restriction sites to facilitate the introduction of coding sequences.

First, the CFD1 coding sequence was amplified from S. cerevisiae genomic DNA by PCR, using primers 2195 and 2196, which also added 5' XhoI and 3' NotI sites, respectively. The resulting ~890 bp product was digested with XhoI plus NotI and ligated into pGV2074 that had been digested with XhoI plus NotI, yielding the plasmid pGV2127. All sequences amplified by PCR were confirmed by DNA sequencing. Next, the NAR1 coding sequence was amplified from S. cerevisiae genomic DNA by PCR, using primers 2197 and 2198, which added 5' SalI and 3' BamHI sites, respectively. The resulting ~1485 bp product was digested with SalI plus BamHI and cloned into pGV2127 which had also been digested with SalI plus BamHI, thereby yielding pGV2138. Next, the NBP35 coding sequence was amplified S. cerevisiae genomic DNA by PCR, using primers 2259 and 2260, which added 5' BglII and 3' KpnI and XhoI (from 5' to 3') sites, respectively. The resulting ~995 bp product was digested with BglII plus XhoI and ligated into pGV2074 that had been digested with BglII plus SalI, yielding pGV2144. Finally, pGV2144 was digested with AvrII plus BamHI, and the resulting 1.78 kb fragment (which contained the PGK1 promoter and the NBP35 ORF sequence) was gel purified and ligated into the vector pGV2138 that had been digested with AvrII plus BglII, yielding pGV2147.

Example 14

Cloning of Heterologous Cytosolic Iron-Sulfur Cluster Assembly Machinery for Overexpression in S. Cerevisiae The purpose of this example is to describe how one or more cytosolic iron-sulfur assembly machinery components, from various species, can be cloned to permit their overexpression in S. cerevisiae, thereby increasing cytosolic DHAD activity.

In addition to the endogenous cytosolic iron-sulfur assembly machinery found in S. cerevisiae, homologous sequences and activities have been identified in other microbial and eukaryotic species. In one example, the ApbC protein of *Salmonella enterica* serovar Typhimurium has been shown, in vitro, to bind and effectively transfer iron-sulfur clusters to a known cytosolic [Fe—S] cluster-containing *S. cerevisiae* substrate, Leu1 (Boyd et al., 2008, *Biochemistry*, 47: 8195-202). Thus, a number of other useful homologs of the known *S. cerevisiae* cytosolic iron-sulfur assembly machinery components exist and present attractive candidates for overexpression in *S. cerevisiae*. Table 28 lists several exemplary homologs and their GenBank accession numbers, as identified by previous homology searches (Boyd et al., 2009, *J. Biol Chem* 284: 110-118). Also included in the table are two closely related *S. cerevisiae* homologs, Nbp35 and Cfd1. Of note, Ind1 is reported to be localized to and functional in the mitochondria (Bych et al., 2008, *EMBO J.* 27: 1736-46), whereas Hcf101 is reported to participate in iron-sulfur cluster assembly in *Arabidopsis* chloroplasts (Lezhneva et al., 2004, *Plant J. Cell Mol Biol* 37: 174-185).

TABLE 28

Functionally homologous proteins involved in iron-sulfur cluster formation.

| Gene | Source, Accession Number |
|---|---|
| ApbC | *Salmonella enterica* serovar Typhimurium LT2, NP_461098 |
| Ind1 | *Yarrowia lypolytica*, YALI0B18590g |
| Hcf101 | *Arabidopsis thaliana*, AAR97892.1 |
| Nubp1 | *Homo sapiens*, NP_002475.2 |
| Nbp35 | *S. cerevisiae*, CAA96797.1 |
| Cfd1 | *S. cerevisiae*, AAS56623 |

The cloning of one or more of these genes is carried out using techniques well known to one skilled in the art. Oligonucleotide primers are designed that are homologous to the 5' and 3' ends of each desired reading, and which furthermore incorporate a restriction site sequence convenient for the cloning of each reading frame into vector pGV2074. A standard PCR reaction is used to amplify each gene, either from the genome of each host organism, or from an in vitro synthesized DNA fragment, and the resulting PCR product is cloned into an expression vector (pGV2074). In the case of a protein known to be targeted to the mitochondria, such as *Yarrowia lypolytica* Ind1, PCR primers are designed to amplify the majority of the coding sequence while excluding the known N-terminal mitochondrial targeting sequence (Bych et al., 2008, *EMBO J.* 27: 1736-46).

Example 15

Overexpression of *S. Cerevisiae* Cytosolic Iron-Sulfur Assembly Machinery to Increase Cytosolic DHAD Activity The purpose of this example is to describe how a plasmid expressing one or more iron-sulfur assembly machinery components is co-expressed with a DHAD, thereby increasing the cytosolic activity of the DHAD.

Strain GEVO2244 is simultaneously co-transformed with one of: pGV1851, pGV1852, pGV1853, pGV1854, pGV1855, pGV1904, pGV1905, pGV1906, or pGV1907 (pGV1851-55 and pGV1904-07 are described in Table 20); plus, one of either: pGV2074 (Table 27) (which serves as an empty-vector control) or pGV2147 (Table 27) (which serves as the cytosolic Fe—S cluster machinery overexpression plasmid), and doubly-transformed cells are selected by plating onto SCD-Ura+9xIV containing 0.1 g/L Hygromycin B.

Three independent isolates from each transformation are cultured in SCD-Ura+9xIV containing 0.1 g/L Hygromycin B to obtain a cell mass suitable for preparation of a lysate, as described in Example 3. Lysates are prepared from each culture, and the resulting lysates are assayed for DHAD activity as described in Example 3. To further confirm that the increased DHAD activity is due specifically to increased cytosolic activity, cultures of GEVO2244 containing pGV1855 plus either pGV2074 or pGV2147 are grown in SCD-Ura+9xIV containing 0.1 g/L Hygromycin B as otherwise described in Example 11. Fractionated lysates are prepared and in vitro assays to measure DHAD activity are further carried out as described in Example 11.

Example 16

Deletion of LEU1

The purpose of this example is to describe the deletion of LEU1 to increase the iron-sulfur cluster availability in the yeast cytosol.

TABLE 29

Plasmids disclosed in Example 16.

| pGV No. | Genotype |
|---|---|
| pGV1299 | *K. lactis* URA3, bla, pUC-ori (GEVO) |
| PGV1981 | $P_{TEF1}$:*Lactococcus lactis* ilvD-coSc:$P_{TDH3}$: Ec_ilvC$^{Q110V}$-coSc:$T_{CYC1}$, HIS3, 2-micron, bla, pUC-ori |
| pGV2001 | $P_{TEF1}$:$P_{TDH3}$:Ec_ilvC$^{Q110V}$-coSc:$T_{CYC1}$, HIS3, 2-micron, bla, pUC-ori |

The LEU1 gene was deleted by transforming cells with a leu1::*K. lactis* URA3 deletion cassette that was generated by two rounds of PCR. Initially, the *K. lactis* URA3 gene was amplified with primers 2171 and 2172 from pGV1299 (described in Example 2). These primers add 40 bp of the LEU1 promoter and terminator sequences to the 5' and 3' ends of the *K. lactis* URA3 gene. This PCR product was then used as a template for a PCR using primers 2170 and 2173. Primer 2170 adds an additional 36 bp of the LEU1 promoter sequence at the 5' end and primer 2173 adds an additional 38 bp of the LEU1 terminator sequence at the 3' end. This PCR product was transformed into GEVO2244 (described in Example 2) to generate GEVO2570. The 5' junction of the integrations were confirmed by colony PCR using primers 2226 and 587. The 3' junction of the integrations were confirmed by colony PCR using primers 588 and 2175. The loss of the LEU1 gene was confirmed by a lack of PCR product using primers 2167 and 2227.

GEVO2570 has a deletion in ILV3. GEVO2570 is used to measure DHAD activity in the presence of *L. lactis* ilvD overexpressed as described in Examples 2 and 4. A plasmid (pGV2001) with no DHAD is used as a negative control.

Example 17

Conserved Motif Amongst Cytosolically Active DHAD Enzymes

This example illustrates that a DHAD enzymes with a specific amino acid sequence motif are more likely to be functional when expressed in the yeast cytosol.

Based on the data from biochemical assays (see Example 10), several DHAD homologs were identified that exhibit at least some cytosolic activity. A total of ten different homologs were tested using biochemical assays. The DHADs were expressed from 2 micron yeast vectors and transformed into GEVO2244. The homologs were then ranked based on their measured specific activity in both whole cell lysates and in cytosolic fractions.

Based on these data, four DHAD homologs: *L. lactis* (SEQ ID NO: 18), *G. forsetii* (SEQ ID NO: 17), *Acidobacteria* (SEQ ID NO: 16), and *S. erythraea* (SEQ ID NO: 19) exhibit cytosolic DHAD activity. Four DHAD homologs exhibit no cytosolic DHAD activity: *R. eutropha* (SEQ ID NO: 22), *C. salexigens* (SEQ ID NO: 23), *P. torridus* (SEQ ID NO: 24), and *S. tokodaii* (SEQ. ID NO: 25). One motif-containing homolog was inconclusive: *Piromyces* sp. E2 (SEQ ID NO: 21), which did not complement the GEVO2242 valine auxotrophy and had detectable biochemical DHAD activity. Since, this homolog has a putative organellar targeting sequence, the protein is likely to be mitochondrially located explaining its inability to complement the GEVO2242 auxotrophy, despite containing the motif.

Figure 5:
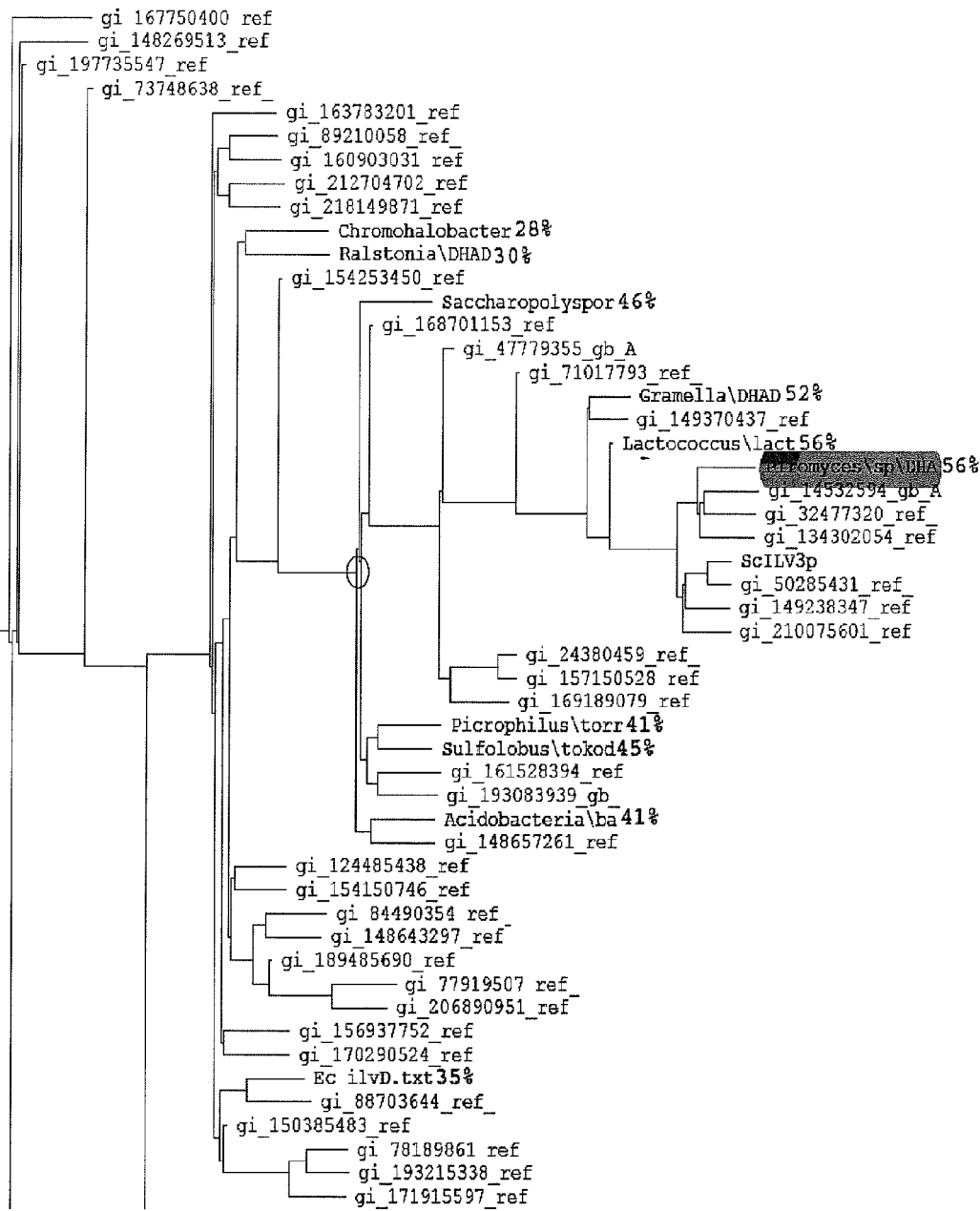
FIG. 5 illustrates a phylogenetic tree of 53 representative DHAD homologs following pairwise global alignments and progressive assembly of alignments using Neighbor-Joining phylogeny.

A multiple sequence alignment (MSA) was created using the Align Multiple Sequences tool of Clone Manager 9 Professional Addition Software using the "Multi-Way" function. This function performs exhaustive pairwise global alignments of all sequences and progressive assembly of alignments using Neighbor-Joining phylogeny. A total of 53 representative DHAD homologs (FIG. 5) were aligned using the following using the BLOSUM62 scoring matrix setting. This alignment generated the tree in FIG. 5.

Many of the DHAD homologs exhibiting cytosolic activity are related by overall homology (>40%) homology when compared to the *S. cerevisiae* DHAD encoded by *S. cerevisiae* ILV3 (e.g. *L. lactis, G. forsetii, Acidobacteria,* and *S. erythraea*). However, the 40% homology cut-off still includes several DHAD homologs that do not exhibit cytosolic DHAD activity (e.g. *R. eutropha, C. salexigens, P. torridus,* and *S. tokodaii*). The *Piromyces* sp. E2 DHAD failed to complement in the genetic/biochemistry assay but this result is still consistent with our motif hypothesis since the protein still retained its mitochondrial localization signal. Therefore, a common sequence motif, unique to DHAD homologs that are cytosolically active, was identified: P(I/L)XXXGX(I/L)XIL (SEQ ID NO: 27), where (I/L) indicates an isoleucine or leucine at that position, and X indicates any natural or non-natural amino acid. This motif can be found in all DHAD homologs exhibiting cytosolically activity. Furthermore, an even more specific version of this motif was identified that is conserved in all of DHAD homologs exhibiting cytosolic activity except for the *S. erythraea* DHAD: PIKXXGX(I/L)XIL (SEQ ID NO: 28). This motif is conserved amongst the majority if not all eukaryotic homologs of DHAD.

Six additional DHAD homologs were identified: SEQ ID NOs: 10-15 as specified in Table 1. These DHAD homologs (SEQ ID NOs: 10-15) contain the motifs PYHKEGGLGIL (SEQ ID NO: 145), PYSEKGGLAIL (SEQ ID NO: 146), PYKPEGGIAIL (SEQ ID NO: 147), PLKPSGHLQIL (SEQ ID NO: 148), PIKKTGHLQIL (SEQ. ID NO: 149), and PIKETGHIQIL (SEQ ID NO: 150), respectively.

Example 18

Use of Cytosolically Localized DHADs for the Production of Isobutanol

The following example illustrates the use of DHADs that have cytosolic activity in yeast and when expressed in the context of an isobutanol biosynthetic pathway lead to isobutanol production.

A yeast strain that contains one integrated copy of the *B. subtilis* alsS gene codon-optimized for expression in *S. cerevisiae* (SEQ ID NO: 144), two integrated copies of the *L. lactis* kivD gene (SEQ ID NOs: 99 and 151), one integrated copy of *L. lactis* adhA$^{RE1}$ gene (SEQ ID NO: 152), and one integrated copy of the *S. cerevisiae* AFT1 gene (SEQ ID NO: 153) was transformed with high copy three-component isobutanol pathway plasmids containing a KARI (Ec_ilvC_coSc$^{P2D1-A1-his6}$, SEQ ID NO: 154), an ADH (*L. lactis* adhA$^{RE1}$, SEQ ID NO: 152) and a DHAD which was expressed from the *S. cerevisiae* PDC1-286 promoter. The DHAD varied according to Table 31. Isobutanol titer and DHAD activity of each strain was compared to that of a control strain that did not express a DHAD in the plasmid. Strains, plasmids, and DHADs are listed in Tables 30, 31, and 32, respectively.

TABLE 30

Genotype of strains disclosed in Example 18.

| GEVO No. | Genotype |
|---|---|
| GEVO3868 | *S. cerevisiae*, CEN.PK2, MATa ura3 leu2 his3 trp1 gpd1::T$_{Kl\_URA3}$ gpd2::T$_{Kl\_URA3}$ tma29::T$_{Kl\_URA3}$ pdc1::P$_{PDC1}$-Ll_kivD2_coSc5-P$_{FBA1}$-LEU2-T$_{LEU2}$-P$_{ADH1}$-Bs_alsS1_coSc-T$_{CYC1}$-P$_{PGK1}$-Ll_kivD2_coEc-P$_{ENO2}$-Sp_HIS5 pdc5::T$_{Kl\_URA3}$ pdc6::P$_{TDH3}$-Sc_AFT1-P$_{ENO2}$-Ll_adhA$^{RE1}$-T$_{Kl\_URA3\_short}$-P$_{FBA1}$-Kl_URA3-T$_{Kl\_URA3}$ {evolved for C2 supplement-independence, glucose tolerance and faster growth} |

TABLE 31

Plasmids disclosed in Example 18.

| Plasmid Name | DHAD | Genotype |
|---|---|---|
| pGV2663 | none | P$_{TDH3}$-Ec_ilvC_coSc$^{P2D1-A1-his6}$, P$_{ENO2}$-Ll_adhA$^{RE1}$, 2μ-ori, pUC ori, bla, G418r |
| pGV2635 | *L. lactis* | P$_{PDC1-286}$-Ll_ilvD_coSc, P$_{TDH3}$-Ec_ilvC_coSc$^{P2D1-A1-his6}$, P$_{ENO2}$-Ll_adhA$^{RE1}$, 2μ-ori, pUC ori, bla, G418r |
| pGV2671 | *S. cerevisiae* | P$_{PDC1-286}$-Sc_ilv3_ΔN20, P$_{TDH3}$-Ec_ilvC_coSc$^{P2D1-A1-his6}$, P$_{ENO2}$-Ll_adhA$^{RE1}$, 2μ-ori, pUC ori, bla, G418r |
| pGV2672 | *G. forsetii* | P$_{PDC1-286}$-Gf_ilvD_coSc, P$_{TDH3}$-Ec_ilvC_coSc$^{P2D1-A1-his6}$, P$_{ENO2}$-Ll_adhA$^{RE1}$, 2μ-ori, pUC ori, bla, G418r |
| pGV2673 | *S. erythraea* | P$_{PDC1-286}$-Se_ilvD_coSc, P$_{TDH3}$-Ec_ilvC_coSc$^{P2D1-A1-his6}$, P$_{ENO2}$-Ll_adhA$^{RE1}$, 2μ-ori, pUC ori, bla, G418r |

TABLE 31-continued

Plasmids disclosed in Example 18.

| Plasmid Name | DHAD | Genotype |
|---|---|---|
| pGV2674 | F. tularensis | $P_{PDC1-286}$-Ft_ilvD_coSc, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2675 | S. cerevisiae ilv3ΔN19 | $P_{PDC1-286}$-Sc_ilv3_ΔN19, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2676 | S. cerevisiae ilv3ΔN23 | $P_{PDC1-286}$-Sc_ilv3_ΔN23, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2677 | N. crassa ilvD2 | $P_{PDC1-286}$-Nc_ilvD2_coSc, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2678 | Acidobacteria bacterium | $P_{PDC1-286}$-Ab_ilvD_coSc, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2679 | Acaryochloris marina | $P_{PDC1-286}$-Am_ilvD_coSc, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2680 | Lyngbya spp. | $P_{PDC1-286}$-Lsp_ilvD_coSc, $P_{TDH3}$-Ec_ilvC_coSc$^{P2D1-A1-his6}$, $P_{ENO2}$-Ll_adhA$^{RE1}$ 2μ-ori, pUC ori, bla, G418r |
| pGV2681 | E. coli | $P_{PDC1-286}$-Ec_ilvD_coKl, $P_{TDH3}$-Ec_ilvC_coSc$^{P2D1-A1-his6}$, $P_{ENO2}$-Ll_adhA$^{RE1}$ 2μ-ori, pUC ori, bla, G418r |

TABLE 32

DHAD sequences disclosed in Example 18.

| DHAD | Abbreviation | SEQ ID NO (DNA) | SEQ ID NO (protein) |
|---|---|---|---|
| L. lactis | Ll_ilvD_coSc | 155 | 18 |
| S. cerevisiae ilv3ΔN20 | Sc_ilv3_ΔN20 | 89 | 26 |
| G. forsetii | Gf_ilvD_coSc | 90 | 17 |
| S. erythraea | Se_ilvD_coSc | 91 | 19 |
| F. tularensis | Ft_ilvD_coSc | 156 | 14 |
| S. cerevisiae ilv3ΔN19 | Sc_ilv3_ΔN19 | 157 | 163 |
| S. cerevisiae ilv3ΔN23 | Sc_ilv3_ΔN23 | 158 | 164 |
| N. crassa ilvD2 | Nc_ilvD2_coSc | 159 | 165 |
| A. bacterium | Ab_ilvD_coSc | 92 | 16 |
| A. marina | Am_ilvD_coSc | 160 | 166 |
| Lyngbya spp. | Lsp_ilvD_coSc | 161 | 167 |
| E. coli | Ec_ilvD_coKl | 162 | 168 |

Cloning techniques included digestion with restriction enzymes, gel purification of DNA fragments (using the Zymoclean Gel DNA Recovery Kit, Cat# D4002, Zymo Research Corp, Orange, Calif.), ligation of two DNA fragments using the DNA Ligation Kit (Mighty Mix Cat# TAK 6023, Clontech Laboratories, Madison, Wis.), and bacterial transformations into competent E. coli cells (Xtreme Efficiency DH5α Competent Cells, Cat# ABP-CE-CC02096P, Allele Biotechnology, San Diego, Calif.). Plasmid DNA was purified from E. coli cells using the Qiagen QIAprep Spin Miniprep Kit (Cat#27106, Qiagen, Valencia, Calif.).

Yeast media used for this example include YP medium (1% (w/v) yeast extract, 2% (w/v) peptone), YPD medium (YP medium containing 2% (w/v) glucose), YPD supplemented with glycerol and ethanol (YPD medium containing 1% (v/v) 80% glycerol and 1% (v/v) ethanol. The antibiotic G418 was added to agar plates to a final concentration of 0.2 g/L. Precultures were grown in YP medium supplemented with 5% glucose, 1% ethanol, and 0.2 g/L G418. Fermentations were carried out in YP medium containing 8% glucose, 1% v/v of ergosterol and Tween-80 in 100% ethanol, 200 mM MES (pH 6.5), and 0.2 μg/mL G418.

A large patch of S. cerevisiae strain. GEVO3868 was grown on an YPD plate. Cells from the patch were scraped from the plate, resuspended in 2 mL YPD containing 1% v/v ethanol containing 1% v/v 80% glycerol and placed in the 30° C. orbital shaker overnight. The following morning, 1 mL of the overnight culture was used to inoculate 50 mL YPD containing 1% ethanol containing 1% v/v 80% glycerol and returned to the 30° C. orbital shaker. After 6 hours, the cells were at an $OD_{600}$ of 0.55. They were diluted to an $OD_{600}$ of 0.1 in the same media and grown overnight at 30° C. In the morning the cells were diluted to an $OD_{600}$ of 0.6, grown for 3 hours at 30° C. until the $OD_{600}$ was 1.1, and the cells were collected by centrifugation at 2700 rcf for 2 min at room temperature. The medium was removed, 50 mL sterile milliQ water was used to wash the cells, and the cells were centrifuged for 2 min at 2700 rcf at room temperature. After removing the supernatant, the cells were washed with 25 mL sterile milliQ water and centrifuged at 2700 rcf for 2 min at room temperature. The supernatant was removed and the cells were resuspended in 1 mL 100 mM lithium acetate. The cells were centrifuged for 10 sec, the supernatant removed, and the cells resuspended in 400 μL 100 mM lithium acetate. The cells were transformed as follows. First, a mixture of plasmid DNA (final volume of 15 μl with sterile water), 72 μl 50% PEG, 10 μl 1M lithium acetate, and 3 μl of denatured salmon sperm DNA (10 mg/mL) was prepared for each transformation. In a sterile 1.5 mL tube, 15 μl of the cell suspension was added to the DNA mixture (100 μl), and the transformation suspension was vortexed for 5 short pulses. The transformation was incubated for 30 min at 30° C., followed by incubation for 22 min at 42° C. The cells were collected by centrifugation (18,000× g, 10 seconds, 25° C.). After removing the supernatant, the cells were resuspended in 400 μl YPD. After an overnight recovery shaking at 30° C. and 250 RPM, the cells were spread over selective plates, YPD containing 0.2 g/L G418. Transformants were then single colony purified onto selective plates.

For fermentations, 3 mL cultures of GEVO3868 transformed with each 2p plasmid were started in YPD containing 1% ethanol containing 0.2 g/L G418 and incubated overnight at 30° C. and 250 RPM. There were three biological replicates of each strain for 39 cultures total. After the $OD_{600}$ of these cultures were taken the next day, the appropriate amount of culture was used to inoculate 50 mL of YP with 5% glucose containing 1% ethanol containing 0.2 g/L G418 (baffled flask) to an $OD_{600}$ of approximately 0.1. These cultures were incubated at 30° C. and 250 RPM overnight. The next day, the cultures containing the S. cerevisiae ilv3ΔN20, the S. cerevisiae ilv3ΔN19, and the S. cerevisiae ilv3ΔN23 did not reach an $OD_{600}$ of 5 (0.6-2.4) so incubation continued for another 24 h at 30° C. and 250 RPM. The remaining 30 cultures had reached an $OD_{600}$ of approximately 5 and were centrifuged in 50 mL Falcon tubes at 2700 rcf for 5 min at 25° C. The cells from the 30 cultures were resuspended in 50 mL YP with 8% glucose, 1% (v/v) ethanol, ergosterol, Tween-80, 200 mM MES (pH 6.5), and 0.2 g/L G418. The cultures were transferred to 250 mL unbaffled flasks with closed screw caps and incubated at 30° C. and 75 RPM. The next day, the remaining 9 cultures were at a higher $OD_{600}$ (3-5) and prepared for the fermentation as described above. At 24 and 48 h after transfer to 250 mL unbaffled flasks with closed screw caps, samples of each of the 39 flasks were taken to determine $OD_{600}$ and prepared for gas chromatography as follows. 2 mL of sample (per flask) was removed and $OD_{600}$ was determined. The remaining sample was centrifuged for 10 min at maximum speed. 1 mL of the supernatant was analyzed by gas chromatography as described. For the final 72 h timepoint, the same procedures were used for measuring $OD_{600}$ and analysis by gas chromatography. In addition samples were analyzed by high performance liquid chromatography. Cells were also prepared for enzyme assays. After 3×15 mL Falcon tubes per flask were weighed (total of 117), 14 mL of the appropriate sample was transferred into the Falcon tubes. After centrifugation at 3000×g for 5 min at 4° C., the supernatant was removed and the cells washed in 3 mL cold, sterile water. The tubes were centrifuged as per above for 2 min, the supernatant removed, and the tubes reweighed to determine total cell weight. The Falcon tubes were stored at −80° C.

Analysis of organic acid metabolites was performed on an HP-1200 HPLC system equipped with two Restek RFQ 150× 7.8 mm columns in series. Organic acid metabolites were detected using an HP-1100 UV detector (210 nm) and refractive index. The column temperature was 60° C. This method was isocratic with 0.0180 $NH_2SO_4$ (in Milli-Q water) as mobile phase. Flow was set to 1.1 mL/min. Injection volume was 20 µL and run time was 16 min. Analysis was performed using authentic standards (>99%, obtained from Sigma-Aldrich, with the exception of 2,3-dihydroxyisovalerate (DHIV), which was custom synthesized according to Cioffi et al., 1980, *Anal Biochem* 104: 485 and a 5-point calibration curve.

Analysis of volatile organic compounds, including ethanol and isobutanol was performed on a HP 5890, 6890 or 7890 gas chromatograph fitted with an HP 7673 Autosampler, a DB-FFAP column (J&W; 30 m length, 0.32 mm ID, 0.25 µM film thickness) or equivalent connected to a flame ionization detector (FID). The temperature program was as follows: 230° C. for the injector, 300° C. for the detector, 100° C. oven for 1 minute, 70° C./minute gradient to 230° C., and then hold for 2.5 min. Analysis was performed using authentic standards (>99%, obtained from Sigma-Aldrich, and a 5-point calibration curve with 1-pentanol as the internal standard.

For DHAD activity assays cells were thawed on ice and resuspended in lysis buffer (50 mM Tris pH 8.0 and 5 mM $MgSO_4$) for a 20% cell suspension by mass. 1000 µl of glass beads (0.5 mm diameter) were added to a 1.5 ml Eppendorf tube and 875 µl of cell suspension was added. Yeast cells were lysed using a Retsch MM301 mixer mill (Retsch Inc. Newtown, Pa.), mixing 6×1 min each at full speed with 1 min incubations on ice between each bead-beating step. The tubes were centrifuged for 10 min at 23,500×g at 4° C. and the supernatant was removed for use. These lysates were held on ice until assayed. Yeast lysate protein concentration was determined using the BioRad Bradford Protein Assay Reagent Kit (Cat#500-0006, BioRad Laboratories, Hercules, Calif.) and using BSA for the standard curve. Briefly 10 µL standard or lysate were added into a microcentrifuge tube. The samples were diluted to fit in the linear range of the standard curve (1:40). 500 µL of diluted and filtered Bio-Rad protein assay dye was added to the blank and samples and then vortexed. Samples were incubated at room temperature for 6 min, transferred into cuvettes and the $OD_{595}$ was determined in a spectrophotometer. The linear regression of the standards was then used to calculate the protein concentration in each sample. For DHAD assays technical triplicates were performed for each sample. In addition, a no lysate control with lysis buffer was performed. To assay each sample, 10 µL of an appropriate dilution of lysate in assay buffer was mixed with 90 µL of assay buffer (5 µL of 0.1 M $MgSO_4$, 10 µL of 0.1 M DHIV, and 75 µL 50 mM Tris pH 8.0), and incubated in a thermocycler for 30 minutes at 35° C., then at 95° C. for 5 minutes. Cell debris and precipitant were removed from the samples by centrifugation at 3000×g for 5 min.

Finally, 75 µL of supernatant was transferred to new PCR tubes and analyzed by Liquid Chromatography for the 2-keto-isovalerate (KIV) product. DNPH reagent (12 mM 2,4-Dinitrophenyl Hydrazine 20 mM Citric Acid pH 3.0 80% Acetonitrile 20% MilliQ $H_2O$) was added to each sample in a 1:1 ratio. Samples were incubated for 30 min at 70° C. in a thermo-cycler (Eppendorf, Mastercycler). Analysis of KIV was performed on an HP-1200 High Performance Liquid Chromatography system equipped with an Eclipse XDB C-18 reverse phase column (Agilent) and a C-18 reverse phase column guard (Phenomenex). Ketoisovalerate was detected using an HP-1100 UV detector (360 nm). The column temperature was 50° C. This method was isocratic with 70% acetonitrile 2.5% phosphoric acid (4%), 27.5% water as mobile phase. Flow was set to 3 mL/min. Injection size was 10 µL and run time was 2 min.

The data at 72 hours are summarized in Table 33. The data demonstrates that the DHADs contained in plasmids pGV2635, 2677, 2674, 2672, 2673 and 2676 led to production of isobutanol titers of at least 2.5 g/L and are considered to be significantly active in the cytosolic isobutanol pathway. The DHADs contained in plasmids pGV2675, 2681, 2680, 2678, 2679, 2671, and 2676 led to production of isobutanol titers below 2.5 g/L and are considered to be inactive or poorly active in the cytosolic isobutanol pathway.

TABLE 33

Isobutanol production with selected DHADs.

| Plasmid (DHAD Gene) | $OD_{600}$ | Isobutanol produced [g/L] | DHAD activity (U/mg) |
|---|---|---|---|
| pGV2635 (*L. lactis*) | 8.6 ± 0.6 | 9.02 ± 0.28 | 0.62 ± 0.01 |
| pGV2677 (*N. crassa*) | 9.4 ± 0.6 | 6.30 ± 0.85 | 0.42 ± 0.02 |
| pGV2674 (*F. tularensis*) | 7.5 ± 0.7 | 6.22 ± 0.31 | 0.30 ± 0.00 |
| pGV2672 (*G. forsetii*) | 8.1 ± 0.6 | 6.10 ± 0.26 | 0.20 ± 0.00 |
| pGV2673 (*S. erythraea*) | 8.0 ± 1.1 | 3.23 ± 0.12 | 0.03 ± 0.00 |
| pGV2676 (*S. cerevisiae* ilv3ΔN23) | 5.2 ± 0.2 | 2.67 ± 0.06 | 0.02 ± 0.00 |
| pGV2675 (*S. cerevisiae* ilv3ΔN19) | 5.0 ± 0.2 | 2.27 ± 0.16 | 0.09 ± 0.00 |
| pGV2681 (*E. coli*) | 6.9 ± 0.6 | 2.21 ± 0.09 | 0.03 ± 0.00 |
| pGV2680 (*Lyngbya* spp.) | 6.9 ± 1.3 | 2.13 ± 0.09 | 0.02 ± 0.00 |
| pGV2678 (*Acidobacteria*) | 7.5 ± 0.2 | 2.06 ± 0.17 | 0.03 ± 0.00 |
| pGV2679 (*A. marina*) | 7.5 ± 0.6 | 2.05 ± 0.06 | 0.03 ± 0.00 |
| pGV2671 (*S. cerevisiae*) | 5.5 ± 0.0 | 1.92 ± 0.03 | 0.44 ± 0.01 |
| pGV2663 (none) | 6.7 ± 0.2 | 1.53 ± 0.18 | 0.01 ± 0.01 |

Example 19

Overexpression of the L. Lactis ilvD in K. Lactis and K. Marxianus

The purpose of this example is to demonstrate activity of L. lactis DHAD in K. lactis and in K. marxianus.

Strains, plasmids, and sequences disclosed herein are listed in Tables 34, 35, and 36, respectively.

TABLE 34

Genotype of strains disclosed in Example 19.

| GEVO Number | Genotype |
| --- | --- |
| K. marxianus strain GEVO2504 | K. marxianus NRRL-Y-7571 ura3-delta2 pdc1Δ::Ll.kivd2 coSc. $P_{TDH3}$:Dm_ADH:$P_{FBA1}$: URA3:$P_{Sc\_FBA1}$:31COX4_MTS:Bs_alsS1_coSc |
| K. marxianus strain GEVO2543 | ura3-delta2 pdc1Δ::Δ::{Ll_kivd2 co:$P_{Sc\_TDH3}$: Ec_ilvC$^{Q110V}$coSC:$P_{Sc\_TPI1}$:G418$^R$:$P_{Sc\_CUP1}$: Bs_alsS1_coSc} |
| K. marxianus strain GEVO2598 | ura3-delta2 pdc1Δ::{Ll_kivd2 co:$P_{Sc\_TDH3}$: Ec_ilvC$^{Q110V}$coSC:$P_{Sc\_TPI1}$:G418$^R$:$P_{Sc\_CUP1}$: Bs_alsS1_coSc} + random integration of {$P_{Sc\_TEF1}$:Ll_ilvD_coSc URA3} |
| K. lactis strain GEVO1287 | MATalpha uraA1 trp1 leu2 lysA1 ade1 lac4-8 [pKD1] ATCC 200826 |

TABLE 35

Plasmids disclosed in Example 19.

| Plasmid Name | Relevant Genes/Usage | Genotype |
| --- | --- | --- |
| pGV2271 | Empty 1.6 micron vector that can be maintained in K. lactis. Encodes hygromycin resistance. | 1.6μ ori, bla, hygroR |
| pGV2273 | 1.6 micron vector for expression of KARI, KIVD, DHAD and ADH in K. lactis | $P_{TDH3}$:Ec_ilvC_P2D1-A1, $P_{TEF1}$: Ll_ilvD_coSc, $P_{PGK1}$: Ll_kivd2_coEc, $P_{ENO2}$:Ll_adhA 1.6μ ori, bla, HygroR |
| pGV2069 | 2 micron plasmid for expression of KIVD, DHAD, KARI, and ALS in K. marxianus | $P_{TDH3}$:Ec_ilvC_coScQ$^{110V}$, p$^{TEF1}$: Ll_ilvD_coSc, $P_{PGK1}$: Ll_kivD2_coEc, $P_{CUP1}$: Bs_alsS1_coSc, $P_{ENO2}$: Dm_adhA, 2μ ori, bla, G418 |
| pGV1855 | 2 micron plasmid for expression of DHAD in K. marxianus | $P_{TEF1}$:Ll_ilvD, 2μ ori, bla, URA |

TABLE 36

Amino acid and nucleotide sequences of enzymes and genes disclosed in Example 19.

| Enz. | Source | Gene (SEQ ID NO) | Corresponding Protein (SEQ ID NO) |
| --- | --- | --- | --- |
| ALS | B. subtilis | Bs_alsS1_coSc (SEQ ID NO: 144) | Bs_AlsS1_coSc (SEQ ID NO: 169) |
| KARI | E. coli | Ec_ilvC_coSc$^{Q110V}$ (SEQ ID NO: 98) | Ec_ilvC_coSc$^{Q110V}$ (SEQ ID NO: 170) |
| | E. coli | Ec_ilvC_coSc$^{P2D1-A1}$ (SEQ ID NO: 171) | Ec_ilvC_coSc$^{P2D1-A1}$ (SEQ ID NO: 172) |
| KIVD | L. lactis | Ll_kivd2_coEc (SEQ ID NO: 99) | Ll_Kivd2_coEc (SEQ ID NO: 173) |
| DHAD | L. lactis | Ll_ilvD_coSc (SEQ ID NO: 155) | Ll_ilvD_coSc (SEQ ID NO: 18) |
| ADH | L. lactis | Ll_adhA (SEQ ID NO: 174) | Ll_adhA (SEQ ID NO: 175) |
| | D. melanogaster | Dm_adh (SEQ ID NO: 116) | Dm_adh (SEQ ID NO: 176) |

To generate GEVO2543, GEVO2504 was transformed with pGV2069 to integrate into the genome three genes: Bs_alsS1_coSc (SEQ ID NO: 144), Ec_ilvC_coSc$^{Q110V}$ (SEQ ID NO: 98), and Ll_kivd2_coEc (SEQ ID NO: 99). To generate GEVO2598, GEVO2543 was transformed pGV1855 to integrate the L. lactis ilvD gene which was codon optimized for S. cerevisiae (gene sequence SEQ ID NO: 155, also referred to as Ll_ilvD_coSc; protein sequence SEQ ID NO: 18) into the chromosome. GEVO1287 was transformed with either pGV2271 (control plasmid) or pGV2273, which contains Ll_ilvD_coSc.

GEVO2543, GEVO2598 and GEVO1287 transformed with pGV2271 or pGV2273 were inoculated into 3 mL of YPD (for GEVO2543 and GEVO2598) or YPD supplemented with 0.1 g/L hygromycin (for GEVO1287) for an overnight culture. After approximately 18 hours, a 50 ml YPD culture in a baffled 250 ml shake flask was inoculated to 0.15 OD$_{600}$ and shaken at 250 rpms for approximately 9 hours. Next, DHAD activity and protein concentrations were measured.

Over-expression of the L. lactis ilvD gene resulted in an increase in DHAD activity (U/mg total cell lysate protein). Table 37 shows the DHAD activity (U/mg total cell lysate protein) averages from technical triplicates comparing strains expressing the L. lactis DHAD to strains not expressing the L. lactis DHAD gene.

TABLE 37

DHAD activity in whole cell yeast lysates.

| Strain | Activity [mU/mg] |
| --- | --- |
| K. marxianus strain GEVO2543 (no DHAD) | 0.010 ± 0.002 |
| K. marxianus strain GEVO2598 (DHAD) | 0.016 ± 0.001 |
| K. lactis strain GEVO1287 + pGV2271 (No DHAD) | 0.052 ± 0.003 |
| K. lactis strain GEVO1287 + pGV2273 (DHAD) | 0.122 ± 0.011 |

Example 20

L. Lactis ilvD Activity is Localized to the Yeast Cytosol

The purpose of this example is to demonstrate that the Lactococcus lactis ilvD protein localizes to the cytosol when expressed in a yeast strain.

The S. cerevisiae strain GEVO1187 (S. cerevisiae CEN.PK2, MATa ura3 leu2 his3 trp1 ADE2) was transformed with plasmid pGV2484, a 2 micron plasmid expressing the L. lactis ilvD gene which was codon optimized for S. cerevisiae (gene sequence SEQ ID NO: 155, also referred to as Ll_ilvD_coSc; protein sequence SEQ ID NO: 18) under the *S. cerevisiae* TEF1 promoter ($P_{TEF_1}$:LL1_ilvD_coSc, 2μ ori, bla, G418R). Briefly, the strain was grown in YPD to an $OD_{600}$ of 0.6-0.8. Cells were washed in $H_2O$, and then resuspended in 100 mM Lithium acetate. In a 1.5 mL tube, 15 μL of the cell suspension was added to a mixture of DNA (final volume of 15 μl with sterile water), 72 μl 50% PEG, 10 μl 1M lithium acetate, and 3 μl of denatured salmon sperm DNA (10 mg/mL). The transformation suspension was vortexed for 5 short pulses. The mixture was incubated at 30° C. for 30 minutes, followed by incubation for 22 minutes at 42° C. The cells were collected by centrifugation (18,000×g, 10 seconds, 25° C.). The cells were resuspended in 1 ml YPD medium (1% (w/v) yeast extract, 2% (w/v) peptone, 2% (w/v) glucose, pH 5) and after an overnight recovery shaking at 30° C. and 250 rpms, the cells were spread over YPD agar plates supplemented with 0.2 g/L G418. Transformants were then single colony purified onto G418 selective plates.

All isolations of crude mitochondrial fractions were performed in duplicate. GEVO1187 and GEVO1187 transformed with pGV2484 were each grown in 100 mL of YPG medium (1% (w/v) yeast extract, 2% (w/v) peptone, 3% (v/v) glycerol, pH5) overnight at 30° C. and 250 rpm. This overnight culture was used to inoculate 840 mL of YPG in a 2800 mL baffled flask at an $OD_{600}$ of 0.03, and cells were grown at 30° C. and 250 rpm for 20-28 h. At an $OD_{600}$ of about 2.0, cells were harvested by centrifugation at 3000×g for 5 minutes, resuspended in 100 mL $H_2O$ followed by centrifugation at 3000×g for 5 minutes. Cells were incubated in 2 mL/g CWW (cell wet weight) of DTT buffer (100 mM Tris-$H_2SO_4$ pH 9.4, 10 mM DTT) for 20 minutes at 30° C. Cells were resuspended in 7 mL/g CWW Zymolyase buffer (1.2 M sorbitol, 20 mM Potassium phosphate pH 7.4) and then centrifuged at 3000×g for 5 minutes. Cells were spheroplasted by incubating in Zymolyase buffer with Zymolyase (Seikagaku Biobusiness Corporation #120491-1; 3 mg/g CWW) for 45 minutes at 30° C. on a rocking platform. 100 OD of spheroplasts were set aside for whole cell lysate preparation (see below). Spheroplasts were resuspended in Zymolyase buffer and centrifuged at 3000×g for 5 minutes before resuspension in 6.5 mL/g CWW homogenization buffer (chilled to 4° C.; 6.5 mL/g 0.6 M sorbitol, 10 mM Tris-HCl pH 7.4, 1 mM EDTA, 1 mM PMSF, 0.2% (w/v) BSA). Spheroplasts were homogenized on ice with 15 strokes of a pre-chilled glass-Teflon homogenizer (40 mL capacity), and the sample was diluted 2-fold with homogenization buffer. Cell debris and nuclei were pelleted by serial supernatant centrifugations of 1500×g for 5 minutes, and 4000×g for 5 minutes. The mitochondrial fraction was isolated by centrifugation at 12,000×g for 15 minutes. The crude mitochondrial pellet was resuspended in 10 mL SEM buffer (250 mM sucrose, 1 mM EDTA, 10 mM MOPS-KOH pH 7.2), centrifuged at 4000×g for 5 minutes to further remove cellular debris and nuclei before recovering the mitochondrial fraction by centrifugation at 12,000×g for 15 minutes. The mitochondrial fraction may contain markers of the plasma membrane, the endoplasmic reticulum, and vacuoles in addition to markers of the mitochondria. Mitochondrial pellet was resuspended in 750 μL SEM Buffer+Protease Arrest (GBiosciences #786-108).

Preparation of whole cell yeast lysates was performed using the 100 ODs of yeast cells set aside after spheroplasting (see above) by resuspending cells in 20% (w/v) SEM Buffer+ 1× Protease Arrest (GBiosciences #786-108). 1000 μl of glass beads (0.5 mm diameter) were added to a 1.5 ml eppendorf tube, and 875 μl of cell suspension was added. Yeast cells were lysed using a Retsch MM301 mixer mill (Retsch Inc. Newtown, Pa.), mixing 6×1 min each at full speed with 1 min incubations on ice between each bead-beating step. The tubes were centrifuged for 10 min at 23,500×g at 4° C., the supernatant was removed, aliquoted, flash frozen in liquid nitrogen, and stored at −80° C.

The resuspended mitochondrial fraction (see above) was added to 1000 μl of glass beads (0.1 mm diameter) in a 1.5 ml Eppendorf tube. Additional buffer was added if necessary to fill the tube completely. The mitochondrial fraction was lysed using a Retsch MM301 mixer mill (Retsch Inc. Newtown, Pa.), mixing 3×1 minute each at full speed with 1 minute incubations on ice between each bead-beating step. The tubes were centrifuged for 10 min at 23,500×g at 4° C., the supernatant was removed, aliquoted, flash frozen in liquid nitrogen, and stored at −80° C.

Whole cell yeast lysate and mitochondrial fraction lysate protein concentration was determined using the BioRad Bradford Protein Assay Reagent Kit (Cat#500-0006, BioRad Laboratories, Hercules, Calif.) and using BSA for the standard curve. Briefly, 10 μL standard or lysate were added into a microcentrifuge tube. The samples were diluted to fit in the linear range of the standard curve (1:10-1:40). 500 μL of diluted and filtered Bio-Rad protein assay dye was added to the blank and samples and then vortexed. Samples were incubated at room temperature for 6 mins, transferred into cuvettes and the $OD_{595}$ was determined in a spectrophotometer. The linear regression of the standards was then used to calculate the protein concentration in each sample.

Three samples of each of the mitochondrial and whole cell yeast lysates were assayed for DHAD activity, along with no lysate controls. Table 38 shows the DHAD activity (U/mg protein) averages from duplicate cultures comparing strains GEVO1187 (no DHAD expression) to GEVO1187 transformed with pGV2484 (*L. lactis* DHAD expressed from pGV2484). DHAD activity was measured in the whole cell yeast lysate and the mitochondrial fraction lysate. Expression of DHAD from pGV2484 resulted in about a 7-fold increase in DHAD activity in the whole cell yeast lysate. Expression of DHAD from pGV2484 did not affect DHAD activity localized to the mitochondrial fraction. Subtracting the background activity in the GEVO1187 whole cell yeast lysate of 0.27 mU/mg from the activity in the whole cell yeast lysate of GEVO1187 transformed with pGV2484 of 1.87 mU/mg shows an increase in 1.60 mU/mg. These data suggest that *L. lactis* DHAD activity does not localize to the organellar structures harvested in the mitochondrial fraction, and is therefore cytosolic when expressed in a yeast strain.

TABLE 38

DHAD activity in whole cell yeast lysates and mitochondrial fraction lysates.

| Strain | Lysate | Activity [mU/mg] |
|---|---|---|
| GEVO1187 | Whole cell | 0.27 ± 0.07 |
| GEVO1187 transformed with pGV2484 | Whole cell | 1.87 ± 0.14 |
| GEVO1187 | Mitochondrial | 3.76 ± 0.01 |
| GEVO1187 transformed with pGV2484 | Mitochondrial | 3.85 ± 0.13 |

Example 21

Overexpression of the *L. Lactis* ilvD in *Issatchenkia Orientalis*

The purpose of this example is to demonstrate cytosolic activity of *L. lactis* DHAD in *I. orientalis*.

An engineered strain derived from the wild-type *I. orientalis* strain ATCC PTA-6658 was further modified to contain copies of all five isobutanol pathway genes integrated into the chromosome. First, both alleles of the PDC1 locus were deleted in series (See e.g. WO/2007/106524, which is herein incorporated by reference in its entirety). The deletion event also simultaneously integrated a copy of *B. subtilis* alsS gene and a copy of the *L. lactis* kivD gene which encode SEQ ID NOs: 169 and 173, respectively. This resulted in a Pdc– strain with two integrated copies of the *B. subtilis* alsS gene and two integrated copies of the *L. lactis* kivD gene (pdc1Δ::Ll_kivD: Bs_alsS pdc1Δ::Ll_kivD: Bs_alsS). This strain was further engineered to delete a single allele of the GPD1 locus (See e.g. WO/2007/106524). The deletion event also simultaneously integrated a single copy of the *L. lactis* adhA$^{RE1}$, the *E. coli* ilvC$^{P2D1-A1}$, and *L. lactis* ilvD which encode the proteins shown in SEQ ID NOs: 177, 172, and 18, respectively. This results in a Pdc– Gpd+ strain with one integrated copy of the Ll_adhA$^{RE1}$, Ec_ilvC$^{P2D1-A1}$, and Ll_ilvD genes (GPD1/gpd1Δ::[Ll_adhA$^{RE1}$: Ec_ilvC$^{P2D1-A1}$: URA3: Ll_ilvD]). This strain is GEVO4306 (Table 39).

To generate a control strain which does not express the pathway genes, both alleles of the PDC1 locus were deleted in series but with no simultaneous integration of heterologous genes. Next one of the two GPD1 alleles was deleted with no simultaneous integration of heterologous genes. The resulting control strain is GEVO4308 (pdc1Δ::loxP/pdc1Δ::loxP GPD1/gpd1Δ::loxP:URA3:loxP) (Table 39).

TABLE 39

Genotype of strains disclosed in Example 21.

| GEVO Number | Genotype |
|---|---|
| 4306 | pdc1Δ::[Ll_kivD:Bs_alsS1 pdc1Δ::Ll_kivD:Bs_alsS] GPD1/gpd1Δ::[Ll_adhA$^{RE1}$: Ec_ilvC$^{P2D1-A1}$:URA3:Ll_ilvD] |
| 4308 | pdc1Δ::loxP/pdc1Δ::loxP GPD1/gpd1Δ::loxP:URA3:loxP |

Over-expression of the *L. lactis* ilvD gene resulted in an increase in DHAD activity (U/mg total cell lysate protein). Table 40 shows the DHAD activity (U/mg total cell lysate protein) averages from technical triplicates comparing the strain expressing the *L. lactis* DHAD gene to the strain not expressing the *L. lactis* DHAD gene. Expression of the *L. lactis* ilvD gene, when expressed with the remainder of the isobutanol pathway, resulted in isobutanol production as seen in Table 40.

TABLE 40

DHAD activity in whole cell yeast lysates and isobutanol titer after 72 hr fermentation.

| Strain | Activity [mU/mg] | Isobutanol titer g/L |
|---|---|---|
| GEVO4306 | 0.041 ± 0.009 | 0.56 ± 0.01 |
| GEVO4308 | 0.012 ± 0.002 | 0.00 ± 0.00 |

Example 22

Cytosolic ALS Homologs that Support Isobutanol Production

This example demonstrates isobutanol production using expression of cytosolically localized ALS genes in the presence of the rest of the isobutanol pathway. The ALS genes were integrated into the PDC1 locus of *S. cerevisiae* strain GEVO1187 and isobutanol production was achieved by expression from plasmid of the other genes in the isobutanol pathway. Isobutanol production in strains carrying the ALS genes from *T. atroviride* (Ta_ALS) and *T. stipitatus* (Ts_ALS) was compared to isobutanol production in strains carrying the ALS gene from *B. subtilis*. Plasmids described in this example are listed in Table 41.

TABLE 41

Plasmids disclosed in Example 22.

| Plasmid name | Relevant Genes/Usage | Genotype |
|---|---|---|
| pGV1730 | Integration plasmid that will integrate P$_{CUP1-1}$:Bs_alsS2 into PDC1 using digestion with NruI for targeting. This was the parent vector for cloning the ALS homologs. | See Table 14. |
| pGV1773 | Vector with *Bacillus subtilis* AlsS codon optimized for *S. cerevisiae*. | P$_{PDC1}$:Bs_AlsS1_coSc, P$_{TDH3}$:Ll_kivD, P$_{ADH1}$:Sc_ADH7_coSc, URA3 5'-end, pUC ORI, kan$^R$. |
| pGV1802 | DNA2.0 plasmid carrying the *Trichoderma atroviride* ALS. | Ta_ALS_coSc in DNA 2.0 vector |
| pGV1803 | DNA2.0 plasmid carrying the *Talaromyces stipitatus* ALS. | Ts_ALS_coSc in DNA 2.0 vector |
| pGV2082 | High copy 2μ plasmid with 4 isobutanol pathway genes without an ALS gene. | Ec_ilvC_coSc$^{Q110V}$, Ll_ilvD_coSc, Ll_kivD2_coEc, and Dm_ADH, 2μ ori, bla, G418R. |
| pGV2114 | Integration plasmid that will integrate into PDC1 using digestion with NruI for targeting. It carries the *Bacillus subtilis* AlsS gene codon optimized for *S. cerevisiae*. | See Table 14. |
| pGV2117 | Integration plasmid that will integrate into PDC1 using digestion with NruI for targeting. It carries the *Trichoderma atroviride* ALS gene codon optimized for *S. cerevisiae*. | See Table 14. |
| pGV2118 | Integration plasmid that will integrate into PDC1 using digestion with NruI for targeting. It carries the *Talaromyces stipitatus* ALS gene codon optimized for *S. cerevisiae*. | See Table 14. |

Strains with integrated ALS genes expressed from the CUP1 promoter were transformed with pGV2082 (which carries the other 4 isobutanol pathway genes Ec_ilvC_coScQ110V (SEQ ID NO: 98), Ll_ilvD (SEQ ID NO: 155), Ll_kivd2_coEc (SEQ ID NO: 99), and Dm_ADH (SEQ ID NO: 116).

GEVO2618, GEVO2621, and GEVO2622 (see Table 13) were each transformed with pGV2082. Control strains GEVO2280 (*B. subtilis* alsS2) (Table 13) and GEVO1187 (no ALS) (Table 13) were also transformed with pGV2082.

Fermentations of the transformed strains GEVO1187, GEVO2280, GEVO2618, GEVO2621, GEVO2622 were performed. Strains encoding the ALS from *T. atroviride* (SEQ ID NO: 71) and *T. stipitatus* (SEQ ID NO: 72) produced more isobutanol than the strain containing the *B. subtilis* als2. The strain containing Bs_Als1_coSc produced the most isobutanol. Table 42 shows the final OD, glucose consumption, and isobutanol titer for each of the strains. The integration of the cytosolic genes Ta_ALS_coSc and Ts_ALS_coSc led to production of isobutanol that was in each case 6-fold above that of a strain without an integrated ALS gene, demonstrating that these strains are producing isobutanol using a cytosolic pathway.

TABLE 42

Results of fermentations with cytosolic ALS homologs at 72 hrs.

| Strain | $OD_{600}$ | Glucose consumed g/L | Isobutanol produced g/L |
|---|---|---|---|
| GEVO1187 | 10.9 ± 0.3 | 233 ± 36 | 0.3 ± 0.0 |
| GEVO2280 | 9.9 ± 0.3 | 274 ± 26 | 1.3 ± 0.11 |
| GEVO2618 | 9.4 ± 0.2 | 138 ± 9 | 2.6 ± .09 |
| GEVO2621 | 9.9 ± 0.3 | 161 ± 52 | 1.9 ± .18 |
| GEVO2622 | 10.8 ± 0.6 | 182 ± 47 | 1.8 ± .15 |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A recombinant yeast microorganism for producing isobutanol, the recombinant yeast microorganism comprising an isobutanol producing metabolic pathway, wherein said isobutanol producing metabolic pathway comprises the following substrate to product conversions:
   (i) pyruvate to acetolactate;
   (ii) acetolactate to 2,3-dihydroxyisovalerate;
   (iii) 2,3-dihydroxyisovalerate to α-ketoisovalerate;
   (iv) α-ketoisovalerate to isobutyraldehyde; and
   (v) isobutyraldehyde to isobutanol;
wherein said recombinant yeast microorganism expresses:
   an exogenous nucleic acid encoding dihydroxy acid dehydratase to catalyze the conversion of 2,3-dihydroxyisovalerate to α-ketoisovalerate, said exogenous nucleic acid encoding dihydroxy acid dehydratase comprising an amino acid motif which is at least 90% identical to the motif of SEQ ID NO: 27, wherein said dihydroxy acid dehydratase is active in the cytosol of said recombinant yeast microorganism, and wherein the recombinant yeast microorganism has been engineered to inactivate one or more endogenous pyruvate decarboxylase (PDC) genes.

2. The recombinant yeast microorganism of claim 1, wherein said dihydroxy acid dehydratase is obtained from a prokaryotic organism.

3. The recombinant yeast microorganism of claim 2, wherein said prokaryotic organism is selected from the group consisting of *Lactococcus lactis, Francisella tularensis, Acidobacteria bacterium, Saccharopolyspora erythraea, Thermotoga petrophila, Gramella forsetii*, and *Victivallis vadensis*.

4. The recombinant yeast microorganism of claim 1, wherein said dihydroxy acid dehydratase is obtained from a eukaryotic organism.

5. The recombinant yeast microorganism of claim 4, wherein said eukaryotic organism is selected from the group consisting of *Yarrowia lipolytica, Neurospora crassa, Arabidopsis thaliana*, and *Piromyces* sp. E2.

6. The recombinant yeast microorganism of claim 1, wherein said one or more endogenous PDC genes is selected from the group consisting of PDC1, PDC5, and PDC6.

7. The recombinant yeast microorganism of claim 1, wherein said recombinant yeast microorganism has been engineered to reduce the activity of one or more endogenous glycerol-3-phosphate dehydrogenase (GPD) genes.

8. The recombinant yeast microorganism of claim 7, wherein said one or more GPD genes is selected from the group consisting of GPD1 and GPD2.

9. The recombinant yeast microorganism of claim 1, wherein said recombinant yeast microorganism is a yeast microorganism of the *Saccharomyces* clade.

10. A method of producing isobutanol, comprising:
    (a) providing a recombinant yeast microorganism according to claim 1; and
    (b) cultivating said recombinant yeast microorganism in a culture medium containing a feedstock providing a carbon source, until the isobutanol is produced.

11. The recombinant yeast microorganism of claim 1, wherein the substrate to product conversion of (i) is catalyzed by an exogenous acetolactate synthase encoded by alsS of *Bacillus subtilis*.

12. The recombinant yeast microorganism of claim 1, wherein the substrate to product conversion of (i) is catalyzed by an exogenous acetolactate synthase encoded by alsS of *Lactococcus lactis*.

13. The recombinant yeast microorganism of claim 1, wherein the substrate to product conversion of (i) is catalyzed by an endogenous acetolactate synthase encoded by ILV2.

14. The recombinant yeast microorganism of claim 1, wherein the substrate to product conversion of (ii) is catalyzed by an exogenous ketol-acid reductoisomerase obtained from a microorganism selected from the group consisting of *Escherichia coli, Bacillus subtilis, Lactococcus lactis, Methanococcus maripaludis*, and *Shewanella* sp.

15. The recombinant yeast microorganism of claim 1, wherein the substrate to product conversion of (ii) is catalyzed by an endogenous ketol-acid reductoisomerase encoded by ILV5.

16. The recombinant yeast microorganism of claim 1, wherein the substrate to product conversion of (iv) is catalyzed by an exogenous 2-keto-acid decarboxylase encoded by kivD of *Lactococcus lactis*.

17. The recombinant yeast microorganism of claim 1, wherein the substrate to product conversion of (iv) is catalyzed by an exogenous 2-keto-acid decarboxylase obtained from a microorganism selected from the group consisting of *Enterobacter cloacae, Mycobacterium smegmatis, Mycobacterium tuberculosis, Mycobacterium avium, Azospirillum brasilense*, and *Bacillus subtilis*.

18. The recombinant yeast microorganism of claim 1, wherein the substrate to product conversion of (v) is catalyzed by an exogenous alcohol dehydrogenase obtained from a microorganism selected from the group consisting of *Lactococcus lactis, Lactococcus brevis, Pediococcus acidilactici, Bacillus cereus, Bacillus thuringiensis, Leptotrichia goodfellowii, Actinobacillus pleuropneumonias, Streptococcus sanguinis, Eikenella corrodens, Neisseria elongate, Escherichia coli, Neisseria meningitidis, Erwinia pyrifoliae*, and *Colwellia psychrerythraea*.

19. The recombinant yeast microorganism of claim 1, wherein the substrate to product conversion of (v) is catalyzed by an engineered alcohol dehydrogenase obtained from *Lactococcus lactis*, wherein said engineered alcohol dehydrogenase comprises SEQ ID NO: 177.

20. The recombinant yeast microorganism of claim 1, wherein the substrate to product conversion of (v) is catalyzed by an endogenous alcohol dehydrogenase encoded by a gene selected from the group consisting of ADH2, ADH6, and ADH7.

\* \* \* \* \*

(12) INTER PARTES REEXAMINATION CERTIFICATE (1036th)
United States Patent
Urano et al.

(10) Number: US 8,232,089 C1
(45) Certificate Issued: Jan. 22, 2015

(54) CYTOSOLIC ISOBUTANOL PATHWAY LOCALIZATION FOR THE PRODUCTION OF ISOBUTANOL

(75) Inventors: Jun Urano, Englewood, CO (US); Catherine Asleson Dundon, Englewood, CO (US)

(73) Assignee: Gevo, Inc., Englewood, CO (US)

Reexamination Request:
No. 95/002,227, Sep. 14, 2012

Reexamination Certificate for:
Patent No.: 8,232,089
Issued: Jul. 31, 2012
Appl. No.: 12/855,276
Filed: Aug. 12, 2010

Related U.S. Application Data

(60) Provisional application No. 61/272,058, filed on Aug. 12, 2009, provisional application No. 61/272,059, filed on Aug. 12, 2009.

(51) Int. Cl.
| | |
|---|---|
| *C12N 1/00* | (2006.01) |
| *C07H 21/02* | (2006.01) |
| *C12P 7/16* | (2006.01) |
| *C12N 9/04* | (2006.01) |
| *C12N 15/81* | (2006.01) |
| *C12N 9/88* | (2006.01) |
| *C12N 9/10* | (2006.01) |

(52) U.S. Cl.
CPC ............. *C12P 7/16* (2013.01); *C12N 9/0006* (2013.01); *C12N 15/81* (2013.01); *C12N 9/88* (2013.01); *C12N 9/1022* (2013.01); *Y02E 50/10* (2013.01)
USPC ................. 435/254.2; 435/160; 536/23.1

(58) Field of Classification Search
None
See application file for complete search history.

(56) References Cited

To view the complete listing of prior art documents cited during the proceeding for Reexamination Control Number 95/002,227, please refer to the USPTO's public Patent Application Information Retrieval (PAIR) system under the Display References tab.

*Primary Examiner* — Gary Kunz

(57) ABSTRACT

The present invention provides recombinant microorganisms comprising isobutanol producing metabolic pathway with at least one isobutanol pathway enzyme localized in the cytosol, wherein said recombinant microorganism is selected to produce isobutanol from a carbon source. Methods of using said recombinant microorganisms to produce isobutanol are also provided. In various aspects of the invention, the recombinant microorganisms may comprise a cytosolically active isobutanol pathway enzymes. In some embodiments, the invention provides mutated, modified, and/or chimeric isobutanol pathway enzymes with cytosolic activity. In various embodiments described herein, the recombinant microorganisms may be microorganisms of the Saccharomyces clade, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-18 and 20 are cancelled.

New claim 21 is added and determined to be patentable.

Claim 19 was not reexamined.

*21. A recombinant yeast microorganism for producing isobutanol, the recombinant yeast microorganism comprising an isobutanol producing metabolic pathway, wherein said isobutanol producing metabolic pathway comprises the following substrate to product conversions:*
  *(i) pyruvate to acetolactate;*
  *(ii) acetolactate to 2,3-dihydroxyisovalerate;*
  *(iii) 2,3-dihydroxyisovalerate to α-ketoisovalerate;*
  *(iv) α-ketoisovalerate to isobutyraldehyde; and*
  *(v) isobutyraldehyde to isobutanol;*
*wherein said recombinant yeast microorganism expresses: an exogenous nucleic acid encoding dihydroxy acid dehydratase to catalyze conversion of 2.3-dihydroxyisovalerate to α-ketoisovalerate, said exogenous nucleic acid encoding dihydroxy acid dehydratase comprising an amino acid motif which is at least 90% identical to the motif of SEQ ID NO: 27, wherein said dihydroxy acid dehydratase is active in the cytosol of said recombinant yeast microorganism, and wherein the recombinant yeast microorganism has been engineered to inactivate one or more endogenous pyruvate decarboxylase (PDC) genes, wherein the substrate to product conversion of (v) is catalyzed by an engineered alcohol dehydrogenase obtained from Lactococcus lactis, wherein said engineered alcohol dehydrogenase comprises SEQ ID NO: 177.*

\* \* \* \* \*

SEQUENCE LISTING

<160> NUMBER OF SEQ ID NOS: 177

<210> SEQ ID NO 1
<211> LENGTH: 491
<212> TYPE: PRT
<213> ORGANISM: Escherichia coli

<400> SEQUENCE: 1

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
             245                 250                 255

Gly Trp Glu Thr Ile Thr Glu Ala Leu Lys Gln Gly Gly Ile Thr Leu
             260                 265                 270

Met Met Asp Arg Leu Ser Asn Pro Ala Lys Leu Arg Ala Tyr Ala Leu
             275                 280                 285

Ser Glu Gln Leu Lys Glu Ile Met Ala Pro Leu Phe Gln Lys His Met
290                 295                 300

Asp Asp Ile Ile Ser Gly Glu Phe Ser Gly Met Met Ala Asp Trp
305                 310                 315                 320

Ala Asn Asp Asp Lys Lys Leu Leu Thr Trp Arg Glu Glu Thr Gly Lys
             325                 330                 335

Thr Ala Phe Glu Thr Ala Pro Gln Tyr Glu Gly Lys Ile Gly Glu Gln
             340                 345                 350

Glu Tyr Phe Asp Lys Gly Val Leu Met Ile Ala Met Val Lys Ala Gly
             355                 360                 365

Val Glu Leu Ala Phe Glu Thr Met Val Asp Ser Gly Ile Ile Glu Glu
             370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
             405                 410                 415

Ala Glu Tyr Gly Asn Tyr Leu Phe Ser Tyr Ala Cys Val Pro Leu Leu
             420                 425                 430

Lys Pro Phe Met Ala Glu Leu Gln Pro Gly Asp Leu Gly Lys Ala Ile
             435                 440                 445

Pro Glu Gly Ala Val Asp Asn Gly Gln Leu Arg Asp Val Asn Glu Ala
             450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
             485                 490

<210> SEQ ID NO 2
<211> LENGTH: 395
<212> TYPE: PRT
<213> ORGANISM: Saccharomyces cerevisiae

<400> SEQUENCE: 2

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
             20                  25                  30

Arg Pro Ala Ala Arg Phe Val Lys Pro Met Ile Thr Thr Arg Gly Leu
             35                  40                  45

Lys Gln Ile Asn Phe Gly Gly Thr Val Glu Thr Val Tyr Glu Arg Ala
             50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
             85                  90                  95

Arg Asp Asn Gly Leu Asn Val Ile Ile Gly Val Arg Lys Asp Gly Ala
             100                 105                 110

Ser Trp Lys Ala Ala Ile Glu Asp Gly Trp Val Pro Gly Lys Asn Leu
             115                 120                 125

```
Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395

<210> SEQ ID NO 3
<211> LENGTH: 578
<212> TYPE: PRT
<213> ORGANISM: Oryza sativa

<400> SEQUENCE: 3

Met Ala Ala Ser Thr Thr Leu Ala Leu Ser His Pro Lys Thr Leu Ala
1               5                   10                  15

Ala Ala Ala Ala Ala Pro Lys Ala Pro Thr Ala Pro Ala Ala Val
            20                  25                  30

Ser Phe Pro Val Ser His Ala Ala Cys Ala Pro Leu Ala Ala Arg Arg
        35                  40                  45

Arg Ala Val Thr Ala Met Val Ala Ala Pro Ala Val Gly Ala Ala
    50                  55                  60

Met Pro Ser Leu Asp Phe Asp Thr Ser Val Phe Asn Lys Glu Lys Val
65                  70                  75                  80

Ser Leu Ala Gly His Glu Glu Tyr Ile Val Arg Gly Gly Arg Asn Leu
                85                  90                  95

Phe Pro Leu Leu Pro Glu Ala Phe Lys Gly Ile Lys Gln Ile Gly Val
            100                 105                 110
```

```
Ile Gly Trp Gly Ser Gln Gly Pro Ala Gln Ala Gln Asn Leu Arg Asp
            115                 120                 125

Ser Leu Ala Glu Ala Lys Ser Asp Ile Val Val Lys Ile Gly Leu Arg
    130                 135                 140

Lys Gly Ser Lys Ser Phe Asp Glu Ala Arg Ala Ala Gly Phe Thr Glu
145                 150                 155                 160

Glu Ser Gly Thr Leu Gly Asp Ile Trp Glu Thr Val Ser Gly Ser Asp
                165                 170                 175

Leu Val Leu Leu Leu Ile Ser Asp Ala Ala Gln Ala Asp Asn Tyr Glu
            180                 185                 190

Lys Ile Phe Ser His Met Lys Pro Asn Ser Ile Leu Gly Leu Ser His
        195                 200                 205

Gly Phe Leu Leu Gly His Leu Gln Ser Ala Gly Leu Asp Phe Pro Lys
    210                 215                 220

Asn Ile Ser Val Ile Ala Val Cys Pro Lys Gly Met Gly Pro Ser Val
225                 230                 235                 240

Arg Arg Leu Tyr Val Gln Gly Lys Glu Ile Asn Gly Ala Gly Ile Asn
                245                 250                 255

Ser Ser Phe Ala Val His Gln Asp Val Asp Gly Arg Ala Thr Asp Val
            260                 265                 270

Ala Leu Gly Trp Ser Val Ala Leu Gly Ser Pro Phe Thr Phe Ala Thr
        275                 280                 285

Thr Leu Glu Gln Glu Tyr Lys Ser Asp Ile Phe Gly Glu Arg Gly Ile
    290                 295                 300

Leu Leu Gly Ala Val His Gly Ile Val Glu Ala Leu Phe Arg Arg Tyr
305                 310                 315                 320

Thr Glu Gln Gly Met Asp Glu Glu Met Ala Tyr Lys Asn Thr Val Glu
                325                 330                 335

Gly Ile Thr Gly Ile Ile Ser Lys Thr Ile Ser Lys Lys Gly Met Leu
            340                 345                 350

Glu Val Tyr Asn Ser Leu Thr Glu Glu Gly Lys Lys Glu Phe Asn Lys
        355                 360                 365

Ala Tyr Ser Ala Ser Phe Tyr Pro Cys Met Asp Ile Leu Tyr Glu Cys
    370                 375                 380

Tyr Glu Asp Val Ala Ser Gly Ser Glu Ile Arg Ser Val Val Leu Ala
385                 390                 395                 400

Gly Arg Arg Phe Tyr Glu Lys Glu Gly Leu Pro Ala Phe Pro Met Gly
                405                 410                 415

Asn Ile Asp Gln Thr Arg Met Trp Lys Val Gly Glu Lys Val Arg Ser
            420                 425                 430

Thr Arg Pro Glu Asn Asp Leu Gly Pro Leu His Pro Thr Ala Gly
        435                 440                 445

Val Tyr Val Ala Leu Met Met Ala Gln Ile Glu Val Leu Arg Lys Lys
    450                 455                 460

Gly His Ser Tyr Ser Glu Ile Ile Asn Glu Ser Val Ile Glu Ser Val
465                 470                 475                 480

Asp Ser Leu Asn Pro Phe Met His Ala Arg Gly Val Ala Phe Met Val
                485                 490                 495

Asp Asn Cys Ser Thr Thr Ala Arg Leu Gly Ser Arg Lys Trp Ala Pro
            500                 505                 510

Arg Phe Asp Tyr Ile Leu Thr Gln Gln Ala Phe Val Thr Val Asp Lys
        515                 520                 525

Asp Ala Pro Ile Asn Gln Asp Leu Ile Ser Asn Phe Met Ser Asp Pro
```

```
                530             535             540
Val His Gly Ala Ile Glu Val Cys Ala Glu Leu Arg Pro Thr Val Asp
545                 550                 555                 560

Ile Ser Val Pro Ala Asn Ala Asp Phe Val Arg Pro Glu Leu Arg Gln
                565                 570                 575

Ser Ser

<210> SEQ ID NO 4
<211> LENGTH: 329
<212> TYPE: PRT
<213> ORGANISM: Methanococcus maripaludis

<400> SEQUENCE: 4

Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Gly Leu Arg Lys
        35                  40                  45

Asn Gly Ala Ser Trp Glu Asn Ala Lys Ala Asp Gly His Asn Val Met
50                  55                  60

Thr Ile Glu Glu Ala Ala Glu Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
            100                 105                 110

Tyr Gly Phe Ile Val Pro Pro Lys Gly Val Asn Val Leu Val Ala
        115                 120                 125

Pro Lys Ser Pro Gly Lys Met Val Arg Arg Thr Tyr Glu Glu Gly Phe
130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ala Pro Glu Met Ala Tyr
210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Lys Glu Ile Gln Asp Gly Arg Phe Thr Lys
        275                 280                 285

Glu Phe Val Leu Glu Lys Gln Val Asn His Ala His Leu Lys Ala Met
290                 295                 300

Arg Arg Ile Glu Gly Asp Leu Gln Ile Glu Glu Val Gly Ala Lys Leu
305                 310                 315                 320

Arg Lys Met Cys Gly Leu Glu Lys Glu
            325
```

<210> SEQ ID NO 5
<211> LENGTH: 339
<212> TYPE: PRT
<213> ORGANISM: Acidiphilium cryptum

<400> SEQUENCE: 5

Met Arg Val Tyr Tyr Asp Ser Asp Ala Asp Val Asn Leu Ile Lys Ala
1               5                   10                  15

Lys Lys Val Ala Val Val Gly Tyr Gly Ser Gln Gly His Ala His Ala
            20                  25                  30

Leu Asn Leu Lys Glu Ser Gly Val Lys Glu Leu Val Val Ala Leu Arg
        35                  40                  45

Lys Gly Ser Ala Ala Val Ala Lys Ala Glu Ala Ala Gly Leu Arg Val
    50                  55                  60

Met Thr Pro Glu Glu Ala Ala Trp Ala Asp Val Val Met Ile Leu
65                  70                  75                  80

Thr Pro Asp Glu Gly Gln Gly Asp Leu Tyr Arg Asp Ser Leu Ala Ala
                85                  90                  95

Asn Leu Lys Pro Gly Ala Ala Ile Ala Phe Ala His Gly Leu Asn Ile
            100                 105                 110

His Phe Asn Leu Ile Glu Pro Arg Ala Asp Ile Asp Val Phe Met Ile
        115                 120                 125

Ala Pro Lys Gly Pro Gly His Thr Val Arg Ser Glu Tyr Gln Arg Gly
    130                 135                 140

Gly Gly Val Pro Cys Leu Val Ala Val Ala Gln Asn Pro Ser Gly Asn
145                 150                 155                 160

Ala Leu Asp Ile Ala Leu Ser Tyr Ala Ser Ala Ile Gly Gly Gly Arg
                165                 170                 175

Ala Gly Ile Ile Glu Thr Thr Phe Lys Glu Glu Cys Glu Thr Asp Leu
            180                 185                 190

Phe Gly Glu Gln Thr Val Leu Cys Gly Gly Leu Val Glu Leu Ile Lys
        195                 200                 205

Ala Gly Phe Glu Thr Leu Val Glu Ala Gly Tyr Ala Pro Glu Met Ala
    210                 215                 220

Tyr Phe Glu Cys Leu His Glu Val Lys Leu Ile Val Asp Leu Ile Tyr
225                 230                 235                 240

Glu Gly Gly Ile Ala Asn Met Asn Tyr Ser Ile Ser Asn Thr Ala Glu
                245                 250                 255

Tyr Gly Glu Tyr Val Thr Gly Pro Arg Met Ile Thr Pro Glu Thr Lys
            260                 265                 270

Ala Glu Met Lys Arg Val Leu Asp Asp Ile Gln Lys Gly Arg Phe Thr
        275                 280                 285

Arg Asp Trp Met Leu Glu Asn Lys Val Asn Gln Thr Asn Phe Lys Ala
    290                 295                 300

Met Arg Arg Ala Asn Ala Ala His Pro Ile Glu Glu Val Gly Glu Lys
305                 310                 315                 320

Leu Arg Ala Met Met Pro Trp Ile Lys Lys Gly Ala Leu Val Asp Lys
                325                 330                 335

Thr Arg Asn

<210> SEQ ID NO 6
<211> LENGTH: 555
<212> TYPE: PRT
<213> ORGANISM: Chlamydomonas reinhardtii

```
<400> SEQUENCE: 6

Met Gln Leu Leu Asn Ser Lys Ser Arg Val Leu Ser Gly Ser Arg Gln
1               5                   10                  15

Gln Ala Ala Lys Ala Val Arg Val Ala Pro Ser Gly Arg Arg Ser
            20                  25                  30

Ala Val Arg Val Ser Ala Val His Leu Asp Phe Asn Thr Lys Val
        35                  40                  45

Phe Gln Lys Glu His Ala Lys Phe Gly Pro Thr Glu Glu Tyr Ile Val
    50                  55                  60

Arg Gly Gly Arg Asp Lys Tyr Pro Leu Leu Lys Glu Ala Phe Lys Gly
65                  70                  75                  80

Ile Lys Lys Val Ser Val Ile Gly Trp Gly Ser Gln Ala Pro Ala Gln
                85                  90                  95

Ala Gln Asn Leu Arg Asp Ser Ile Ala Glu Ala Gly Met Asp Ile Lys
            100                 105                 110

Val Ala Ile Gly Leu Arg Pro Asp Ser Pro Ser Trp Ala Glu Ala Glu
        115                 120                 125

Ala Cys Gly Phe Ser Lys Thr Asp Gly Thr Leu Gly Glu Val Phe Glu
    130                 135                 140

Gln Ile Ser Ser Ser Asp Phe Val Ile Leu Leu Ile Ser Asp Ala Ala
145                 150                 155                 160

Gln Ala Lys Leu Tyr Pro Arg Ile Leu Ala Ala Met Lys Pro Gly Ala
                165                 170                 175

Thr Leu Gly Leu Ser His Gly Phe Leu Leu Gly Val Met Arg Asn Asp
            180                 185                 190

Gly Val Asp Phe Arg Lys Asp Ile Asn Val Val Leu Val Ala Pro Lys
        195                 200                 205

Gly Met Gly Pro Ser Val Arg Arg Leu Tyr Glu Gln Gly Lys Ser Val
    210                 215                 220

Asn Gly Ala Gly Ile Asn Cys Ser Phe Ala Ile Gln Gln Asp Ala Thr
225                 230                 235                 240

Gly Gln Ala Ala Asp Ile Ala Ile Gly Trp Ala Ile Gly Val Gly Ala
                245                 250                 255

Pro Phe Ala Phe Pro Thr Thr Leu Glu Ser Glu Tyr Lys Ser Asp Ile
            260                 265                 270

Tyr Gly Glu Arg Cys Val Leu Leu Gly Ala Val His Gly Ile Val Glu
        275                 280                 285

Ala Leu Phe Arg Arg Tyr Thr Arg Gln Gly Met Ser Asp Glu Glu Ala
    290                 295                 300

Phe Lys Gln Ser Val Glu Ser Ile Thr Gly Pro Ile Ser Arg Thr Ile
305                 310                 315                 320

Ser Thr Lys Gly Met Leu Ser Val Tyr Asn Ser Phe Asn Glu Ala Asp
                325                 330                 335

Lys Lys Ile Phe Glu Gln Ala Tyr Ser Ala Ser Tyr Lys Pro Ala Leu
            340                 345                 350

Asp Ile Cys Phe Glu Ile Tyr Glu Asp Val Ala Ser Gly Asn Glu Ile
        355                 360                 365

Lys Ser Val Val Gln Ala Val Gln Arg Phe Asp Arg Phe Pro Met Gly
    370                 375                 380

Lys Ile Asp Gln Thr Tyr Met Trp Lys Val Gly Gln Lys Val Arg Ala
385                 390                 395                 400

Glu Arg Asp Glu Ser Lys Ile Pro Val Asn Pro Phe Thr Ala Gly Val
                405                 410                 415
```

```
Tyr Val Ala Val Met Met Ala Thr Val Glu Val Leu Arg Glu Lys Gly
            420                 425                 430

His Pro Phe Ser Glu Ile Cys Asn Glu Ser Ile Ile Glu Ala Val Asp
            435                 440                 445

Ser Leu Asn Pro Tyr Met His Ala Arg Gly Val Ala Phe Met Val Asp
450                 455                 460

Asn Cys Ser Tyr Thr Ala Arg Leu Gly Ser Arg Lys Trp Ala Pro Arg
465                 470                 475                 480

Phe Asp Tyr Ile Ile Glu Gln Gln Ala Phe Val Asp Ile Asp Ser Gly
                485                 490                 495

Lys Ala Ala Asp Lys Glu Val Met Ala Glu Phe Leu Ala His Pro Val
            500                 505                 510

His Ser Ala Leu Ala Thr Cys Ser Ser Met Arg Pro Ser Val Asp Ile
            515                 520                 525

Ser Val Gly Gly Glu Asn Ser Ser Val Gly Val Gly Ala Gly Ala Ala
            530                 535                 540

Arg Thr Glu Phe Arg Ser Thr Ala Ala Lys Val
545                 550                 555
```

<210> SEQ ID NO 7
<211> LENGTH: 329
<212> TYPE: PRT
<213> ORGANISM: Picrophilus torridus

<400> SEQUENCE: 7

```
Met Glu Lys Val Tyr Thr Glu Asn Asp Leu Lys Glu Asn Leu Met Arg
1               5                   10                  15

Asn Lys Lys Ile Ala Val Leu Gly Tyr Gly Ser Gln Gly Arg Ala Trp
            20                  25                  30

Ala Leu Asn Met Arg Asp Ser Gly Leu Asn Val Thr Val Gly Leu Glu
        35                  40                  45

Arg Gln Gly Lys Ser Trp Glu Lys Ala Val Ala Asp Gly Phe Lys Pro
    50                  55                  60

Leu Lys Ser Arg Asp Ala Val Arg Asp Ala Asp Ala Val Ile Phe Leu
65                  70                  75                  80

Val Pro Asp Met Ala Gln Arg Glu Leu Tyr Lys Asn Ile Met Asn Asp
                85                  90                  95

Ile Lys Asp Asp Ala Asp Ile Val Phe Ala His Gly Phe Asn Val His
            100                 105                 110

Tyr Gly Leu Ile Asn Pro Lys Asn His Asp Val Tyr Met Val Ala Pro
        115                 120                 125

Lys Ala Pro Gly Pro Ser Val Arg Glu Phe Tyr Glu Arg Gly Gly Gly
    130                 135                 140

Val Pro Val Leu Ile Ala Val Ala Asn Asp Val Ser Gly Arg Ser Lys
145                 150                 155                 160

Glu Lys Ala Leu Ser Ile Ala Tyr Ser Leu Gly Ala Leu Arg Ala Gly
                165                 170                 175

Ala Ile Glu Thr Thr Phe Lys Glu Glu Thr Glu Thr Asp Leu Ile Gly
            180                 185                 190

Glu Gln Leu Asp Leu Val Gly Gly Ile Thr Glu Leu Leu Arg Ser Thr
        195                 200                 205

Phe Asn Ile Met Val Glu Met Gly Tyr Lys Pro Glu Met Ala Tyr Phe
    210                 215                 220

Glu Ala Ile Asn Glu Met Lys Leu Ile Val Asp Gln Val Phe Glu Lys
225                 230                 235                 240
```

```
Gly Ile Ser Gly Met Leu Arg Ala Val Ser Asp Thr Ala Lys Tyr Gly
                245                 250                 255

Gly Leu Thr Thr Gly Lys Tyr Ile Ile Asn Asp Val Arg Lys Arg
            260                 265                 270

Met Arg Glu Arg Ala Glu Tyr Ile Val Ser Gly Lys Phe Ala Glu Glu
        275                 280                 285

Trp Ile Glu Glu Tyr Gly Glu Gly Ser Lys Asn Leu Glu Ser Met Met
    290                 295                 300

Leu Asp Ile Asp Asn Ser Leu Glu Glu Gln Val Gly Lys Gln Leu Arg
305                 310                 315                 320

Glu Ile Val Leu Arg Gly Arg Pro Lys
                325

<210> SEQ ID NO 8
<211> LENGTH: 339
<212> TYPE: PRT
<213> ORGANISM: Zymomonas mobilis

<400> SEQUENCE: 8

Met Lys Val Tyr Tyr Asp Ser Asp Ala Asp Leu Gly Leu Ile Lys Ser
1               5                   10                  15

Lys Lys Ile Ala Ile Leu Gly Tyr Gly Ser Gln Gly His Ala His Ala
            20                  25                  30

Gln Asn Leu Arg Asp Ser Gly Val Ala Glu Val Ala Ile Ala Leu Arg
        35                  40                  45

Pro Asp Ser Ala Ser Val Lys Lys Ala Gln Asp Ala Gly Phe Lys Val
    50                  55                  60

Leu Thr Asn Ala Glu Ala Ala Lys Trp Ala Asp Ile Leu Met Ile Leu
65                  70                  75                  80

Ala Pro Asp Glu His Gln Ala Ala Ile Tyr Ala Glu Asp Leu Lys Asp
                85                  90                  95

Asn Leu Arg Pro Gly Ser Ala Ile Ala Phe Ala His Gly Leu Asn Ile
            100                 105                 110

His Phe Gly Leu Ile Glu Pro Arg Lys Asp Ile Asp Val Phe Met Ile
        115                 120                 125

Ala Pro Lys Gly Pro Gly His Thr Val Arg Ser Glu Tyr Val Arg Gly
    130                 135                 140

Gly Gly Val Pro Cys Leu Val Ala Val Asp Gln Asp Ala Ser Gly Asn
145                 150                 155                 160

Ala His Asp Ile Ala Leu Ala Tyr Ala Ser Gly Ile Gly Gly Gly Arg
                165                 170                 175

Ser Gly Val Ile Glu Thr Thr Phe Arg Glu Glu Val Glu Thr Asp Leu
            180                 185                 190

Phe Gly Glu Gln Ala Val Leu Cys Gly Gly Leu Thr Ala Leu Ile Thr
        195                 200                 205

Ala Gly Phe Glu Thr Leu Thr Glu Ala Gly Tyr Ala Pro Glu Met Ala
    210                 215                 220

Phe Phe Glu Cys Met His Glu Met Lys Leu Ile Val Asp Leu Ile Tyr
225                 230                 235                 240

Glu Ala Gly Ile Ala Asn Met Arg Tyr Ser Ile Ser Asn Thr Ala Glu
                245                 250                 255

Tyr Gly Asp Ile Val Ser Gly Pro Arg Val Ile Asn Glu Glu Ser Lys
            260                 265                 270

Lys Ala Met Lys Ala Ile Leu Asp Asp Ile Gln Ser Gly Arg Phe Val
        275                 280                 285
```

```
Ser Lys Phe Val Leu Asp Asn Arg Ala Gly Gln Pro Glu Leu Lys Ala
            290                 295                 300

Ala Arg Lys Arg Met Ala Ala His Pro Ile Glu Gln Val Gly Ala Arg
305                 310                 315                 320

Leu Arg Lys Met Met Pro Trp Ile Ala Ser Asn Lys Leu Val Asp Lys
                325                 330                 335

Ala Arg Asn

<210> SEQ ID NO 9
<211> LENGTH: 10
<212> TYPE: PRT
<213> ORGANISM: Artificial Sequence
<220> FEATURE:
<223> OTHER INFORMATION: c-myc epitope tag

<400> SEQUENCE: 9

Glu Gln Lys Leu Ile Ser Glu Glu Asp Leu
1               5                   10

<210> SEQ ID NO 10
<211> LENGTH: 554
<212> TYPE: PRT
<213> ORGANISM: Thermotoga petrophila

<400> SEQUENCE: 10

Met Arg Ser Asp Val Ile Lys Lys Gly Leu Glu Arg Ala Pro His Arg
1               5                   10                  15

Ser Leu Leu Lys Ala Leu Gly Ile Thr Asp Asp Glu Met Arg Arg Pro
                20                  25                  30

Phe Ile Gly Ile Val Ser Ser Trp Asn Glu Ile Ile Pro Gly His Val
            35                  40                  45

His Leu Asp Lys Val Val Glu Ala Val Lys Ala Gly Val Arg Met Ala
        50                  55                  60

Gly Gly Val Pro Phe Val Phe Pro Thr Ile Gly Ile Cys Asp Gly Ile
65                  70                  75                  80

Ala Met Asp His Arg Gly Met Lys Phe Ser Leu Pro Ser Arg Glu Leu
                85                  90                  95

Ile Ala Asp Ser Ile Glu Ile Val Ala Ser Gly Phe Pro Phe Asp Gly
            100                 105                 110

Leu Val Phe Val Pro Asn Cys Asp Lys Ile Thr Pro Gly Met Met Met
        115                 120                 125

Ala Met Gly Arg Leu Asn Ile Pro Ser Val Leu Ile Ser Gly Gly Pro
130                 135                 140

Met Leu Ala Gly Arg Tyr Asn Gly Arg Asp Ile Asp Leu Ile Thr Val
145                 150                 155                 160

Phe Glu Ala Val Gly Gly Tyr Lys Val Gly Lys Val Asp Glu Glu Thr
                165                 170                 175

Leu Lys Ala Ile Glu Asp Leu Ala Cys Pro Gly Ala Gly Ser Cys Ala
            180                 185                 190

Gly Leu Phe Thr Ala Asn Thr Met Asn Ser Leu Ala Glu Ala Leu Gly
        195                 200                 205

Ile Ala Pro Arg Gly Asn Gly Thr Val Pro Ala Val His Ala Lys Arg
    210                 215                 220

Leu Arg Met Ala Lys Glu Ala Gly Met Leu Val Glu Leu Val Lys
225                 230                 235                 240

Arg Asp Val Lys Pro Arg Asp Ile Val Thr Leu Asp Ser Phe Met Asn
                245                 250                 255
```

```
Ala Val Met Val Asp Leu Ala Thr Gly Gly Ser Thr Asn Thr Val Leu
            260                 265                 270

His Leu Lys Ala Ile Ala Glu Ser Phe Gly Ile Asp Phe Asp Ile Lys
            275                 280                 285

Leu Phe Asp Glu Leu Ser Arg Lys Ile Pro His Ile Cys Asn Ile Ser
            290                 295                 300

Pro Val Gly Pro Tyr His Ile Gln Asp Leu Asp Ala Gly Gly Ile
305                 310                 315                 320

Tyr Ala Val Met Lys Arg Leu Gln Glu Asn Gly Leu Leu Lys Glu Asp
                325                 330                 335

Ala Met Thr Ile Tyr Leu Arg Lys Ile Gly Asp Leu Val Arg Glu Ala
            340                 345                 350

Lys Ile Leu Asn Glu Asp Val Ile Arg Pro Phe Asp Asn Pro Tyr His
            355                 360                 365

Lys Glu Gly Gly Leu Gly Ile Leu Phe Gly Asn Leu Ala Pro Glu Gly
            370                 375                 380

Ala Val Ala Lys Leu Ser Gly Val Pro Glu Lys Met Met His Val
385                 390                 395                 400

Gly Pro Ala Val Val Phe Glu Asp Gly Glu Ala Thr Lys Ala Ile
                405                 410                 415

Leu Ser Gly Lys Ile Lys Lys Gly Asp Val Val Ile Arg Tyr Glu
            420                 425                 430

Gly Pro Lys Gly Gly Pro Gly Met Arg Glu Met Leu Ser Pro Thr Ser
            435                 440                 445

Ala Ile Val Gly Met Gly Leu Ala Glu Asp Val Ala Leu Ile Thr Asp
            450                 455                 460

Gly Arg Phe Ser Gly Gly Ser His Gly Ala Val Ile Gly His Val Ser
465                 470                 475                 480

Pro Glu Ala Ala Glu Gly Gly Pro Ile Gly Ile Val Lys Asp Gly Asp
                485                 490                 495

Leu Ile Glu Ile Asp Phe Glu Lys Arg Thr Leu Asn Leu Leu Ile Ser
            500                 505                 510

Asp Glu Glu Phe Glu Arg Arg Met Lys Glu Phe Thr Pro Leu Val Lys
            515                 520                 525

Glu Val Asp Ser Asp Tyr Leu Arg Arg Tyr Ala Phe Phe Val Gln Ser
530                 535                 540

Ala Ser Lys Gly Ala Ile Phe Arg Lys Pro
545                 550

<210> SEQ ID NO 11
<211> LENGTH: 561
<212> TYPE: PRT
<213> ORGANISM: Victivallis vadensis

<400> SEQUENCE: 11

Met Arg Ser Asp Thr Met Lys Lys Gly Pro Glu Arg Ala Pro His Arg
1               5                   10                  15

Gly Leu Met Arg Ala Thr Gly Leu Lys Lys Glu Asp Phe Asp Lys Pro
            20                  25                  30

Phe Ile Gly Val Cys Asn Ser Tyr Thr Asn Ile Val Pro Gly His Cys
            35                  40                  45

His Leu Lys Lys Val Gly Glu Ile Ile Cys Asp Ala Ile Arg Glu Ala
            50                  55                  60

Gly Gly Val Pro Tyr Glu Phe Asn Thr Ile Ala Val Cys Asp Gly Ile
65                  70                  75                  80
```

```
Ala Met Gly His Lys Gly Met Lys Tyr Ser Leu Ala Ser Arg Glu Ile
                85                  90                  95

Ile Ala Asp Ser Val Glu Thr Met Gly Thr Ala His Pro Phe Asp Ala
            100                 105                 110

Met Ile Cys Ile Pro Asn Cys Asp Lys Val Val Pro Gly Met Leu Met
        115                 120                 125

Gly Ala Met Arg Leu Asn Ile Pro Thr Ile Phe Ala Ser Gly Gly Pro
    130                 135                 140

Met Arg Ala Gly Lys Pro Gln Ala Glu Gly Gly Pro Asp Thr Asp Leu
145                 150                 155                 160

Ile Ser Ile Phe Glu Gly Val Ala Ala Asn Arg Ile Gly Lys Leu Ser
                165                 170                 175

Asp Glu Gly Leu Glu Ala Leu Glu Cys Ser Ala Cys Pro Gly Pro Gly
            180                 185                 190

Ser Cys Ser Gly Met Phe Thr Ala Asn Ser Met Asn Cys Leu Cys Glu
        195                 200                 205

Ala Leu Gly Ile Ala Leu Pro Gly Asn Gly Thr Ile Ala Ala Asp Ser
    210                 215                 220

Pro Glu Arg Val Glu Leu Trp Lys Arg Ala Ala Arg Arg Ala Val Glu
225                 230                 235                 240

Leu Ala Arg Met Glu Asn Pro Pro Thr Ala Lys Asp Phe Ala Thr Pro
                245                 250                 255

Ala Ala Phe Gln Asn Ala Leu Val Leu Asp Met Ala Met Gly Gly Ser
            260                 265                 270

Ser Asn Thr Val Leu His Thr Leu Ala Val Ala Thr Glu Ala Gly Thr
        275                 280                 285

Lys Leu Asp Leu Lys Lys Leu Asp Glu Ile Ser Ala Arg Thr Pro Asn
    290                 295                 300

Ile Cys Lys Leu Ser Pro Ser Val Gln Tyr His Ile Val Glu Asp Gly
305                 310                 315                 320

Asn Arg Val Gly Gly Ile Met Ala Ile Leu Lys Glu Ile Ser Lys Val
                325                 330                 335

Pro Gly Leu Ile Asp Gly Ser Ala Pro Thr Val Ser Gly Lys Thr Leu
            340                 345                 350

Ala Glu Glu Phe Asn Gly Ala Pro Asp Pro Asp Gly Thr Ile Ile Arg
        355                 360                 365

Pro Leu Ser Asn Pro Tyr Ser Glu Lys Gly Gly Leu Ala Ile Leu Phe
    370                 375                 380

Gly Asn Leu Ala Glu Lys Gly Cys Val Val Lys Ala Ala Gly Val Ala
385                 390                 395                 400

Lys Ala Met Leu Thr His Lys Gly Pro Ala Val Ile Phe Asp Ser Glu
                405                 410                 415

Glu Glu Ala Gly Glu Gly Ile Leu Ala Gly Lys Val Lys Ala Gly Asp
            420                 425                 430

Val Val Val Ile Arg Tyr Glu Gly Pro Lys Gly Gly Pro Gly Met Gln
        435                 440                 445

Glu Met Leu Ala Pro Thr Ser Tyr Ile Met Gly Arg Gly Leu Gly Glu
    450                 455                 460

Ser Val Ala Leu Val Thr Asp Gly Arg Phe Ser Gly Gly Thr Arg Gly
465                 470                 475                 480

Ala Cys Ile Gly His Val Ser Pro Glu Ala Ala Gly Gly Leu Ile
                485                 490                 495

Gly Leu Val Glu Pro Gly Asp Ile Ile Glu Ile Asp Ile Pro Asn Arg
            500                 505                 510
```

Ser Ile Lys Leu Asp Val Pro Asp Glu Val Ile Ala Glu Arg Arg Lys
            515                 520                 525

Asn Trp Lys Pro Arg Glu Pro Lys Ile Lys Thr Gly Tyr Leu Ala Lys
            530                 535                 540

Tyr Ala Ser Leu Ala Thr Ser Ala Asp Thr Gly Gly Val Leu Lys Val
545                 550                 555                 560

Asn

<210> SEQ ID NO 12
<211> LENGTH: 549
<212> TYPE: PRT
<213> ORGANISM: Termite Group 1 Bacterium Phylotype Rs-D17

<400> SEQUENCE: 12

Met Arg Ser Asp Gln Ile Lys Arg Gly Ala Val Arg Ala Pro Asn Arg
1               5                   10                  15

Cys Leu Leu Tyr Ser Thr Gly Ile Ser Pro Gly Asp Leu Asp Lys Pro
            20                  25                  30

Phe Ile Gly Ile Ala Ser Ser Phe Thr Asp Leu Val Pro Gly His Val
        35                  40                  45

Ala Met Arg Asp Leu Glu Arg Tyr Val Glu Arg Gly Ile Ala Ala Gly
    50                  55                  60

Gly Gly Val Pro Phe Ile Phe Gly Ala Pro Ala Val Cys Asp Gly Ile
65                  70                  75                  80

Ala Met Gly His Ser Gly Met His Tyr Ser Leu Gly Ser Arg Glu Ile
                85                  90                  95

Ile Ala Asp Leu Val Glu Thr Val Ala Asn Ala His Met Leu Asp Gly
            100                 105                 110

Leu Ile Leu Leu Ser Asn Cys Asp Lys Val Thr Pro Gly Met Leu Met
        115                 120                 125

Ala Ala Ala Arg Leu Asn Ile Pro Ala Ile Val Val Thr Ala Gly Ala
    130                 135                 140

Met Met Thr Gly Met Tyr Asp Lys Lys Arg Arg Ser Met Val Arg Asp
145                 150                 155                 160

Thr Phe Glu Ala Val Gly Gln Phe Gln Ala Gly Lys Ile Thr Glu Lys
                165                 170                 175

Gln Leu Ser Glu Leu Glu Met Ala Ala Cys Pro Gly Ala Gly Ala Cys
            180                 185                 190

Gln Gly Met Tyr Thr Ala Asn Thr Met Ala Cys Leu Thr Glu Thr Met
        195                 200                 205

Gly Met Ser Met Arg Gly Cys Ala Thr Thr Leu Ala Val Ser Ala Lys
    210                 215                 220

Lys Lys Arg Ile Ala Tyr Glu Ser Gly Ile Arg Val Val Ala Leu Val
225                 230                 235                 240

Lys Lys Asp Val Lys Pro Arg Asp Ile Leu Thr Leu Ala Ala Phe Lys
                245                 250                 255

Asn Ala Ile Val Ala Asp Met Ala Leu Gly Gly Ser Thr Asn Thr Val
            260                 265                 270

Leu His Leu Pro Ala Ile Ala Asn Glu Ala Gly Ile Glu Leu Pro Leu
        275                 280                 285

Glu Leu Phe Asp Glu Ile Ser Lys Lys Thr Pro Gln Ile Ala Cys Leu
    290                 295                 300

Glu Pro Ala Gly Asp His Tyr Met Glu Asp Leu Asp Asn Ala Gly Gly
305                 310                 315                 320

```
Ile Pro Ala Val Leu Phe Ala Ile Gln Lys Asn Leu Ala His Ser Lys
                325                 330                 335

Thr Val Ser Gly Phe Asp Ile Ile Glu Ile Ala Asn Ser Ala Glu Ile
            340                 345                 350

Leu Asp Glu Tyr Val Ile Arg Ala Lys Asn Pro Tyr Lys Pro Glu Gly
        355                 360                 365

Gly Ile Ala Ile Leu Arg Gly Asn Ile Ala Pro Arg Gly Cys Val Val
    370                 375                 380

Lys Gln Ala Ala Val Ser Glu Lys Met Lys Val Phe Ser Gly Arg Ala
385                 390                 395                 400

Arg Val Phe Asn Ser Glu Asp Asn Ala Met Lys Ala Ile Leu Asp Asn
                405                 410                 415

Lys Ile Val Pro Gly Asp Ile Val Val Ile Arg Tyr Glu Gly Pro Ala
            420                 425                 430

Gly Gly Pro Gly Met Arg Glu Met Leu Ser Pro Thr Ser Ala Leu His
        435                 440                 445

Gly Met Gly Leu Ser Asp Ser Val Ala Leu Leu Thr Asp Gly Arg Phe
    450                 455                 460

Ser Gly Gly Thr Arg Gly Pro Cys Ile Gly His Ile Ser Pro Glu Ala
465                 470                 475                 480

Ala Ala Asp Gly Ala Ile Val Ala Ile Asn Glu Gly Asp Thr Ile Asn
                485                 490                 495

Ile Asn Ile Pro Glu Arg Thr Leu Asn Val Glu Leu Thr Asp Asp Glu
            500                 505                 510

Ile Lys Ala Arg Ile Gly Lys Val Ile Lys Pro Glu Pro Lys Ile Lys
        515                 520                 525

Thr Gly Tyr Met Ala Arg Tyr Ala Lys Leu Val Gln Ser Ala Asp Thr
    530                 535                 540

Gly Ala Val Leu Lys
545

<210> SEQ ID NO 13
<211> LENGTH: 573
<212> TYPE: PRT
<213> ORGANISM: Yarrowia lipolytica

<400> SEQUENCE: 13

Met Ile Arg Ala Arg Asn Tyr Ala Thr Lys Ala His Thr Leu Asn Lys
1               5                   10                  15

Phe Ser Lys Ile Ile Thr Glu Pro Lys Ser Gln Gly Ala Ser Gln Ala
            20                  25                  30

Met Leu Tyr Ala Cys Gly Phe Asn Glu Ala Asp Leu Gly Lys Pro Gln
        35                  40                  45

Val Gly Val Ala Ser Val Trp Trp Ser Gly Asn Pro Cys Asn Met His
    50                  55                  60

Leu Leu Asp Leu Asn Phe Lys Val Lys Glu Gly Ile Glu Lys His Asn
65                  70                  75                  80

Leu Lys Ala Met Gln Phe Asn Thr Ile Gly Val Ser Asp Gly Ile Ser
                85                  90                  95

Met Gly Thr Lys Gly Met Arg Tyr Ser Leu Gln Ser Arg Asp Met Ile
            100                 105                 110

Ala Asp Ser Ile Glu Thr Leu Met Met Ala Gln His Tyr Asp Ala Asn
        115                 120                 125

Ile Ser Ile Pro Gly Cys Asp Lys Asn Met Pro Gly Val Leu Met Ala
    130                 135                 140
```

```
Met Gly Arg Val Asn Arg Pro Ser Ile Met Leu Tyr Gly Gly Thr Ile
145                 150                 155                 160

His Pro Gly Lys Ala Glu Thr Arg Lys Gly Asp Ile Asp Ile Val
            165                 170                 175

Ser Ala Phe Gln Ala Tyr Gly Gln Tyr Ile Ala Gly Gly Ile Ser Glu
            180                 185                 190

Thr Glu Arg Ala Asp Val Ile Arg His Ala Cys Pro Gly Gln Gly Ala
            195                 200                 205

Cys Gly Gly Met Tyr Thr Ala Asn Thr Met Ala Ser Ala Ala Glu Val
210                 215                 220

Leu Gly Met Thr Leu Pro Gly Ser Ser Ala Pro Ala Ile Ser Lys
225                 230                 235                 240

Glu Lys Met Ala Glu Cys Glu Ala Leu Gly Pro Ala Ile Asn Lys Leu
                245                 250                 255

Leu Glu Met Asp Leu Lys Pro Lys Asp Ile Met Thr Arg Gln Ala Phe
            260                 265                 270

Glu Asn Ala Ile Ala Tyr Ile Ile Ala Thr Gly Gly Ser Thr Asn Ala
            275                 280                 285

Val Leu His Leu Leu Ala Ile Ala His Thr Val Asp Val Pro Leu Thr
    290                 295                 300

Ile Asp Asp Phe Gln Arg Ile Ser Asp Asn Thr Pro Leu Leu Ala Asp
305                 310                 315                 320

Phe Lys Pro Ser Gly Ala His Val Met Ala Asp Leu Gln Lys Trp Gly
            325                 330                 335

Gly Thr Pro Ala Val Ile Lys Met Leu Ile Glu Gln Gly Phe Ile Asp
            340                 345                 350

Gly Ser Pro Met Thr Cys Ser Gly Glu Ser Leu Lys Asp Thr Val Ala
            355                 360                 365

Lys Tyr Pro Ser Leu Pro Lys Glu Gln Asp Ile Phe Ala Ser Val Asp
            370                 375                 380

Ala Pro Leu Lys Pro Ser Gly His Leu Gln Ile Leu Lys Gly Ser Leu
385                 390                 395                 400

Ala Pro Gly Gly Ser Val Gly Lys Ile Thr Gly Lys Glu Gly Thr Phe
            405                 410                 415

Phe Lys Gly Thr Ala Arg Cys Phe Asp Glu Glu Asp Leu Phe Ile Glu
            420                 425                 430

Ala Leu Glu Lys Gly Glu Ile Lys Lys Gly Glu Lys Thr Cys Val Ile
            435                 440                 445

Ile Arg Tyr Glu Gly Pro Lys Gly Gly Pro Gly Met Pro Glu Met Leu
            450                 455                 460

Lys Pro Ser Ser Ala Leu Met Gly Tyr Gly Leu Gly Lys Asp Val Ala
465                 470                 475                 480

Leu Leu Thr Asp Gly Arg Phe Ser Gly Gly Ser His Gly Phe Leu Ile
            485                 490                 495

Gly His Ile Val Pro Glu Ala Tyr Glu Gly Gly Pro Ile Gly Leu Val
            500                 505                 510

Glu Asp Gly Asp Glu Ile Ile Ile Asp Ala Asp Asn Asn Ile Ile Asp
            515                 520                 525

Leu Leu Val Asp Glu Lys Thr Met Ala Glu Arg Lys Ala Lys Trp Thr
530                 535                 540

Pro Pro Ala Pro Arg Tyr Thr Ser Gly Thr Leu His Lys Tyr Ser Lys
545                 550                 555                 560

Leu Val Ser Asp Ala Ser Thr Gly Cys Ile Thr Asp Ala
            565                 570
```

<210> SEQ ID NO 14
<211> LENGTH: 560
<212> TYPE: PRT
<213> ORGANISM: Francisella tularensis

<400> SEQUENCE: 14

Met Lys Lys Val Leu Asn Lys Tyr Ser Arg Arg Leu Thr Glu Asp Lys
1               5                   10                  15

Ser Gln Gly Ala Ser Gln Ala Met Leu Tyr Gly Thr Glu Met Asn Asp
            20                  25                  30

Ala Asp Met His Lys Pro Gln Ile Gly Ile Gly Ser Val Trp Tyr Glu
        35                  40                  45

Gly Asn Thr Cys Asn Met His Leu Asn Gln Leu Ala Gln Phe Val Lys
    50                  55                  60

Asp Ser Val Glu Lys Glu Asn Leu Lys Gly Met Arg Phe Asn Thr Ile
65                  70                  75                  80

Gly Val Ser Asp Gly Ile Ser Met Gly Thr Asp Gly Met Ser Tyr Ser
                85                  90                  95

Leu Gln Ser Arg Asp Leu Ile Ala Asp Ser Ile Glu Thr Val Met Ser
            100                 105                 110

Ala His Trp Tyr Asp Gly Leu Val Ser Ile Pro Gly Cys Asp Lys Asn
        115                 120                 125

Met Pro Gly Cys Met Met Ala Leu Gly Arg Leu Asn Arg Pro Gly Phe
    130                 135                 140

Val Ile Tyr Gly Gly Thr Ile Gln Ala Gly Val Met Arg Gly Lys Pro
145                 150                 155                 160

Ile Asp Ile Val Thr Ala Phe Gln Ser Tyr Gly Ala Cys Leu Ser Gly
                165                 170                 175

Gln Ile Thr Glu Gln Glu Arg Gln Glu Thr Ile Lys Lys Ala Cys Pro
            180                 185                 190

Gly Ala Gly Ala Cys Gly Gly Met Tyr Thr Ala Asn Thr Met Ala Cys
        195                 200                 205

Ala Ile Glu Ala Leu Gly Met Ser Leu Pro Phe Ser Ser Ser Thr Ser
    210                 215                 220

Ala Thr Ser Val Glu Lys Val Gln Glu Cys Asp Lys Ala Gly Glu Thr
225                 230                 235                 240

Ile Lys Asn Leu Leu Glu Leu Asp Ile Lys Pro Arg Asp Ile Met Thr
                245                 250                 255

Arg Lys Ala Phe Glu Asn Ala Met Val Leu Ile Thr Val Met Gly Gly
            260                 265                 270

Ser Thr Asn Ala Val Leu His Leu Leu Ala Met Ala Ser Ser Val Asp
        275                 280                 285

Val Asp Leu Ser Ile Asp Asp Phe Gln Glu Ile Ala Asn Lys Thr Pro
    290                 295                 300

Val Leu Ala Asp Phe Lys Pro Ser Gly Lys Tyr Val Met Ala Asn Leu
305                 310                 315                 320

His Ala Ile Gly Gly Thr Pro Ala Val Met Lys Met Leu Leu Lys Ala
                325                 330                 335

Gly Met Leu His Gly Asp Cys Leu Thr Val Thr Gly Lys Thr Leu Ala
            340                 345                 350

Glu Asn Leu Glu Asn Val Ala Asp Leu Pro Glu Asp Asn Thr Ile Ile
        355                 360                 365

His Lys Leu Asp Asn Pro Ile Lys Lys Thr Gly His Leu Gln Ile Leu
    370                 375                 380

Lys Gly Asn Val Ala Pro Glu Gly Ser Val Ala Lys Ile Thr Gly Lys
385                 390                 395                 400

Glu Gly Glu Ile Phe Glu Gly Val Ala Asn Val Phe Asp Ser Glu Glu
            405                 410                 415

Glu Met Val Ala Val Glu Thr Gly Lys Val Lys Lys Gly Asp Val
        420                 425                 430

Ile Val Ile Arg Tyr Glu Gly Pro Lys Gly Gly Pro Gly Met Pro Glu
        435                 440                 445

Met Leu Lys Pro Thr Ser Leu Ile Met Gly Ala Gly Leu Gly Gln Asp
    450                 455                 460

Val Ala Leu Ile Thr Asp Gly Arg Phe Ser Gly Ser His Gly Phe
465                 470                 475                 480

Ile Val Gly His Ile Thr Pro Glu Ala Tyr Glu Gly Met Ile Ala
            485                 490                 495

Leu Leu Glu Asn Gly Asp Lys Ile Thr Ile Asp Ala Ile Asn Asn Val
            500                 505                 510

Ile Asn Val Asp Leu Ser Asp Gln Glu Ile Ala Gln Arg Lys Ser Lys
        515                 520                 525

Trp Arg Ala Ser Lys Gln Lys Ala Ser Arg Gly Thr Leu Lys Lys Tyr
    530                 535                 540

Ile Lys Thr Val Ser Ser Ala Ser Thr Gly Cys Val Thr Asp Leu Asp
545                 550                 555                 560

<210> SEQ ID NO 15
<211> LENGTH: 581
<212> TYPE: PRT
<213> ORGANISM: Arabidopsis thaliana

<400> SEQUENCE: 15

Met Pro Ser Ile Ile Ser Cys Ser Ala Gln Ser Val Thr Ala Asp Pro
1               5                   10                  15

Ser Pro Pro Ile Thr Asp Thr Asn Lys Leu Asn Lys Tyr Ser Ser Arg
            20                  25                  30

Ile Thr Glu Pro Lys Ser Gln Gly Gly Ser Gln Ala Ile Leu His Gly
        35                  40                  45

Val Gly Leu Ser Asp Asp Asp Leu Leu Lys Pro Gln Ile Gly Ile Ser
    50                  55                  60

Ser Val Trp Tyr Glu Gly Asn Thr Cys Asn Met His Leu Leu Lys Leu
65              70                  75                  80

Ser Glu Ala Val Lys Glu Gly Val Glu Asn Ala Gly Met Val Gly Phe
            85                  90                  95

Arg Phe Asn Thr Ile Gly Val Ser Asp Ala Ile Ser Met Gly Thr Arg
        100                 105                 110

Gly Met Cys Phe Ser Leu Gln Ser Arg Asp Leu Ile Ala Asp Ser Ile
    115                 120                 125

Glu Thr Val Met Ser Ala Gln Trp Tyr Asp Gly Asn Ile Ser Ile Pro
130                 135                 140

Gly Cys Asp Lys Asn Met Pro Gly Thr Ile Met Ala Met Gly Arg Leu
145                 150                 155                 160

Asn Arg Pro Gly Ile Met Val Tyr Gly Gly Thr Ile Lys Pro Gly His
            165                 170                 175

Phe Gln Asp Lys Thr Tyr Asp Ile Val Ser Ala Phe Gln Ser Tyr Gly
        180                 185                 190

Glu Phe Val Ser Gly Ser Ile Ser Asp Glu Gln Arg Lys Thr Val Leu
    195                 200                 205

His His Ser Cys Pro Gly Ala Gly Ala Cys Gly Gly Met Tyr Thr Ala
    210                 215                 220

Asn Thr Met Ala Ser Ala Ile Gly Ala Met Gly Met Ser Leu Pro Tyr
225                 230                 235                 240

Ser Ser Ser Ile Pro Ala Glu Asp Pro Leu Lys Leu Asp Glu Cys Arg
                245                 250                 255

Leu Ala Gly Lys Tyr Leu Leu Glu Leu Leu Lys Met Asp Leu Lys Pro
            260                 265                 270

Arg Asp Ile Ile Thr Pro Lys Ser Leu Arg Asn Ala Met Val Ser Val
        275                 280                 285

Met Ala Leu Gly Gly Ser Thr Asn Ala Val Leu His Leu Ile Ala Ile
    290                 295                 300

Ala Arg Ser Val Gly Leu Glu Leu Thr Leu Asp Asp Phe Gln Lys Val
305                 310                 315                 320

Ser Asp Ala Val Pro Phe Leu Ala Asp Leu Lys Pro Ser Gly Lys Tyr
                325                 330                 335

Val Met Glu Asp Ile His Lys Ile Gly Gly Thr Pro Ala Val Leu Arg
            340                 345                 350

Tyr Leu Leu Glu Leu Gly Leu Met Asp Gly Asp Cys Met Thr Val Thr
        355                 360                 365

Gly Gln Thr Leu Ala Gln Asn Leu Glu Asn Val Pro Ser Leu Thr Glu
    370                 375                 380

Gly Gln Glu Ile Ile Arg Pro Leu Ser Asn Pro Ile Lys Glu Thr Gly
385                 390                 395                 400

His Ile Gln Ile Leu Arg Gly Asp Leu Ala Pro Asp Gly Ser Val Ala
                405                 410                 415

Lys Ile Thr Gly Lys Glu Gly Leu Tyr Phe Ser Gly Pro Ala Leu Val
            420                 425                 430

Phe Glu Gly Glu Glu Ser Met Leu Ala Ala Ile Ser Ala Asp Pro Met
        435                 440                 445

Ser Phe Lys Gly Thr Val Val Ile Arg Gly Glu Gly Pro Lys Gly
    450                 455                 460

Gly Pro Gly Met Pro Glu Met Leu Thr Pro Thr Ser Ala Ile Met Gly
465                 470                 475                 480

Ala Gly Leu Gly Lys Glu Cys Ala Leu Leu Thr Asp Gly Arg Phe Ser
                485                 490                 495

Gly Gly Ser His Gly Phe Val Val Gly His Ile Cys Pro Glu Ala Gln
            500                 505                 510

Glu Gly Gly Pro Ile Gly Leu Ile Lys Asn Gly Asp Ile Ile Thr Ile
        515                 520                 525

Asp Ile Gly Lys Lys Arg Ile Asp Thr Gln Val Ser Pro Glu Glu Met
    530                 535                 540

Asn Asp Arg Arg Lys Lys Trp Thr Ala Pro Ala Tyr Lys Val Asn Arg
545                 550                 555                 560

Gly Val Leu Tyr Lys Tyr Ile Lys Asn Val Gln Ser Ala Ser Asp Gly
                565                 570                 575

Cys Val Thr Asp Glu
            580

<210> SEQ ID NO 16
<211> LENGTH: 573
<212> TYPE: PRT
<213> ORGANISM: Candidatus Koribacter versatilis

<400> SEQUENCE: 16

```
Met Thr Glu Lys Ser Pro Lys Pro His Lys Arg Ser Asp Ala Ile Thr
1               5                   10                  15
Glu Gly Pro Asn Arg Ala Pro Ala Arg Ala Met Leu Arg Ala Ala Gly
            20                  25                  30
Phe Thr Pro Glu Asp Leu Arg Lys Pro Ile Ile Gly Ile Ala Asn Thr
        35                  40                  45
Trp Ile Glu Ile Gly Pro Cys Asn Leu His Leu Arg Glu Leu Ala Glu
50                  55                  60
His Ile Lys Gln Gly Val Arg Glu Ala Gly Gly Thr Pro Met Glu Phe
65                  70                  75                  80
Asn Thr Val Ser Ile Ser Asp Gly Ile Thr Met Gly Ser Glu Gly Met
                85                  90                  95
Lys Ala Ser Leu Val Ser Arg Glu Val Ile Ala Asp Ser Ile Glu Leu
                100                 105                 110
Val Ala Arg Gly Asn Leu Phe Asp Gly Leu Ile Ala Leu Ser Gly Cys
            115                 120                 125
Asp Lys Thr Ile Pro Gly Thr Ile Met Ala Leu Glu Arg Leu Asp Ile
        130                 135                 140
Pro Gly Leu Met Leu Tyr Gly Gly Ser Ile Ala Pro Gly Lys Phe His
145                 150                 155                 160
Ala Gln Lys Val Thr Ile Gln Asp Val Phe Glu Ala Val Gly Thr His
                165                 170                 175
Ala Arg Gly Lys Met Ser Asp Ala Asp Leu Glu Glu Leu Glu His Asn
                180                 185                 190
Ala Cys Pro Gly Ala Gly Ala Cys Gly Gly Gln Phe Thr Ala Asn Thr
            195                 200                 205
Met Ser Met Cys Gly Glu Phe Leu Gly Ile Ser Pro Met Gly Ala Asn
        210                 215                 220
Ser Val Pro Ala Met Thr Val Glu Lys Gln Gln Val Ala Arg Arg Cys
225                 230                 235                 240
Gly His Leu Val Met Glu Leu Val Arg Arg Asp Ile Arg Pro Ser Gln
                245                 250                 255
Ile Ile Thr Arg Lys Ala Ile Glu Asn Ala Ile Ala Ser Val Ala Ala
                260                 265                 270
Ser Gly Gly Ser Thr Asn Ala Val Leu His Leu Leu Ala Ile Ala His
            275                 280                 285
Glu Met Asp Val Glu Leu Asn Ile Glu Asp Phe Asp Lys Ile Ser Ser
        290                 295                 300
Arg Thr Pro Leu Leu Cys Glu Leu Lys Pro Ala Gly Arg Phe Thr Ala
305                 310                 315                 320
Thr Asp Leu His Asp Ala Gly Gly Ile Pro Leu Val Ala Gln Arg Leu
                325                 330                 335
Leu Glu Ala Asn Leu Leu His Ala Asp Ala Leu Thr Val Thr Gly Lys
                340                 345                 350
Thr Ile Ala Glu Glu Ala Lys Gln Ala Lys Glu Thr Pro Gly Gln Glu
            355                 360                 365
Val Val Arg Pro Leu Thr Asp Pro Ile Lys Ala Thr Gly Gly Leu Met
        370                 375                 380
Ile Leu Lys Gly Asn Leu Ala Ser Glu Gly Cys Val Val Lys Leu Val
385                 390                 395                 400
Gly His Lys Lys Leu Phe Phe Glu Gly Pro Ala Arg Val Phe Glu Ser
                405                 410                 415
Glu Glu Glu Ala Phe Ala Gly Val Glu Asp Arg Thr Ile Gln Ala Gly
```

```
                420                 425                 430
Glu Val Val Val Arg Tyr Glu Gly Pro Lys Gly Gly Pro Gly Met
            435                 440                 445

Arg Glu Met Leu Gly Val Thr Ala Ala Ile Ala Gly Thr Glu Leu Ala
450                 455                 460

Glu Thr Val Ala Leu Ile Thr Asp Gly Arg Phe Ser Gly Ala Thr Arg
465                 470                 475                 480

Gly Leu Ser Val Gly His Val Ala Pro Glu Ala Asn Gly Gly Ala
            485                 490                 495

Ile Ala Val Val Arg Asn Gly Asp Ile Ile Thr Leu Asp Val Glu Arg
            500                 505                 510

Arg Glu Leu Arg Val His Leu Thr Asp Ala Glu Leu Glu Ala Arg Leu
            515                 520                 525

Arg Asn Trp Arg Ala Pro Glu Pro Arg Tyr Lys Arg Gly Val Phe Ala
            530                 535                 540

Lys Tyr Ala Ser Thr Val Ser Ser Ala Ser Phe Gly Ala Val Thr Gly
545                 550                 555                 560

Ser Thr Ile Glu Asn Lys Thr Leu Ala Gly Ser Thr Lys
                565                 570

<210> SEQ ID NO 17
<211> LENGTH: 562
<212> TYPE: PRT
<213> ORGANISM: Gramella forsetii

<400> SEQUENCE: 17

Met Asp Lys Thr Ala Met Asn Asn Lys Tyr Ser Ser Thr Ile Thr Gln
1               5                   10                  15

Ser Asp Ser Gln Pro Ala Ser Gln Ala Met Leu His Ala Ile Gly Leu
            20                  25                  30

Asn Lys Glu Asp Leu Lys Lys Pro Phe Val Gly Ile Gly Ser Thr Gly
            35                  40                  45

Tyr Glu Gly Asn Pro Cys Asn Met His Leu Asn Asp Leu Ala Lys Glu
    50                  55                  60

Val Lys Lys Gly Thr Gln Asn Ala Asp Leu Asn Gly Leu Ile Phe Asn
65                  70                  75                  80

Thr Ile Gly Val Ser Asp Gly Ile Ser Met Gly Thr Pro Gly Met Arg
                85                  90                  95

Phe Ser Leu Pro Ser Arg Asp Leu Ile Ala Asp Ser Met Glu Thr Val
            100                 105                 110

Val Gly Gly Met Ser Tyr Asp Gly Leu Val Thr Val Gly Cys Asp
            115                 120                 125

Lys Asn Met Pro Gly Ala Leu Met Ala Met Leu Arg Leu Asn Arg Pro
    130                 135                 140

Ser Val Leu Val Tyr Gly Gly Thr Ile Ala Ser Gly Cys His Asn Gly
145                 150                 155                 160

Lys Lys Leu Asp Val Val Ser Ala Phe Glu Ala Trp Gly Ser Lys Val
            165                 170                 175

Ser Gly Asp Met Gln Glu Glu Glu Tyr Gln Gln Val Ile Glu Lys Ala
            180                 185                 190

Cys Pro Gly Ala Gly Ala Cys Gly Gly Met Tyr Thr Ala Asn Thr Met
    195                 200                 205

Ala Ser Ser Ile Glu Ala Leu Gly Met Ser Leu Pro Phe Asn Ser Ser
210                 215                 220

Asn Pro Ala Thr Gly Pro Glu Lys Thr Gln Glu Ser Val Lys Ala Gly
```

```
                225                 230                 235                 240
Glu Ala Met Lys Tyr Leu Leu Glu Asn Asp Leu Lys Pro Lys Asp Ile
            245                 250                 255

Val Thr Ala Lys Ser Leu Glu Asn Ala Ile Arg Leu Leu Thr Val Leu
        260                 265                 270

Gly Gly Ser Thr Asn Ala Val Leu His Phe Leu Ala Ile Ala Lys Ala
    275                 280                 285

Ala Glu Ile Asn Phe Gly Leu Lys Asp Phe Thr Arg Ile Cys Glu Glu
290                 295                 300

Thr Pro Phe Leu Ala Asp Leu Lys Pro Ser Gly Lys Tyr Leu Met Glu
305                 310                 315                 320

Asp Ile His Arg Ile Gly Gly Ile Pro Ala Val Met Lys Tyr Met Leu
                325                 330                 335

Glu Lys Gly Leu Leu His Gly Glu Cys Met Thr Val Thr Gly Lys Thr
            340                 345                 350

Ile Ala Glu Asn Leu Glu Asn Val Lys Pro Leu Pro Asp Asp Gln Asp
        355                 360                 365

Val Ile His Pro Val Glu Lys Pro Ile Lys Ala Thr Gly His Ile Arg
    370                 375                 380

Ile Leu Tyr Gly Asn Leu Ala Ser Glu Gly Ser Val Ala Lys Ile Thr
385                 390                 395                 400

Gly Lys Glu Gly Leu Glu Phe Gln Gly Lys Ala Arg Val Phe Asn Gly
                405                 410                 415

Glu Phe Glu Ala Asn Glu Gly Ile Ser Ser Gly Lys Val Gln Lys Gly
            420                 425                 430

Asp Val Val Ile Arg Tyr Glu Gly Pro Lys Gly Gly Pro Gly Met
        435                 440                 445

Pro Glu Met Leu Lys Pro Thr Ser Ala Ile Met Gly Ala Gly Leu Gly
    450                 455                 460

Lys Ser Val Ala Leu Ile Thr Asp Gly Arg Phe Ser Gly Gly Thr His
465                 470                 475                 480

Gly Phe Val Val Gly His Ile Thr Pro Glu Ala Gln Gln Gly Gly Leu
                485                 490                 495

Ile Gly Leu Leu Lys Asp Gly Asp Glu Ile Ser Ile Asn Ala Glu Lys
            500                 505                 510

Asn Thr Ile Glu Ala His Leu Ser Ala Glu Ile Asn Arg Arg Lys
        515                 520                 525

Glu Ala Trp Lys Ala Pro Ala Leu Lys Val Asn Gly Gly Val Leu Tyr
    530                 535                 540

Lys Tyr Ala Lys Thr Val Ala Ser Ala Ser Glu Gly Cys Val Thr Asp
545                 550                 555                 560

Glu Phe

<210> SEQ ID NO 18
<211> LENGTH: 570
<212> TYPE: PRT
<213> ORGANISM: Lactococcus lactis

<400> SEQUENCE: 18

Met Glu Phe Lys Tyr Asn Gly Lys Val Glu Ser Val Glu Leu Asn Lys
1               5                   10                  15

Tyr Ser Lys Thr Leu Thr Gln Asp Pro Thr Gln Pro Ala Thr Gln Ala
            20                  25                  30

Met Tyr Tyr Gly Ile Gly Phe Lys Asp Glu Asp Phe Lys Lys Ala Gln
        35                  40                  45
```

-continued

Val Gly Ile Val Ser Met Asp Trp Asp Gly Asn Pro Cys Asn Met His
       50                  55                  60

Leu Gly Thr Leu Gly Ser Lys Ile Lys Ser Ser Val Asn Gln Thr Asp
 65                  70                  75                  80

Gly Leu Ile Gly Leu Gln Phe His Thr Ile Gly Val Ser Asp Gly Ile
                 85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125

Ile Val Ala Ile Pro Gly Cys Asp Lys Asn Met Pro Gly Ser Ile Ile
    130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ser Leu Gly Gln Lys Ile Thr Gly Asn Ile Ser Asp Glu Asp
                180                 185                 190

Tyr His Gly Val Ile Cys Asn Ala Ile Pro Gly Gln Gly Ala Cys Gly
            195                 200                 205

Gly Met Tyr Thr Ala Asn Thr Leu Ala Ala Ala Ile Glu Thr Leu Gly
    210                 215                 220

Met Ser Leu Pro Tyr Ser Ser Asn Pro Ala Val Ser Gln Glu Lys
225                 230                 235                 240

Gln Glu Glu Cys Asp Glu Ile Gly Leu Ala Ile Lys Asn Leu Leu Glu
                245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
        275                 280                 285

His Ile Ile Ala Met Ala Asn Ala Ile Gly Val Glu Ile Thr Gln Asp
    290                 295                 300

Asp Phe Gln Arg Ile Ser Asp Ile Thr Pro Val Leu Gly Asp Phe Lys
305                 310                 315                 320

Pro Ser Gly Lys Tyr Met Met Glu Asp Leu His Lys Ile Gly Gly Leu
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
        355                 360                 365

Leu Asp Leu Asp Phe Asp Ser Gln Asp Ile Met Arg Pro Leu Lys Asn
    370                 375                 380

Pro Ile Lys Ala Thr Gly His Leu Gln Ile Leu Tyr Gly Asn Leu Ala
385                 390                 395                 400

Gln Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430

Ile Glu Ser Gly Arg Leu His Ala Gly Asp Val Ala Val Ile Arg Asn
        435                 440                 445

Ile Gly Pro Val Gly Gly Pro Gly Met Pro Glu Met Leu Lys Pro Thr
    450                 455                 460

Ser Ala Leu Ile Gly Ala Gly Leu Gly Lys Ser Cys Ala Leu Ile Thr

```
                465                 470                 475                 480
Asp Gly Arg Phe Ser Gly Gly Thr His Gly Phe Val Val Gly His Ile
                    485                 490                 495

Val Pro Glu Ala Val Glu Gly Gly Leu Ile Gly Leu Val Glu Asp Asp
                500                 505                 510

Asp Ile Ile Glu Ile Asp Ala Val Asn Asn Ser Ile Ser Leu Lys Val
            515                 520                 525

Ser Asp Glu Glu Ile Ala Lys Arg Arg Ala Asn Tyr Gln Lys Pro Thr
        530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                    565                 570

<210> SEQ ID NO 19
<211> LENGTH: 568
<212> TYPE: PRT
<213> ORGANISM: Saccharopolyspora erythraea

<400> SEQUENCE: 19

Met Ser Thr Ser Thr Asp Gly Thr Gly Gln Ser Gly Arg Gly Leu Lys
1               5                   10                  15

Pro Arg Ser Gly Asp Val Thr Glu Gly Ile Glu Arg Ala Ala Ala Arg
            20                  25                  30

Gly Met Leu Arg Ala Val Gly Met Gln Asp Ala Asp Phe Ala Lys Pro
        35                  40                  45

Gln Ile Gly Val Ala Ser Ser Trp Asn Glu Ile Thr Pro Cys Asn Leu
    50                  55                  60

Ser Leu Gln Arg Leu Ala Gln Ala Ser Lys Glu Gly Val His Ala Ala
65                  70                  75                  80

Gly Gly Phe Pro Met Glu Phe Gly Thr Ile Ser Val Ser Asp Gly Ile
                85                  90                  95

Ser Met Gly His Val Gly Met His Tyr Ser Leu Val Ser Arg Glu Val
            100                 105                 110

Ile Ala Asp Ser Val Glu Thr Val Met Glu Ala Glu Arg Leu Asp Gly
        115                 120                 125

Ser Val Leu Leu Ala Gly Cys Asp Lys Ser Leu Pro Gly Met Leu Met
    130                 135                 140

Ala Ala Ala Arg Leu Asp Val Ala Ala Val Phe Val Tyr Ala Gly Ser
145                 150                 155                 160

Ile Leu Pro Gly Arg Val Asp Asp Arg Glu Val Thr Ile Ile Asp Ala
                165                 170                 175

Phe Glu Ala Val Gly Ala Cys Ala Arg Gly Leu Ile Ser Glu Ala Glu
            180                 185                 190

Val Asp Arg Ile Glu Arg Ala Ile Cys Pro Gly Glu Gly Ala Cys Gly
        195                 200                 205

Gly Met Tyr Thr Ala Asn Thr Met Ala Cys Ala Ala Glu Ala Met Gly
    210                 215                 220

Met Ser Leu Pro Gly Ser Ala Ser Pro Pro Ser Val Asp Arg Arg Arg
225                 230                 235                 240

Asp Ala Gly Ala Arg Glu Ala Gly Arg Ala Val Val Gly Met Ile Glu
                245                 250                 255

Arg Gly Leu Thr Ala Arg Gln Ile Leu Thr Lys Glu Ala Phe Glu Asn
            260                 265                 270

Ala Ile Ala Val Val Met Ala Phe Gly Gly Ser Thr Asn Ala Val Leu
```

```
                 275                 280                 285
His Leu Leu Ala Ile Ala Arg Glu Ala Glu Val Asp Leu Thr Leu Asp
    290                 295                 300

Asp Phe Asn Arg Ile Gly Asp Arg Val Pro His Leu Ala Asp Val Lys
305                 310                 315                 320

Pro Phe Gly Arg His Val Met Thr Ala Val Asp Arg Ile Gly Gly Val
                325                 330                 335

Pro Val Val Met Lys Ala Leu Leu Asp Ala Gly Leu Leu His Gly Asp
            340                 345                 350

Cys Met Thr Val Thr Gly Lys Thr Val Ala Glu Asn Leu Ala Glu Leu
        355                 360                 365

Asp Pro Pro Glu Leu Asp Gly Glu Val Leu His Lys Leu Ser Asn Pro
    370                 375                 380

Leu His Pro Thr Gly Gly Leu Thr Ile Leu Arg Gly Ser Leu Ala Pro
385                 390                 395                 400

Glu Gly Ala Val Val Lys Ser Ala Gly Phe Asp Ser Ala Thr Phe Glu
                405                 410                 415

Gly Thr Ala Arg Val Phe Asp Gly Glu Gln Gly Ala Met Asp Ala Val
            420                 425                 430

Glu Asp Gly Ser Leu Lys Ala Gly Asp Val Val Ile Arg Tyr Glu
        435                 440                 445

Gly Pro Arg Gly Gly Pro Gly Met Arg Glu Met Leu Ala Val Thr Gly
    450                 455                 460

Ala Ile Lys Gly Ala Gly Leu Gly Lys Asp Val Leu Leu Leu Thr Asp
465                 470                 475                 480

Gly Arg Phe Ser Gly Gly Thr Thr Gly Leu Cys Ile Gly His Val Ala
                485                 490                 495

Pro Glu Ala Thr Asp Gly Gly Pro Ile Ala Phe Val Arg Asp Gly Asp
            500                 505                 510

Pro Ile Arg Leu Asp Leu Ala Gly Arg Thr Leu Asp Leu Leu Val Asp
        515                 520                 525

Glu Ala Glu Leu Ala Arg Arg Lys Glu Gly Trp Val Pro Arg Glu Pro
    530                 535                 540

Lys Phe Arg Gln Gly Val Leu Gly Lys Tyr Ala Arg Leu Val Arg Ser
545                 550                 555                 560

Ala Ala Val Gly Ala Val Cys Ser
                565

<210> SEQ ID NO 20
<211> LENGTH: 585
<212> TYPE: PRT
<213> ORGANISM: Saccharomyces cerevisiae

<400> SEQUENCE: 20

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
                20                  25                  30

Pro Lys Gly Gln Gly Ala Ser Gln Ala Met Leu Tyr Ala Thr Gly Phe
            35                  40                  45

Lys Lys Glu Asp Phe Lys Lys Pro Gln Val Gly Val Gly Ser Cys Trp
        50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
```

```
            85                  90                  95
Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
            115                 120                 125

Met Met Ala Gln His Tyr Asp Ala Asn Ile Ala Ile Pro Ser Cys Asp
            130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
            165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
            195                 200                 205

Asp Val Val Glu His Ala Cys Pro Gly Pro Ser Cys Gly Gly Met
210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
            245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
            275                 280                 285

Thr Tyr Val Val Ala Thr Gly Gly Ser Thr Asn Ala Val Leu His Leu
            290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
            325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
            355                 360                 365

Thr Val Thr Gly Asp Thr Leu Ala Glu Arg Ala Lys Lys Ala Pro Ser
            370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
            405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
            435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
            485                 490                 495

Gly Arg Phe Ser Gly Gly Ser His Gly Phe Leu Ile Gly His Ile Val
            500                 505                 510
```

Pro Glu Ala Ala Glu Gly Gly Pro Ile Gly Leu Val Arg Asp Gly Asp
            515                 520                 525

Glu Ile Ile Ile Asp Ala Asp Asn Asn Lys Ile Asp Leu Leu Val Ser
            530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
                580                 585

<210> SEQ ID NO 21
<211> LENGTH: 592
<212> TYPE: PRT
<213> ORGANISM: Piromyces sp

<400> SEQUENCE: 21

Met Ser Phe Ser Leu Ala Asn Leu Ala Ala Lys Gly Ser Asn Leu Phe
1               5                   10                  15

Lys Phe Thr Pro Ala Leu Leu Ser Ala Lys Arg Phe Gly Ser Ser Gly
            20                  25                  30

Lys Pro Ile Asn Lys Phe Ser Lys Ile Ile Thr Glu Pro Lys Ser Arg
        35                  40                  45

Gly Gly Ser Gln Ala Met Leu Ile Ala Thr Gly Ile Lys Pro Glu Asp
    50                  55                  60

Leu Lys Lys Pro Gln Ile Gly Ile Gly Ser Val Trp Tyr Asp Gly Asn
65                  70                  75                  80

Pro Cys Asn Met His Leu Leu Asp Leu Gly Ser Val Val Lys Lys Ala
                85                  90                  95

Val Gln Lys Gln Asn Met Asn Gly Met Arg Phe Asn Met Ile Gly Val
            100                 105                 110

Ser Asp Gly Ile Ser Asn Gly Thr Asp Gly Met Ser Phe Ser Leu Gln
        115                 120                 125

Ser Arg Glu Ile Ile Ala Asp Ser Ile Glu Thr Ile Met Ser Ala Gln
    130                 135                 140

Tyr Tyr Asp Ala Asn Ile Ser Leu Pro Gly Cys Asp Lys Asn Met Pro
145                 150                 155                 160

Gly Cys Leu Ile Ala Ala Ala Arg Leu Asn Arg Pro Thr Ile Ile Ile
                165                 170                 175

Tyr Gly Gly Thr Ile Lys Pro His His Thr Lys Lys Gly Glu Thr Ile
            180                 185                 190

Asp Leu Val Ser Ala Phe Gln Cys Tyr Gly Gln Tyr Leu Ala Gly Glu
        195                 200                 205

Ile Thr Glu Glu Gln Arg Glu Glu Ile Val Asn Asn Ala Cys Pro Gly
    210                 215                 220

Ala Gly Ala Cys Gly Gly Met Tyr Thr Ala Asn Thr Met Ala Ser Ile
225                 230                 235                 240

Ile Glu Ser Met Gly Met Ser Leu Pro Tyr Ser Ala Ser Thr Pro Ala
                245                 250                 255

Glu Asp Pro Leu Lys Glu Leu Glu Cys Ile Asn Ala Ala Ala Ala Ile
            260                 265                 270

Lys Asn Leu Met Glu Lys Asp Ile Lys Pro Leu Asp Ile Met Thr Arg
        275                 280                 285

Lys Ala Phe Glu Asn Ala Ile Thr Ile Thr Leu Ile Leu Gly Gly Ser
    290                 295                 300

```
Thr Asn Ser Val Leu His Leu Leu Ala Ile Ala Arg Ala Cys Lys Val
305                 310                 315                 320

Pro Leu Thr Ile Asp Asp Phe Gln Glu Phe Ser Asn Arg Ile Pro Val
            325                 330                 335

Leu Ala Asp Leu Lys Pro Ser Gly Lys Tyr Val Met Glu Asp Leu Gln
        340                 345                 350

Leu Ile Gly Gly Leu Pro Ala Ile Gln Lys Tyr Leu Leu Asn Glu Gly
    355                 360                 365

Leu Leu His Gly Asp Ile Met Thr Val Thr Gly Lys Thr Leu Ala Glu
370                 375                 380

Asn Leu Lys Asp Val Ala Pro Ile Asp Phe Glu Thr Gln Asp Ile Ile
385                 390                 395                 400

Arg Pro Leu Ser Asn Pro Ile Lys Lys Asn Gly His Ile Ile Ile Met
            405                 410                 415

Lys Gly Asn Val Ser Pro Asp Gly Gly Val Ala Lys Ile Thr Gly Lys
        420                 425                 430

Gln Gly Leu Phe Phe Glu Gly Val Ala Asn Cys Phe Asp Cys Glu Glu
    435                 440                 445

Asp Met Leu Ala Ala Leu Glu Arg Gly Glu Ile Lys Lys Gly Gln Val
450                 455                 460

Ile Ile Ile Arg Tyr Glu Gly Pro Thr Gly Gly Pro Gly Met Pro Glu
465                 470                 475                 480

Met Leu Thr Pro Thr Ser Ala Ile Met Gly Ala Gly Leu Gly Lys Asp
            485                 490                 495

Val Ala Leu Leu Thr Asp Gly Arg Phe Ser Gly Gly Ser His Gly Phe
        500                 505                 510

Ile Ile Gly His Ile Thr Pro Glu Ala Gln Val Gly Gly Pro Ile Ala
    515                 520                 525

Leu Ile Lys Asn Gly Asp Lys Ile Thr Ile Asp Ala Asn Lys Arg Thr
530                 535                 540

Ile His Ala His Val Ser Glu Glu Phe Ala Lys Arg Arg Ala Glu
545                 550                 555                 560

Trp Lys Ala Pro Pro Tyr Arg Ala Thr Gln Gly Thr Leu Lys Lys Tyr
            565                 570                 575

Ile Lys Leu Val Lys Pro Ala Asn Phe Gly Cys Val Thr Asp Glu Trp
        580                 585                 590

<210> SEQ ID NO 22
<211> LENGTH: 587
<212> TYPE: PRT
<213> ORGANISM: Ralstonia eutropha

<400> SEQUENCE: 22

Met Pro Tyr Ala Asp Asp Pro Lys Leu Pro Gln Asp Gly Ala Ala Pro
1               5                   10                  15

Thr Glu Gly Leu Ala Lys Gly Leu Thr Asn Tyr Gly Asp Thr Gly Phe
            20                  25                  30

Ser Leu Phe Leu Arg Lys Ala Phe Ile Lys Gly Ala Gly Phe Thr Asp
        35                  40                  45

Asp Ala Leu Ser Arg Pro Val Ile Gly Ile Val Asn Thr Gly Ser Ser
    50                  55                  60

Tyr Asn Pro Cys His Gly Asn Ala Pro Gln Leu Val Glu Ala Val Lys
65                  70                  75                  80

Arg Gly Val Met Leu Ala Gly Gly Leu Pro Val Asp Phe Pro Thr Ile
            85                  90                  95
```

```
Ser Val His Glu Ser Phe Ser Ala Pro Thr Ser Met Tyr Leu Arg Asn
            100                 105                 110

Leu Met Ser Met Asp Thr Glu Met Ile Arg Ala Gln Pro Met Asp
        115                 120                 125

Ala Val Val Leu Ile Gly Gly Cys Asp Lys Thr Val Pro Ala Gln Leu
130                 135                 140

Met Gly Ala Ala Ser Ala Gly Val Pro Ala Ile Gln Leu Val Thr Gly
145                 150                 155                 160

Ser Met Leu Thr Gly Ser His Arg Ser Glu Arg Val Gly Ala Cys Thr
                165                 170                 175

Asp Cys Arg Arg Tyr Trp Gly Arg Tyr Arg Ala Glu Glu Ile Asp Ser
            180                 185                 190

Ala Glu Ile Ala Asp Val Asn Asn Gln Leu Val Ala Ser Val Gly Thr
        195                 200                 205

Cys Ser Val Met Gly Thr Ala Ser Thr Met Ala Cys Val Ala Glu Ala
    210                 215                 220

Leu Gly Met Met Val Ser Gly Ala Ser Ala Pro Ala Val Thr Ala
225                 230                 235                 240

Asp Arg Val Arg Val Ala Glu Arg Thr Gly Thr Thr Ala Val Gly Met
                245                 250                 255

Ala Ala Ala Arg Leu Thr Pro Asp Arg Ile Leu Thr Gly Lys Ala Phe
            260                 265                 270

Glu Asn Ala Leu Arg Val Leu Ala Ile Gly Gly Ser Thr Asn Gly
        275                 280                 285

Ile Val His Leu Thr Ala Ile Ala Gly Arg Leu Gly Ile Asp Ile Asp
    290                 295                 300

Leu Ala Gly Leu Asp Arg Met Ser Arg Glu Thr Pro Val Leu Val Asp
305                 310                 315                 320

Leu Lys Pro Ser Gly Gln His Tyr Met Glu Asp Phe His Lys Ala Gly
                325                 330                 335

Gly Met Leu Thr Leu Leu Arg Glu Leu Arg Pro Leu Leu His Leu Asp
            340                 345                 350

Thr Leu Thr Val Ser Gly Arg Thr Leu Gly Glu Glu Leu Asp Ala Ala
        355                 360                 365

Pro Pro Leu Phe Pro Gln Asp Val Ile Arg Ser Ala Gly Asn Pro Ile
    370                 375                 380

Tyr Pro Ala Gly Gly Leu Ala Val Leu Arg Gly Asn Leu Ala Pro Gly
385                 390                 395                 400

Gly Ala Ile Ile Lys Gln Ser Ala Ala Asn Pro Ala Leu Met Glu His
                405                 410                 415

Glu Gly Arg Ala Val Val Phe Glu Asn Ala Glu Asp Met Ala Gln Arg
            420                 425                 430

Ile Asp Asp Glu Ser Leu Asp Val Lys Ala Asp Ile Leu Val Leu
        435                 440                 445

Lys Arg Ile Gly Pro Thr Gly Ala Pro Gly Met Pro Glu Ala Gly Tyr
    450                 455                 460

Met Pro Ile Pro Lys Lys Leu Ala Arg Ala Gly Val Lys Asp Met Val
465                 470                 475                 480

Arg Val Ser Asp Gly Arg Met Ser Gly Thr Ala Ala Gly Thr Ile Val
                485                 490                 495

Leu His Val Thr Pro Glu Ala Ala Ile Gly Gly Pro Leu Ala Leu Val
            500                 505                 510

Gln Ser Gly Asp Arg Ile Arg Leu Ser Val Ala Asn Arg Glu Ile Ala
        515                 520                 525
```

```
Leu Leu Val Asp Asp Ala Glu Leu Ala Arg Arg Ala Ala Ala Gln Pro
        530                 535                 540

Val Glu Arg Pro Arg Ala Glu Arg Gly Tyr Arg Lys Leu Phe Leu Glu
545                 550                 555                 560

Thr Val Thr Gln Ala Asp Gln Gly Val Asp Phe Asp Phe Leu Arg Ala
                565                 570                 575

Ala Gln Thr Val Asp Thr Val Pro Lys Gln Gly
            580                 585

<210> SEQ ID NO 23
<211> LENGTH: 581
<212> TYPE: PRT
<213> ORGANISM: Chromohalobacter salexigens

<400> SEQUENCE: 23

Met Thr His Lys Lys Arg Pro Leu Arg Ser Ala Glu Trp Phe Gly Asn
1               5                   10                  15

Asp Asp Lys Asn Gly Phe Met Tyr Arg Ser Trp Met Lys Asn Gln Gly
            20                  25                  30

Ile Pro Asp His Glu Phe Arg Gly Lys Pro Ile Ile Gly Ile Cys Asn
        35                  40                  45

Thr Phe Ser Glu Leu Thr Pro Cys Asn Ala His Phe Arg Lys Leu Ala
    50                  55                  60

Glu His Val Lys Lys Gly Val Leu Glu Ala Gly Tyr Pro Val Glu
65                  70                  75                  80

Phe Pro Val Phe Ser Asn Gly Glu Ser Asn Leu Arg Pro Thr Ala Met
                85                  90                  95

Phe Thr Arg Asn Leu Ala Ser Met Asp Val Glu Glu Ala Ile Arg Gly
            100                 105                 110

Asn Pro Leu Asp Ala Val Val Leu Leu Val Gly Cys Asp Lys Thr Thr
        115                 120                 125

Pro Ala Leu Leu Met Gly Ala Ala Ser Cys Asp Ile Pro Thr Ile Val
    130                 135                 140

Val Thr Gly Gly Pro Met Leu Asn Gly Lys His Lys Gly Arg Asp Ile
145                 150                 155                 160

Gly Ser Gly Thr Val Val Trp Gln Leu Ser Glu Glu Val Lys Ala Gly
                165                 170                 175

Lys Ile Ser Leu His Asp Phe Met Ala Ala Glu Ala Gly Met Ser Arg
            180                 185                 190

Ser Ala Gly Thr Cys Asn Thr Met Gly Thr Ala Ser Thr Met Ala Cys
        195                 200                 205

Met Ala Glu Ser Leu Gly Thr Ser Leu Pro His Asn Ala Ala Ile Pro
    210                 215                 220

Ala Val Asp Ser Arg Arg Tyr Val Leu Ala His Leu Ser Gly Asn Arg
225                 230                 235                 240

Ile Val Glu Met Val Asp Glu Asp Leu Thr Leu Ser Lys Val Leu Thr
                245                 250                 255

Lys Ser Ala Phe Glu Asn Ala Ile Arg Thr Asn Ala Ala Ile Gly Gly
            260                 265                 270

Ser Thr Asn Ala Val Ile His Leu Gln Ala Ile Ala Gly Arg Met Gly
        275                 280                 285

Val Asp Leu Thr Leu Asp Asp Trp Thr Arg Val Gly Arg Gly Thr Pro
    290                 295                 300

Thr Ile Val Asp Leu Gln Pro Ser Gly Arg Tyr Leu Met Glu Glu Phe
305                 310                 315                 320
```

```
Tyr Tyr Ala Gly Gly Leu Pro Ala Val Leu Arg Arg Leu Gly Glu Ala
                325                 330                 335

Asp Arg Leu Pro His Lys Asp Ala Leu Thr Val Asn Gly Lys Thr Leu
            340                 345                 350

Trp Glu Asn Val Gln Asp Ala Pro Leu Tyr Asn Asp Ala Val Ile Leu
        355                 360                 365

Pro Leu Asp Ala Pro Leu Arg Glu Asp Gly Gly Met Cys Val Met Arg
    370                 375                 380

Gly Asn Leu Ala Pro Asn Gly Ala Val Leu Lys Pro Ser Ala Ala Thr
385                 390                 395                 400

Pro Ala Leu Met Gln His Arg Gly Arg Ala Val Val Phe Glu Asn Phe
                405                 410                 415

Asp Asp Tyr Lys Ala Arg Ile Asn Asp Pro Asp Leu Asp Val Thr Ala
            420                 425                 430

Asp Asp Ile Leu Val Met Lys Asn Cys Gly Pro Arg Gly Tyr His Gly
        435                 440                 445

Met Ala Glu Val Gly Asn Met Gly Leu Pro Ala Lys Leu Leu Glu Gln
    450                 455                 460

Gly Val Thr Asp Met Val Arg Ile Ser Asp Ala Arg Met Ser Gly Thr
465                 470                 475                 480

Ala Tyr Gly Thr Val Val Leu His Val Ala Pro Glu Ala Ala Ala Gly
                485                 490                 495

Gly Pro Leu Ala Ala Val Arg Asn Gly Asp Trp Ile Ala Leu Asp Ala
            500                 505                 510

Tyr Ser Gly Lys Leu His Leu Glu Val Asp Ala Glu Ile Ala Ser
        515                 520                 525

Arg Leu Ala Glu Ala Asp Pro Thr Ala Glu Ser Thr Arg Ile Ala Ser
    530                 535                 540

Thr Gly Gly Tyr Arg Gln Leu Tyr Ile Glu His Val Leu Gln Ala Asp
545                 550                 555                 560

Gln Gly Cys Asp Phe Asp Phe Leu Val Gly Cys Arg Gly Ala Glu Val
                565                 570                 575

Pro Arg His Ser His
            580

<210> SEQ ID NO 24
<211> LENGTH: 329
<212> TYPE: PRT
<213> ORGANISM: Picrophilus torridus

<400> SEQUENCE: 24

Met Glu Lys Val Tyr Thr Glu Asn Asp Leu Lys Glu Asn Leu Met Arg
1               5                   10                  15

Asn Lys Lys Ile Ala Val Leu Gly Tyr Gly Ser Gln Gly Arg Ala Trp
            20                  25                  30

Ala Leu Asn Met Arg Asp Ser Gly Leu Asn Val Thr Val Gly Leu Glu
        35                  40                  45

Arg Gln Gly Lys Ser Trp Glu Lys Ala Val Ala Asp Gly Phe Lys Pro
    50                  55                  60

Leu Lys Ser Arg Asp Ala Val Arg Asp Ala Asp Ala Val Ile Phe Leu
65                  70                  75                  80

Val Pro Asp Met Ala Gln Arg Glu Leu Tyr Lys Asn Ile Met Asn Asp
                85                  90                  95

Ile Lys Asp Asp Ala Asp Ile Val Phe Ala His Gly Phe Asn Val His
            100                 105                 110
```

```
Tyr Gly Leu Ile Asn Pro Lys Asn His Asp Val Tyr Met Val Ala Pro
            115                 120                 125

Lys Ala Pro Gly Pro Ser Val Arg Glu Phe Tyr Glu Arg Gly Gly
        130                 135                 140

Val Pro Val Leu Ile Ala Val Ala Asn Asp Val Ser Gly Arg Ser Lys
145                 150                 155                 160

Glu Lys Ala Leu Ser Ile Ala Tyr Ser Leu Gly Ala Leu Arg Ala Gly
                165                 170                 175

Ala Ile Glu Thr Thr Phe Lys Glu Thr Glu Thr Asp Leu Ile Gly
            180                 185                 190

Glu Gln Leu Asp Leu Val Gly Ile Thr Glu Leu Leu Arg Ser Thr
        195                 200                 205

Phe Asn Ile Met Val Glu Met Gly Tyr Lys Pro Glu Met Ala Tyr Phe
    210                 215                 220

Glu Ala Ile Asn Glu Met Lys Leu Ile Val Asp Gln Val Phe Glu Lys
225                 230                 235                 240

Gly Ile Ser Gly Met Leu Arg Ala Val Ser Asp Thr Ala Lys Tyr Gly
                245                 250                 255

Gly Leu Thr Thr Gly Lys Tyr Ile Ile Asn Asp Asp Val Arg Lys Arg
            260                 265                 270

Met Arg Glu Arg Ala Glu Tyr Ile Val Ser Gly Lys Phe Ala Glu Glu
        275                 280                 285

Trp Ile Glu Glu Tyr Gly Glu Gly Ser Lys Asn Leu Glu Ser Met Met
    290                 295                 300

Leu Asp Ile Asp Asn Ser Leu Glu Glu Gln Val Gly Lys Gln Leu Arg
305                 310                 315                 320

Glu Ile Val Leu Arg Gly Arg Pro Lys
                325

<210> SEQ ID NO 25
<211> LENGTH: 560
<212> TYPE: PRT
<213> ORGANISM: Picrophilus torridus

<400> SEQUENCE: 25

Met Asn Pro Asp Lys Lys Arg Ser Asn Leu Ile Tyr Gly Gly Tyr
1               5                   10                  15

Glu Lys Ala Pro Asn Arg Ala Phe Leu Lys Ala Met Gly Leu Thr Asp
            20                  25                  30

Asp Asp Ile Ala Lys Pro Ile Val Gly Val Ala Val Ala Trp Asn Glu
        35                  40                  45

Ala Gly Pro Cys Asn Ile His Leu Leu Gly Leu Ser Asn Ile Val Lys
    50                  55                  60

Glu Gly Val Arg Ser Gly Gly Thr Pro Arg Val Phe Thr Ala Pro
65                  70                  75                  80

Val Val Ile Asp Gly Ile Ala Met Gly Ser Glu Gly Met Lys Tyr Ser
                85                  90                  95

Leu Val Ser Arg Glu Ile Val Ala Asn Thr Val Glu Leu Val Val Asn
            100                 105                 110

Ala His Gly Tyr Asp Gly Phe Val Ala Leu Ala Gly Cys Asp Lys Thr
        115                 120                 125

Pro Pro Gly Met Met Met Ala Met Ala Arg Leu Asn Ile Pro Ser Ile
    130                 135                 140

Ile Met Tyr Gly Gly Thr Thr Leu Pro Gly Asn Phe Lys Gly Lys Pro
145                 150                 155                 160
```

```
Ile Thr Ile Gln Asp Val Tyr Glu Ala Val Gly Ala Tyr Ser Lys Gly
                165                 170                 175

Lys Ile Thr Ala Glu Asp Leu Arg Leu Met Glu Asp Asn Ala Ile Pro
            180                 185                 190

Gly Pro Gly Thr Cys Gly Gly Leu Tyr Thr Ala Asn Thr Met Gly Leu
        195                 200                 205

Met Thr Glu Ala Leu Gly Leu Ala Leu Pro Gly Ser Ala Ser Pro Pro
    210                 215                 220

Ala Val Asp Ser Ala Arg Val Lys Tyr Ala Tyr Glu Thr Gly Lys Ala
225                 230                 235                 240

Leu Met Asn Leu Ile Glu Ile Gly Leu Lys Pro Arg Asp Ile Leu Thr
                245                 250                 255

Phe Glu Ala Phe Glu Asn Ala Ile Thr Val Leu Met Ala Ser Gly Gly
            260                 265                 270

Ser Thr Asn Ala Val Leu His Leu Leu Ala Ile Ala Tyr Glu Ala Gly
        275                 280                 285

Val Lys Leu Thr Leu Asp Asp Phe Asp Arg Ile Ser Gln Arg Thr Pro
    290                 295                 300

Glu Ile Val Asn Met Lys Pro Gly Gly Glu Tyr Ala Met Tyr Asp Leu
305                 310                 315                 320

His Arg Val Gly Gly Ala Pro Leu Ile Met Lys Lys Leu Leu Glu Ala
                325                 330                 335

Asp Leu Leu His Gly Asp Val Ile Thr Val Thr Gly Lys Thr Val Lys
            340                 345                 350

Gln Asn Leu Glu Glu Tyr Lys Leu Pro Asn Val Pro His Glu His Ile
        355                 360                 365

Val Arg Pro Ile Ser Asn Pro Phe Asn Pro Thr Gly Gly Ile Arg Ile
    370                 375                 380

Leu Lys Gly Ser Leu Ala Pro Glu Gly Ala Val Ile Lys Val Ser Ala
385                 390                 395                 400

Thr Lys Val Arg Tyr His Lys Gly Pro Ala Arg Val Phe Asn Ser Glu
                405                 410                 415

Glu Glu Ala Phe Lys Ala Val Leu Glu Glu Lys Ile Gln Glu Asn Asp
            420                 425                 430

Val Val Val Ile Arg Tyr Glu Gly Pro Lys Gly Gly Pro Gly Met Arg
        435                 440                 445

Glu Met Leu Ala Val Thr Ser Ala Ile Val Gly Gln Gly Leu Gly Glu
    450                 455                 460

Lys Val Ala Leu Ile Thr Asp Gly Arg Phe Ser Gly Ala Thr Arg Gly
465                 470                 475                 480

Ile Met Val Gly His Val Ala Pro Glu Ala Val Gly Gly Pro Ile
                485                 490                 495

Ala Leu Leu Arg Asp Gly Asp Thr Ile Ile Asp Ala Asn Asn Gly
            500                 505                 510

Arg Leu Asp Val Asp Leu Pro Gln Glu Glu Leu Lys Lys Arg Ala Asp
        515                 520                 525

Glu Trp Thr Pro Pro Pro Lys Tyr Lys Ser Gly Leu Leu Ala Gln
    530                 535                 540

Tyr Ala Arg Leu Val Ser Ser Ser Leu Gly Ala Val Leu Leu Thr
545                 550                 555                 560

<210> SEQ ID NO 26
<211> LENGTH: 566
<212> TYPE: PRT
```

<213> ORGANISM: Artificial Sequence
<220> FEATURE:
<223> OTHER INFORMATION: Saccharomyces cerevisiae ILV3deltaN

<400> SEQUENCE: 26

Met Lys Lys Leu Asn Lys Tyr Ser Tyr Ile Ile Thr Glu Pro Lys Gly
1               5                   10                  15

Gln Gly Ala Ser Gln Ala Met Leu Tyr Ala Thr Gly Phe Lys Lys Glu
            20                  25                  30

Asp Phe Lys Lys Pro Gln Val Gly Val Gly Ser Cys Trp Trp Ser Gly
        35                  40                  45

Asn Pro Cys Asn Met His Leu Leu Asp Leu Asn Asn Arg Cys Ser Gln
    50                  55                  60

Ser Ile Glu Lys Ala Gly Leu Lys Ala Met Gln Phe Asn Thr Ile Gly
65                  70                  75                  80

Val Ser Asp Gly Ile Ser Met Gly Thr Lys Gly Met Arg Tyr Ser Leu
                85                  90                  95

Gln Ser Arg Glu Ile Ile Ala Asp Ser Phe Glu Thr Ile Met Met Ala
            100                 105                 110

Gln His Tyr Asp Ala Asn Ile Ala Ile Pro Ser Cys Asp Lys Asn Met
        115                 120                 125

Pro Gly Val Met Met Ala Met Gly Arg His Asn Arg Pro Ser Ile Met
    130                 135                 140

Val Tyr Gly Gly Thr Ile Leu Pro Gly His Pro Thr Cys Gly Ser Ser
145                 150                 155                 160

Lys Ile Ser Lys Asn Ile Asp Ile Val Ser Ala Phe Gln Ser Tyr Gly
                165                 170                 175

Glu Tyr Ile Ser Lys Gln Phe Thr Glu Glu Arg Glu Asp Val Val
            180                 185                 190

Glu His Ala Cys Pro Gly Pro Gly Ser Cys Gly Gly Met Tyr Thr Ala
        195                 200                 205

Asn Thr Met Ala Ser Ala Ala Glu Val Leu Gly Leu Thr Ile Pro Asn
    210                 215                 220

Ser Ser Ser Phe Pro Ala Val Ser Lys Glu Lys Leu Ala Glu Cys Asp
225                 230                 235                 240

Asn Ile Gly Glu Tyr Ile Lys Lys Thr Met Glu Leu Gly Ile Leu Pro
                245                 250                 255

Arg Asp Ile Leu Thr Lys Glu Ala Phe Glu Asn Ala Ile Thr Tyr Val
            260                 265                 270

Val Ala Thr Gly Gly Ser Thr Asn Ala Val Leu His Leu Val Ala Val
        275                 280                 285

Ala His Ser Ala Gly Val Lys Leu Ser Pro Asp Asp Phe Gln Arg Ile
    290                 295                 300

Ser Asp Thr Thr Pro Leu Ile Gly Asp Phe Lys Pro Ser Gly Lys Tyr
305                 310                 315                 320

Val Met Ala Asp Leu Ile Asn Val Gly Gly Thr Gln Ser Val Ile Lys
                325                 330                 335

Tyr Leu Tyr Glu Asn Asn Met Leu His Gly Asn Thr Met Thr Val Thr
            340                 345                 350

Gly Asp Thr Leu Ala Glu Arg Ala Lys Lys Ala Pro Ser Leu Pro Glu
        355                 360                 365

Gly Gln Glu Ile Ile Lys Pro Leu Ser His Pro Ile Lys Ala Asn Gly
    370                 375                 380

His Leu Gln Ile Leu Tyr Gly Ser Leu Ala Pro Gly Gly Ala Val Gly
385                 390                 395                 400

```
Lys Ile Thr Gly Lys Glu Gly Thr Tyr Phe Lys Gly Arg Ala Arg Val
                405                 410                 415

Phe Glu Glu Glu Gly Ala Phe Ile Glu Ala Leu Glu Arg Gly Glu Ile
            420                 425                 430

Lys Lys Gly Glu Lys Thr Val Val Ile Arg Tyr Glu Gly Pro Arg
        435                 440                 445

Gly Ala Pro Gly Met Pro Glu Met Leu Lys Pro Ser Ser Ala Leu Met
    450                 455                 460

Gly Tyr Gly Leu Gly Lys Asp Val Ala Leu Leu Thr Asp Gly Arg Phe
465                 470                 475                 480

Ser Gly Gly Ser His Gly Phe Leu Ile Gly His Ile Val Pro Glu Ala
                485                 490                 495

Ala Glu Gly Gly Pro Ile Gly Leu Val Arg Asp Gly Asp Glu Ile Ile
            500                 505                 510

Ile Asp Ala Asp Asn Asn Lys Ile Asp Leu Leu Val Ser Asp Lys Glu
        515                 520                 525

Met Ala Gln Arg Lys Gln Ser Trp Val Ala Pro Pro Arg Tyr Thr
    530                 535                 540

Arg Gly Thr Leu Ser Lys Tyr Ala Lys Leu Val Ser Asn Ala Ser Asn
545                 550                 555                 560

Gly Cys Val Leu Asp Ala
                565

<210> SEQ ID NO 27
<211> LENGTH: 11
<212> TYPE: PRT
<213> ORGANISM: Artificial Sequence
<220> FEATURE:
<223> OTHER INFORMATION: Conserved DHAD motif
<220> FEATURE:
<221> NAME/KEY: Feature
<222> LOCATION: (2)..(2)
<223> OTHER INFORMATION: X may either be isoleucine or leucine
<220> FEATURE:
<221> NAME/KEY: Feature
<222> LOCATION: (3)..(3)
<223> OTHER INFORMATION: X may be any natural or non-natural amino acid
<220> FEATURE:
<221> NAME/KEY: Feature
<222> LOCATION: (4)..(4)
<223> OTHER INFORMATION: X may be any natural or non-natural amino acid
<220> FEATURE:
<221> NAME/KEY: Feature
<222> LOCATION: (5)..(5)
<223> OTHER INFORMATION: X may be any natural or non-natural amino acid
<220> FEATURE:
<221> NAME/KEY: Feature
<222> LOCATION: (7)..(7)
<223> OTHER INFORMATION: X may be any natural or non-natural amino acid
<220> FEATURE:
<221> NAME/KEY: Feature
<222> LOCATION: (8)..(8)
<223> OTHER INFORMATION: X may either be isoleucine or leucine
<220> FEATURE:
<221> NAME/KEY: Feature
<222> LOCATION: (9)..(9)
<223> OTHER INFORMATION: X may be any natural or non-natural amino acid

<400> SEQUENCE: 27

Pro Xaa Xaa Xaa Xaa Gly Xaa Xaa Xaa Ile Leu
1               5                   10

<210> SEQ ID NO 28
<211> LENGTH: 11
<212> TYPE: PRT
<213> ORGANISM: Artificial Sequence
```

```
<220> FEATURE:
<223> OTHER INFORMATION: Conserved DHAD motif
<220> FEATURE:
<221> NAME/KEY: Feature
<222> LOCATION: (4)..(4)
<223> OTHER INFORMATION: X may be any natural or non-natural amino acid
<220> FEATURE:
<221> NAME/KEY: Feature
<222> LOCATION: (5)..(5)
<223> OTHER INFORMATION: X may be any natural or non-natural amino acid
<220> FEATURE:
<221> NAME/KEY: Feature
<222> LOCATION: (7)..(7)
<223> OTHER INFORMATION: X may be any natural or non-natural amino acid
<220> FEATURE:
<221> NAME/KEY: Feature
<222> LOCATION: (8)..(8)
<223> OTHER INFORMATION: X may either be isoleucine or leucine
<220> FEATURE:
<221> NAME/KEY: Feature
<222> LOCATION: (9)..(9)
<223> OTHER INFORMATION: X may be any natural or non-natural amino acid

<400> SEQUENCE: 28

Pro Ile Lys Xaa Xaa Gly Xaa Xaa Xaa Ile Leu
1               5                   10

<210> SEQ ID NO 29
<211> LENGTH: 36
<212> TYPE: DNA
<213> ORGANISM: Artificial Sequence
<220> FEATURE:
<223> OTHER INFORMATION: Primer 387

<400> SEQUENCE: 29
gtcacagtcg acatggctaa ctacttcaat acactg                              36

<210> SEQ ID NO 30
<211> LENGTH: 33
<212> TYPE: DNA
<213> ORGANISM: Artificial Sequence
<220> FEATURE:
<223> OTHER INFORMATION: Primer 388

<400> SEQUENCE: 30
gcataaggat ccttaacccg caacagcaat acg                                 33

<210> SEQ ID NO 31
<211> LENGTH: 36
<212> TYPE: DNA
<213> ORGANISM: Artificial Sequence
<220> FEATURE:
<223> OTHER INFORMATION: Primer 410

<400> SEQUENCE: 31
gactttgtcg acatgcttta cccagaaaaa tttcag                              36

<210> SEQ ID NO 32
<211> LENGTH: 41
<212> TYPE: DNA
<213> ORGANISM: Artificial Sequence
<220> FEATURE:
<223> OTHER INFORMATION: Primer 411

<400> SEQUENCE: 32
ctaatagcgg ccgcctattt atggaatttc ttatcataat c                        41

<210> SEQ ID NO 33
<211> LENGTH: 35
<212> TYPE: DNA
```

```
<213> ORGANISM: Artificial Sequence
<220> FEATURE:
<223> OTHER INFORMATION: Primer 637

<400> SEQUENCE: 33
ttttgagctc gccgatccca ttaccgacat ttggg                          35

<210> SEQ ID NO 34
<211> LENGTH: 96
<212> TYPE: DNA
<213> ORGANISM: Artificial Sequence
<220> FEATURE:
<223> OTHER INFORMATION: Primer 638

<400> SEQUENCE: 34
aaagtcgaca ccgatatacc tgtatgtgtc accaccaatg tatctataag tatccatgct    60
agccctaggt ttatgtgatg attgattgat tgattg                             96

<210> SEQ ID NO 35
<211> LENGTH: 36
<212> TYPE: DNA
<213> ORGANISM: Artificial Sequence
<220> FEATURE:
<223> OTHER INFORMATION: Primer 697

<400> SEQUENCE: 35
gagtacggat ccctagagag ctttcgtttt catgag                         36

<210> SEQ ID NO 36
<211> LENGTH: 37
<212> TYPE: DNA
<213> ORGANISM: Artificial Sequence
<220> FEATURE:
<223> OTHER INFORMATION: Primer 767

<400> SEQUENCE: 36
caagaagtcg acatgttgac aaaagcaaca aaagaac                        37

<210> SEQ ID NO 37
<211> LENGTH: 32
<212> TYPE: DNA
<213> ORGANISM: Artificial Sequence
<220> FEATURE:
<223> OTHER INFORMATION: Primer 1149

<400> SEQUENCE: 37
cgcttactcg agatgggccg cgatgaattc gc                             32

<210> SEQ ID NO 38
<211> LENGTH: 33
<212> TYPE: DNA
<213> ORGANISM: Artificial Sequence
<220> FEATURE:
<223> OTHER INFORMATION: Primer 1150

<400> SEQUENCE: 38
gcataaagat ctttaacccg caacagcaat acg                            33

<210> SEQ ID NO 39
<211> LENGTH: 35
<212> TYPE: DNA
<213> ORGANISM: Artificial Sequence
<220> FEATURE:
<223> OTHER INFORMATION: Primer 1151

<400> SEQUENCE: 39
```

```
agacgtgtcg acatgactgg catgactgat gcaga                                35

<210> SEQ ID NO 40
<211> LENGTH: 34
<212> TYPE: DNA
<213> ORGANISM: Artificial Sequence
<220> FEATURE:
<223> OTHER INFORMATION: Primer 1152

<400> SEQUENCE: 40
gtttagggat cctcatccac ccaacttcga tttg                                 34

<210> SEQ ID NO 41
<211> LENGTH: 31
<212> TYPE: DNA
<213> ORGANISM: Artificial Sequence
<220> FEATURE:
<223> OTHER INFORMATION: Primer 1006

<400> SEQUENCE: 41
gtagaagacg tcacctggta gaccaaagat g                                    31

<210> SEQ ID NO 42
<211> LENGTH: 32
<212> TYPE: DNA
<213> ORGANISM: Artificial Sequence
<220> FEATURE:
<223> OTHER INFORMATION: Primer 1009

<400> SEQUENCE: 42
catcgtgacg tcgctcaatt gactgctgct ac                                   32

<210> SEQ ID NO 43
<211> LENGTH: 32
<212> TYPE: DNA
<213> ORGANISM: Artificial Sequence
<220> FEATURE:
<223> OTHER INFORMATION: Primer 1016

<400> SEQUENCE: 43
actaagcgac acgtgcggtt tctgtggtat ag                                   32

<210> SEQ ID NO 44
<211> LENGTH: 36
<212> TYPE: DNA
<213> ORGANISM: Artificial Sequence
<220> FEATURE:
<223> OTHER INFORMATION: Primer 1017

<400> SEQUENCE: 44
gaaaccgcac gtgtcgctta gtttacattt ctttcc                               36

<210> SEQ ID NO 45
<211> LENGTH: 1647
<212> TYPE: DNA
<213> ORGANISM: Artificial Sequence
<220> FEATURE:
<223> OTHER INFORMATION: L. lactis kivD (codon optimized for E. coli) in
      pGV1590

<400> SEQUENCE: 45
atgtatactg ttggtgatta tctgctggac cgtctgcatg aactgggtat cgaagaaatc     60
ttcggcgttc cgggtgatta caatctgcag ttcctggatc agatcatctc tcataaagac    120
atgaaatggg tgggtaacgc taacgaactg aacgcaagct acatggcaga tggttatgca    180
cgtaccaaga aagccgcggc atttctgacc actttcggtg ttggcgaact gagcgccgtc    240
```

```
aacggtctgg cgggctccta cgccgaaaac ctgccggtgg tggagatcgt aggcagccca    300
acgagcaaag ttcagaacga aggtaaattc gtccaccaca ctctggctga cggcgatttc    360
aaacacttca tgaaaatgca tgaacctgtg actgcggcac gtacgctgct gactgcagag    420
aacgctactg tggaaatcga ccgcgttctg tctgcgctgc tgaaagaacg caaaccagtt    480
tacatcaacc tgcctgtgga tgttgcggca gctaaagcgg aaaaaccgag cctgccgctg    540
aagaaagaaa actccacttc taacactagc gaccaggaaa tcctgaacaa atccaggag    600 tctctgaaaa acgcaaagaa accaatcgtg atcaccggcc acgaaatcat ttcttttggt    660
ctggagaaga ccgtgaccca attcatcagc aaaaccaaac tgccgattac caccctgaac    720
ttcggcaagt cctctgttga cgaggctctg ccgtctttcc tgggcatcta acggtact     780 ctgagcgaac cgaacctgaa agaatttgtt gaatctgcgg acttcatcct gatgctgggc    840
gttaaactga ccgactcttc taccggtgca ttcactcacc atctgaacga aaacaaaatg    900
attagcctga acatcgacga gggtaaaatc ttcaacgagc gtatccagaa cttcgacttc    960
gaaagcctga tcagctctct gctggacctg tccgaaatcg agtataaagg caaatacatt   1020
gacaaaaagc aagaagattt cgtaccatct aacgcactgc tgtcccagga tcgcctgtgg   1080
caggccgtgg agaacctgac ccagagcaat gaaaccatcg tggcggaaca aggtacgagc   1140 ttttcggcg cgtcttctat ctttctgaaa tccaaaagcc attttatcgg tcagccgctg   1200 tgggtagca ttggctatac tttcccggca gcgctgggct ctcagatcgc tgataaagaa   1260
tctcgtcatc tgctgttcat cggtgacggt tccctgcagc tgaccgtaca ggaactgggt   1320
ctggcaattc gtgaaaagat caacccgatt tgcttcatta ttaacaatga cggctacacc   1380
gttgagcgtg agatccacgg tccgaaccag tcttacaacg atatccctat gtggaactac   1440
tctaaactgc cggagtcctt cggcgcaact gaggaccgtg ttgtgtctaa aattgtgcgt   1500
accgaaaacg aatttgtgag cgtgatgaaa gaggcccagg ccgatccgaa ccgtatgtac   1560
tggatcgaac tgatcctggc gaaagaaggc gcaccgaagg tactgaagaa aatgggcaag   1620
ctgtttgctg aacagaataa atcctaa                                      1647

<210> SEQ ID NO 46
<211> LENGTH: 1086
<212> TYPE: DNA
<213> ORGANISM: Artificial Sequence
<220> FEATURE:
<223> OTHER INFORMATION: S. cerevisiae ADH7 in pGV1590

<400> SEQUENCE: 46
atgctttacc cagaaaaatt tcagggcatc ggtatttcca acgcaaagga ttggaagcat     60
cctaaattag tgagttttga cccaaaaccc tttggcgatc atgacgttga tgttgaaatt    120
gaagcctgtg gtatctgcgg atctgatttt catatagccg ttggtaattg gggtccagtc    180
ccagaaaatc aaatccttgg acatgaaata attggccgcg tggtgaaggt tggatccaag    240
tgccacactg gggtaaaaat cggtgaccgt gttggtgttg gtgcccaagc cttggcgtgt    300
tttgagtgtg aacgttgcaa aagtgacaac gagcaatact gtaccaatga ccacgtttg    360 actatgtgga ctccttacaa ggacggctac attcacaag gaggctttgc ctcccacgtg    420
aggcttcatg aacactttgc tattcaaata ccagaaaata ttccaagtcc gctagccgct    480
ccattattgt gtggtggtat tacagttttc tctccactac taagaaatgg ctgtggtcca    540
ggtaagaggg taggtattgt tggcatcggt ggtattgggc atatggggat tctgttggct    600
aaagctatgg gagccgaggt ttatgcgttt tcgcgaggcc actccaagcg ggaggattct    660
```

```
atgaaactcg gtgctgatca ctatattgct atgttggagg ataaaggctg gacagaacaa      720
tactctaacg ctttggacct tcttgtcgtt tgctcatcat ctttgtcgaa agttaatttt      780
gacagtatcg ttaagattat gaagattgga ggctccatcg tttcaattgc tgctcctgaa      840
gttaatgaaa agcttgtttt aaaaccgttg ggcctaatgg gagtatcaat ctcaagcagt      900
gctatcggat ctaggaagga aatcgaacaa ctattgaaat tagtttccga aaagaatgtc      960
aaaatatggg tggaaaaact tccgatcagc gaagaaggcg tcagccatgc ctttacaagg     1020
atggaaagcg gagacgtcaa atacagattt actttggtcg attatgataa gaaattccat     1080
aaatag                                                                1086
```

`<210>` SEQ ID NO 47  
`<211>` LENGTH: 1716  
`<212>` TYPE: DNA  
`<213>` ORGANISM: Artificial Sequence  
`<220>` FEATURE:  
`<223>` OTHER INFORMATION: B. subtilis alsS in pGV1726

`<400>` SEQUENCE: 47

```
atgttgacaa aagcaacaaa agaacaaaaa tcccttgtga aaagcagagg ggcggagctt       60
gttgttgatt gcttagcgga gcaaggtgtc acacatgtat ttggcattcc aggtgcaaaa      120
attgatgcgg tatttgacgc tttacaagat aaagggcctg aaattatcgt tgcccggcat      180
gaacaaaatg cagcatttat ggcgcaagca gtcggccgtt taactggaaa accgggagtc      240
gtgttagtca catcaggacc aggtgcttcg aacttggcaa caggactgct gacagcaaac      300
actgaaggtg accctgtcgt tgcgcttgct gggaacgtga tccgtgcaga tcgtttaaaa      360
cggacacatc aatctttgga taatgcggcg ctattccagc cgattacaaa atacagtgta      420
gaagttcaag atgtaaaaaa taccggaaa gctgttacaa atgcgtttag atagcgtca       480 gcagggcagg ctggggccgc ttttgtgagt tttccgcaag atgttgtgaa tgaagtcaca      540
aatacaaaaa acgtacgtgc tgtcgcagcg ccaaaacttg gtcccgcagc agatgacgca      600
atcagtatgg ccattgcaaa aattcaaaca gcaaaacttc ctgtcgtttt agtcggcatg      660
aagggcggaa gaccggaagc gattaaagcg gttcgcaagc tattgaaaaa agtgcagctt      720
ccattcgttg aaacatatca gctgccggt actcttacga gagatttaga ggatcagtat      780
tttggccgga tcggtttatt ccgcaaccag cctggcgatc tgctgcttga gcaggctgat      840
gttgttctga caatcggcta tgacccaatt gaatatgatc cgaaattctg gaatgtcaat      900
ggagaccgga cgatcatcca tttagacgag attctggctg acattgatca tgcttaccag      960
ccggatcttg aactgatcgg tgatattcca tctacgatca atcatatcga acacgatgct     1020
gtgaaagtag actttgcgga acgtgagcag aagatccttt ctgatttaaa acaatatatg     1080
catgagggtg agcaggtgcc tgcagattgg aaatcagaca gagtgcatcc tcttgaaatc     1140
gttaaagaat tgcgaaacgc agtcgatgat catgttacag tgacttgcga tatcggttca     1200
cacgcgattt ggatgtcacg ttatttccgc agctacgagc cgttaacatt aatgattagt     1260
aacggtatgc aaacactcgg cgttgcgctt ccttgggcaa tcggcgcttc attggtgaaa     1320
ccgggagaaa aagtagtatc agtctccggt gatggcggtt tcttattctc agctatggaa     1380
ttagagacag cagttcgttt aaaagcacca attgtacaca ttgtatggaa cgacagcaca     1440
tatgacatgg ttgcattcca gcaattgaaa aaatataatc gtacatctgc ggtcgatttc     1500
ggaaatatcg atatcgtgaa atacgcggaa agcttcggag caactggctt acgcgtagaa     1560
tcaccagacc agctggcaga tgttctgcgt caaggcatga acgctgaggg gcctgtcatc     1620
```

```
attgatgtcc cggttgacta cagtgataac gttaatttag caagtgacaa gcttccgaaa    1680
gaattcgggg aactcatgaa aacgaaagct ctctag                              1716
```

<210> SEQ ID NO 48
<211> LENGTH: 1410
<212> TYPE: DNA
<213> ORGANISM: Artificial Sequence
<220> FEATURE:
<223> OTHER INFORMATION: E. coli ilvCdeltaN in pGV1727

<400> SEQUENCE: 48

```
atgggccgcg atgaattcgc cgatggcgcg agctaccttc agggtaaaaa agtagtcatc      60
gtcggctgtg cgcacagggg tctgaaccag ggcctgaaca tgcgtgattc tggtctcgat     120
atctcctacg ctctgcgtaa agaagcgatt gccgagaagc gcgcgtcctg gcgtaaagcg     180
accgaaaatg gttttaaagt gggtacttac gaagaactga tcccacaggc ggatctggtg     240
attaacctga cgccggacaa gcagcactct gatgtagtgc gcaccgtaca gccactgatg     300
aaagacggcg cggcgctggg ctactcgcac ggtttcaaca tcgtcgaagt gggcgagcag     360
atccgtaaag atatcaccgt agtgatggtt gcgccgaaat gcccaggcac cgaagtgcgt     420
gaagagtaca acgtgggttt cggcgtaccg acgctgattg ccgttcaccc ggaaaacgat     480
ccgaaaggcg aaggcatggc gattgccaaa gcctgggcgg ctgcaaccgg tgtcaccgt     540 gcgggtgtgc tggaatcgtc cttcgttgcg gaagtgaaat ctgacctgat gggcgagcaa     600
accatcctgt gcggtatgtt gcaggctggc tctctgctgt gcttcgacaa gctggtggaa     660
gaaggtaccg atccagcata cgcagaaaaa ctgattcagt tcggttggga aaccatcacc     720
gaagcactga acagggcgg catcaccctg atgatggacc gtctctctaa cccggcgaaa     780
ctgcgtgctt atgcgctttc tgaacagctg aaagagatca tggcaccccct gttccagaaa     840 catatggacg acatcatctc cggcgaattc tcttccggta tgatggcgga ctgggccaac     900
gatgataaga aactgctgac ctggcgtgaa gagaccggca aaaccgcgtt tgaaaccgcg     960
ccgcagtatg aaggcaaaat cggcgagcag gagtacttcg ataaaggcgt actgatgatt    1020
gcgatggtga agcgggcgt tgaactggcg ttcgaaacca tggtcgattc cggcatcatt    1080
gaagagtctg catattatga atcactgcac gagctgccgc tgattgccaa ccatcgcc    1140 cgtaagcgtc tgtacgaaat gaacgtggtt atctctgata ccgctgagta cggtaactat    1200
ctgttctctt acgcttgtgt gccgttgctg aaaccgttta tggcagagct gcaaccgggc    1260
gacctgggta aagctattcc ggaaggcgcg gtagataacg gcaactgcg tgatgtgaac    1320 gaagcgattc gcagccatgc gattgagcag gtaggtaaga aactgcgcgg ctatatgaca    1380
gatatgaaac gtattgctgt tgcgggttaa                                      1410
```

<210> SEQ ID NO 49
<211> LENGTH: 1782
<212> TYPE: DNA
<213> ORGANISM: Artificial Sequence
<220> FEATURE:
<223> OTHER INFORMATION: E. coli ilvDdeltaN (codon optimized for K.
      lactis) in pGV1727

<400> SEQUENCE: 49

```
atgactggca tgactgatgc agatttcgga aagccaatca ttgccgtcgt caactctttt      60
acacaattcg ttccgggtca tgtccatttg cgtgatctag gtaagcttgt tgccgaacaa     120
attgaagctg caggtggtgt cgcaaaagag tttaatacta ttgctgtgga cgacggtata     180
```

-continued

```
gctatggggc atggcggtat gttatactct ttaccatcga gagaattaat tgcagactca     240
gtcgaatata tggttaatgc tcattgtgcc gatgcaatgg tttgtatctc taattgtgat     300
aagataacgc ctggtatgtt gatggcgtcc ttgagattga acatcccagt aatcttcgta     360
tctggcggcc caatggaggc tggtaaaact aagttaagtg atcagatcat caaacttgat     420
cttgtggatg caatgattca aggtgcagat ccaaaagttt cagactcgca gtcagaccaa     480
gttgaaagaa gtgcatgtcc aacttgtggt tcttgcagtg gaatgttcac ggctaactct     540
atgaattgct tgactgaagc tctaggttta tctcaaccag gaaatggttc attattagcg     600
acccatgcag acagaaagca attgttctta aatgccggaa aaagaattgt ggaactaacg     660
aaaaggtatt acgaacaaaa tgatgaatca gcattaccga gaatatagc ttcaaaggct      720 gcattcgaaa atgccatgac attggatatt gcaatgggtg gtagtacaaa cacggtctta    780
catcttctag ctgcagccca agaagctgag atagatttca ccatgtctga tatcgacaag    840
ctttcacgta aggttccaca gttatgtaag gttgcaccat caactcaaaa gtatcacatg    900
gaagacgttc atcgtgcagg agggggttatt ggtatttttag gggagttgga cagagccggt  960
cttttaaaca gggatgtgaa gaatgtattg ggtttaacac ttccacagac attagagcaa    1020
tacgatgtca tgttaactca agatgatgcc gtgaaaaaca tgttcagggc aggtccagca    1080
gggatcagaa ccacccaagc attctcgcaa gactgtaggt gggacacttt ggacgatgat    1140
agagcaaatg gatgtataag atcgcttgag catgcttata gtaaggatgg tggtttagca    1200
gtattatatg gaaacttcgc tgaaaatggt tgcattgtga aaactgctgg tgtagatgat    1260
agtattttga aatttactgg acccgctaaa gtttacgaaa gtcaagacga tgctgttgag    1320
gctatacttg gcggaaaggt ggtagcagga gacgtggtag tgataagata tgagggacca    1380
aagggaggac caggtatgca ggaaatgctt tacccaactt catttttgaa gtccatggga    1440
ctaggaaaag cttgtgccct tatcactgac ggtagattct ctggtggcac ttcgggttta    1500
agtatcggtc acgtatcacc agaggcagct tctggtggtt cgattggatt gattgaagat    1560
ggagatttga tcgccataga tatcccaaat agaggtatcc aattacaagt ctcagacgct    1620
gaattggctg caagaagaga agcacaagat gccagaggag ataaggcttg gactcctaaa    1680
aatagagaac gtcaagtaag tttcgcccctt agggcttatg cttcattggc tacttcagcc    1740 gataagggg cagtaagaga caaatcgaag ttgggtggat ga                        1782
```

<210> SEQ ID NO 50
<211> LENGTH: 39
<212> TYPE: DNA
<213> ORGANISM: Artificial Sequence
<220> FEATURE:
<223> OTHER INFORMATION: Primer 575

<400> SEQUENCE: 50
ttttgaattc tggttctatc gaggagaaaa agcgacaag                            39

<210> SEQ ID NO 51
<211> LENGTH: 35
<212> TYPE: DNA
<213> ORGANISM: Artificial Sequence
<220> FEATURE:
<223> OTHER INFORMATION: Primer 576

<400> SEQUENCE: 51
ttttggatcc ggatgtgaag tcgttgacac agtcg                                35

<210> SEQ ID NO 52

```
<211> LENGTH: 22
<212> TYPE: DNA
<213> ORGANISM: Artificial Sequence
<220> FEATURE:
<223> OTHER INFORMATION: Primer 1623

<400> SEQUENCE: 52
gtctctgata aggaaatggc tc                                              22

<210> SEQ ID NO 53
<211> LENGTH: 60
<212> TYPE: DNA
<213> ORGANISM: Artificial Sequence
<220> FEATURE:
<223> OTHER INFORMATION: Primer 1886

<400> SEQUENCE: 53
tcaagaagcc tcaagtcggg gttggttcct gttggtggtc cggtaaccca tgtaacatgc     60

<210> SEQ ID NO 54
<211> LENGTH: 60
<212> TYPE: DNA
<213> ORGANISM: Artificial Sequence
<220> FEATURE:
<223> OTHER INFORMATION: Primer 1887

<400> SEQUENCE: 54
cggtaaccca tgtaacatgc atctattgga cttgaataac attctggttc tatcgaggag     60

<210> SEQ ID NO 55
<211> LENGTH: 60
<212> TYPE: DNA
<213> ORGANISM: Artificial Sequence
<220> FEATURE:
<223> OTHER INFORMATION: Primer 1888

<400> SEQUENCE: 55
ctttcgttaa caagcccatc tctactttt tcttggctgt atccggatgt gaagtcgttg      60

<210> SEQ ID NO 56
<211> LENGTH: 60
<212> TYPE: DNA
<213> ORGANISM: Artificial Sequence
<220> FEATURE:
<223> OTHER INFORMATION: Primer 1889

<400> SEQUENCE: 56
gatgggcttg ttaacgaaag ttgctacatc tagacaattc tgcattatag gccccaatcg     60

<210> SEQ ID NO 57
<211> LENGTH: 20
<212> TYPE: DNA
<213> ORGANISM: Artificial Sequence
<220> FEATURE:
<223> OTHER INFORMATION: Primer 1890

<400> SEQUENCE: 57
ttagtggcag caaagcagag                                                 20

<210> SEQ ID NO 58
<211> LENGTH: 20
<212> TYPE: DNA
<213> ORGANISM: Artificial Sequence
<220> FEATURE:
<223> OTHER INFORMATION: Primer 1892

<400> SEQUENCE: 58
```
acatgatgcc cgttcacaac                                              20

<210> SEQ ID NO 59
<211> LENGTH: 20
<212> TYPE: DNA
<213> ORGANISM: Artificial Sequence
<220> FEATURE:
<223> OTHER INFORMATION: Primer 1916

<400> SEQUENCE: 59
caggatgaca gttcgatgag                                              20

<210> SEQ ID NO 60
<211> LENGTH: 20
<212> TYPE: DNA
<213> ORGANISM: Artificial Sequence
<220> FEATURE:
<223> OTHER INFORMATION: Primer 1917

<400> SEQUENCE: 60
tgtcaacgac ttcacatccg                                              20

<210> SEQ ID NO 61
<211> LENGTH: 20
<212> TYPE: DNA
<213> ORGANISM: Artificial Sequence
<220> FEATURE:
<223> OTHER INFORMATION: Primer 1920

<400> SEQUENCE: 61
tgcagcctag ctttgaagac                                              20

<210> SEQ ID NO 62
<211> LENGTH: 20
<212> TYPE: DNA
<213> ORGANISM: Artificial Sequence
<220> FEATURE:
<223> OTHER INFORMATION: Primer 1921

<400> SEQUENCE: 62
tacgttagga ccccagtatc                                              20

<210> SEQ ID NO 63
<211> LENGTH: 67
<212> TYPE: DNA
<213> ORGANISM: Artificial Sequence
<220> FEATURE:
<223> OTHER INFORMATION: Primer 271

<400> SEQUENCE: 63
ctagcatgga acaaaaactc atctcagaag aagatggtgt cgacgaattc ccgggatccg   60
cggccgc                                                            67

<210> SEQ ID NO 64
<211> LENGTH: 67
<212> TYPE: DNA
<213> ORGANISM: Artificial Sequence
<220> FEATURE:
<223> OTHER INFORMATION: Primer 272

<400> SEQUENCE: 64
tcgagcggcc gcggatcccg ggaattcgtc gacaccatct tcttctgaga tgagttttg    60 ttccatg                                                            67

<210> SEQ ID NO 65

```
<211> LENGTH: 34
<212> TYPE: DNA
<213> ORGANISM: Artificial Sequence
<220> FEATURE:
<223> OTHER INFORMATION: Primer 421

<400> SEQUENCE: 65
gccaacggat cctcaagcat ctaaaacaca accg                                34

<210> SEQ ID NO 66
<211> LENGTH: 36
<212> TYPE: DNA
<213> ORGANISM: Artificial Sequence
<220> FEATURE:
<223> OTHER INFORMATION: Primer 551

<400> SEQUENCE: 66
gctcatgtcg acatgaagaa gctcaacaag tactcg                              36

<210> SEQ ID NO 67
<211> LENGTH: 35
<212> TYPE: DNA
<213> ORGANISM: Artificial Sequence
<220> FEATURE:
<223> OTHER INFORMATION: Primer 1617

<400> SEQUENCE: 67
cgttgagtcg acatgggctt gttaacgaaa gttgc                               35

<210> SEQ ID NO 68
<211> LENGTH: 34
<212> TYPE: DNA
<213> ORGANISM: Artificial Sequence
<220> FEATURE:
<223> OTHER INFORMATION: Primer 1618

<400> SEQUENCE: 68
gccaacggat cctcaagcat ctaaaacaca accg                                34

<210> SEQ ID NO 69
<211> LENGTH: 6654
<212> TYPE: DNA
<213> ORGANISM: Artificial Sequence
<220> FEATURE:
<223> OTHER INFORMATION: pGV1730

<400> SEQUENCE: 69
caggcaagtg cacaaacaat acttaaataa atactactca gtaataacct atttcttagc    60
atttttgacg aaatttgcta ttttgttaga gtcttttaca ccatttgtct ccacacctcc   120
gcttacatca acaccaataa cgccatttaa tctaagcgca tcaccaacat tttctggcgt   180
cagtccacca gctaacataa aatgtaagct ttcggggctc tcttgccttc caacccagtc   240
agaaatcgag ttccaatcca aaagttcacc tgtcccacct gcttctgaat caaacaaggg   300
aataaacgaa tgaggtttct gtgaagctgc actgagtagt atgttgcagt cttttggaaa   360
tacgagtctt ttaataactg gcaaaccgag gaactcttgg tattcttgcc acgactcatc   420
tccatgcagt tggacgatat caatgccgta atcattgacc agagccaaaa catcctcctt   480
aggttgatta cgaaacacgc caaccaagta tttcggagtg cctgaactat ttttatatgc   540
ttttacaaga cttgaaattt tccttgcaat aaccgggtca attgttctct ttctattggg   600
cacacatata atacccagca agtcagcatc ggaatctaga gcacattctg cggcctctgt   660
gctctgcaag ccgcaaactt tcaccaatgg accagaacta cctgtgaaat taataacaga   720
```

-continued

```
catactccaa gctgcctttg tgtgcttaat cacgtatact cacgtgctca atagtcacca    780
atgccctccc tcttggccct ctccttttct tttttcgacc gaattaattc ttaatcggca    840
aaaaaagaaa agctccggat caagattgta cgtaaggtga caagctattt ttcaataaag    900
aatatcttcc actactgcca tctggcgtca taactgcaaa gtacacatat attacgatgc    960
tgtctattaa atgcttccta tattatatat atagtaatgt cgttgacgtc gccggcagga   1020
gagtgaaaga gccttgttta tatttttttt tttcctatgt tcaacgagga cagctaggtt   1080
tatgcaaaaa tgtgccatca ccataagctg attcaaatga gctaaaaaaa aaatagttag   1140
aaaataaggt ggtgttgaac gatagcaagt agatcaagac accgtctaac agaaaagggg   1200
gcagcggaca atattatgca attatgaaga aaagtactca aagggtcgga aaaatattca   1260
aacgatattt gcattaaatc ctcaattgat tgattattcc atagtaaaat accgtaacaa   1320
cacaaaattg ttctcaaatt cataaattat tcattttttc cacgagcctc atcacacgaa   1380
aagtcagaag agcatacata atcttttaaa tgcataggtt atgcattttg caaatgccac   1440
caggcaacaa aaatatgcgt ttagcgggcg gaatcgggaa ggaagccgga accaccaaaa   1500
actggaagct acgttttaa ggaaggtatg ggtgcagtgt gcttatctca agaaatatta   1560
gttatgatat aaggtgttga agtttagaga taggtaaata aacgcggggt gtgtttatta   1620
catgaagaag aagttagttt ctgccttgct tgtttatctt gcacatcaca tcagcggaac   1680
atatgctcac ccagtcgcga catccaattt atagaaatca gcttgtgggt attgttcaga   1740 gaattttttca atcattggag caatcatttt acatggaccg caccaagtgg cgtagaaatc   1800
tacgacaact agcttgtctt gagcaattgc agagtcgaat tcgctggcag ttttgaattg   1860
agtaaccatt atttgtatcg aggtgtctag tcttctatta cactaatgca gtttcagggt   1920
tttgaaaacc acactgttta aacagtgttc cttaatcaag gatacctctt ttttttttcct   1980 tggttccact aattcatcgg tttttttttt ggaagacatc ttttccaacg aaaagaatat   2040
acatatcgtt taagagaaat tctccaaatt tgtaaagaag cggacccaga cttaagccta   2100
accaggccaa ttcaacagac tgtcggcaac ttcttgtctg gtctttccat ggtaagtgac   2160
agtgcagtaa taatatgaac caatttattt ttcgttacat aaaaatgctt ataaaacttt   2220
aactaataat tagagattaa atcgcggccg cggatccctt gagagctttc gttttcatga   2280
gttccccgaa ttctttcgga agcttgtcac ttgctaaatt aacgttatca ctgtagtcaa   2340
ccgggacatc aatgatgaca ggcccctcag cgttcatgcc ttgacgcaga acatctgcca   2400
gctggtctgg tgattctacg cgtaagccag ttgctccgaa gctttccgcg tatttcacga   2460
tatcgatatt tccgaaatcg accgcagatg tacgattata ttttttcaat tgctggaatg   2520
caaccatgtc atatgtgctg tcgttccata caatgtgtac aattggtgct tttaaacgaa   2580
ctgctgtctc taattccata gctgagaata agaaaccgcc atcaccggag actgatacta   2640
ctttttctcc cggtttcacc aatgaagcgc cgattgccca aggaagcgca acgccgagtg   2700
tttgcatacc gttactaatc attaatgtta acggctcgta gctgcggaaa taacgtgaca   2760
tccaaatcgc gtgtgaaccg atatcgcaag tcactgtaac atgatcatcg actgcgtttc   2820
gcaattcttt aacgatttca agaggatgca ctctgtctga tttccaatct gcaggcacct   2880 gctcacccctc atgcatatat tgttttaaat cagaaaggat cttctgctca cgttccgcaa   2940
agtctacttt cacagcatcg tgttcgatat gattgatcgt agatggaata tcaccgatca   3000
gttcaagatc cggctggtaa gcatgatcaa tgtcagccag aatctcgtct aaatggatga   3060
tcgtccggtc tccattgaca ttccagaatt tcggatcata ttcaattggg tcatagccga   3120
```

```
ttgtcagaac aacatcagcc tgctcaagca gcagatcgcc aggctggttg cggaataaac    3180
cgatccggcc aaaatactga tcctctaaat ctctcgtaag agtaccggca gcttgatatg    3240
tttcaacgaa tggaagctgc actttttca atagcttgcg aaccgcttta atcgcttccg    3300
gtcttccgcc cttcatgccg actaaaacga caggaagttt tgctgtttga attttttgcaa   3360
tggccatact gattgcgtca tctgctgcgg gaccaagttt tggcgctgcg acagcacgta    3420
cgttttttgt atttgtgact tcattcacaa catcttgcgg aaaactcaca aaagcggccc    3480
cagcctgccc tgctgacgct atcctaaacg catttgtaac agcttccggt atatttttta   3540
catcttgaac ttctacactg tatttttgtaa tcggctggaa tagcgccgca ttatccaaag   3600
attgatgtgt ccgttttaaa cgatctgcac ggatcacgtt cccagcaagc gcaacgacag    3660
ggtcaccttc agtgtttgct gtcagcagtc ctgttgccaa gttcgaagca cctggtcctg    3720
atgtgactaa cacgactccc ggttttccag ttaaacggcc gactgcttgc gccataaatg    3780
ctgcattttg ttcatgccgg gcaacgataa tttcaggccc tttatcttgt aaagcgtcaa    3840
ataccgcatc aattttgca cctggaatgc caaatacatg tgtgacacct tgctccgcta    3900
agcaatcaac aacaagctcc gccctctgc ttttcacaag ggattttgtt tcttttgttg    3960
cttttgtcaa catgtcgact ttatgtgatg attgattgat tgattgtaca gtttgttttt    4020
cttaatatct atttcgatga cttctatatg atattgcact aacaagaaga tattataatg    4080
caattgatac aagacaagga gttatttgct tctctttat atgattctga caatccatat    4140
tgcgttggta gtcttttttg ctggaacggt tcagcggaaa agacgcatcg ctcttttgc    4200
ttctagaaga aatgccagca aaagaatctc ttgacagtga ctgacagcaa aaatgtcttt    4260
ttctaactag taacaaggct aagatatcag cctgaaataa agggtggtga agtaataatt    4320
aaatcatccg tataaaccta tacacatata tgaggaaaaa taatacaaaa gtgttttaaa    4380
tacagataca tacatgaaca tatgcacgta tagcgcccaa atgtcggtaa tgggatcggc    4440
gagctccagc ttttgttccc tttagtgagg gttaattgcg cgcttggcgt aatcatggtc    4500
atagctgttt cctgtgtgaa attgttatcc gctcacaatt ccacacaaca taggagccgg    4560
aagcataaag tgtaaagcct ggggtgccta atgagtgagg taactcacat taattgcgtt    4620
gcgctcactg cccgctttcc agtcgggaaa cctgtcgtgc cagctgcatt aatgaatcgg    4680
ccaacgcgcg gggagaggcg gtttgcgtat tgggcgctct tccgcttcct cgctcactga    4740
ctcgctgcgc tcggtcgttc ggctgcggcg agcggtatca gctcactcaa aggcggtaat    4800
acggttatcc acagaatcag gggataacgc aggaaagaac atgtgagcaa aaggccagca    4860
aaaggccagg aaccgtaaaa aggccgcgtt gctggcgttt ttccataggc tccgcccccc    4920
tgacgagcat cacaaaaatc gacgctcaag tcagaggtgg cgaaacccga caggactata    4980
aagataccag gcgtttcccc ctggaagctc cctcgtgcgc tctcctgttc cgaccctgcc    5040
gcttaccgga tacctgtccg cctttctccc ttcgggaagc gtggcgcttt ctcatagctc    5100
acgctgtagg tatctcagtt cggtgtaggt cgttcgctcc aagctgggct gtgtgcacga    5160
accccccgtt cagcccgacc gctgcgcctt atccggtaac tatcgtcttg agtccaaccc    5220
ggtaagacac gacttatcgc cactggcagc agccactggt aacaggatta gcagagcgag    5280
gtatgtaggc ggtgctacag agttcttgaa gtggtggcct aactacggct acactagaag    5340
gacagtattt ggtatctgcg ctctgctgaa gccagttacc ttcggaaaaa gagttggtag    5400
ctcttgatcc ggcaaacaaa ccaccgctgg tagcggtggt ttttttgttt gcaagcagca    5460
gattacgcgc agaaaaaaag gatctcaaga agatcctttg atcttttcta cggggtctga    5520
```

```
cgctcagtgg aacgaaaact cacgttaagg gattttggtc atgagattat caaaaaggat    5580
cttcacctag atccttttaa attaaaaatg aagttttaaa tcaatctaaa gtatatatga    5640
gtaaacttgg tctgacagtt accaatgctt aatcagtgag gcacctatct cagcgatctg    5700
tctatttcgt tcatccatag ttgcctgact ccccgtcgtg tagataacta cgatacggga    5760
gggcttacca tctggcccca gtgctgcaat gataccgcga acccacgct caccggctcc     5820 agatttatca gcaataaacc agccagccgg aagggccgag cgcagaagtg gtcctgcaac    5880
tttatccgcc tccatccagt ctattaattg ttgccgggaa gctagagtaa gtagttcgcc    5940
agttaatagt ttgcgcaacg ttgttgccat tgctacaggc atcgtggtgt cacgctcgtc    6000
gtttggtatg gcttcattca gctccggttc ccaacgatca aggcgagtta catgatcccc    6060
catgttgtgc aaaaaagcgg ttagctcctt cggtcctccg atcgttgtca gaagtaagtt    6120
ggccgcagtg ttatcactca tggttatggc agcactgcat aattctctta ctgtcatgcc    6180
atccgtaaga tgcttttctg tgactggtga gtactcaacc aagtcattct gagaatagtg    6240
tatgcggcga ccgagttgct cttgcccggc gtcaatacgg gataataccg cgccacatag    6300
cagaacttta aaagtgctca tcattggaaa acgttcttcg gggcgaaaac tctcaaggat    6360
cttaccgctg ttgagatcca gttcgatgta acccactcgt gcacccaact gatcttcagc    6420
atcttttact ttcaccagcg tttctgggtg agcaaaaaca ggaaggcaaa atgccgcaaa    6480
aaagggaata agggcgacac ggaaatgttg aatactcata ctcttccttt ttcaatatta    6540
ttgaagcatt tatcagggtt attgtctcat gagcggatac atatttgaat gtatttagaa    6600
aaataaacaa atagggggttc cgcgcacatt tccccgaaaa gtgccacctg acgt          6654
```

<210> SEQ ID NO 70
<211> LENGTH: 1728
<212> TYPE: DNA
<213> ORGANISM: Artificial Sequence
<220> FEATURE:
<223> OTHER INFORMATION: B. subtilis alsS in pGV1730

<400> SEQUENCE: 70

```
gtcgacatgt tgactaaagc tacaaaagag cagaaatcat tggtgaaaaa tagggggtgca    60 gaacttgttg tggactgttt ggtagaacag ggcgtaacac atgttttttgg tatcccaggt   120 gcaaaaatcg acgccgtgtt tgatgcatta caagacaagg gtccagaaat tattgttgct   180
agacatgagc aaaatgccgc atttatggcg caagctgtag gtaggcttac aggtaaacct   240
ggtgttgtcc tagttacgtc tggcccagga gcctccaatt tagcaactgg tctattgaca   300
gctaatactg agggagatcc tgtagttgcg ttagccggta atgtaattag agctgatagg   360
cttaagagaa ctcaccagtc tctagacaac gctgctttat tccaaccgat caccaagtac   420
tcagtagagg tacaagacgt aaagaatata cctgaagctg tgacaaacgc atttcgtata   480
gcttctgctg gtcaggctgg tgccgcgttt gtttctttttc ctcaagacgt tgtcaatgaa   540
gtgaccaata ctaaaaacgt tagagcggtt gcagccccta aactaggtcc agccgcagac   600
gacgcaatta gcgctgcaat tgctaaaatt cagacggcga aactaccagt agtccttgtc   660
ggtatgaagg gcggaagacc agaagcaata aaagctgttc gtaagttatt gaagaaagtc   720
caattacctt tcgttgagac ttaccaagca gcaggtactc tatctagaga tttagaggat   780
cagtattttg gaaggatagg tctatttaga aaccaaccag gagatttact attagaacaa   840
gctgatgttg tacttactat cggttatgat cctatagagt atgacccaaa gttttggaac   900
ataaatgggg atagaacaat tatacatcta gacgagataa tcgccgacat cgatcacgct   960
```

-continued

| | |
|---|---|
| tatcaaccag atttagaact aatcggagat atcccgtcaa caatcaatca tattgaacat | 1020 |
| gatgctgtaa aggttgagtt cgctgaacgt gagcagaaaa tcttatctga tctaaagcaa | 1080 |
| tatatgcatg agggtgaaca agttccagca gactggaaat ctgaccgtgc acatcctttg | 1140 |
| gaaatcgtta aggaactaag aaatgcggtc gatgatcatg tgactgttac atgtgatatc | 1200 |
| ggttcacatg caatttggat gtcacgttat tttaggagct acgaaccatt aactttaatg | 1260 |
| atatctaacg ggatgcaaac tctgggggtt gcacttcctt gggctattgg cgctagttta | 1320 |
| gttaagcccg gtgagaaggt ggtatcggta tcaggtgatg gtggctttct gttttcggct | 1380 |
| atggaattag aaactgcagt ccgtttaaaa gctcccattg tgcatattgt ctggaatgat | 1440 |
| tctacttacg acatggttgc tttttcaacag ttgaagaaat acaatagaac ttcggctgta | 1500 |
| gactttggta acatcgatat tgtgaaatat gctgagtctt ttggcgcaac aggcctgagg | 1560 |
| gtggaaagtc cagatcagtt agctgatgtg ttgagacaag ggatgaatgc cgagggaccg | 1620 |
| gtaatcatag atgtgccagt tgactactca gacaatatta atttggcttc tgataaactt | 1680 |
| cctaaagagt ttggcgagct aatgaagacc aaagccttat aaggatcc | 1728 |

<210> SEQ ID NO 71
<211> LENGTH: 1698
<212> TYPE: DNA
<213> ORGANISM: Trichoderma atraviride

<400> SEQUENCE: 71

| | |
|---|---|
| gtcgacatga caaaggatac cgttgacatt ttgattgatt ctttaaaagc agcaggtgta | 60 |
| aaatatgttt tcggcgttcc gggagcgaaa attgactccg tgtttaatgc cctaatcgat | 120 |
| catccagaca tcaagttagt tgtatgtaga cacgaacaaa acgccgcctt tatcgcagca | 180 |
| gctatgggta aggttaccgg tagacctggt gtctgcatcg ctacaagtgg gcctgggact | 240 |
| tctaatttgg ttacaggcct ggttacagcg accgacgaag gggcgccggt tgttgctata | 300 |
| gtgggttcag ttaaacgtag tcaatcatta caaagaactc atcagtcgct aaggggagcc | 360 |
| gacctgttgg ctcccgttac caagaaggtg gtaagtgccg ttgtcgaaga tcaagttgcc | 420 |
| gaaatcatgt tggatgcatt tcgtgttgca gctgcttccc ctccaggcgc taccgctgtg | 480 |
| tctcttccca tcgatctgat gacgccagcc aaatctactt ctaccgttac ggccttccca | 540 |
| gctgaatgtt tcatacctcc aaaatacggc aaaagccctg aaactacatt acaagccgca | 600 |
| gccgatttga taagcgccgc caaagctcca gttctattct tagggatgcg tgttagcgag | 660 |
| tctgacgata caattagcgc agtacacggt tttcttcgta agcatcctgt tccagttgtg | 720 |
| gaaacctttc aagctgcagg cgcgatttcc aaagagctag tgcacttatt ttatggtaga | 780 |
| atcggtttat tttctaatca accgggtgat caattgctac aacatgcgga cctagtaata | 840 |
| gcgatcggct tagatcaagc tgagtatgac gctaatatgt ggaacgccag aggcacaaca | 900 |
| attttacatg tcgatataca accagcggac tttgttgctc attataaacc taagatcgag | 960 |
| ctggtcggtt cactagcaga caacatgaca gatttgactt ctaggttgga tacggtcgct | 1020 |
| aggctacaat taacgaaacc tggtgaagcc attagaacca acatgtggga atggcaaaat | 1080 |
| tccccggaag cctccggtag atcaacgggt cctgttcatc cattgcactt tattagacta | 1140 |
| tttcaatcca ttattgaccc gagcaccact gtaattagtg atgtaggtag tgtgtatatc | 1200 |
| tggttgtgca gatacttcta ctcttacgct cgtagaactt tcctgatgag taacgtgcag | 1260 |
| caaaacacttg gagtcgctat gccttgggcg ataggggtat cttatctctca gacgccacct | 1320 |
| agtagtaaga aagttgtatc cattagcggt gatggtggtt ttatgttctc ttcacaagag | 1380 |

| | |
|---|---|
| ttggtgacag ctgttcaaca aggttgcaac atcactcatt ttatatggaa cgatggaaaa | 1440 |
| tataacatgg tggaatttca agaagttaat aagtatggta ggtcatccgg cgtggatcta | 1500 |
| ggtggagtgg attttgtaaa gttagctgat agtatgggag ccaagggttt aagagtatca | 1560 |
| agtgctggcg atcttgaagc cgtaatgaag gaagcattag catacgacgg tgtatgtttg | 1620 |
| gttgacatag aaattgacta ctctcaaaac cataacttaa tgatggattt ggtaacatcc | 1680 |
| gatgtatctt aaggatcc | 1698 |

<210> SEQ ID NO 72
<211> LENGTH: 1720
<212> TYPE: DNA
<213> ORGANISM: Talaromyces stipitatus

<400> SEQUENCE: 72

| | |
|---|---|
| agtcgacatg tctaacagga acccttctca cgtgatagtg gagtcattat ctaatgccgg | 60 |
| cgttaagata gttttcggga taccaggtgc aaaggtcgat ggtatctttg atgcattgtc | 120 |
| agatcatcct actatcaagt tgattgtgtg tagacatgaa cagaacgctg cctttatggc | 180 |
| agccgcagtt ggacgtctta ctggcgcccc gggtgtctgc ttagtaacga gtgggcctgg | 240 |
| aacttctaat ttggtaaccg gtttagctac tgccactaca gaaggtgatc ctgttttagc | 300 |
| aatagctgga acagtctcta gattgcaagc agctaggcat actcatcaaa gtttagatgt | 360 |
| taacaaagta ttagaagggg tctgtaagag tgtaatacaa gtcggggtgg aagatcaagt | 420 |
| gagtgaagta atcgctaatg cttttagaca tgcgaggcaa ttcccacaag gagccaccgc | 480 |
| agttgcgctg ccaatggata taataaaatc tacttccgtg ggtgtgccac cttttccatc | 540 |
| tctatcattc gaggcaccag gttatggtag ttccaatacg aaactttgta agtagcggt | 600 |
| cgataaacta attgcggcga aatatccagt gatactgctg ggaatgagat cctcagaccc | 660 |
| tgagattgta gcttcagtcc gtcgtatgat aaaagatcat accttgcctg tagttgaaac | 720 |
| ttttcaagct gcgggagcca tctcagaaga tttgcttcat agatactatg ggagggtggg | 780 |
| tttattccgt aatcaacctg gtgacaaagt actagcaaga gcagacctga ttattgcagt | 840 |
| tggctacgat ccatacgaat atgatgcaga acatggaat gtcaataatc cagcaaccat | 900 |
| acacaacatt attcacattg attacacaca ttccagggtg tcacaacact atatgcctca | 960 |
| tgttgagcta ctgggaaacc cagcggatat cgtcgatgaa ttgacggcca gtttacaggc | 1020 |
| cctaaaacca aacttttggt ctggggctga agatacctta gaaaatatta ggcaagaaat | 1080 |
| agctcgttgt gaagccactg ccactcatac tgaatctttg caagatggcg cggttcagcc | 1140 |
| tactcacttc gtatatcaat tgaggcatct gttaccaaag gaaactattg ttgctgttga | 1200 |
| tgtaggaacc gtctatatct acatgatgag atacttccaa acctattcac cgagacactt | 1260 |
| gctgtgtagt aatggacaac aaactttggg agttggtttg ccttgggcta gctgcttc | 1320 |
| actaattcaa gaacctcctt gcagtaggaa ggttgtctct atatctggtg atggcgggtt | 1380 |
| tatgtttagt agccaagaac tggctacggc agtcttgcaa aagtgtaaca taacccattt | 1440 |
| tatttggaat gacagcggct acaacatggt tgaatttcaa gaggaggcta agtatggtcg | 1500 |
| tagctctggt ataaaactag gcggtattga tttcgtcaaa tttgcagagg ctttcgacgg | 1560 |
| tgcgcgtgga ttccgtataa acagcaccaa agaagttaag gaggtcatta agaggcact | 1620 |
| agcctttgaa ggcgttgcta tagttgatgt cagaatcgat tattctagga gtcatgaatt | 1680 |
| aatgaaagat attattccaa aggactacca ataaggatcc | 1720 |

<210> SEQ ID NO 73

<211> LENGTH: 1635
<212> TYPE: DNA
<213> ORGANISM: Artificial Sequence
<220> FEATURE:
<223> OTHER INFORMATION: Piromyces ilvD with predicted MTS removed

<400> SEQUENCE: 73

```
atgggtagtc aagcgatgtt aatcgcaact ggtataaaac cagaagattt aaaaaagcca      60
cagatcggca taggcagtgt ttggtatgat ggaaatccat gcaacatgca tctattggat     120
cttggctccg tggtaaaaaa ggccgttcaa aacaaaata tgaatggtat gagattcaat      180
atgattggag tgtcagacgg gatctccaac ggtacggatg aatgtccttt ctctttgcag     240
tcccgtgaaa ttattgcgga ttctatcgaa acaatcatgt ctgcacaata ttatgatgct     300
aacatcagct tacctggctg cgacaagaac atgcctggtt gtttaatcgc cgctgccaga     360
ttgaacagac cgactataat tatctacggt ggcacgatca agcccggaca tacaaaaaag     420
ggagagacga ttgatttagt ctcggccttc aatgttatg gcaatactt ggctggagaa       480
attactgaag agcaaagaga agaaatagtg aataatgcat gtcctggcgc aggtgcatgc     540
ggtggaatgt atacagctaa tacaatggct tccataatcg aatcaatggg tatgagttta    600
ccttactccg cctcgacccc ggcagaagac ccattgaaag agcttgaatg tataaacgcg    660
gcagctgcaa ttaagaattt aatggaaaaa gacatcaagc cattagacat aatgacaaga    720
aaagcgtttg agaacgctat aactattact ttgattcttg gagggagtac aaactccgtt    780
ctgcaccttt tggctatcgc tagggcctgc aaagtcccat taactattga cgatttccag    840
gaatttctta taggatacc cgttttagcc gacttaaaac ctagtggtaa atatgtcatg     900
gaagatttgc agttgatcgg cggtcttcca gctattcaga aatatcttct gaatgaaggt     960
ctacttcatg gtgatattat gactgttacc ggaaagaccc tagcagagaa tttgaaagac    1020
gttgctccaa tcgattttga aactcaagat ataattagac ctttatcgaa tcccattaaa    1080
aagaatggtc acattatcat tatgaaaggt aacgtctctc cggacggtgg tgttgctaaa    1140
attacaggta gcagggatt gttttttcgaa ggcgtggcga attgctttga ttgtgaagaa    1200
gacatgttag ctgcactgga aagaggcgaa attaaaaaag gtcaagtgat tataataagg    1260
tatgaaggcc ccactggagg gcctggtatg ccggagatgc taactccgac cagtgctatt    1320
atgggtgctg ggtaggaaaa agatgtagca ctattaacag atggcagatt ttcaggcggg    1380
tcacacggct tcattattgg tcatattacg cctgaggcac aagtaggtgg tccaattgcc    1440
ctaatcaaaa acgtgataa gataactata gacgcgaata acgtaccat acatgcccat    1500
gtcagcgaag aagaatttgc taaaagacgt gccgagtgga aagcaccacc ttacagagct    1560
actcaaggta ctttaaagaa atacattaag ctggttaaac ccgcaaactt tggatgtgtt    1620
accgatgagt ggtaa                                                    1635
```

<210> SEQ ID NO 74
<211> LENGTH: 24
<212> TYPE: DNA
<213> ORGANISM: Artificial Sequence
<220> FEATURE:
<223> OTHER INFORMATION: Primer 351

<400> SEQUENCE: 74

```
cttcttgctc attagaaaga aagc                                              24
```

<210> SEQ ID NO 75
<211> LENGTH: 21
<212> TYPE: DNA

<213> ORGANISM: Artificial Sequence
<220> FEATURE:
<223> OTHER INFORMATION: Primer 1625

<400> SEQUENCE: 75
caaggttacg gtcaaggttt g                                    21

<210> SEQ ID NO 76
<211> LENGTH: 22
<212> TYPE: DNA
<213> ORGANISM: Artificial Sequence
<220> FEATURE:
<223> OTHER INFORMATION: Primer 1626

<400> SEQUENCE: 76
cattggttcc ggttacgttt ac                                   22

<210> SEQ ID NO 77
<211> LENGTH: 46
<212> TYPE: DNA
<213> ORGANISM: Artificial Sequence
<220> FEATURE:
<223> OTHER INFORMATION: Primer 1615

<400> SEQUENCE: 77
caactcgcgg ccgcggatcc taggttattg gttttctggt ctcaac         46

<210> SEQ ID NO 78
<211> LENGTH: 32
<212> TYPE: DNA
<213> ORGANISM: Artificial Sequence
<220> FEATURE:
<223> OTHER INFORMATION: Primer 1616

<400> SEQUENCE: 78
cgccgactcg agatgttgag aactcaagcc gc                        32

<210> SEQ ID NO 79
<211> LENGTH: 44
<212> TYPE: DNA
<213> ORGANISM: Artificial Sequence
<220> FEATURE:
<223> OTHER INFORMATION: Primer 1809

<400> SEQUENCE: 79
cgccgactcg aggtcgacat gggtttgaag caaatcaact tcgg           44

<210> SEQ ID NO 80
<211> LENGTH: 7564
<212> TYPE: DNA
<213> ORGANISM: Artificial Sequence
<220> FEATURE:
<223> OTHER INFORMATION: pGV1354

<400> SEQUENCE: 80
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctggc ttaactatgc ggcatcagag cagattgta ctgagagtgc    180 accataaacg acattactat atatataata taggaagcat taatagaca gcatcgtaat    240 atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420

-continued

```
tgagcacgtg agtatacgtg attaagcaca caaaggcagc ttggagtatg tctgttatta    480
atttcacagg tagttctggt ccattggtga agtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttgggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc ttattggttt tctggtctca actttctgac ttccttacca accttccaga   2220
tttccatgtt tctgatggtg tctaattcct tttctagctt ttctctgtag tcaggttgag   2280
agttgaattc caaagatctc ttggtttcgg taccgttctt ggtagattcg tacaagtctt   2340
ggaaaacagg cttcaaagca ttcttgaaga ttgggtacca gtccaaagca cctcttctgg   2400
cggtggtgga acaagcatcg tacatgtaat ccataccgta cttaccgatc aatgggtata   2460
gagattgggt agcttcttcg acggtttcgt tgaaagcttc agatggggag tgaccgtttt   2520
ctctcaagac gtcgtattga gccaagaaca taccgtggat accacccatt aaacaacctc   2580
tttcaccgta caagtcagag ttgacttctc tttcgaaagt ggtttggtaa cgtaaccgg   2640 aaccaatggc aacggccaaa gcttgggcct tttcgtgagc cttaccggtg acatcgttcc   2700
agacggcgta agaagagtta ataccacgac cttccttgaa caaagatctg acagttctac   2760
cggaacccct tggagcaacc aagataacat ctaagtcctt tggtggttca acgtgagtca   2820
```

```
agtccttgaa gactggggag aaaccgtggg agaagtacaa agtcttaccc ttggtcaaca    2880
atggcttgat agcaggccag gtttctgatt gagcggcatc ggacaacaag ttcataacgt    2940
aactacctct cttgatagca tcttcaacag tgaacaagtt cttgcctgga acccaaccgt    3000
cttcgatggc agccttccaa gaagcaccat ctttacggac accaatgata acgttcaaac    3060
cgttgtctct caagttcaaa ccttgaccgt aaccttggga accgtaaccg atcaaagcaa    3120
aagtgtcgtt cttgaagtag tccaacaact tttctcttgg ccagtcagct ctttcgtaga    3180
cggtttcaac agtaccaccg aagttgattt gcttcaacat gtcgacacca tcttcttctg    3240
agatgagttt ttgttccatg ctagttctag aatccgtcga aactaagttc tggtgtttta    3300
aaactaaaaa aaagactaac tataaaagta gaatttaaga agtttaagaa atagatttac    3360
agaattacaa tcaatacctc ccgtctttat atacttatta gtcaagtagg ggaataattt    3420
cagggaactg gtttcaacct ttttttttcag ctttttccaa atcagagaga gcagaaggta    3480
atagaaggtg taagaaaatg agatagatac atgcgtgggt caattgcctt gtgtcatcat    3540
ttactccagg caggttgcat cactccattg aggttgtgcc cgttttttgc ctgtttgtgc    3600
ccctgttctc tgtagttgcg ctaagagaat ggacctatga actgatggtt ggtgaagaaa    3660
acaatatttt ggtgctggga ttctttttttt ttctggatgc cagcttaaaa agcgggctcc    3720
attatattta gtggatgcca ggaataaact gttcacccag acacctacga tgttatatat    3780
tctgtgtaac ccgcccccta ttttgggcat gtacgggtta cagcagaatt aaaaggctaa    3840
ttttttgact aaataaagtt aggaaaatca ctactattaa ttatttacgt attctttgaa    3900
atggcgagta ttgataatga taaactgagc tagatctggg cccgagctcc agcttttgtt    3960 cccctttagtg agggttaatt gcgcgcttgg cgtaatcatg gtcatagctg tttcctgtgt    4020
gaaattgtta tccgctcaca attccacaca acataggagc cggaagcata aagtgtaaag    4080
cctggggtgc ctaatgagtg aggtaactca cattaattgc gttgcgctca ctgcccgctt    4140
tccagtcggg aaacctgtcg tgccagctgc attaatgaat cggccaacgc gcggggagag    4200
gcggtttgcg tattgggcgc tcttccgctt cctcgctcac tgactcgctg cgctcggtcg    4260
ttcggctgcg gcgagcggta tcagctcact caaaggcggt aatacggtta tccacagaat    4320
caggggataa cgcaggaaag aacatgtgag caaaaggcca gcaaaaggcc aggaaccgta    4380
aaaaggccgc gttgctggcg tttttccata ggctccgccc ccctgacgag catcacaaaa    4440
atcgacgctc aagtcagagg tggcgaaacc cgacaggact ataaagatac caggcgtttc    4500
cccctggaag ctccctcgtg cgctctcctg ttccgaccct gccgcttacc ggatacctgt    4560
ccgcctttct cccttcggga agcgtggcgc tttctcatag ctcacgctgt aggtatctca    4620
gttcggtgta ggtcgttcgc tccaagctgg gctgtgtgca cgaaccccc gttcagcccg    4680 accgctgcgc cttatccggt aactatcgtc ttgagtccaa cccggtaaga cacgacttat    4740
cgccactggc agcagccact ggtaacagga ttagcagagc gaggtatgta ggcggtgcta    4800
cagagttctt gaagtggtgg cctaactacg gctacactag aaggacagta tttggtatct    4860
gcgctctgct gaagccagtt accttcggaa aaagagttgg tagctcttga tccggcaaac    4920
aaaccaccgc tggtagcggt ggtttttttg tttgcaagca gcagattacg cgcagaaaaa    4980
aaggatctca agaagatcct ttgatctttt ctacggggtc tgacgctcag tggaacgaaa    5040
actcacgtta agggattttg gtcatgagat tatcaaaaag gatcttcacc tagatccttt    5100
taaattaaaa atgaagtttt aaatcaatct aaagtatata tgagtaaact tggtctgaca    5160
gttaccaatg cttaatcagt gaggcaccta tctcagcgat ctgtctattt cgttcatcca    5220
```

```
tagttgcctg actccccgtc gtgtagataa ctacgatacg ggagggctta ccatctggcc    5280
ccagtgctgc aatgataccg cgagacccac gctcaccggc tccagattta tcagcaataa    5340
accagccagc cggaagggcc gagcgcagaa gtggtcctgc aactttatcc gcctccatcc    5400
agtctattaa ttgttgccgg gaagctagag taagtagttc gccagttaat agtttgcgca    5460
acgttgttgc cattgctaca ggcatcgtgg tgtcacgctc gtcgtttggt atggcttcat    5520
tcagctccgg ttcccaacga tcaaggcgag ttacatgatc ccccatgttg tgcaaaaaag    5580
cggttagctc cttcggtcct ccgatcgttg tcagaagtaa gttggccgca gtgttatcac    5640
tcatggttat ggcagcactg cataattctc ttactgtcat gccatccgta agatgctttt    5700
ctgtgactgg tgagtactca accaagtcat tctgagaata gtgtatgcgg cgaccgagtt    5760
gctcttgccc ggcgtcaata cgggataata ccgcgccaca tagcagaact ttaaaagtgc    5820
tcatcattgg aaaacgttct cggggcgaaa actctcaag gatcttaccg ctgttgagat    5880
ccagttcgat gtaacccact cgtgcaccca actgatcttc agcatctttt actttcacca    5940
gcgtttctgg gtgagcaaaa acaggaaggc aaaatgccgc aaaaaaggga ataagggcga    6000
cacgaaaatg ttgaatactc atactcttcc ttttcaata ttattgaagc atttatcagg    6060
gttattgtct catgagcgga tacatatttg aatgtattta gaaaaataaa caaatagggg    6120
ttccgcgcac atttccccga aaagtgccac ctgaacgaag catctgtgct tcattttgta    6180
gaacaaaaat gcaacgcgag agcgctaatt tttcaaacaa agaatctgag ctgcattttt    6240
acagaacaga aatgcaacgc gaaagcgcta ttttaccaac gaagaatctg tgcttcattt    6300
ttgtaaaaca aaaatgcaac gcgagagcgc taattttttca acaaagaat ctgagctgca    6360 tttttacaga acgaaatgc aacgcgagag cgctatttta ccaacaaaga atctatactt    6420
cttttttgtt ctacaaaaat gcatcccgag agcgctattt ttctaacaaa gcatcttaga    6480 ttacttttt tctcctttgt gcgctctata atgcagtctc ttgataactt tttgcactgt    6540
aggtccgtta aggttagaag aaggctactt tggtgtctat tttctcttcc ataaaaaaag    6600
cctgactcca cttcccgcgt ttactgatta ctagcgaagc tgcgggtgca ttttttcaag    6660
ataaaggcat ccccgattat attctatacc gatgtggatt gcgcatactt tgtgaacaga    6720
aagtgatagc gttgatgatt cttcattggt cagaaaatta tgaacggttt cttctatttt    6780
gtctctatat actacgtata ggaaatgttt acatttcgt attgttttcg attcactcta    6840
tgaatagttc ttactacaat ttttttgtct aaagagtaat actagagata aacataaaaa    6900
atgtagaggt cgagtttaga tgcaagttca aggagcgaaa ggtggatggg taggttatat    6960
agggatatag cacagagata tatagcaaag agatactttt gagcaatgtt tgtggaagcg    7020
gtattcgcaa tattttagta gctcgttaca gtccggtgcg ttttttggttt tttgaaagtg    7080 cgtcttcaga gcgcttttgg ttttcaaaag cgctctgaag ttcctatact ttctagagaa    7140
taggaacttc ggaataggaa cttcaaagcg tttccgaaaa cgagcgcttc cgaaaatgca    7200
acgcgagctg cgcacataca gctcactgtt cacgtcgcac ctatatctgc gtgttgcctg    7260
tatatatata tacatgagaa gaacggcata gtgcgtgttt atgcttaaat gcgtacttat    7320
atgcgtctat ttatgtagga tgaaaggtag tctagtacct cctgtgatat tatcccattc    7380
catgcggggt atcgtatgct tccttcagca ctacccttta gctgttctat atgctgccac    7440
tcctcaattg gattagtctc atccttcaat gctatcattt ccttgatat tggatcatat    7500 taagaaacca ttattatcat gacattaacc tataaaaata ggcgtatcac gaggcccttt    7560
cgtc                                                                  7564
```

<210> SEQ ID NO 81
<211> LENGTH: 7955
<212> TYPE: DNA
<213> ORGANISM: Artificial Sequence
<220> FEATURE:
<223> OTHER INFORMATION: pGV1662

<400> SEQUENCE: 81

| | | | | | |
|---|---|---|---|---|---|
| ttggatcata | ctaagaaacc | attattatca | tgacattaac | ctataaaaat | aggcgtatca | 60 |
| cgaggccctt | tcgtctcgcg | cgtttcggtg | atgacggtga | aaacctctga | cacatgcagc | 120 |
| tcccggagac | ggtcacagct | tgtctgtaag | cggatgccgg | gagcagacaa | gcccgtcagg | 180 |
| gcgcgtcagc | gggtgttggc | gggtgtcggg | gctggcttaa | ctatgcggca | tcagagcaga | 240 |
| ttgtactgag | agtgcaccat | accacagctt | tcaattcaa | ttcatcattt | tttttttatt | 300 |
| cttttttttg | atttcggttt | cttttgaaatt | ttttgattc | ggtaatctcc | gaacagaagg | 360 |
| aagaacgaag | gaaggagcac | agacttagat | tggtatatat | acgcatatgt | agtgttgaag | 420 |
| aaacatgaaa | ttgcccagta | ttcttaaccc | aactgcacag | aacaaaaacc | tgcaggaaac | 480 |
| gaagataaat | catgtcgaaa | gctacatata | aggaacgtgc | tgctactcat | cctagtcctg | 540 |
| ttgctgccaa | gctatttaat | atcatgcacg | aaaagcaaac | aaacttgtgt | gcttcattgg | 600 |
| atgttcgtac | caccaaggaa | ttactggagt | tagttgaagc | attaggtccc | aaaatttgtt | 660 |
| tactaaaaac | acatgtggat | atcttgactg | atttttccat | ggagggcaca | gttaagccgc | 720 |
| taaaggcatt | atccgccaag | tacaattttt | tactcttcga | agacagaaaa | tttgctgaca | 780 |
| ttggtaatac | agtcaaattg | cagtactctg | cgggtgtata | cagaatagca | gaatgggcag | 840 |
| acattacgaa | tgcacacggt | gtggtgggcc | caggtattgt | tagcggtttg | aagcaggcgg | 900 |
| cagaagaagt | aacaaaggaa | cctagaggcc | ttttgatgtt | agcagaattg | tcatgcaagg | 960 |
| gctccctatc | tactgagaa | tatactaagg | gtactgttga | cattgcgaag | agcgacaaag | 1020 |
| attttgttat | cggctttatt | gctcaaagag | acatgggtgg | aagagatgaa | ggttacgatt | 1080 |
| ggttgattat | gacacccggt | gtgggtttag | atgacaaggg | agacgcattg | ggtcaacagt | 1140 |
| atagaaccgt | ggatgatgtg | gtctctacag | gatctgacat | tattattgtt | ggaagaggac | 1200 |
| tatttgcaaa | gggaagggat | gctaaggtag | agggtgaacg | ttacagaaaa | gcaggctggg | 1260 |
| aagcatattt | gagaagatgc | ggccagcaaa | actaaaaaac | tgtattataa | gtaaatgcat | 1320 |
| gtatactaaa | ctcacaaatt | agagcttcaa | tttaattata | tcagttatta | ccctatgcgg | 1380 |
| tgtgaaatac | cgcacagatg | cgtaaggaga | aaataccgca | tcaggaaatt | gtaaacgtta | 1440 |
| atattttgtt | aaaattcgcg | ttaaattttt | gttaaatcag | ctcatttttt | aaccaatagg | 1500 |
| ccgaaatcgg | caaaatccct | tataaatcaa | agaatagac | cgagataggg | ttgagtgttg | 1560 |
| ttccagtttg | gaacaagagt | ccactattaa | agaacgtgga | ctccaacgtc | aaagggcgaa | 1620 |
| aaaccgtcta | tcagggcgat | ggcccactac | gtgaaccatc | accctaatca | agttttttgg | 1680 |
| ggtcgaggtg | ccgtaaagca | ctaaatcgga | accctaaagg | gagcccccga | tttagagctt | 1740 |
| gacggggaaa | gccggcgaac | gtggcgagaa | aggaagggaa | gaaagcgaaa | ggagcgggcg | 1800 |
| ctagggcgct | ggcaagtgta | gcggtcacgc | tgcgcgtaac | caccacaccc | gccgcgctta | 1860 |
| atgcgccgct | acagggcgcg | tcgcgccatt | cgccattcag | gctgcgcaac | tgttgggaag | 1920 |
| ggcgatcggt | gcgggcctct | tcgctattac | gccagctggc | gaaagggga | tgtgctgcaa | 1980 |
| ggcgattaag | ttgggtaacg | ccagggtttt | cccagtcacg | acgttgtaaa | acgacggcca | 2040 |
| gtgagcgcgc | gtaatacgac | tcactatagg | gcgaattggg | taccggccgc | aaattaaagc | 2100 |

```
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggag ggcgtgaatg taagcgtgac ataactaatt acatgactcg   2340
agcggccgcg gatccttagg atttattctg ttcagcaaac agcttgccca ttttcttcag   2400
taccttcggt gcgccttctt tcgccaggat cagttcgatc cagtacatac ggttcggatc   2460
ggcctgggcc tctttcatca cgctcacaaa ttcgttttcg gtacgcacaa ttttagacac   2520
aacacggtcc tcagttgcgc cgaaggactc cggcagttta gagtagttcc acatagggat   2580
atcgttgtaa gactggttcg gaccgtggat ctcacgctca acggtgtagc cgtcattgtt   2640
aataatgaag caaatcgggt tgatcttttc acgaattgcc agacccagtt cctgtacggt   2700
cagctgcagg gaaccgtcac cgatgaacag cagatgacga gattctttat cagcgatctg   2760
agagcccagc gctgccggga agtatagcc aatgctaccc cacagcggct gaccgataaa   2820
atggcttttg gatttcagaa agatagaaga cgcgccgaaa aagctcgtac cttgttccgc   2880
cacgatggtt tcattgctct gggtcaggtt ctccacggcc tgccacaggc gatcctggga   2940
cagcagtgcg ttagatggta cgaaatcttc ttgctttttg tcaatgtatt tgcctttata   3000
ctcgatttcg gacaggtcca gcagagagct gatcaggctt tcgaagtcga agttctggat   3060
acgctcgttg aagattttac cctcgtcgat gttcaggcta atcattttgt tttcgttcag   3120
atggtgagtg aatgcaccgg tagaagagtc ggtcagttta acgcccagca tcaggatgaa   3180
gtccgcagat tcaacaaatt cttttcaggtt cggttcgctc agagtaccgt tgtagatgcc   3240
caggaaagac ggcagagcct cgtcaacaga ggacttgccg aagttcaggg tggtaatcgg   3300
cagtttggtt ttgctgatga attgggtcac ggtcttctcc agaccaaaag aaatgatttc   3360
gtggccggtg atcacgattg gtttcttttgc gttttcaga gactcctgga ttttgttcag   3420
gatttcctgg tcgctagtgt tagaagtgga gttttctttc ttcagcggca ggctcggttt   3480
ttccgcttta gctgccgcaa catccacagg caggttgatg taaactggtt tgcgttcttt   3540
cagcagcgca gacagaacgc ggtcgatttc cacagtagcg ttctctgcag tcagcagcgt   3600
acgtgccgca gtcacaggtt catgcatttt catgaagtgt ttgaaatcgc cgtcagccag   3660
agtgtggtgg acgaatttac cttcgttctg aactttgctc gttgggctgc ctacgatctc   3720
caccaccggc aggttttcgg cgtaggagcc cgccagaccg ttgacggcgc tcagttcgcc   3780
aacaccgaaa gtggtcagaa atgccgcggc tttcttggta cgtgcataac catctgccat   3840
gtagcttgcg ttcagttcgt tagcgttacc cacccatttc atgtctttat gagagatgat   3900
ctgatccagg aactgcagat tgtaatcacc cggaacgccg aagatttctt cgatacccag   3960
ttcatgcaga cggtccagca gataatcacc aacagtatac atgtcgacaa acttagatta   4020
gattgctatg ctttctttct aatgagcaag aagtaaaaaa agttgtaata gaacaagaaa   4080
aatgaaactg aaacttgaga aattgaagac cgtttattaa cttaaatatc aatgggaggt   4140
catcgaaaga gaaaaaatc aaaaaaaaaa ttttcaagaa aaagaaacgt gataaaaatt   4200
tttattgcct ttttcgacga agaaaagaa acgaggcggt ctctttttc ttttccaaac   4260 ctttagtacg ggtaattaac gacaccctag aggaagaaag aggggaaatt tagtatgctg   4320
tgcttgggtg ttttgaagtg gtacggcgat gcgcggagtc cgagaaaatc tggaagagta   4380
aaaaaggagt agaacatttt tgaagctatg agctccagct tttgttccct ttagtgaggg   4440
ttaattgcgc gcttggcgta atcatggtca tagctgtttc ctgtgtgaaa ttgttatccg   4500
```

```
ctcacaattc cacacaacat aggagccgga agcataaagt gtaaagcctg gggtgcctaa    4560
tgagtgaggt aactcacatt aattgcgttg cgctcactgc ccgctttcca gtcgggaaac    4620
ctgtcgtgcc agctgcatta atgaatcggc caacgcgcgg ggagaggcgg tttgcgtatt    4680
gggcgctctt ccgcttcctc gctcactgac tcgctgcgct cggtcgttcg gctgcggcga    4740
gcggtatcag ctcactcaaa ggcggtaata cggttatcca cagaatcagg ggataacgca    4800
ggaaagaaca tgtgagcaaa aggccagcaa aaggccagga accgtaaaaa ggccgcgttg    4860
ctggcgtttt tccataggct ccgcccccct gacgagcatc acaaaaatcg acgctcaagt    4920
cagaggtggc gaaacccgac aggactataa agataccagg cgtttccccc tggaagctcc    4980
ctcgtgcgct ctcctgttcc gaccctgccg cttaccggat acctgtccgc ctttctccct    5040
tcgggaagcg tggcgctttc tcatagctca cgctgtaggt atctcagttc ggtgtaggtc    5100
gttcgctcca agctgggctg tgtgcacgaa ccccccgttc agcccgaccg ctgcgcctta    5160
tccggtaact atcgtcttga gtccaacccg gtaagacacg acttatcgcc actggcagca    5220
gccactggta acaggattag cagagcgagg tatgtaggcg gtgctacaga gttcttgaag    5280
tggtggccta actacggcta cactagaagg acagtatttg gtatctgcgc tctgctgaag    5340
ccagttacct tcggaaaaag agttggtagc tcttgatccg gcaaacaaac caccgctggt    5400
agcggtggtt tttttgtttg caagcagcag attacgcgca gaaaaaaagg atctcaagaa    5460
gatcctttga tcttttctac ggggtctgac gctcagtgga acgaaaactc acgttaaggg    5520
attttggtca tgagattatc aaaaaggatc ttcacctaga tccttttaaa ttaaaaatga    5580
agttttaaat caatctaaag tatatatgag taaacttggt ctgacagtta ccaatgctta    5640
atcagtgagg cacctatctc agcgatctgt ctatttcgtt catccatagt tgcctgactc    5700
cccgtcgtgt agataactac gatacgggag ggcttaccat ctggccccag tgctgcaatg    5760
ataccgcgag acccacgctc accggctcca gatttatcag caataaacca gccagccgga    5820
agggccgagc gcagaagtgg tcctgcaact ttatccgcct ccatccagtc tattaattgt    5880
tgccgggaag ctagagtaag tagttcgcca gttaatagtt tgcgcaacgt tgttgccatt    5940
gctacaggca tcgtggtgtc acgctcgtcg tttggtatgg cttcattcag ctccggttcc    6000
caacgatcaa ggcgagttac atgatccccc atgttgtgca aaaaagcggt tagctccttc    6060
ggtcctccga tcgttgtcag aagtaagttg gccgcagtgt tatcactcat ggttatggca    6120
gcactgcata attctcttac tgtcatgcca tccgtaagat gcttttctgt gactggtgag    6180
tactcaacca agtcattctg agaatagtgt atgcggcgac cgagttgctc ttgcccggcg    6240
tcaatacggg ataataccgc gccacatagc agaactttaa aagtgctcat cattggaaaa    6300
cgttcttcgg ggcgaaaact ctcaaggatc ttaccgctgt tgagatccag ttcgatgtaa    6360
cccactcgtg cacccaactg atcttcagca tcttttactt tcaccagcgt ttctgggtga    6420
gcaaaaacag gaaggcaaaa tgccgcaaaa aagggaataa gggcgacacg gaaatgttga    6480
atactcatac tcttcctttt tcaatattat tgaagcattt atcagggtta ttgtctcatg    6540
agcggataca tatttgaatg tatttagaaa aataaacaaa tagggggttcc gcgcacattt    6600 ccccgaaaag tgccacctga acgaagcatc tgtgcttcat tttgtagaac aaaaatgcaa    6660
cgcgagagcg ctaattttct aaacaaagaa tctgagctgc attttacag aacagaaatg    6720 caacgcgaaa gcgctatttt accaacgaag aatctgtgct tcattttttgt aaaacaaaaa    6780 tgcaacgcga gagcgctaat ttttcaaaca agaatctga gctgcatttt tacagaacag    6840
aaatgcaacg cgagagcgct attttaccaa caaagaatct atacttcttt tttgttctac    6900
```

```
aaaaatgcat cccgagagcg ctattttttct aacaaagcat cttagattac ttttttttctc    6960 ctttgtgcgc tctataatgc agtctcttga taacttttttg cactgtaggt ccgttaaggt    7020
tagaagaagg ctactttggt gtctattttc tcttccataa aaaaagcctg actccacttc    7080
ccgcgtttac tgattactag cgaagctgcg ggtgcatttt ttcaagataa aggcatcccc    7140
gattatattc tataccgatg tggattgcgc atactttgtg aacagaaagt gatagcgttg    7200
atgattcttc attggtcaga aaattatgaa cggtttcttc tattttgtct ctatatacta    7260
cgtataggaa atgtttacat tttcgtattg ttttcgattc actctatgaa tagttcttac    7320 tacaatttttt ttgtctaaag agtaatacta gagataaaca taaaaaatgt agaggtcgag    7380
tttagatgca agttcaagga gcgaaaggtg gatgggtagg ttatataggg atatagcaca    7440
gagatatata gcaaagagat acttttgagc aatgtttgtg gaagcggtat tcgcaatatt    7500
ttagtagctc gttacagtcc ggtgcgtttt tggtttttttg aaagtgcgtc ttcagagcgc    7560
ttttggtttt caaaagcgct ctgaagttcc tatactttct agagaatagg aacttcggaa    7620
taggaacttc aaagcgtttc cgaaaacgag cgcttccgaa aatgcaacgc gagctgcgca    7680
catacagctc actgttcacg tcgcacctat atctgcgtgt tgcctgtata tatatataca    7740
tgagaagaac ggcatagtgc gtgtttatgc ttaaatgcgt acttatatgc gtctatttat    7800
gtaggatgaa aggtagtcta gtacctcctg tgatattatc ccattccatg cggggtatcg    7860
tatgcttcct tcagcactac cctttagctg ttctatatgc tgccactcct caattggatt    7920
agtctcatcc ttcaatgcta tcatttcctt tgata                                7955

<210> SEQ ID NO 82
<211> LENGTH: 8572
<212> TYPE: DNA
<213> ORGANISM: Artificial Sequence
<220> FEATURE:
<223> OTHER INFORMATION: pGV1810

<400> SEQUENCE: 82
tagaaaaact catcgagcat caaatgaaac tgcaatttat tcatatcagg attatcaata      60 ccatatttttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa ataaggtta tcaagtgaga atcaccatg agtgacgact     240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca ccccttgttt gcctggcggc agtagcgcgg tggtcccacc    1020
```

-continued

```
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttaggggtg tcgcccttat tcgactctat agtgaagttc     1200
ctattctcta gaaagtatag gaacttctga agtggggcta gccacgaaaa acaaactaac    1260
ttatgcgcat cattagatgt aagaactact aaagagctac tggagttggt tgaggcttta    1320
ggtccaaaaa tttgtttgtt gaagacacat gttgacatat taacagattt ttctatggag    1380
ggtaccgtta agcctctgaa agcgttaagc gcgaaatata actttctttt atttgaagac    1440
cgtaagtttg ctgatattgg aaatactgtt aagttgcaat atagcgcagg agtttataga    1500
attgccgaat gggctgacat tacgaatgcc cacggtgttg taggtcctgg cattgtgtct    1560
ggattgaaac aagcggcaga ggaagtgact aaggaaccaa gaggtttact aatgctggcg    1620
gaattatctt gcaaaggctc tctagccacc ggtgaatata caaaaggtac tgtggatatt    1680
gcaaagtctg ataaggactt cgtaatcggt tttattgcac aaagagatat gggaggtcgt    1740
gacgagggct acgattggtt aattatgaca ccaggcgtag gattagatga caaaggcgat    1800
gcgttaggcc aacagtatcg tacagtcgat gatgtcgtaa gtaccggttc tgatatcatt    1860
attgtcggga gaggtttatt tgccaagggc cgtgatgcga aagtggaggg ggaaagatat    1920
aggaaggcag gttgggaggc ttacttgaga agatgtggtc agcagaatta agcggccgca    1980
taacaatact gacagtacta ataattgcc tacttggctt cacatacgtt gcatacgtcg     2040
atatagataa taatgataat gacagcagga ttatcgtaat acgtaatagt tgaaaatctc    2100
aaaaatgtgt gggtcattac gtaaataatg ataggaatgg gattcttcta ttttttccttt   2160 ttccattcta gcagccgtcg ggaaaacgtg gcatcctctc tttcgggctc aattggagtc    2220
acgctgccgt gagcatcctc tctttccata tctaacaact gagcacgtaa ccaatggaaa    2280
agcatgagct tagcgttgct ccaaaaaagt attggatggt taataccatt tgtctgttct    2340
cttctgactt tgactcctca aaaaaaaaaa atctacaatc aacagatcgc ttcaattacg    2400
ccctcacaaa aacttttttc cttcttcttc gcccacgtta aattttatcc ctcatgttgt    2460
ctaacggatt tctgcacttg atttattata aaaagacaaa gacataatac ttctctatca    2520
atttcagtta ttgttcttcc ttgcgttatt cttctgttct tcttttttctt ttgtcatata    2580 taaccataac caagtaatac atattcaaac tcgagatgtt gagaactcaa gccgccagat    2640
tgatctgcaa ctcccgtgtc atcactgcta agagaacctt tgctttggcc acccgtgctg    2700
ctgcttacag cagaccagct gcccgtttcg ttaagccaat gatcactacc cgtggtttga    2760
agcaaatcaa cttcggtggt actgttgaaa ccgtctacga aagagctgac tggccaagag    2820
aaaagttgtt ggactacttc aagaacgaca cttttgcttt gatcggttac ggttcccaag    2880
gttacggtca aggtttgaac ttgagagaca acggtttgaa cgttatcatt ggtgtccgta    2940
aagatggtgt cttcttggaag gctgccatcg aagacggttg ggttccaggc aagaacttgt    3000
tcactgttga agatgctatc aagagaggta gttacgttat gaacttgttg tccgatgccg    3060
ctcaatcaga aacctggcct gctatcaagc cattgttgac caagggtaag actttgtact    3120
tctcccacgg tttctcccca gtcttcaagg acttgactca cgttgaacca ccaaaggact    3180
tagatgttat cttggttgct ccaaagggtt ccggtagaac tgtcagatct ttgttcaagg    3240
aaggtcgtgg tattaactct tcttacgccg tctggaacga tgtcaccggt aaggctcacg    3300
aaaaggccca agctttggcc gttgccattg gttccggtta cgtttaccaa accactttcg    3360
aaagagaagt caactctgac ttgtacggtg aaagaggttg tttaatgggt ggtatccacg    3420
```

```
gtatgttctt ggctcaatac gacgtcttga gagaaaacgg tcactcccca tctgaagctt    3480
tcaacgaaac cgtcgaagaa gctacccaat ctctataccc attgatcggt aagtacggta    3540
tggattacat gtacgatgct tgttccacca ccgccagaag aggtgctttg gactggtacc    3600
caatcttcaa gaatgctttg aagcctgttt tccaagactt gtacgaatct accaagaacg    3660
gtaccgaaac caagagatct ttggaattca actctcaacc tgactacaga gaaaagctag    3720
aaaaggaatt agacaccatc agaaacatgg aaatctggaa ggttggtaag gaagtcagaa    3780
agttgagacc agaaaaccaa taacctagga tcttgtttaa agattacgga tatttaactt    3840
acttagaata atgccatttt tttgagttat aataatccta cgttagtgtg agcgggatt t   3900 aaactgtgag gaccttaata cattcagaca cttctgcggt atcaccctac ttattccctt    3960
cgagattata tctaggaacc catcaggttg gtggaagatt acccgttcta agacttttca    4020
gcttcctcta ttgatgttac acctggacac ccctttt ctg gcatccagtt tttaatcttc   4080
agtggcatgt gagattctcc gaaattaatt aaagcaatca cacaattctc tcggatacca    4140
cctcggttga aactgacagg tggtttgtta cgcatgctaa tgcaaaggag cctatatacc    4200
tttggctcgg ctgctgtaac agggaatata aagggcagca taatttagga gtttagtgaa    4260
cttgcaacat ttactatttt cccttcttac gtaaatattt ttcttttta a ttctaaatca   4320 atctttttca attttttgtt tgtattcttt tcttgcttaa atctataact acaaaaaaca    4380
catacataaa ctaaaagtcg acatgtaccc atacgatgtt ccagattacg caggtggtgg    4440
tgtcgacatg cctaaataca gatcagctac gactacacac ggtagaaata tggccggagc    4500
cagggcccta tggagagcca ccggcatgac agatgcagat tttggtaaac ctataattgc    4560
tgtagttaac tcttttacac agtttgttcc aggtcatgta catctaagag acttgggcaa    4620
attggtggca gaacaaatcg aggctgctgg tggtgttgca aaagaattta acactattgc    4680
cgtagacgac ggcattgcga tgggtcatgg cggtatgctt tattcgctac cctccagaga    4740
attaattgca gacagcgttg aatatatggt aaatgcccac tgcgcagatg ccatggtttg    4800
catttccaat tgtgacaaaa tcacgccggg catgttgatg gcgtcattga gactaaaatat   4860 tcctgtgatc ttcgttagcg gaggtccca t ggaagccggg aaaactaaac tttccgatca   4920
gataatcaag ttagacttgg tcgatgccat gatccagggt gcggaccccaaagtaagcga    4980 ctctcaatcc gatcaagttg aaagatccgc atgtccaact tgcgggagtt gctctgggat    5040
gttcacggcg aactctatga attgcctaac agaggccctg gcctgtcac aacctggcaa     5100 cggttcgctt ttagcaactc atgctgatag aaagcaatta tttctaaatg ctggtaaaag    5160
aatcgttgaa ttaacaaaaa gatattacga acaaaacgat gaatctgcac tgccaaggaa    5220
cattgcttca aaggccgctt tcgaaaacgc tatgacattg gatattgcaa tgggtggaag    5280
cacaaatact gtccttcatc tactggcggc tgctcaagaa gcagaaattg atttcacaat    5340
gagcgatatc gacaagctat cacgtaaggt cccgcagctg tgtaaagtgg caccgtctac    5400
tcaaaaatac cacatggaag atgtccatcg tgctggaggc gttatcggaa tcttggggga    5460 gttgacagg gccggtctat taaacagaga tgttaagaac gtgctaggtc taactttgcc     5520
tcaaacctta gagcagtacg acgttatgtt aactcaagat gacgcagtca aaacatgtt     5580 cagagcgggg ccagctggaa taaggactac ccaagcgttc tcgcaagatt gcagatggga    5640
tactctggac gatgatagag ctaacggttg cataagatca ctagagcatg cttactcgaa    5700
agatggaggt ttagctgttt tatacggtaa ttttgccgaa aacggatgta tagtgaagac    5760 cgctgggggtt gatgattcaa ttctaaaatt cactgggcca gccaaggtat acgagtcaca    5820
```

```
agatgatgct gttgaagcca tcttaggtgg gaaagtggtg gcaggggacg tggtggtaat    5880
aagatatgaa ggtccaaagg gtggtccagg tatgcaagaa atgctgtacc ctacttcttt    5940
ccttaaatct atgggtttag gcaaggcttg tgctcttata accgatggta gattttctgg    6000
aggtacatca ggccttttcca taggacatgt tagccccgaa gctgcctcag gtggtagtat   6060
tggcttaatc gaggatggtg acttaattgc tattgacatt cctaacaggg gtattcaact    6120
acaggttagc gatgcagaat tagccgctag aagagaggca caagatgcga gaggcgataa    6180
agcatggaca cctaagaaca gggagagaca agtgagcttt gccctgagag cttatgcctc    6240
gctggcgacg agcgcagaca aaggagccgt aagagataaa tcaaaattgg gtggttaggg    6300
atccgcgatt taatctctaa ttattagtta agttttata agcatttta tgtaacgaaa      6360
aataaattgg ttcatattat tactgcactg tcacttacca tggaaagacc agacaagaag    6420
ttgccgacag tctgttgaat tggcctggtt aggcttaagt ctgggtccgc ttctttacaa    6480
atttggagaa tttctcttaa acgatatgta tattcttttc gttggaaaag atgtcttcca    6540
aaaaaaaac cgatgaatta gtggaaccaa ggaaaaaaaa agaggtatcc ttgattaagg      6600
aacactgttt aaacagtgtg gtttccaaaa ccctgaaact gcattagtgt aatagaagac    6660
tagacacctc gatacaaata atggttactc aattcaaaac tgccagcgaa ttcgactctg    6720
caattgctca agacaagcta gttgtcgtag atttctacgc cacttggtgc ggtccatgta    6780
aaatgattgc tccaatgatt gaaaaattct ctgaacaata cccacaagct gatttctata    6840
aattggatgt cgatgaattg ggtgatgttg cacaaaagaa tgaagtttcc gctatgccaa    6900
ctttgcttct attcaagaac ggtaaggaag ttgcaaaggt tgttggtgcc aacccagcgg    6960
ctattaagca agccattgct gctaatgctt aaactcaccc aatgaccgat atattgtgtt    7020
tctatactgt gtttgttata tatagtttac ctttaagctt aaaatgaagt gaagttccta    7080
tactttctag agaataggaa cttctatagt gagtcgaata agggcgacac aaaatttatt    7140
ctaaatgcat aataaatact gataacatct tatagtttgt attatatttt gtattatcgt    7200
tgacatgtat aattttgata tcaaaaactg attttccctt tattattttc gagatttatt    7260
ttcttaattc tctttaacaa actagaaata ttgtatatac aaaaaatcat aaataataga    7320
tgaatagttt aattataggt gttcatcaat cgaaaaagca acgtatctta tttaaagtgc    7380
gttgcttttt tctcatttat aaggttaaat aattctcata tatcaagcaa agtgacaggc    7440
gcccttaaat attctgacaa atgctctttc cctaaactcc ccccataaaa aaacccgccg    7500
aagcgggttt ttacgttatt tgcggattaa cgattactcg ttatcagaac cgcccagggg    7560
gcccgagctt aagactggcc gtcgttttac aacacagaaa gagtttgtag aaacgcaaaa    7620
aggccatccg tcaggggcct tctgcttagt ttgatgcctg gcagttccct actctcgcct    7680
tccgcttcct cgctcactga ctcgctgcgc tcggtcgttc ggctgcggcg agcggtatca    7740
gctcactcaa aggcggtaat acggttatcc acagaatcag gggataacgc aggaaagaac    7800
atgtgagcaa aaggccagca aaaggccagg aaccgtaaaa aggccgcgtt gctggcgttt    7860
ttccataggc tccgcccccc tgacgagcat cacaaaaatc gacgctcaag tcagaggtgg    7920
cgaaacccga caggactata aagataccag gcgtttcccc ctggaagctc cctcgtgcgc    7980
tctcctgttc cgaccctgcc gcttaccgga tacctgtccg cctttctccc ttcgggaagc    8040
gtggcgcttt ctcatagctc acgctgtagg tatctcagtt cggtgtaggt cgttcgctcc    8100
aagctgggct gtgtgcacga accccccgtt cagcccgacc gctgcgcctt atccggtaac    8160
tatcgtcttg agtccaaccc ggtaagacac gacttatcgc cactggcagc agccactggt    8220
```

| | |
|---|---|
| aacaggatta gcagagcgag gtatgtaggc ggtgctacag agttcttgaa gtggtgggct | 8280 |
| aactacggct acactagaag aacagtattt ggtatctgcg ctctgctgaa gccagttacc | 8340 |
| ttcggaaaaa gagttggtag ctcttgatcc ggcaaacaaa ccaccgctgg tagcggtggt | 8400 |
| ttttttgttt gcaagcagca gattacgcgc agaaaaaaag gatctcaaga agatcctttg | 8460 |
| atctttctta cggggtctga cgctcagtgg aacgacgcgc gcgtaactca cgttaaggga | 8520 |
| ttttggtcat gagcttgcgc cgtcccgtca agtcagcgta atgctctgct tt | 8572 |

<210> SEQ ID NO 83
<211> LENGTH: 1488
<212> TYPE: DNA
<213> ORGANISM: Artificial Sequence
<220> FEATURE:
<223> OTHER INFORMATION: E. coli codon optimized ilvC for expression in
      S. cerevisiae

<400> SEQUENCE: 83

| | |
|---|---|
| ctcgagatgg ccaactattt taacacatta aatttgagac aacaattggc tcaactgggt | 60 |
| aagtgcagat ttatgggaag ggacgagttt gctgatggtg cttcttatct gcaaggaaag | 120 |
| aaaagtagtaa ttgttggctg cggtgctcag ggtctaaacc aaggtttaaa catgagagat | 180 |
| tcaggtctgg atatttcgta tgcattgagg aaagaggcaa ttgcagaaaa gagggcctcc | 240 |
| tggcgtaaag cgacggaaaa tgggttcaaa gttggtactt acgaagaact gatccctcag | 300 |
| gcagatttag tgattaacct aacaccagat aagcaacact cagacgtagt aagaacagtt | 360 |
| caaccgctga tgaaggatgg ggcagcttta ggttactctc atggctttaa tatcgttgaa | 420 |
| gtgggcgagc agatcagaaa agatataaca gtcgtaatgg ttgcaccaaa gtgcccaggt | 480 |
| acggaagtca gagaggagta caagaggggt tttggtgtac ctacattgat cgccgtacat | 540 |
| cctgaaaatg acccccaaagg tgaaggtatg gcaattgcga aggcatgggc agccgcaacc | 600 |
| ggaggtcata gagcgggtgt gttagagagt tcttttcgtag ctgaggtcaa gagtgactta | 660 |
| atgggtgaac aaaccattct gtgcggaatg ttgcaggcag ggtctttact atgctttgat | 720 |
| aaattggtcg aagagggtac agatcctgcc tatgctgaaa agttgataca atttggttgg | 780 |
| gagacaatca ccgaggcact taaacaaggt ggcataacat tgatgatgga tagactttca | 840 |
| aatccggcca agctaagagc ctacgcctta tctgagcaac taaaagagat catggcacca | 900 |
| ttattccaaa agcacatgga cgatattatc tccggtgagt tttcctcagg aatgatggca | 960 |
| gattgggcaa acgatgataa aaagttattg acgtggagag aagaaaccgg caagacggca | 1020 |
| ttcgagacag ccccacaata cgaaggtaaa attggtgaac aagaatactt tgataaggga | 1080 |
| gtattgatga tagctatggt gaaggcaggg gtagaacttg cattcgaaac tatggttgac | 1140 |
| tccggtatca ttgaagaatc tgcatactat gagtctttgc atgaattgcc tttgatagca | 1200 |
| aatactattg caagaaaaag acttttacgag atgaatgttg tcatatcaga cactgcagaa | 1260 |
| tatggtaatt acttatttag ctacgcatgt gtcccgttgt taaagcccctt catggccgag | 1320 |
| ttacaacctg gtgatttggg gaaggctatt ccggaaggag cggttgacaa tggccaactg | 1380 |
| agagacgtaa atgaagctat tcgttcacat gctatagaac aggtgggtaa aaagctgaga | 1440 |
| ggatatatga ccgatatgaa aagaattgca gtggcaggat gaagatct | 1488 |

<210> SEQ ID NO 84
<211> LENGTH: 38
<212> TYPE: DNA
<213> ORGANISM: Artificial Sequence
<220> FEATURE:
<223> OTHER INFORMATION: Primer 1792

<400> SEQUENCE: 84
ttttctcgag atgcagattt tgtgaagac cctcactg                                  38

<210> SEQ ID NO 85
<211> LENGTH: 51
<212> TYPE: DNA
<213> ORGANISM: Artificial Sequence
<220> FEATURE:
<223> OTHER INFORMATION: Primer 1794

<400> SEQUENCE: 85
ttttgcggcc gcggatccgt cgacacctcg caggcgcaac accaggtgca g                  51

<210> SEQ ID NO 86
<211> LENGTH: 228
<212> TYPE: DNA
<213> ORGANISM: Artificial Sequence
<220> FEATURE:
<223> OTHER INFORMATION: M. musculus ubiquitin gene codon-optimized for
      expression in S. cerevisiae

<400> SEQUENCE: 86
atgcagattt tgtgaagac cctcactggc aaaaccatca cccttgaggt cgagcccagt          60
gacaccattg agaatgtcaa agccaaaatt caagacaagg agggtatccc acctgaccag        120
cagcgtctga tatttgccgg caaacagctg gaggatggcc gcactctctc agactacaac        180
atccagaaag agtccaccct gcacctggtg ttgcgcctgc gaggtgga                     228

<210> SEQ ID NO 87
<211> LENGTH: 1713
<212> TYPE: DNA
<213> ORGANISM: Lactococcus lactis

<400> SEQUENCE: 87
atggagttta agtataacgg caaagttgaa tctgttgaac tgaataagta cagcaaaacg         60
ttgacacaag atcccacaca acccgccaca caggcaatgt attacggcat cgggtttaaa       120
gacgaagatt tcaagaaagc tcaagtgggt atagtgtcga tggactggga tggaaatcca       180
tgcaacatgc atttaggaac ccttggatca agattaaaa gctcagtaaa tcagacagat       240
ggtctgatcg gcttacaatt tcatacgata ggagtttctg atgggatagc aaatggaaag       300
ttgggaatga gatactccct tgtttccaga gaagttatag ctgactctat tgaaaccaac       360
gctggcgctg aatactatga tgcaattgta gccatcccag ttgtgacaa aaatatgcca       420 ggttctatta ttggtatggc aagacttaat aggccaagca ttatggtgta tggaggaaca       480
atagaacacg gtaatataa aggtgagaaa ttgaacatcg tatcggcttt tgaatctcta       540
ggccagaaaa ttaccggcaa tatctctgat gaagattatc acggtgttat ttgtaatgct       600
attcctggtc aaggggcatg tgggggatg tacacagcta ataccttagc tgccgctatc       660
gaaacactag gtatgtcatt gccgtattct tcttcgaacc ctgcagtatc tcaagaaaaa       720
caagaagaat gtgatgagat tggattagcc attaagaatc ttttggaaaa agacatcaag       780
cctagtgata taatgactaa ggaggcgttc gagaacgcta ttaccattgt gatggtcttg       840
gggggtagta ctaatgctgt cttgcatatt attgcaatgg ctaacgcgat aggtgtcgaa       900
ataactcagg atgacttcca agaattagt gacattactc cagtactagg tgattttaaa       960
ccttcaggta atatatgat ggaagatttg cataaaattg gaggcttgcc agcagtgctt      1020
aagtaccttc taaggaagg aaaattgcat ggtgactgcc ttactgtgac gggtaaaaca      1080

```
ttagccgaga atgtcgagac tgccctagac ttggatttcg actcacaaga tatcatgagg    1140
ccactaaaga atcctatcaa ggccaccggc cacttgcaga ttctgtacgg taatttagct    1200 caaggggtt ccgtagcaaa aattagcggt aaagaaggag agttcttcaa aggcactgcc    1260
agagtctttg atggtgaaca acattttatc gacggcatag aatctggtcg tttgcatgct    1320
ggagatgtag cggtaattag gaatataggt cccgtcggcg gacctggtat gcccgaaatg    1380
ctgaagccta catcagcatt aattggtgcg ggtttaggga aaagttgcgc gttaattacg    1440
gatggtagat tctccggtgg cactcacggt tttgttgtcg gccatattgt gcctgaagcc    1500
gttgagggtg gactaatcgg cttagttgaa gatgacgata aatagagat agatgcagtc    1560 aacaactcta tatccctgaa agtttccgat gaagaaatcg caaagagaag agctaattat    1620
cagaagccaa ctccgaaagc caccagggga gttttggcaa aattcgctaa attaacccgt    1680
cctgcatcgg aagggtgtgt tactgatctg taa                                  1713

<210> SEQ ID NO 88
<211> LENGTH: 1758
<212> TYPE: DNA
<213> ORGANISM: Saccharomyces cerevisiae

<400> SEQUENCE: 88
atgggcttgt taacgaaagt tgctacatct agacaattct ctacaacgag atgcgttgca      60
aagaagctca acaagtactc gtatatcatc actgaaccta agggccaagg tgcgtcccag     120
gccatgcttt atgccaccgg tttcaagaag gaagatttca agaagcctca agtcggggtt     180
ggttcctgtt ggtggtccgg taacccatgt aacatgcatc tattggactt gaataacaga     240
tgttctcaat ccattgaaaa agcgggtttg aaagctatgc agttcaacac catcggtgtt     300
tcagacggta tctctatggg tactaaaggt atgagatact cgttacaaag tagagaaatc     360
attgcagact cctttgaaac catcatgatg gcacaacact acgatgctaa catcgccatc     420
ccatcatgtg acaaaaacat gcccggtgtc atgatggcca tgggtagaca taacagacct     480
tccatcatgg tatatggtgg tactatcttg cccggtcatc caacatgtgg ttcttcgaag     540
atctctaaaa acatcgatat cgtctctgcg ttccaatcct acggtgaata tatttccaag     600
caattcactg aagaagaaag agaagatgtt gtggaacatg catgcccagg tcctggttct     660
tgtggtggta tgtatactgc caacacaatg gcttctgccg ctgaagtgct aggttttgacc     720 attccaaaact cctcttcctt cccagccgtt tccaaggaga agttagctga gtgtgacaac     780
attggtgaat acatcaagaa gacaatggaa ttgggtattt tacctcgtga tatcctcaca     840
aaagaggctt ttgaaaacgc cattacttat gtcgttgcaa ccggtgggtc cactaatgct     900
gttttgcatt tggtggctgt tgctcactct gcgggtgtca agttgtcacc agatgattttc     960 caagaatca gtgatactac accattgatc ggtgacttca accttctgg taaatacgtc    1020 atggccgatt tgattaacgt tggtggtacc caatctgtga ttaagtatct atatgaaaac    1080
aacatgttgc acggtaacac aatgactgtt accggtgaca ctttggcaga acgtgcaaag    1140
aaagcaccaa gcctacctga aggacaagag attattaagc cactctccca cccaatcaag    1200
gccaacggtc acttgcaaat tctgtacggt tcattggcac aggtggagc tgtgggtaaa    1260 attaccggta aggaaggtac ttacttcaag ggtagagcac gtgtgttcga agaggaaggt    1320
gcctttattg aagccttgga agaggtgaaa atcaagaagg gtgaaaaac cgttgttgtt    1380 atcagatatg aaggtccaag aggtgcacca ggtatgcctg aaatgctaaa gccttcctct    1440
gctctgatgg gttacggttt gggtaaagat gttgcattgt tgactgatgg tagattctct    1500
```

-continued

| | |
|---|---|
| ggtggttctc acgggttctt aatcggccac attgttcccg aagccgctga aggtggtcct | 1560 |
| atcgggttgg tcagagacgg cgatgagatt atcattgatg ctgataataa caagattgac | 1620 |
| ctattagtct ctgataagga aatggctcaa cgtaaacaaa gttgggttgc acctccacct | 1680 |
| cgttacacaa gaggtactct atccaagtat gctaagttgg tttccaacgc ttccaacggt | 1740 |
| tgtgttttag atgcttga | 1758 |

<210> SEQ ID NO 89
<211> LENGTH: 1701
<212> TYPE: DNA
<213> ORGANISM: Saccharomyces cerevisiae

<400> SEQUENCE: 89

| | |
|---|---|
| atgaagaagc tcaacaagta ctcgtatatc atcactgaac ctaagggcca aggtgcgtcc | 60 |
| caggccatgc tttatgccac cggtttcaag aaggaagatt tcaagaagcc tcaagtcggg | 120 |
| gttggttcct gttggtggtc cggtaaccca tgtaacatgc atctattgga cttgaataac | 180 |
| agatgttctc aatccattga aaaagcgggt ttgaaagcta tgcagttcaa caccatcggt | 240 |
| gtttcagacg gtatctctat gggtactaaa ggtatgagat actcgttaca agtagagaa | 300 |
| atcattgcag actcctttga aaccatcatg atggcacaac actacgatgc taacatcgcc | 360 |
| atcccatcat gtgacaaaaa catgcccggt gtcatgatgg ccatgggtag acataacaga | 420 |
| ccttccatca tggtatatgg tggtactatc ttgcccggtc atccaacatg tggttcttcg | 480 |
| aagatctcta aaaacatcga tatcgtctct gcgttccaat cctacggtga atatatttcc | 540 |
| aagcaattca ctgaagaaga agagaagat gttgtggaac atgcatgccc aggtcctggt | 600 |
| tcttgtggtg gtatgtatac tgccaacaca atggcttctg ccgctgaagt gctaggtttg | 660 |
| accattccaa actcctcttc cttcccagcc gtttccaagg agaagttagc tgagtgtgac | 720 |
| aacattggtg aatacatcaa gaagacaatg gaattgggta ttttacctcg tgatatcctc | 780 |
| acaaaagagg cttttgaaaa cgccattact tatgtcgttg caaccggtgg gtccactaat | 840 |
| gctgttttgc atttggtggc tgttgctcac tctgcgggtg tcaagttgtc accagatgat | 900 |
| ttccaaagaa tcagtgatac tacaccattg atcggtgact caaacccttc tggtaaatac | 960 |
| gtcatggccg atttgattaa cgttggtggt acccaatctg tgattaagta tctatatgaa | 1020 |
| aacaacatgt tgcacggtaa cacaatgact gttaccggtg acacttttggc agaacgtgca | 1080 |
| aagaaagcac aagcctacct gaaggacaa gagattatta agccactctc ccacccaatc | 1140 |
| aaggccaacg tcacttgca aattctgtac ggttcattgg caccaggtgg agctgtgggt | 1200 |
| aaaattaccg gtaaggaagg tacttacttc aagggtagag cacgtgtgtt cgaagaggaa | 1260 |
| ggtgccttta ttgaagcctt ggaaagaggt gaaatcaaga agggtgaaaa accgttgtt | 1320 |
| gttatcagat atgaaggtcc aagaggtgca ccaggtatgc ctgaaatgct aaagccttcc | 1380 |
| tctgctctga tgggttacgg tttgggtaaa gatgttgcat tgttgactga tggtagattc | 1440 |
| tctggtggtt ctcacgggtt cttaatcggc cacattgttc ccgaagccgc tgaaggtggt | 1500 |
| cctatcgggt tggtcagaga cggcgatgag attatcattg atgctgataa taacaagatt | 1560 |
| gacctattag tctctgataa ggaaatggct caacgtaaac aaagttgggt tgcacctcca | 1620 |
| cctcgttaca caagaggtac tctatccaag tatgctaagt tggtttccaa cgcttccaac | 1680 |
| ggttgtgttt tagatgcttg a | 1701 |

<210> SEQ ID NO 90
<211> LENGTH: 1689
<212> TYPE: DNA

<213> ORGANISM: Gramella forsetii

<400> SEQUENCE: 90

```
atggataaaa cagccatgaa taacaaatac tcttctacta ttacacaaag tgactcacaa      60
ccagcgtcac aagcaatgct tcacgccatc ggccttaata aggaagattt gaaaaagcct     120
tttgtaggca tcggcagtac cggatatgaa ggaaacccat gcaacatgca cctgaatgat     180
ttggctaagg aagtgaaaaa aggcactcag aatgcagatt taaacggtct gatctttaat     240
acaattggcg tcagcgatgg aatatctatg ggtactccag gtatgaggtt ctcattgcca     300
tcccgtgact tgattgcaga tagcatggaa acagtagttg gtggaatgtc gtatgatggt     360
ttagttaccg tagttgggtg tgataaaaac atgccaggag cattaatggc aatgttgagg     420
ttaaatcgtc cgtcggtttt agtgtatggg ggaacaattg ctagtggttg ccacaatgga     480
aagaagttag atgttgtgtc tgcttttcgag gcctgggggtt ctaaagtttc aggtgatatg     540
caggaagaag aataccagca agtcattgaa aaggcatgtc ctggtgcagg tgcttgtggg     600
ggtatgtaca cagccaacac catggcttca tctattgaag ccttggggat gtccttgcct     660
tttaactcat ccaatcctgc aactggtccg gaaaaaactc aagaatctgt caaagctggc     720
gaggctatga atacttact agaaaatgat ctgaaaccca agatattgt gacggccaag     780
tcgctggaaa atgctattag attgctaacg gttttgggtg gtagtaccaa tgccgtcttg     840
cacttcttgg ctatagctaa ggcagccgaa ataaactttg gtttgaaaga ttttacaaga     900
atatgtgagg aaactccctt cttggccgac ttaaaaccat ctggtaagta tctgatggaa     960
gacattcata ggataggcgg aatccccgcg gttatgaagt acatgttaga gaaaggatta    1020
cttcatggtg agtgcatgac ggtaactggc aagactatcg cagaaaacct tgaaaatgtg    1080
aaacctctgc cagatgatca ggacgtgatt catccagtcg aaaaacctat taaagctact    1140
ggacatatca ggatttttgta tgcaatttta gccagcgaag ctccgtagc caagattact    1200
gggaaggaag gattagaatt tcaaggtaag gccagagtct ttaatggcga atttgaggcc    1260
aatgaaggga tcagtagcgg aaaggtccaa aaaggcgacg tagtagtaat tagatatgag    1320
ggtcccaagg ggggtccggg tatgccggaa atgctaaaac ccacgtcagc aataatggga    1380
gctggtcttg gtaagagtgt cgctttaata actgacggta gattcagcgg cggtactcat    1440
ggttttgtcg tgggtcatat aaccctgaa gcgcaacaag tggactaat agggctattg    1500
aaagatggtg atgaaatttc gatcaacgcg gagaaaaaca cgattgaagc acatttatcc    1560
gcagaagaaa ttaatagaag aaaggaggct tggaaggctc ctgctctaaa agttaacggt    1620
ggggtacttt acaaatatgc gaagacagtt gctagtgcat cagaggggtg tgttacagac    1680
gagttctaa                                                            1689
```

<210> SEQ ID NO 91
<211> LENGTH: 1707
<212> TYPE: DNA
<213> ORGANISM: Saccharopolyspora erythraea

<400> SEQUENCE: 91

```
atgagtacga gtacagatgg tacgggtcaa tcaggtagag gactaaaacc aaggtccgga      60
gacgtaaccg agggtataga aagagccgcc gcaagaggca tgttacgtgc agtcggtatg     120
caagatgctg acttcgccaa gcctcaaatt ggtgtcgctt cgtcttggaa cgagataact     180
ccctgtaatc tttcccttca gcgtttagca caagcgtcta aggaaggagt gcatgcagct     240
ggtgggttcc caatggaatt tggcactatt tcagtgagtg atgggatatc tatgggccat     300
```

-continued

```
gttggaatgc attactctct agtgagtagg gaggtgattg ctgattcggt tgagacggta      360
atggaagctg aaaggctgga cggttccgtt ttgttagccg gttgtgacaa gagcctaccg      420
ggtatgctaa tggccgcagc acgtttagat gtcgccgctg tattcgtgta tgcaggttcc      480
atactgcctg aagagtaga cgatagagaa gtaactatta ttgacgcttt tgaagccgtc      540
ggagcttgtg caaggggctt gatctcagaa gccgaggtgg ataggattga aagggctata      600
tgcccaggtg aaggcgcttg tggaggaatg tatacggcga ataccatggc ttgtgcggct      660
gaagcaatgg gcatgtcgtt accaggatca gcctcccctc ctagcgtaga tcgtagaaga      720
gacgcgggcg cacgtgaagc tggtagagct gtggtcggta tgattgaacg tggtcttaca      780
gccagacaaa tattgactaa agaggcgttc gaaaacgcta tcgcggttgt tatggctttt      840
ggcggcagta ctaatgctgt tctgcatttg ctggcaattg cacgtgaggc agaagttgat      900
ttaacattag atgattttaa caggattggt gatagagtgc ctcatctggc tgatgttaag      960
ccatttggaa ggcacgtgat gaccgcagtc gataggatag tggagtacc agtagtaatg     1020 aaagccttgt tggatgctgg tttgcttcat ggagactgta tgacagttac tgggaaaact     1080
gtcgccgaga atctagctga attagaccca ccagaattag acggggaagt tcttcacaaa     1140
ctgtctaacc ccttacaccc taccggcggc ttgaccatct tgagagggag cttggcccct     1200
gagggagctg ttgtcaaaag cgctggcttt gactccgcaa cattcgaggg tactgcacgt     1260
gttttcgatg gagagcaggg tgccatggat gctgttgagg atggttcatt gaaagcgggt     1320
gacgtggtag tcatcagata tgaaggtcca agaggcggtc caggtatgag ggaaatgctt     1380
gctgtaacag gggctatcaa aggtgcaggg ttagggaagg acgttctatt gttaactgat     1440
ggtagatttt cggtggaac cacaggttta tgcatcggac acgtcgcgcc cgaagcaact     1500
gacggcggtc cgattgcttt tgttcgtgac ggtgatccta ttagactgga tttagcgggt     1560
agaactttgg atctattagt agatgaagcc gaacttgcaa gaagaaaga aggctgggtt     1620 ccgagagaac ccaagtttag acaaggtgtt ttgggcaaat acgctagact ggttaggtct     1680
gctgcagttg gagccgtctg ctccttga                                        1707
```

<210> SEQ ID NO 92
<211> LENGTH: 1722
<212> TYPE: DNA
<213> ORGANISM: Candidatus Koribacter versatilis

<400> SEQUENCE: 92

```
atgactgaga agtcaccaaa accccataag agatccgatg caatcacaga ggggccaaat       60
cgtgctcctg ctcgtgctat gttaagggct gcaggtttta ctcctgagga tttgagaaaa      120
cccattatcg gtatagccaa cacatggatt gaaattggcc cttgcaactt acatctaaga      180
gaattggccg aacatatcaa gcaaggtgta agagaagctg gagggacacc catggaattt      240
aatacagttt ccatctccga cgggataacc atgggatcag aagtatgaa agctagtcta      300 gtgagtcgtg aggtaatagc cgattcaatt gagttagttg ccagaggaaa cttgtttgat      360
ggactaatag ctttatctgg atgtgataag acaatcccag gtacaattat ggcattggag      420
agacttgata tcccaggcct tatgctttat ggtggttcaa ttgctccggg caaattccac      480
gcacagaagg ttacgatcca agatgtattc gaagccgttg gtacccacgc tagggggtaaa      540 atgagcgatg cagacttaga agagcttgag cacaatgctt gtcctggtgc tggggcgtgc      600
ggaggacagt tcagagctaa tactatgtct atgtgtggtg aatttctggg tatatctcct      660
atgggagcga atagcgttcc cgcaatgacg gtcgagaaac aacaagtcgc gcgtagatgt      720
```

```
ggacatttag ttatggagtt ggtgagaaga gacatcaggc cgtctcaaat cataacaaga    780
aaagcaattg agaacgcaat agcatcagtt gcggctagtg gaggtagtac taacgcggtc    840
ctgcatctgt tagctattgc acacgagatg gatgtcgaat tgaacattga agattttgat    900
aagataagct ctcgtactcc acttctttgt gaactgaaac cagccggtag gtttacggct    960
acagatttgc atgacgctgg tggtattcca ttagttgctc aaagactgtt ggaagcaaat   1020
ttgttacacg ctgacgcttt gacagtaact ggcaagacta ttgcagaaga agctaaacag   1080
gccaaagaaa ccccgggcca agaagtagtc aggcccttga ccgacccaat taaggctacc   1140
ggcggattaa tgatcttaaa aggtaatcta gcatcagaag ggtgcgtggt aaagttggtt   1200
ggtcacaaga agttattctt cgaaggtcct gcgagagttt ttgaatctga agaagaagca   1260
tttgccggcg tcgaggatag gacgattcaa gcgggtgaag ttgtagtggt cagatacgaa   1320
gggccaaaag gcggacctgg aatgcgtgaa atgttaggcg ttactgctgc gatagctggc   1380
accgagttag ctgaaactgt ggccctaatc accgacggta gattttcggg tgcaacaaga   1440
ggtctatccg tggggcatgt cgcacctgaa gccgcaaatg gtggtgccat tgccgtagtt   1500
aggaatggtg acattattac gctggatgtt gagagaagag aattaagggt tcatttgact   1560
gatgctgaat tggaggccag attgcgtaac tggagagcgc ctgaaccgag atacaaacgt   1620
ggtgttttcg ctaaatatgc ttctacggtc tcatcagcat cgttcggagc tgtaacaggt   1680
tctaccatag aaaacaaaac actggcaggc tcgactaagt aa                     1722

<210> SEQ ID NO 93
<211> LENGTH: 1779
<212> TYPE: DNA
<213> ORGANISM: Piromyces sp

<400> SEQUENCE: 93
atgtctttct cactggctaa cctggccgct aagggttcga acttgttcaa atttactcct     60
gcgcttctaa gcgcaaagcg ttttggttca tcaggaaagc caattaataa gttcagcaag    120
attataacag agccaaagtc tagaggggt agtcaagcga tgttaatcgc aactggtata    180
aaaccagaag atttaaaaaa gccacagatc ggcataggca gtgtttggta tgatggaaat    240
ccatgcaaca tgcatctatt ggatcttggc tccgtggtaa aaaaggccgt tcaaaaacaa    300
aatatgaatg gtatgagatt caatatgatt ggagtgtcag acgggatctc caacggtacg    360
gatggaatgt cctttttcttt gcagtcccgt gaaattattg cggattctat cgaaacaatc    420
atgtctgcac aatattatga tgctaacatc agcttacctg gctgcgacaa gaacatgcct    480
ggttgtttaa tcgccgctgc cagattgaac agaccgacta taattatcta cggtggcacg    540
atcaagcccg gacatacaaa aaagggagag acgattgatt tagtctcggc cttccaatgt    600
tatgggcaat acttggctgg agaaattact gaagagcaaa gagaagaaat agtgaataat    660
gcatgtcctg gcgcaggtgc atgcggtgga atgtatacag ctaatacaat ggcttccata    720
atcgaatcaa tgggtatgag tttaccttac tccgcctcga ccccggcaga agacccattg    780
aaagagcttg aatgtataaa cgcggcagct gcaattaaga atttaatgga aaaagacatc    840
aagccattag acataatgac aagaaaagcg tttgagaacg ctataactat actttttgatt    900 cttgagggga gtacaaactc cgttctgcac cttttggcta tcgctagggc ctgcaaagtc    960
ccattaacta ttgacgattt ccaggaattt tctaatagga tacccgtttt agccgactta   1020
aaacctagtg gtaaatatgt catggaagat ttgcagttga tcggcggtct tccagctatt   1080
cagaaatatc ttctgaatga aggtctactt catggtgata ttatgactgt taccggaaag   1140
```

-continued

| | |
|---|---|
| accctagcag agaatttgaa agacgttgct ccaatcgatt ttgaaactca agatataatt | 1200 |
| agacctttat cgaatcccat taaaaagaat ggtcacatta tcattatgaa aggtaacgtc | 1260 |
| tctccggacg gtggtgttgc taaaattaca ggtaagcagg gattgttttt cgaaggcgtg | 1320 |
| gcgaattgct ttgattgtga agaagacatg ttagctgcac tggaaagagg cgaaattaaa | 1380 |
| aaaggtcaag tgattataat aaggtatgaa ggccccactg gagggcctgg tatgccggag | 1440 |
| atgctaactc cgaccagtgc tattatgggt gctgggttag gaaaagatgt agcactatta | 1500 |
| acagatggca gattttcagg cgggtcacac ggcttcatta ttggtcatat tacgcctgag | 1560 |
| gcacaagtag gtggtccaat tgccctaatc aaaaacggtg ataagataac tatagacgcg | 1620 |
| aataaacgta ccatacatgc ccatgtcagc gaagaagaat ttgctaaaag acgtgccgag | 1680 |
| tggaaagcac caccttacag agctactcaa ggtactttaa agaaatacat taagctggtt | 1740 |
| aaacccgcaa actttggatg tgttaccgat gagtggtaa | 1779 |

<210> SEQ ID NO 94
<211> LENGTH: 1764
<212> TYPE: DNA
<213> ORGANISM: Ralstonia eutropha

<400> SEQUENCE: 94

| | |
|---|---|
| atgccgtacg cagatgaccc aaaattacct caagatgggg ctgcgcctac agaaggtttg | 60 |
| gccaagggcc ttactaatta tggtgatact ggtttctctt tattcctgag gaaggctttt | 120 |
| atcaaaggtg caggttttac cgatgatgca ctatcaaggc cggtgatagg aattgtaaat | 180 |
| actggatctt cttataaccc atgccacggc aacgcccctc aattagtgga ggcggtgaag | 240 |
| agaggtgtca tgttggcagg tggtttaccc gtagacttcc ctactatatc cgtccacgag | 300 |
| tcatttagcg cacccactag tatgtattta aggaacttga tgtccatgga taccgaagaa | 360 |
| atgattcgtg ctcagccgat ggacgccgtc gttctgatag ggggttgtga caaaacagtt | 420 |
| ccagcccaac tgatgggtgc cgcatcagct ggagtaccag ccatccaatt agtcacaggt | 480 |
| tctatgctaa ctggtagcca tagaagtgag agagtcggag cgtgtacgga ttgtcgtaga | 540 |
| tactggggta gataccgtgc tgaggagatt gattcagccg agatcgcaga tgttaataat | 600 |
| cagttggttg cctcagttgg tacatgctcg gtcatgggga cagcttcaac aatggcttgt | 660 |
| gtagcagagg ccttgggtat gatggtttct ggcggtgctt cggcacctgc tgtgaccgcg | 720 |
| gatagagtta gggtcgcgga acgtaccggg acgactgctg ttggaatggc ggcggccagg | 780 |
| ttgacacctg atagaatatt aacaggtaaa gcctttgaaa acgctttgag agttctactg | 840 |
| gcaatcggcg gttcaacaaa tgggatagta catctaacgg ctattgctgg tagactagga | 900 |
| atcgacatcg acctagcagg gttggacaga atgtctcgtg aaacgcctgt tctggttgac | 960 |
| ttgaaaccta gcggtcaaca ttacatggaa gattttcata aggccggagg aatgttaacg | 1020 |
| ttgttacgtg aactgagacc actattacac ttagatactt tgaccgttag tggaaggacc | 1080 |
| cttggcgaag aattagatgc agcacccccct ctgttcccac aagatgtcat tagaagtgca | 1140 |
| ggtaatccta tttatcccgc aggtggatta gcggtccttc gtggtaattt ggctccaggc | 1200 |
| ggggctatca tcaaacaatc cgctgcgaac ccagctctta tggagcatga aggaagagcc | 1260 |
| gtagttttg aaaatgcaga agacatggct caaagaattg acgacgaatc cttagacgtg | 1320 |
| aaagctgacg atattcttgt acttaaaagg attggtccaa ctggcgcccc gggtatgcct | 1380 |
| gaagctggct atatgccgat accaaagaag ttagcaagag cagggggttaa ggatatggta | 1440 |
| agagttagtg atggtcgtat gtctggaacg gcagctggca caatagtttt gcatgtgaca | 1500 |

```
ccagaagcag ccatagggggg acccttagcc cttgttcagt cgggagatag aattaggcta     1560
tctgtggcca accgtgaaat tgcattgtta gtagatgatg ccgaattagc aaggagggcc     1620
gctgctcaac ccgtagaaag accaagggct gagagaggtt atagaaaatt gtttctggag     1680
acagtaactc aggcggatca gggtgttgat ttcgactttt tgagagctgc tcaaactgtg     1740
gatacagtcc caaagcaagg ctaa                                            1764
```

<210> SEQ ID NO 95
<211> LENGTH: 1746
<212> TYPE: DNA
<213> ORGANISM: Chromohalobacter salexigens

<400> SEQUENCE: 95

```
atgactcata agaagagacc tttaagaagt gccgagtggt tcggtaatga tgacaaaaat      60
ggatttatgt atagatcgtg gatgaaaaac caaggtatac ccgatcacga gtttagaggt     120
aaaccgataa ttggtatctg caataccttt agtgaactaa ctccatgcaa cgcccatttc     180
agaaagttag cagaacatgt gaaaaaaggt gtattagaag caggcggtta cccggttgaa     240
tttccagtat tttctaacgg ggaatctaat ttgagaccaa ctgctatgtt cacaaggaat     300
ttggctagta tggatgtcga ggaagccatt agaggcaatc cattagacgc agtcgtgttg     360
cttgtgggtt gtgataaaac aacaccagcc ttacttatgg gtgctgcttc ttgtgacatt     420
ccgactatag ttgttacagg tgggccaatg cttaacggga acacaagggg aagagacatc     480
ggatcaggta cggtcgtgtg gcagcttttct gaagaggtta aggccgggaa aatttcctta     540
catgatttca tggcggctga ggctggaatg agccgttccg ctggcacttg taacactatg     600
ggaaccgcct ctaccatggc atgcatggcc gaatctcttg gtacttcatt gccacacaat     660
gccgctattc cggccgtgga tagccgtagg tatgtacttg cacatttgag tggtaatagg     720
attgtcgaaa tggtcgatga agacctaaca ctgagcaaag tgctgaccaa gagcgctttt     780
gaaaacgcta tcagaacgaa tgctgcgatt ggcgggtcaa ccaatgcagt aatccatcta     840
caggcaatcg caggtagaat gggggtggac ttgacactag atgactggac aagagtaggt     900
cgtggcacgc ctactatcgt cgatttacaa ccctcgggta ggtacttgat ggaggaattt     960
tattatgcgg gaggtctgcc tgcagtttta aggagattgg gggaagctga tagactaccc    1020
cataaagatg ccttaaccgt taatggcaag accctgtggg aaaacgttca agatgcgcca    1080
ttatacaacg acgccgttat tttgccattg gatgctccct acgtgagga cggaggcatg    1140 tgtgtgatgc gtggtaatct tgcgcctaac ggggctgtat taaaacctag cgcagcaact    1200
cctgctctaa tgcagcacag gggcagagcg gttgttttg agaattttga tgattacaaa    1260
gccaggataa atgatcctga cttggatgtt actgccgatg atatattagt aatgaagaac    1320
tgtggtccta gaggttatca tggtatggca gaagtaggca acatgggact gcctgcaaaa    1380
ctactggagc agggtgtcac ggacatggtc cgtatttcag atgcaagaat gagtggaacc    1440
gcttacggta ctgttgtatt gcatgtagct cctgaagctg ctgccggtgg tcccttagct    1500
gccgttcgta tggcgattg gatcgcacta gacgcatatt caggaaaatt acacttggag    1560
gtcgatgatg ctgaaatagc gtccagatta gcagaggcag acccaacagc tgaatcaact    1620
aggatagcgt caacaggagg ttacagacaa ctttacattg aacatgtttt gcaagctgat    1680
caaggctgtg atttcgattt cttagttgga tgcagggggcg cagaagtccc aagacattcc    1740
cactaa                                                              1746
```

<210> SEQ ID NO 96

<211> LENGTH: 990
<212> TYPE: DNA
<213> ORGANISM: Picrophilus torridus

<400> SEQUENCE: 96

```
atggaaaagg tttatacgga gaacgaccta aaggaaaact tgatgcgtaa caaaaagata     60
gcagttctag gttatggctc acaaggtaga gcttgggcat aaatatgag agacagcgga    120
ttaaatgtga cagtgggatt ggaaagacag gggaaatctt gggaaaaagc cgttgctgat    180
ggctttaagc cacttaagtc aagagatgct gttagagacg ctgacgcagt cattttctta    240
gtcccagaca tggcccagag agaattatat aagaatatta tgaatgatat aaagatgac    300
gcagacatcg tttttgccca cggctttaac gttcattatg gtcttattaa tcctaaaaac    360
catgatgttt acatggtggc tcctaaagca cccggcccat cggtaaggga gttttacgaa    420
agaggggag gggtcccggt tcttattgct gttgcaaatg atgtctcggg ccgttctaaa    480
gaaaaggcgt taagtatagc gtatagcttg ggtgccttga gcagggtgc gattgaaacc    540
accttcaaag aggaaactga aacagaccta atcggtgaac aattggatct ggttggaggt    600
attactgaat tactaagatc aacgtttaat attatggttg aaatgggtta taaaccagaa    660
atggcttatt ttgaggccat caatgagatg aagttgatag tagaccaggt attcgaaaaa    720
ggtatttctg gtatgcttag agccgtaagt gataccgcta atatggagg tctgacaact    780
ggtaagtaca ataaaatga tgatgtaaga aaaaggatga gggaaagggc agaatacatt    840
gtgtcaggaa aattcgctga ggagtggatt gaagaatacg gcgagggttc taagaatctg    900
gaaagtatga tgttggatat cgataactcc ctagaagagc aagttggaaa gcaattaaga    960
gaaatcgtct aagggggacg tcctaagtaa                                     990
```

<210> SEQ ID NO 97
<211> LENGTH: 1683
<212> TYPE: DNA
<213> ORGANISM: Sulfolobus tokodaii

<400> SEQUENCE: 97

```
atgaacccag acaagaaaaa acgttcgaat ctgatatatg gtggatacga gaaggctcct     60
aacagggcct tcttgaaagc catgggcttg acggatgatg acatcgctaa accaatagtc    120
ggtgtcgctg ttgcttggaa tgaagctggc ccatgtaata ttcatttact aggtttatct    180
aatattgtta agaaggagt gaggtcaggg ggtggcactc cgagggtatt taccgcccct    240
gttgtgattg acggtatcgc aatgggttct gaagggatga gtattccct tgtttcaaga    300
gaaattgtgg caaatacggt cgagcttgtg ttaatgctc acgggtacga tggtttcgtt    360
gcattagctg gtgtgacaa gactccacca ggaatgatga tggcaatggc tagattaaac    420
attcccagca ttatcatgta tggaggcaca cactacctg taatttcaa aggaaaaccc    480
atcactatcc aggatgtata tgaggctgtt ggggcttatt ctaaaggaaa gattacagca    540
gaagatttaa gattgatgga agataatgct attccaggtc cgggaacctg cggcggtcta    600
tacacagcca atactatggg cttaatgaca gaagcccttg gtcttgcgct accaggcagt    660
gcttctcctc cagcagtgga tagtgcaagg gtaaatatg catacgaaac gggtaaagcc    720
ctaatgaatt taatcgaaat cggggttaaa ccctcgtgaca ttcttacctt tgaagccttt    780
gaaaacgcaa taaccgtatt gatggcgtcg gcggatcaa ccaacgcagt gttgcattta    840
ctggcgatag catacgaagc aggcgttaaa ttaactttag atgattttga tcgtatatcc    900
caaagaacac cagaaattgt taacatgaag cctggaggtg aatacgctat gtacgatttg    960
```

```
cataggggtcg gtggtgctcc cctgataatg aagaaattgc ttgaggccga cttattgcac    1020
ggtgatgtaa taactgttac tggtaagacc gtcaaacaga atcttgagga gtataagttg    1080
ccaaatgttc cacacgaaca cattgtcagg cccatatcca acccttttaa cccaacagga    1140
gggataagaa ttttgaaggg ttcactggct ccagagggcg cagtaattaa agtctccgcc    1200
actaaggtga gataccataa gggtccagcg agagtcttca attccgaaga ggaagccttt    1260
aaggcagttc tggaagaaaa aatccaagag aatgatgtag ttgttatcag atatgaagga    1320
cctaagggcg gtcctggaat gcgtgaaatg ttggctgtca cgtcggctat cgtgggtcaa    1380
ggtttaggtg aaaaagttgc cttgattact gacggtagat tttcaggagc cacgagaggt    1440
attatggtcg acatgtagc tcccgaggcg gcagtaggtg gtccgatagc tttgctgagg    1500
gacggtgaca caatcataat tgatgcaaat aatggcagac tagacgtcga tctacctcaa    1560
gaagaattaa agaaaagagc tgatgagtgg acgcctcctc ccccgaaata taaaagtgga    1620
ttattggctc aatacgctag actagttagc agttcttcac taggtgcggt gctattgact    1680
taa                                                                  1683

<210> SEQ ID NO 98
<211> LENGTH: 1476
<212> TYPE: DNA
<213> ORGANISM: Artificial Sequence
<220> FEATURE:
<223> OTHER INFORMATION: E. coli ilvC(Q110V)

<400> SEQUENCE: 98
atggccaact attttaacac attaaatttg agacaacaat ggctcaact gggtaagtgc      60 agatttatgg aagggacga gtttgctgat ggtgcttctt atctgcaagg aaagaaagta    120
gtaattgttg gctgcggtgc tcagggtcta aaccaaggtt taaacatgag agattcaggt    180
ctggatattt cgtatgcatt gaggaaagag gcaattgcag aaaagagggc ctcctggcgt    240
aaagcgacgg aaaatgggtt caaagttggt acttacgaag aactgatccc tcaggcagat    300
ttagtgatta acctaacacc agataaggtt cactcagacg tagtaagaac agttcaaccg    360
ctgatgaagg atggggcagc tttaggttac tctcatggct taatatcgt tgaagtgggc    420 gagcagatca gaaagatat aacagtcgta atggttgcac caaagtgccc aggtacggaa    480
gtcagagagg agtacaagag ggggttttggt gtacctacat tgatcgccgt acatcctgaa    540 aatgaccoca aggtgaagg tatggcaatt gcgaaggcat gggcagccgc aaccggaggt    600
catagagcgg gtgtgttaga gagttctttc gtagctgagg tcaagagtga cttaatgggt    660
gaacaaacca ttctgtgcgg aatgttgcag gcagggtctt tactatgctt tgataaattg    720
gtcgaagagg gtacagatcc tgcctatgct gaaaagttga tacaattgg ttgggagaca    780 atcaccgagg cacttaaaca aggtggcata acattgatga tggatagact ttcaaatccg    840
gccaagctaa gagcctacgc cttatctgag caactaaaag agatcatggc accattattc    900
caaaagcaca tggacgatat tatctccggt gagttttcct caggaatgat ggcagattgg    960
gcaaacgatg ataaaaagtt attgacgtgg agagaagaaa ccggcaagac ggcattcgag    1020
acagccccac aatacgaagg taaaattggt gaacaagaat actttgataa gggagtattg    1080
atgatagcta tggtgaaggc aggggtagaa cttgcattcg aaactatggt tgactccggt    1140
atcattgaag aatctgcata ctatgagtct ttgcatgaat tgccttttgat agcaaatact    1200 attgcaagaa aaagacttta cgagatgaat gttgtcatat cagacactgc agaatatggt    1260
aattacttat ttagctacgc atgtgtcccg ttgttaaagc ccttcatggc cgagttacaa    1320
```

```
cctggtgatt tggggaaggc tattccggaa ggagcggttg acaatggcca actgagagac     1380
gtaaatgaag ctattcgttc acatgctata gaacaggtgg gtaaaaagct gagaggatat     1440
atgaccgata tgaaaagaat tgcagtggca ggatga                              1476

<210> SEQ ID NO 99
<211> LENGTH: 1647
<212> TYPE: DNA
<213> ORGANISM: Lactococcus lactis

<400> SEQUENCE: 99
atgtatactg ttggtgatta tctgctggac cgtctgcatg aactgggtat cgaagaaatc       60
ttcggcgttc cgggtgatta caatctgcag ttcctggatc agatcatctc tcataaagac      120
atgaaatggg tgggtaacgc taacgaactg aacgcaagct acatggcaga tggttatgca      180
cgtaccaaga aagccgcggc atttctgacc actttcggtg ttggcgaact gagcgccgtc      240
aacggtctgg cgggctccta cgccgaaaac ctgccggtgg tggagatcgt aggcagccca      300
acgagcaaag ttcagaacga aggtaaattc gtccaccaca ctctggctga cggcgatttc      360
aaacacttca tgaaaatgca tgaacctgtg actgcggcac gtacgctgct gactgcagag      420
aacgctactg tggaaatcga ccgcgttctg tctgcgctgc tgaaagaacg caaaccagtt      480
tacatcaacc tgcctgtgga tgttgcggca gctaaagcgg aaaaaccgag cctgccgctg      540
aagaaagaaa actccacttc taacactagc gaccaggaaa tcctgaacaa atccaggag       600 tctctgaaaa acgcaaagaa accaatcgtg atcaccggcc acgaaatcat ttcttttggt      660
ctggagaaga ccgtgaccca attcatcagc aaaaccaaac tgccgattac caccctgaac      720
ttcggcaagt cctctgttga cgaggctctg ccgtctttcc tgggcatcta acggtact       780 ctgagcgaac cgaacctgaa agaatttgtt gaatctgcgg acttcatcct gatgctgggc      840
gttaaactga ccgactcttc taccggtgca ttcactcacc atctgaacga aaacaaaatg      900
attagcctga acatcgacga gggtaaaatc ttcaacgagc gtatccagaa cttcgacttc      960
gaaagcctga tcagctctct gctggaccotg tccgaaatcg agtataaagg caaatacatt     1020
gacaaaaagc aagaagattt cgtaccatct aacgcactgc tgtcccagga tcgcctgtgg     1080
caggccgtgg agaacctgac ccagagcaat gaaaccatcg tggcggaaca aggtacgagc     1140
tttttcggcg cgtcttctat ctttctgaaa tccaaaagcc attttatcgg tcagccgctg     1200
tggggtagca ttggctatac tttcccggca gcgctgggct ctcagatcgc tgataaagaa     1260
tctcgtcatc tgctgttcat cggtgacggt tccctgcagc tgaccgtaca ggaactgggt     1320
ctggcaattc gtgaaaagat caacccgatt tgcttcatta ttaacaatga cggctacacc     1380
gttgagcgtg agatccacgg tccgaaccag tcttacaacg atatccctat gtggaactac     1440
tctaaactgc cggagtcctt cggcgcaact gaggaccgtg ttgtgtctaa aattgtgcgt     1500
accgaaaacg aatttgtgag cgtgatgaaa gaggcccagg ccgatccgaa ccgtatgtac     1560
tggatcgaac tgatcctggc gaaagaaggc gcaccgaagg tactgaagaa aatgggcaag     1620
ctgtttgctg aacagaataa atcctaa                                         1647

<210> SEQ ID NO 100
<211> LENGTH: 1188
<212> TYPE: DNA
<213> ORGANISM: Saccharomyces cerevisiae

<400> SEQUENCE: 100
atgttgagaa ctcaagccgc cagattgatc tgcaactccc gtgtcatcac tgctaagaga       60
```

```
accttttgctt tggccacccg tgctgctgct tacagcagac cagctgcccg tttcgttaag    120
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc caggcaagaa cttgttcact gttgaagatg ctatcaagag aggtagttac    420
gttatgaact tgttgtccga tgccgctcaa tcagaaacct ggcctgctat caagccattg    480
ttgaccaagg gtaagacttt gtacttctcc cacggttttct ccccagtctt caaggacttg    540
actcacgttg aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact cccatctga agctttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa              1188
```

<210> SEQ ID NO 101
<211> LENGTH: 20
<212> TYPE: DNA
<213> ORGANISM: Artificial Sequence
<220> FEATURE:
<223> OTHER INFORMATION: Primer 1321

<400> SEQUENCE: 101
aatcatatcg aacacgatgc                                                 20

<210> SEQ ID NO 102
<211> LENGTH: 20
<212> TYPE: DNA
<213> ORGANISM: Artificial Sequence
<220> FEATURE:
<223> OTHER INFORMATION: Primer 1322

<400> SEQUENCE: 102
tcagaaagga tcttctgctc                                                 20

<210> SEQ ID NO 103
<211> LENGTH: 20
<212> TYPE: DNA
<213> ORGANISM: Artificial Sequence
<220> FEATURE:
<223> OTHER INFORMATION: Primer 1323

<400> SEQUENCE: 103
atcgatatcg tgaaatacgc                                                 20

<210> SEQ ID NO 104
<211> LENGTH: 20
<212> TYPE: DNA
<213> ORGANISM: Artificial Sequence
<220> FEATURE:

```
<223> OTHER INFORMATION: Primer 1324

<400> SEQUENCE: 104
agctggtctg gtgattctac                                               20

<210> SEQ ID NO 105
<211> LENGTH: 38
<212> TYPE: DNA
<213> ORGANISM: Artificial Sequence
<220> FEATURE:
<223> OTHER INFORMATION: Primer 1409

<400> SEQUENCE: 105
attgatgcgg ccgcgattta atctctaatt attagtta                           38

<210> SEQ ID NO 106
<211> LENGTH: 34
<212> TYPE: DNA
<213> ORGANISM: Artificial Sequence
<220> FEATURE:
<223> OTHER INFORMATION: Primer 1410

<400> SEQUENCE: 106
cacccagtcg cgacatccaa tttatagaaa tcag                               34

<210> SEQ ID NO 107
<211> LENGTH: 32
<212> TYPE: DNA
<213> ORGANISM: Artificial Sequence
<220> FEATURE:
<223> OTHER INFORMATION: Primer 1411

<400> SEQUENCE: 107
attggatgtc gcgactgggt gagcatatgt tc                                 32

<210> SEQ ID NO 108
<211> LENGTH: 32
<212> TYPE: DNA
<213> ORGANISM: Artificial Sequence
<220> FEATURE:
<223> OTHER INFORMATION: Primer 1412

<400> SEQUENCE: 108
gagaaagccg gcaggagagt gaaagagcct tg                                 32

<210> SEQ ID NO 109
<211> LENGTH: 21
<212> TYPE: DNA
<213> ORGANISM: Artificial Sequence
<220> FEATURE:
<223> OTHER INFORMATION: Primer 1440

<400> SEQUENCE: 109
atcgtacatc ttccaagcat c                                             21

<210> SEQ ID NO 110
<211> LENGTH: 20
<212> TYPE: DNA
<213> ORGANISM: Artificial Sequence
<220> FEATURE:
<223> OTHER INFORMATION: Primer 1441

<400> SEQUENCE: 110
aatcggaacc ctaaagggag                                               20

<210> SEQ ID NO 111
```

```
<211> LENGTH: 20
<212> TYPE: DNA
<213> ORGANISM: Artificial Sequence
<220> FEATURE:
<223> OTHER INFORMATION: Primer 1443

<400> SEQUENCE: 111
tgcagatgca gatgtgagac                                                     20

<210> SEQ ID NO 112
<211> LENGTH: 24
<212> TYPE: DNA
<213> ORGANISM: Artificial Sequence
<220> FEATURE:
<223> OTHER INFORMATION: Primer 1587

<400> SEQUENCE: 112
cggctgccag aactctacta actg                                                24

<210> SEQ ID NO 113
<211> LENGTH: 23
<212> TYPE: DNA
<213> ORGANISM: Artificial Sequence
<220> FEATURE:
<223> OTHER INFORMATION: Primer 1588

<400> SEQUENCE: 113
gcgacgtcta ctggcaggtt aat                                                 23

<210> SEQ ID NO 114
<211> LENGTH: 24
<212> TYPE: DNA
<213> ORGANISM: Artificial Sequence
<220> FEATURE:
<223> OTHER INFORMATION: Primer 1633

<400> SEQUENCE: 114
tccgtcactg gattcaatgc catc                                                24

<210> SEQ ID NO 115
<211> LENGTH: 20
<212> TYPE: DNA
<213> ORGANISM: Artificial Sequence
<220> FEATURE:
<223> OTHER INFORMATION: Primer 1634

<400> SEQUENCE: 115
ttcgccaggg agctggtgaa                                                     20

<210> SEQ ID NO 116
<211> LENGTH: 771
<212> TYPE: DNA
<213> ORGANISM: Drosophila melanogaster

<400> SEQUENCE: 116
atgtcgttta ctttgaccaa caagaacgtg attttcgttg ccggtctggg aggcattggt         60
ctggacacca gcaaggagct gctcaagcgc gatctgaaga acctggtgat cctcgaccgc        120
attgagaacc cggctgccat tgccgagctg aaggcaatca atccaaaggt gaccgtcacc        180
ttctacccct atgatgtgac cgtgcccatt gccgagacca ccaagctgct gaagaccatc        240
ttcgcccagc tgaagaccgt cgatgtcctg atcaacggag ctggtatcct ggacgatcac        300
cagatcgagc gcaccattgc cgtcaactac actggcctgg tcaacaccac gacggccatt        360
ctggacttct gggacaagcg caagggcggt cccggtggta tcatctgcaa cattggatcc        420
```

-continued

| | |
|---|---|
| gtcactggat tcaatgccat ctaccaggtg cccgtctact ccggcaccaa ggccgccgtg | 480 |
| gtcaacttca ccagctccct ggcgaaactg ccccccatta ccggcgtgac ggcttacact | 540 |
| gtgaaccccg gcatcacccg caccaccctg gtgcacacgt tcaactcctg gttggatgtt | 600 |
| gagcctcagg ttgccgagaa gctcctggct catcccaccc agccctcgtt ggcctgcgcc | 660 |
| gagaacttcg tcaaggctat cgagctgaac cagaacggag ccatctggaa actggacttg | 720 |
| ggcacccctgg aggccatcca gtggaccaag cactgggact ccggcatcta a | 771 |

<210> SEQ ID NO 117
<211> LENGTH: 8870
<212> TYPE: DNA
<213> ORGANISM: Artificial Sequence
<220> FEATURE:
<223> OTHER INFORMATION: pGV1914

<400> SEQUENCE: 117

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cataccacag ctttcaatt | 420 |
| caattcatca ttttttttt attctttttt ttgatttcgg tttccttgaa attttttga | 480 |
| ttcggtaatc tccgaacaga aggaagaacg aaggaaggag cacagactta gattggtata | 540 |
| tatacgcata tgtagtgttg aagaaacatg aaattgccca gtattcttaa cccaactgca | 600 |
| cagaacaaaa acctgcagga aacgaagata atcatgtcg aaagctacat ataaggaacg | 660 |
| tgctgctact catcctagtc ctgttgctgc caagctattt aatatcatgc acgaaaagca | 720 |
| aacaaacttg tgtgcttcat ggatgttcg taccaccaag gaattactgg agttagttga | 780 |
| agcattaggt cccaaaattt gtttactaaa acacatgtg gatatcttga ctgatttttc | 840 |
| catggagggc acagttaagc cgctaaaggc attatccgcc aagtacaatt ttttactctt | 900 |
| cgaagacaga aaatttgctg acattggtaa tacagtcaaa ttgcagtact ctgcgggtgt | 960 |
| atacagaata gcagaatggg cagacattac gaatgcacac ggtgtggtgg gcccaggtat | 1020 |
| tgttagcggt ttgaagcagg cggcagaaga agtaacaaag gaacctagag gccttttgat | 1080 |
| gttagcagaa ttgtcatgca agggctccct atctactgga gaatatacta agggtactgt | 1140 |
| tgacattgcg aagagcgaca agattttgt tatcggcttt attgctcaaa gagacatggg | 1200 |
| tggaagagat gaaggttacg attggttgat tatgacaccc ggtgtgggtt tagatgacaa | 1260 |
| gggagacgca ttgggtcaac agtatagaac cgtggatgat gtggtctcta caggatctga | 1320 |
| cattattatt gttggaagag gactatttgc aaagggaagg gatgctaagg tagagggtga | 1380 |
| acgttacaga aaagcaggct gggaagcata tttgagaaga tgcggccagc aaaactaaaa | 1440 |
| aactgtatta taagtaaatg catgtatact aaactcacaa attagagctt caatttaatt | 1500 |
| atatcagtta ttaccctatg cggtgtgaaa taccgcacag atgcgtaagg agaaaatacc | 1560 |
| gcatcaggaa attgtaaacg ttaatatttt gttaaaattc gcgttaaatt tttgttaaat | 1620 |
| cagctcattt ttaaccaat aggccgaaat cggcaaaatc ccttataaat caaaagaata | 1680 |
| gaccgagata gggttgagtg ttgttccagt ttggaacaag agtccactat taaagaacgt | 1740 |

```
ggactccaac gtcaaagggc gaaaaaccgt ctatcagggc gatggcccac tacgtgaacc   1800
atcaccctaa tcaagttttt tggggtcgag gtgccgtaaa gcactaaatc ggaaccctaa   1860
agggagcccc cgatttagag cttgacgggg aaagccggcg aggactgcaa tagcacaaga   1920
ttaagataga atggcttcaa acagccgcct tttatacata ttggtaaaag ctcgcgaatc   1980
gcaccatatc ccttatcctg taatcaaatc gatctaggtg cagatacaga tcaattcata   2040
aaaagaaatt gaagcaccag tttatcacta ctacactatc tttttctttt tttttttttt   2100
ttgcgcagtt tcgccctttg ttcaatatca cttgataagt tgtgggcttt ttctgtcact   2160
cattcggctt aaaagtatt cgttcttttg tgttttatga aaagggaacg tgatataaaa    2220
aaacatcctt tggtgtggga catgggcttt tgtttagaga atggttatca ctaccgcccc   2280
caccccttgaa agccacagaa aatgaaaaag tatgtgaata aggtgtgaac tctataacat   2340
tttggccaaa tgccacagcc gatctgcata ttccaatgga catgatgcaa caacaattga   2400
tgtcacattc tcttacacac ttcgattggt ccgtacgtag tacttttac ataactgact    2460
caggcgtttc cttcattgaa atgctcatct attgccaagt acatagaatc cacagtgcat   2520
aggttaacgc attgtaccca aacgacggga aacaaggaag gatgcagaat gagcacttgt   2580
tatttataaa aagacacggg aggggaatc ccgtctttcg tccgtcggag ccaaagagat     2640
gagccaaagc agaaaacag gggacgccgc ccttcttccg tcccgtgcgt gagggggggcg    2700
cggccattcg gttttttgcaa tatgacctgt gggccaaaaa tcgaaaaaa aaaaaaaat     2760
aagaggcggc tgcggaattt tataagacaa gcgcagggcc aaagaaaaaa taataattga   2820
cgtggctgaa caacagtctc tccccacccc tttccaaaaa ggggaatgaa atacgagttc   2880
ttttttcccaa ttggtagata ttcaacaaga gacgcgcagt acgtaacatg cgaattgcgt  2940
aattcacggc gataacgtag tatttagatt tagtataatt tgaaccgatg tatttatttg   3000
tctgattgat ttatgtattc aaactgtgta agtttattta tttgcaacaa taattcgttt   3060
gagtacacta ctaatggcgg ccgcttagat gccggagtcc cagtgcttgg tccactggat   3120
ggcctccagg gtgcccaagt ccagttttcca gatggctccg ttctggttca gctcgatagc   3180
cttgacgaag ttctcggcgc aggccaacga gggctgggtg gatgagcca ggagcttctc    3240
ggcaacctga ggctcaacat ccaaccagga gttgaacgtg tgcaccaggg tggtgcgggt   3300
gatgccgggg ttcacagtgt aagccgtcac gccggtaatg ggggccagtt tcgccaggga   3360
gctggtgaag ttgaccacgg cggccttggt gccggagtag acgggcaccct ggtagatggc  3420
attgaatcca gtgacggatc caatgttgca gatgatacca ccgggaccgc ccttgcgctt   3480
gtcccagaag tccagaatgg ccgtcgtggt gttgaccagg ccagtgtagt tgacggcaat   3540
ggtgcgctcg atctggtgat cgtccaggat accagctccg ttgatcagga catcgacggt   3600
cttcagctgg gcgaagatgg tcttcagcag cttggtggtc tcggcaatgg gcacggtcac   3660
atcatagggg tagaaggtga cggtcaccct tggattgatt gccttcagct cggcaatggc   3720
agccgggttc tcaatgcggt cgaggatcac caggttcttc agatcgcgct tgagcagctc   3780
cttgctggtg tccagaccaa tgcctcccag accggcaacg aaaatcacgt tcttgttggt   3840
caaagtaaac gacataccgg tatctcctag atccgtcgaa gtcgaaacta agttctggtg   3900
ttttaaaact aaaaaaaga ctaactataa agtagaattt taagaagttt agaaaatagaa   3960
tttacagaat tacaatcaat acctaccgtc tttatatact tattagtcaa gtaggggaat   4020
aatttcaggg aactggttc aacctttttt ttcagctttt tccaaatcag agagagcaga    4080
aggtaataga aggtgtaaga aaatgagata gatacatgcg tgggtcaatt gccttgtgtc   4140
```

```
atcatttact ccaggcaggt tgcatcactc cattgaggtt gtgcccgttt tttgcctgtt    4200
tgtgcccctg ttctctgtag ttgcgctaag agaatggacc tatgaactga tggttggtga    4260
agaaaacaat attttggtgc tgggattctt ttttttttctg gatgccagct taaaaagcgg    4320
gctccattat atttagtgga tgccaggaat aaactgttca cccagacacc tacgatgtta    4380
tatattctgt gtaacccgcc ccctatttg gcatgtacg ggttacagca gaattaaaag     4440 gctaatttt tgactaaata aagttaggaa aatcactact attaattatt tacgtattct    4500
ttgaaatggc gagtattgat aatgataaac tggatcctta ggatttattc tgttcagcaa    4560
acagcttgcc catttctttc agtaccttcg gtgcgcctc tttcgccagg atcagttcga     4620
tccagtacat acggttcgga tcggcctggg cctctttcat cacgctcaca aattcgtttt    4680
cggtacgcac aattttagac acaacacggt cctcagttgc gccgaaggac tccggcagtt    4740
tagagtagtt ccacataggg atatcgttgt aagactggtt cggaccgtgg atctcacgct    4800
caacggtgta gccgtcattg ttaataatga agcaaatcgg gttgatcttt tcacgaattg    4860
ccagacccag ttcctgtacg gtcagctgca gggaaccgtc accgatgaac agcagatgac    4920
gagattcttt atcagcgatc tgagagccca gcgctgccgg gaaagtatag ccaatgctac    4980
cccacagcgg ctgaccgata aaatggcttt tggatttcag aaagatagaa gacgcgccga    5040
aaaagctcgt accttgttcc gccacgatgg tttcattgct ctgggtcagg ttctccacgg    5100
cctgccacag gcgatcctgg gacagcagtg cgttagatgg tacgaaatct tcttgctttt    5160
tgtcaatgta tttgcccttta tactcgattt cggacaggtc cagcagagag ctgatcaggc    5220
tttcgaagtc gaagttctgg atacgctcgt tgaagatttt accctcgtcg atgttcaggc    5280
taatcatttt gttttcgttc agatggtgag tgaatgcacc ggtagaagag tcggtcagtt    5340
taacgcccag catcaggatg aagtccgcag attcaacaaa ttctttcagg ttcggttcgc    5400
tcagagtacc gttgtagatg cccaggaaag acggcagagc ctcgtcaaca gaggacttgc    5460
cgaagttcag ggtggtaatc ggcagtttgg ttttgctgat gaattgggtc acggtcttct    5520
ccagaccaaa agaaatgatt tcgtggccgg tgatcacgat tggtttcttt gcgttttca    5580 gagactcctg gattttgttc aggatttcct ggtcgctagt gttagaagtg gagttttctt    5640
tcttcagcgg caggctcggt ttttccgctt tagctgccgc aacatccaca ggcaggttga    5700
tgtaaactgg tttgcgttct ttcagcagcg cagacagaac gcggtcgatt tccacagtag    5760
cgttctctgc agtcagcagc gtacgtgccg cagtcacagg ttcatgcatt ttcatgaagt    5820
gtttgaaatc gccgtcagcc agagtgtggt ggacgaattt accttcgttc tgaactttgc    5880
tcgttgggct gcctacgatc tccaccaccg gcaggttttc ggcgtaggag cccgccagac    5940
cgttgacggc gctcagttcg ccaacaccga agtggtcag aaatgccgcg ctttcttgg     6000 tacgtgcata accatctgcc atgtagcttg cgttcagttc gttagcgtta cccacccatt    6060
tcatgtcttt atgagagatg atctgatcca ggaactgcag attgtaatca cccgaacgc     6120 cgaagatttc ttcgataccc agttcatgca gacggtccag cagataatca ccaacagtat    6180
acatgtcgac aaacttagat tagattgcta tgctttcttt ctaatgagca agaagtaaaa    6240
aaagttgtaa tagaacaaga aaaatgaaac tgaaacttga gaaattgaag accgtttatt    6300
aacttaaata tcaatgggag gtcatcgaaa gagaaaaaaa tcaaaaaaaa aattttcaag    6360
aaaaagaaac gtgataaaaa tttttattgc cttttcgac gaagaaaaag aaacgaggcg     6420
gtctcttttt tcttttccaa acctttagta cgggtaatta acgacaccct agaggaagaa    6480
agaggggaaa tttagtatgc tgtgcttggg tgttttgaag tggtacggcg atgcgcggag    6540
```

-continued

```
tccgagaaaa tctggaagag taaaaaagga gtagaaacat tttgaagcta tgagctccag    6600
cttttgttcc ctttagtgag ggttaattgc gcgcttggcg taatcatggt catagctgtt    6660
tcctgtgtga aattgttatc cgctcacaat tccacacaac ataggagccg gaagcataaa    6720
gtgtaaagcc tggggtgcct aatgagtgag gtaactcaca ttaattgcgt tgcgctcact    6780
gcccgctttc cagtcgggaa acctgtcgtg ccagctgcat taatgaatcg gccaacgcgc    6840
ggggagaggc ggtttgcgta ttgggcgctc ttccgcttcc tcgctcactg actcgctgcg    6900
ctcggtcgtt cggctgcggc gagcggtatc agctcactca aaggcggtaa tacggttatc    6960
cacagaatca ggggataacg caggaaagaa catgtgagca aaaggccagc aaaaggccag    7020
gaaccgtaaa aaggccgcgt tgctggcgtt tttccatagg ctccgccccc ctgacgagca    7080
tcacaaaaat cgacgctcaa gtcagaggtg gcgaaacccg acaggactat aaagatacca    7140
ggcgtttccc cctggaagct ccctcgtgcg ctctcctgtt ccgaccctgc cgcttaccgg    7200
atacctgtcc gcctttctcc cttcgggaag cgtggcgctt tctcatagct cacgctgtag    7260
gtatctcagt tcggtgtagg tcgttcgctc caagctgggc tgtgtgcacg aaccccccgt    7320
tcagcccgac cgctgcgcct tatccggtaa ctatcgtctt gagtccaacc cggtaagaca    7380
cgacttatcg ccactggcag cagccactgg taacaggatt agcagagcga ggtatgtagg    7440
cggtgctaca gagttcttga agtggtggcc taactacggc tacactagaa ggacagtatt    7500
tggtatctgc gctctgctga agccagttac cttcggaaaa agagttggta gctcttgatc    7560
cggcaaacaa accaccgctg gtagcggtgg tttttttgtt tgcaagcagc agattacgcg    7620
cagaaaaaaa ggatctcaag aagatccttt gatcttttct acggggtctg acgctcagtg    7680
gaacgaaaac tcacgttaag ggattttggt catgagatta tcaaaaagga tcttcaccta    7740
gatcctttta aattaaaaat gaagttttaa atcaatctaa agtatatatg agtaaacttg    7800
gtctgacagt taccaatgct taatcagtga ggcacctatc tcagcgatct gtctatttcg    7860
ttcatccata gttgcctgac tccccgtcgt gtagataact acgatacggg agggcttacc    7920
atctggcccc agtgctgcaa tgataccgcg agacccacgc tcaccggctc cagatttatc    7980
agcaataaac cagccagccg gaagggccga gcgcagaagt ggtcctgcaa ctttatccgc    8040
ctccatccag tctattaatt gttgccggga agctagagta agtagttcgc cagttaatag    8100
tttgcgcaac gttgttgcca ttgctacagg catcgtggtg tcacgctcgt cgtttggtat    8160
ggcttcattc agctccggtt cccaacgatc aaggcgagtt acatgatccc ccatgttgtg    8220
caaaaaagcg gttagctcct tcggtcctcc gatcgttgtc agaagtaagt tggccgcagt    8280
gttatcactc atggttatgg cagcactgca taattctctt actgtcatgc catccgtaag    8340
atgcttttct gtgactggtg agtactcaac caagtcattc tgagaatagt gtatgcggcg    8400
accgagttgc tcttgcccgg cgtcaatacg ggataatacc gcgccacata gcagaacttt    8460
aaaagtgctc atcattggaa aacgttcttc ggggcgaaaa ctctcaagga tcttaccgct    8520
gttgagatcc agttcgatgt aacccactcg tgcacccaac tgatcttcag catcttttac    8580
tttcaccagc gtttctgggt gagcaaaaac aggaaggcaa aatgccgcaa aaagggaat    8640 aagggcgaca cggaaatgtt gaatactcat actcttcctt tttcaatatt attgaagcat    8700
ttatcagggt tattgtctca tgagcggata catatttgaa tgtatttaga aaataaaca    8760 ataggggtt ccgcgcacat ttccccgaaa agtgccacct gacgtctaag aaaccattat    8820
tatcatgaca ttaacctata aaaataggcg tatcacgagg ccctttcgtc              8870
```

<210> SEQ ID NO 118

<211> LENGTH: 4857
<212> TYPE: DNA
<213> ORGANISM: Artificial Sequence
<220> FEATURE:
<223> OTHER INFORMATION: SacI-NotI fragment

<400> SEQUENCE: 118

| | |
|---|---|
| gagctcatag cttcaaaatg tttctactcc ttttttactc ttccagattt tctcggactc | 60 |
| cgcgcatcgc cgtaccactt caaaacaccc aagcacagca tactaaattt cccctctttc | 120 |
| ttcctctagg gtgtcgttaa ttacccgtac taaaggtttg gaaagaaaaa aagagaccgc | 180 |
| ctcgtttctt tttcttcgtc gaaaaaggca ataaaaattt ttatcacgtt tcttttttctt | 240 |
| gaaaattttt tttttgattt tttttctcttt cgatgacctc ccattgatat ttaagttaat | 300 |
| aaacggtctc caatttctca gtttcagtt tcatttttct tgttctatta caacttttt | 360 |
| tacttcttgc tcattagaaa gaaagcatag caatctaatc taagtttgtc gacatgaaga | 420 |
| agctcaacaa gtactcgtat atcatcactg aacctaaggg ccaaggtgcg tcccaggcca | 480 |
| tgctttatgc caccggtttc aagaaggaag atttcaagaa gcctcaagtc ggggttggtt | 540 |
| cctgttggtg gtccggtaac ccatgtaaca tgcatctatt ggacttgaat aacagatgtt | 600 |
| ctcaatccat tgaaaaagcg ggtttgaaag ctatgcagtt caacaccatc ggtgtttcag | 660 |
| acggtatctc tatgggtact aaaggtatga gatactcgtt acaaagtaga gaaatcattg | 720 |
| cagactcctt tgaaaccatc atgatggcac aacactacga tgctaacatc gccatcccat | 780 |
| catgtgacaa aaacatgccc ggtgtcatga tggccatggg tagacataac agaccttcca | 840 |
| tcatggtata tggtggtact atcttgcccg gtcatccaac atgtggttct tcgaagatct | 900 |
| ctaaaaacat cgatatcgtc tctgcgttcc aatcctacgg tgaatatatt tccaagcaat | 960 |
| tcactgaaga agaaagagaa gatgttgtgg aacatgcatg cccaggtcct ggttcttgtg | 1020 |
| gtggtatgta tactgccaac acaatggctt ctgccgctga agtgctaggt ttgaccattc | 1080 |
| caaactcctc ttccttccca gccgtttcca aggagaagtt agctgagtgt gacaacattg | 1140 |
| gtgaatacat caagaagaca atggaattgg gtatttttacc tcgtgatatc ctcacaaaag | 1200 |
| aggcttttga aaacgccatt acttatgtcg ttgcaaccgg tgggtccact aatgctgttt | 1260 |
| tgcatttggt ggctgttgct cactctgcgg gtgtcaagtt gtcaccagat gatttccaaa | 1320 |
| gaatcagtga tactacacca ttgatcggtga acttcaaacc ttctggtaaa tacgtcatgg | 1380 |
| ccgatttgat taacgttggt ggtacccaat ctgtgattaa gtatctatat gaaaacaaca | 1440 |
| tgttgcacgg taacacaatg actgttaccg gtgacacttt ggcagaacgt gcaaagaaag | 1500 |
| caccaagcct acctgaagga caagagatta ttaagccact ctcccaccca atcaaggcca | 1560 |
| acggtcactt gcaaattctg tacgttcat tggcaccagg tggagctgtg ggtaaaatta | 1620 |
| ccggtaagga aggtacttac ttcaagggta gagcacgtgt gttcgaagag aaggtgcct | 1680 |
| ttattgaagc cttggaaaga ggtgaaatca agaagggta aaaaaccgtt gttgttatca | 1740 |
| gatatgaagg tccaagaggt gcaccaggta tgcctgaaat gctaaagcct tcctctgctc | 1800 |
| tgatgggtta cggtttgggt aaagatgttg cattgttgac tgatggtaga ttctctggtg | 1860 |
| gttctcacgg gttcttaatc ggccacattg ttcccgaagc cgctgaaggt ggtcctatcg | 1920 |
| ggttggtcag agacggcgat gagattatca ttgatgctga taataacaag attgacctat | 1980 |
| tagtctctga taaggaaatg ctcaacgta acaaagttg ggttgcacct ccacctcgtt | 2040 |
| acacaagagg tactctatcc aagtatgcta agttggtttc caacgcttcc aacggttgtg | 2100 |
| ttttagatgc ttgaggatcc agtttatcat tatcaatact cgccatttca aagaatacgt | 2160 |

```
aaataattaa tagtagtgat tttcctaact ttatttagtc aaaaaattag ccttttaatt    2220
ctgctgtaac ccgtacatgc ccaaaatagg gggcgggtta cacagaatat ataacatcgt    2280
aggtgtctgg gtgaacagtt tattcctggc atccactaaa tataatggag cccgcttttt    2340
aagctggcat ccagaaaaaa aaagaatccc agcaccaaaa tattgttttc ttcaccaacc    2400
atcagttcat aggtccattc tcttagcgca actacagaga acaggggcac aaacaggcaa    2460
aaaacgggca caacctcaat ggagtgatgc aacctgcctg gagtaaatga tgacacaagg    2520
caattgaccc acgcatgtat ctatctcatt tcttacaccc ttctattacc ttctgctctc    2580
tctgatttgg aaaaagctga aaaaaaaggt tgaaaccagt tccctgaaat tattccccta    2640
cttgactaat aagtatataa agacggtagg tattgattgt aattctgtaa atctatttct    2700
taaacttctt aaattctact tttatagtta gtcttttttt tagttttaaa acaccagaac    2760
ttagtttcga ctcgagatgg ccaactattt taacacatta aatttgagac aacaattggc    2820
tcaactgggt aagtgcagat ttatgggaag ggacgagttt gctgatggtg cttcttatct    2880
gcaaggaaag aaagtagtaa ttgttggctg cggtgctcag ggtctaaacc aaggtttaaa    2940
catgagagat tcaggtctgg atatttcgta tgcattgagg aaagaggcaa ttgcagaaaa    3000
gagggcctcc tggcgtaaag cgacggaaaa tgggttcaaa gttggtactt acgaagaact    3060
gatccctcag gcagatttag tgattaacct aacaccagat aaggttcact cagacgtagt    3120
aagaacagtt caaccgctga tgaaggatgg ggcagcttta ggttactctc atggctttaa    3180
tatcgttgaa gtgggcgagc agatcagaaa agatataaca gtcgtaatgg ttgcaccaaa    3240
gtgcccaggt acggaagtca gagaggagta caagaggggt tttggtgtac ctacattgat    3300
cgccgtacat cctgaaaatg accccaaagg tgaaggtatg gcaattgcga aggcatgggc    3360
agccgcaacc ggaggtcata gagcgggtgt gttagagagt tctttcgtag ctgaggtcaa    3420
gagtgactta atgggtgaac aaaccattct gtgcggaatg ttgcaggcag ggtctttact    3480
atgctttgat aaattggtcg aagagggtac agatcctgcc tatgctgaaa agttgataca    3540
atttggttgg gagacaatca ccgaggcact taaacaaggt ggcataacat tgatgatgga    3600
tagactttca aatccggcca agctaagagc ctacgcctta tctgagcaac taaaagagat    3660
catggcacca ttattccaaa agcacatgga cgatattatc tccggtgagt tttcctcagg    3720
aatgatggca gattgggcaa acgatgataa aaagttattg acgtggagag aagaaaccgg    3780
caagacggca ttcgagacag ccccacaata cgaaggtaaa attggtgaac aagaatactt    3840
tgataaggga gtattgatga tagctatggt gaaggcaggg gtagaacttg cattcgaaac    3900
tatggttgac tccggtatca ttgaagaatc tgcatactat gagtctttgc atgaattgcc    3960
tttgatagca aatactattg caagaaaaag actttacgag atgaatgttg tcatatcaga    4020
cactgcagaa tatggtaatt acttatttag ctacgcatgt gtcccgttgt taaagccctt    4080
catggccgag ttcaacctg gtgatttggg gaaggctatt ccggaaggag cggttgacaa    4140
tggccaactg agagacgtaa atgaagctat tcgttcacat gctatagaac aggtgggtaa    4200
aaagctgaga ggatatatga ccgatatgaa aagaattgca gtggcaggat gaagatccgc    4260
ggccgctcga gtcatgtaat tagttatgtc acgcttacat tcacgccctc cccccacatc    4320
cgctctaacc gaaaggaag gagttagaca acctgaagtc taggtcccta tttattttt    4380 tatagttatg ttagtattaa gaacgttatt tatatttcaa attttctttt tttttctgta    4440
cagacgcgtg tacgcatgta acattatact gaaaaccttg cttgagaagg ttttgggacg    4500
ctcgaaggct ttaatttgcg gccggtaccc aattcgccct atagtgagtc gtattacgcg    4560
```

```
cgctcactgg ccgtcgtttt acaacgtcgt gactgggaaa accctggcgt tacccaactt    4620
aatcgccttg cagcacatcc cccttttcgcc agctggcgta atagcgaaga ggcccgcacc    4680
gatcgccctt cccaacagtt gcgcagcctg aatggcgaat ggcgcgacgc gccctgtagc    4740
ggcgcattaa gcgcggcggg tgtggtggtt acgcgcagcg tgaccgctac acttgccagc    4800
gccctagcgc ccgctccttt cgctttcttc ccttcctttc tcgccacgtt cgccggc       4857
```

```
<210> SEQ ID NO 119
<211> LENGTH: 34
<212> TYPE: DNA
<213> ORGANISM: Artificial Sequence
<220> FEATURE:
<223> OTHER INFORMATION: Primer 421

<400> SEQUENCE: 119
gccaacggat cctcaagcat ctaaaacaca accg                                 34

<210> SEQ ID NO 120
<211> LENGTH: 36
<212> TYPE: DNA
<213> ORGANISM: Artificial Sequence
<220> FEATURE:
<223> OTHER INFORMATION: Primer 551

<400> SEQUENCE: 120
gctcatgtcg acatgaagaa gctcaacaag tactcg                               36

<210> SEQ ID NO 121
<211> LENGTH: 67
<212> TYPE: DNA
<213> ORGANISM: Artificial Sequence
<220> FEATURE:
<223> OTHER INFORMATION: Primer 269

<400> SEQUENCE: 121
ctagcatgta cccatacgat gttcctgact atgcgggtgt cgacgaattc ccgggatccg     60
cggccgc                                                               67

<210> SEQ ID NO 122
<211> LENGTH: 67
<212> TYPE: DNA
<213> ORGANISM: Artificial Sequence
<220> FEATURE:
<223> OTHER INFORMATION: Primer 270

<400> SEQUENCE: 122
tcgagcggcc gcggatcccg ggaattcgtc gacacccgca tagtcaggaa catcgtatgg     60
gtacatg                                                               67

<210> SEQ ID NO 123
<211> LENGTH: 35
<212> TYPE: DNA
<213> ORGANISM: Artificial Sequence
<220> FEATURE:
<223> OTHER INFORMATION: Primer 1842

<400> SEQUENCE: 123
ttttggatcc ctaccaatcc tggtggactt tatcg                                35

<210> SEQ ID NO 124
<211> LENGTH: 37
<212> TYPE: DNA
<213> ORGANISM: Artificial Sequence
<220> FEATURE:
```

```
<223> OTHER INFORMATION: Primer 2163

<400> SEQUENCE: 124
ttggtagtcg acatggttta cactccatcc aagggtc                              37

<210> SEQ ID NO 125
<211> LENGTH: 32
<212> TYPE: DNA
<213> ORGANISM: Artificial Sequence
<220> FEATURE:
<223> OTHER INFORMATION: Primer 2183

<400> SEQUENCE: 125
acagtagtcg acatgacaga gcagaaagcc ct                                   32

<210> SEQ ID NO 126
<211> LENGTH: 34
<212> TYPE: DNA
<213> ORGANISM: Artificial Sequence
<220> FEATURE:
<223> OTHER INFORMATION: Primer 2184

<400> SEQUENCE: 126
tacatcggat ccctacataa gaacaccttt ggtg                                 34

<210> SEQ ID NO 127
<211> LENGTH: 41
<212> TYPE: DNA
<213> ORGANISM: Artificial Sequence
<220> FEATURE:
<223> OTHER INFORMATION: Primer 2195

<400> SEQUENCE: 127
ttgttcctcg agatggagga acaggagata ggcgttcctg c                         41

<210> SEQ ID NO 128
<211> LENGTH: 42
<212> TYPE: DNA
<213> ORGANISM: Artificial Sequence
<220> FEATURE:
<223> OTHER INFORMATION: Primer 2196

<400> SEQUENCE: 128
gttcttgcgg ccgcttattt tggagattct atctggggtt gc                        42

<210> SEQ ID NO 129
<211> LENGTH: 40
<212> TYPE: DNA
<213> ORGANISM: Artificial Sequence
<220> FEATURE:
<223> OTHER INFORMATION: Primer 2197

<400> SEQUENCE: 129
ttcttggtcg acatgagtgc tctactgtcc gagtctgacc                           40

<210> SEQ ID NO 130
<211> LENGTH: 43
<212> TYPE: DNA
<213> ORGANISM: Artificial Sequence
<220> FEATURE:
<223> OTHER INFORMATION: Primer 2198

<400> SEQUENCE: 130
ttgttcggat ccttaccagg tgctcccaac agagacgaga tcc                       43

<210> SEQ ID NO 131
```

```
<211> LENGTH: 42
<212> TYPE: DNA
<213> ORGANISM: Artificial Sequence
<220> FEATURE:
<223> OTHER INFORMATION: Primer 2259

<400> SEQUENCE: 131
tcagtaagat ctatgactga gatactacca catgtaaacg ac                              42

<210> SEQ ID NO 132
<211> LENGTH: 44
<212> TYPE: DNA
<213> ORGANISM: Artificial Sequence
<220> FEATURE:
<223> OTHER INFORMATION: Primer 2260

<400> SEQUENCE: 132
catatcctcg aggtacccta tacatccccc acagcatctc gcag                            44

<210> SEQ ID NO 133
<211> LENGTH: 7685
<212> TYPE: DNA
<213> ORGANISM: Artificial Sequence
<220> FEATURE:
<223> OTHER INFORMATION: pGV2074

<400> SEQUENCE: 133
ttggatcata ctaagaaacc attattatca tgacattaac ctataaaaat aggcgtatca           60
cgaggccctt tcgtctcgcg cgtttcggtg atgacggtga aacctctga cacatgcagc           120 tcccggagac ggtcacagct tgtctgtaag cggatgccgg gagcagacaa gcccgtcagg          180
gcgcgtcagc gggtgttggc gggtgtcggg gctggcttaa ctatgcggca tcagagcaga          240
ttgtactgag agtgcaccat accacagctt ttcaattcaa ttcatcattt ttttttttatt         300 cttttttttg atttcggttt ctttgaaatt tttttgattc ggtaatctcc gaacagaagg          360
aagaacgaag gaaggagcac agacttagat tggtatatat acgcatatgg caaattaaag          420
ccttcgagcg tcccaaaacc ttctcaagca aggttttcag tataatgtta catgcgtaca          480
cgcgtctgta cagaaaaaaa agaaaaattt gaaatataaa taacgttctt aatactaaca          540
taactataaa aaaataaata gggacctaga cttcaggttg tctaactcct tccttttcgg          600
ttagagcgga tgtgggggga gggcgtgaat gtaagcgtga cataagaatt cttattcctt          660
tgccctcgga cgagtgctgg ggcgtcggtt tccactatcg gcgagtactt ctacacagcc          720
atcggtccag acgccgcgc ttctgcgggc gatttgtgta cgcccgacag tcccggctcc           780
ggatcggacg attgcgtcgc atcgaccctg cgcccaagct gcatcatcga aattgccgtc          840
aaccaagctc tgatagagtt ggtcaagacc aatgcggagc atatacgccc ggaggcgcgg          900
cgatcctgca agctccggat gcctccgctc gaagtagcgc gtctgctgct ccatacaagc          960
caaccacggc ctccagaaga ggatgttggc gacctcgtat tgggaatccc cgaacatcgc         1020
ctcgctccag tcaatgaccg ctgttatgcg gccattgtcc gtcaggacat gttggagcc          1080 gaaatccgca tgcacgaggt gccggacttc ggggcagtcc tcggcccaaa gcatcagctc         1140
atcgagagcc tgcgcgacgg acgcactgac ggtgtcgtcc atcacagttt gccagtgata         1200
cacatgggga tcagcaatcg cgcatatgaa atcacgccat gtagtgtatt gaccgattcc         1260
ttgcggtccg aatgggccga acccgctcgt ctggctaaga tcggccgcag cgatcgcatc         1320
catggcctcc gcgaccggct ggagaacagc gggcagttcg gtttcaggca ggtcttgcaa         1380
cgtgacaccc tgtgcacggc gggagatgca ataggtcagg ctctcgctga actccccaat         1440
```

```
gtcaagcact tccggaatcg ggagcgcggc cgatgcaaag tgccgataaa cataacgatc    1500
tttgtagaaa ccatcggcgc agctatttac ccgcaggaca tatccacgcc ctcctacatc    1560
gaagctgaaa gcacgagatt cttcgccctc cgagagctgc atcaggtcgg agacgctgtc    1620
gaacttttcg atcagaaact tctcgacaga cgtcgcggtg agttcaggct ttttacccat    1680
actagttttt agtttatgta tgtgttttt gtagttatag atttaagcaa gaaaagaata    1740
caaacaaaaa attgaaaaag attgatttag aattaaaaag aaaaatattt acgtaagaag    1800
ggaaaatagt aaatgttgca agttcactaa actcctaaat tatgctgccc tttatattcc    1860
ctgttacagc agccgagcca aaggtatata ggctcctttg cattagcatg cgtaacaaac    1920
cacctgtcag tttcaaccga ggtggtatcc gagagaattg tgtgattgct ttaattaatt    1980
tcggagaatc tcacatgcca ctgaagatta aaaactggat gccagaaaag gggtgtccag    2040
gtgtaacatc aatagaggaa gctgaaaagt cttagaacgg gtaatcttcc accaacctga    2100
tgggttccta gatataatct cgaagggaat aagtagggtg ataccgcaga agtgtctgaa    2160
tgtattaagg tcctcacagt ttaaatcccg ctcacactaa cgtaggatta ttataactca    2220
aaaaaatggc attattctaa gtaagttaaa tatccgtaat cttaaacag cggccgcaga    2280 tctctcgagt cgaaactaag ttctggtgtt ttaaaactaa aaaaaagact aactataaaa    2340
gtagaattta agaagtttaa gaaatagatt tacagaatta caatcaatac ctaccgtctt    2400
tatatactta ttagtcaagt aggggaataa tttcagggaa ctggtttcaa cctttttttt    2460 cagcttttc caaatcagag agagcagaag gtaatagaag gtgtaagaaa atgagataga    2520
tacatgcgtg ggtcaattgc cttgtgtcat catttactcc aggcaggttg catcactcca    2580
ttgaggttgt gcccgttttt tgcctgtttg tgccctgtt ctctgtagtt gcgctaagag    2640
aatggaccta tgaactgatg gttggtgaag aaaacaatat tttggtgctg ggattctttt    2700
tttttctgga tgccagctta aaaagcgggc tccattatat ttagtggatg ccaggaataa    2760
actgttcacc cagacaccta cgatgttata tattctgtgt aacccgcccc ctattttggg    2820
catgtacggg ttacagcaga attaaaaggc taattttttg actaaataaa gttaggaaaa    2880
tcactactat taattattta cgtattcttt gaaatggcga gtattgataa tgataaactg    2940
gatccgtcga caaacttaga ttagattgct atgctttctt tctaatgagc aagaagtaaa    3000
aaaagttgta atagaacaag aaaaatgaaa ctgaaacttg agaaattgaa gaccgttat    3060 taacttaaat atcaatggga ggtcatcgaa agagaaaaaa atcaaaaaaa aattttcaa    3120 gaaaagaaa cgtgataaaa attttttattg cctttttcga cgaagaaaaa gaaacgaggc    3180
ggtctctttt ttcttttcca aacctttagt acgggtaatt aacgacaccc tagaggaaga    3240 aagagggaa atttagtatg ctgtgcttgg gtgttttgaa gtggtacggc gatgcgcgga    3300
gtccgagaaa atctggaaga gtaaaaaagg agtagaaaca ttttgaagct atgagctcag    3360
atctgttaac cttgttttat atttgttgta aaaagtagat aattacttcc ttgatgatct    3420 gtaaaaaga gaaaagaaa gcatctaaga acttgaaaaa ctacgaatta gaaaagacca    3480
aatatgtatt tcttgcattg accaatttat gcaagtttat atatatgtaa atgtaagttt    3540
cacgaggttc tactaaacta aaccaccccc ttggttagaa gaaaagagtg tgtgagaaca    3600
ggctgttgtt gtcacacgat tcggacaatt ctgtttgaaa gagagagagt aacagtacga    3660
tcgaacgaac tttgctctgg agatcacagt gggcatcata gcatgtggta ctaaacccctt    3720 tcccgccatt ccagaacctt cgattgcttg ttacaaaacc tgtgagccgt cgctaggacc    3780
ttgttgtgtg acgaaattgg aagctgcaat caataggaag acaggaagtc gagcgtgtct    3840
```

```
gggttttttc agtttttgttc tttttgcaaa caaatcacga gcgacggtaa tttctttctc    3900
gataagaggc cacgtgcttt atgagggtaa catcaattca agaaggaggg aaacacttcc    3960
tttttctggc cctgataata gtatgagggt gaagccaaaa taaaggattc gcgcccaaat    4020
cggcatcttt aaatgcaggt atgcgatagt tcctcactct ttccttactc acgagtaatt    4080
cttgcaaatg cctattatgc agatgttata atatctgtgc gtcttgagtt gagcctaggg    4140
agctccagct tttgttccct ttagtgaggg ttaattgcgc gcttggcgta atcatggtca    4200
tagctgtttc ctgtgtgaaa ttgttatccg ctcacaattc cacacaacat aggagccgga    4260
agcataaagt gtaaagcctg gggtgcctaa tgagtgaggt aactcacatt aattgcgttg    4320
cgctcactgc ccgctttcca gtcgggaaac ctgtcgtgcc agctgcatta atgaatcggc    4380
caacgcgcgg ggagaggcgg tttgcgtatt gggcgctctt ccgcttcctc gctcactgac    4440
tcgctgcgct cggtcgttcg gctgcggcga gcggtatcag ctcactcaaa ggcggtaata    4500
cggttatcca cagaatcagg ggataacgca ggaaagaaca tgtgagcaaa aggccagcaa    4560
aaggccagga accgtaaaaa ggccgcgttg ctggcgtttt tccataggct ccgcccccct    4620
gacgagcatc acaaaaatcg acgctcaagt cagaggtggc gaaacccgac aggactataa    4680
agataccagg cgtttccccc tggaagctcc ctcgtgcgct ctcctgttcc gaccctgccg    4740
cttaccggat acctgtccgc ctttctccct tcgggaagcg tggcgctttc tcatagctca    4800
cgctgtaggt atctcagttc ggtgtaggtc gttcgctcca agctgggctg tgtgcacgaa    4860
ccccccgttc agcccgaccg ctgcgcctta tccggtaact atcgtcttga gtccaacccg    4920
gtaagacacg acttatcgcc actggcagca gccactggta acaggattag cagagcgagg    4980
tatgtaggcg gtgctacaga gttcttgaag tggtggccta actacggcta cactagaagg    5040
acagtatttg gtatctgcgc tctgctgaag ccagttacct tcggaaaaag agttggtagc    5100
tcttgatccg gcaaacaaac caccgctggt agcggtggtt ttttgtttg caagcagcag    5160
attacgcgca gaaaaaaagg atctcaagaa gatcctttga tcttttctac ggggtctgac    5220
gctcagtgga acgaaaactc acgttaaggg attttggtca tgagattatc aaaaaggatc    5280
ttcacctaga tccttttaaa ttaaaaatga agttttaaat caatctaaag tatatatgag    5340
taaacttggt ctgacagtta ccaatgctta atcagtgagg cacctatctc agcgatctgt    5400
ctatttcgtt catccatagt tgcctgactc cccgtcgtgt agataactac gatacgggag    5460
ggcttaccat ctggccccag tgctgcaatg ataccgcgag acccacgctc accggctcca    5520
gatttatcag caataaacca gccagccgga agggccgagc gcagaagtgg tcctgcaact    5580
ttatccgcct ccatccagtc tattaattgt tgccgggaag ctagagtaag tagttcgcca    5640
gttaatagtt tgcgcaacgt tgttgccatt gctacaggca tcgtggtgtc acgctcgtcg    5700
tttggtatgg cttcattcag ctccggttcc caacgatcaa ggcgagttac atgatccccc    5760
atgttgtgca aaaaagcggt tagctccttc ggtcctccga tcgttgtcag aagtaagttg    5820
gccgcagtgt tatcactcat ggttatggca gcactgcata attctcttac tgtcatgcca    5880
tccgtaagat gcttttctgt gactggtgag tactcaacca agtcattctg agaatagtgt    5940
atgcggcgac cgagttgctc ttgcccggcg tcaatacggg ataataccgc gccacatagc    6000
agaactttaa aagtgctcat cattggaaaa cgttcttcgg ggcgaaaact ctcaaggatc    6060
ttaccgctgt tgagatccag ttcgatgtaa cccactcgtg cacccaactg atcttcagca    6120
tcttttactt tcaccagcgt ttctgggtga gcaaaaacag gaaggcaaaa tgccgcaaaa    6180
aagggaataa gggcgacacg gaaatgttga atactcatac tcttcctttt tcaatattat    6240
```

```
tgaagcattt atcagggtta ttgtctcatg agcggataca tatttgaatg tatttagaaa    6300
aataaacaaa taggggttcc gcgcacattt ccccgaaaag tgccacctga acgaagcatc    6360
tgtgcttcat tttgtagaac aaaaatgcaa cgcgagagcg ctaattttc aaacaaagaa     6420 tctgagctgc attttacag aacagaaatg caacgcgaaa gcgctatttt accaacgaag     6480
aatctgtgct tcattttgt aaaacaaaaa tgcaacgcga gagcgctaat ttttcaaaca    6540
aagaatctga gctgcatttt tacagaacag aaatgcaacg cgagagcgct attttaccaa    6600
caaagaatct atacttcttt tttgttctac aaaaatgcat cccgagagcg ctattttct    6660 aacaaagcat cttagattac ttttttttctc ctttgtgcgc tctataatgc agtctcttga   6720 taacttttg cactgtaggt ccgttaaggt tagaagaagg ctactttggt gtctattttc    6780
tcttccataa aaaagcctg actccacttc ccgcgtttac tgattactag cgaagctgcg    6840
ggtgcatttt ttcaagataa aggcatcccc gattatattc tataccgatg tggattgcgc    6900
atactttgtg aacagaaagt gatagcgttg atgattcttc attggtcaga aaattatgaa    6960
cggtttcttc tattttgtct ctatatacta cgtataggaa atgtttacat tttcgtattg    7020
ttttcgattc actctatgaa tagttcttac tacaattttt ttgtctaaag agtaatacta    7080
gagataaaca taaaaatgt agaggtcgag tttagatgca agttcaagga gcgaaaggtg    7140
gatgggtagg ttataggg atatagcaca gagatatata gcaaagagat acttttgagc     7200
aatgtttgtg gaagcggtat tcgcaatatt ttagtagctc gttacagtcc ggtgcgtttt    7260
tggttttttg aaagtgcgtc ttcagagcgc ttttggtttt caaaagcgct ctgaagttcc    7320
tatactttct agagaatagg aacttcggaa taggaacttc aaagcgtttc cgaaaacgag    7380
cgcttccgaa aatgcaacgc gagctgcgca catacagctc actgttcacg tcgcaccctat  7440 atctgcgtgt tgcctgtata tatatataca tgagaagaac ggcatagtgc gtgtttatgc    7500
ttaaatgcgt acttatatgc gtctatttat gtaggatgaa aggtagtcta gtacctcctg    7560
tgatattatc ccattccatg cggggtatcg tatgcttcct tcagcactac cctttagctg    7620
ttctatatgc tgccactcct caattggatt agtctcatcc ttcaatgcta tcatttcctt    7680
tgata                                                                7685
```

<210> SEQ ID NO 134  
<211> LENGTH: 24  
<212> TYPE: DNA  
<213> ORGANISM: Artificial Sequence  
<220> FEATURE:  
<223> OTHER INFORMATION: Primer 587

<400> SEQUENCE: 134
ccaatgcaga ccgatcttct accc                                              24

<210> SEQ ID NO 135  
<211> LENGTH: 22  
<212> TYPE: DNA  
<213> ORGANISM: Artificial Sequence  
<220> FEATURE:  
<223> OTHER INFORMATION: Primer 588

<400> SEQUENCE: 135
gatcacgtga tctgttgtat tg                                                22

<210> SEQ ID NO 136  
<211> LENGTH: 20  
<212> TYPE: DNA  
<213> ORGANISM: Artificial Sequence  
<220> FEATURE:

<223> OTHER INFORMATION: Primer 2167

<400> SEQUENCE: 136
tacatggggt acttctcctc                                              20

<210> SEQ ID NO 137
<211> LENGTH: 60
<212> TYPE: DNA
<213> ORGANISM: Artificial Sequence
<220> FEATURE:
<223> OTHER INFORMATION: Primer 2170

<400> SEQUENCE: 137
cagtcaacaa atataaagaa tattgaaatt gacagttttt gtcgctatcg attttttatta      60

<210> SEQ ID NO 138
<211> LENGTH: 60
<212> TYPE: DNA
<213> ORGANISM: Artificial Sequence
<220> FEATURE:
<223> OTHER INFORMATION: Primer 2171

<400> SEQUENCE: 138
ttttgtcgct atcgattttt attatttgct gttttaaatc attctggttc tatcgaggag      60

<210> SEQ ID NO 139
<211> LENGTH: 60
<212> TYPE: DNA
<213> ORGANISM: Artificial Sequence
<220> FEATURE:
<223> OTHER INFORMATION: Primer 2172

<400> SEQUENCE: 139
catgttattg acgccaggtt tggacgttgt ttttcactgt atccggatgt gaagtcgttg      60

<210> SEQ ID NO 140
<211> LENGTH: 60
<212> TYPE: DNA
<213> ORGANISM: Artificial Sequence
<220> FEATURE:
<223> OTHER INFORMATION: Primer 2173

<400> SEQUENCE: 140
tggttttaga aaaggatggt gtgcttgtcg ctgagacaca tgttattgac gccaggtttg      60

<210> SEQ ID NO 141
<211> LENGTH: 20
<212> TYPE: DNA
<213> ORGANISM: Artificial Sequence
<220> FEATURE:
<223> OTHER INFORMATION: Primer 2175

<400> SEQUENCE: 141
tctagttcag agcttggtgc                                              20

<210> SEQ ID NO 142
<211> LENGTH: 20
<212> TYPE: DNA
<213> ORGANISM: Artificial Sequence
<220> FEATURE:
<223> OTHER INFORMATION: Primer 2226

<400> SEQUENCE: 142
tgctccattt ggaagtctcg                                              20

<210> SEQ ID NO 143

```
<211> LENGTH: 20
<212> TYPE: DNA
<213> ORGANISM: Artificial Sequence
<220> FEATURE:
<223> OTHER INFORMATION: Primer 2227

<400> SEQUENCE: 143
tatctacgaa gtgacctgcg                                             20

<210> SEQ ID NO 144
<211> LENGTH: 1716
<212> TYPE: DNA
<213> ORGANISM: Artificial Sequence
<220> FEATURE:
<223> OTHER INFORMATION: B. subtilis alsS codon-optimized for expression
      in S. cerevisiae

<400> SEQUENCE: 144
atgttgacta aagctacaaa agagcagaaa tcattggtga aaaatagggg tgcagaactt    60
gttgtggact gtttggtaga acagggcgta acacatgttt ttggtatccc aggtgcaaaa   120
atcgacgccg tgtttgatgc attacaagac aagggtccag aaattattgt tgctagacat   180
gagcaaaatg ccgcatttat ggcgcaagct gtaggtaggc ttacaggtaa acctggtgtt   240
gtcctagtta cgtctggccc aggagcctcc aatttagcaa ctggtctatt gacagctaat   300
actgagggag atcctgtagt tgcgttagcc ggtaatgtaa ttagagctga taggcttaag   360
agaactcacc agtctctaga caacgctgct ttattccaac cgatcaccaa gtactcagta   420
gaggtacaag acgtaaagaa tatacctgaa gctgtgacaa acgcatttcg tatagcttct   480
gctggtcagg ctggtgccgc gtttgtttct tttcctcaag acgttgtcaa tgaagtgacc   540
aatactaaaa acgttagagc ggttgcagcc cctaaactag gtccagccgc agacgacgca   600
attagcgctg caattgctaa aattcagacg gcgaaactac cagtagtcct tgtcggtatg   660
aagggcggaa gaccagaagc aataaaaagc gttcgtaagt tattgaagaa gtccaattca   720
cctttcgttg agacttacca agcagcaggt actttatcta gagatttaga ggatcagtat   780
tttggaagga taggtctatt tagaaaccaa ccaggagatt tactattaga acaagctgat   840
gttgtactta ctatcggtta tgatcctata gagtatgacc caaagttttg gaacataaat   900
ggggatagaa caattataca tctagacgag ataatcgccg acatcgatca cgcttatcaa   960
ccagatttag aactaatcgg agatatcccg tcaacaatca atcatattga acatgatgct  1020
gtaaaggttg agttcgctga acgtgagcag aaaatcttat ctgatctaaa gcaatatatg  1080
catgagggtg aacaagttcc agcagactgg aaatctgacc gtgcacatcc tttggaaatc  1140
gttaaggaac taagaaatgc ggtcgatgat catgtgactg ttacatgtga tatcggttca  1200
catgcaattt ggatgtcacg ttattttagg agctacgaac cattaacttt aatgatatct  1260
aacgggatgc aaactctggg ggttgcactt ccttgggcta ttggcgctag tttagttaag  1320
cccggtgaga aggtggtatc ggtatcaggt gatggtggct tctgttttc ggctatggaa  1380 ttagaaactg cagtccgttt aaaagctccc attgtgcata ttgtctggaa tgattctact  1440
tacgacatgg ttgcttttca acagttgaag aaatacaata gaacttcggc tgtagacttt  1500
ggtaacatcg atattgtgaa atatgctgag tcttttggcg caacaggcct gagggtggaa  1560
agtccagatc agttagctga tgtgttgaga caagggatga tgccgagggg accggtaatc  1620
atagatgtgc cagttgacta ctcagacaat attaatttgg cttctgataa acttcctaaa  1680
gagtttggcg agctaatgaa gaccaaagcc ttataa                             1716
```

<210> SEQ ID NO 145
<211> LENGTH: 11
<212> TYPE: PRT
<213> ORGANISM: Thermotoga petrophila

<400> SEQUENCE: 145

Pro Tyr His Lys Glu Gly Gly Leu Gly Ile Leu
1               5                   10

<210> SEQ ID NO 146
<211> LENGTH: 11
<212> TYPE: PRT
<213> ORGANISM: Victivallis vadensis

<400> SEQUENCE: 146

Pro Tyr Ser Glu Lys Gly Gly Leu Ala Ile Leu
1               5                   10

<210> SEQ ID NO 147
<211> LENGTH: 11
<212> TYPE: PRT
<213> ORGANISM: Termite Group 1 Bacterium Phylotype Rs-D17

<400> SEQUENCE: 147

Pro Tyr Lys Pro Glu Gly Gly Ile Ala Ile Leu
1               5                   10

<210> SEQ ID NO 148
<211> LENGTH: 11
<212> TYPE: PRT
<213> ORGANISM: Yarrowia lipolytica

<400> SEQUENCE: 148

Pro Leu Lys Pro Ser Gly His Leu Gln Ile Leu
1               5                   10

<210> SEQ ID NO 149
<211> LENGTH: 11
<212> TYPE: PRT
<213> ORGANISM: Francisella tularensis

<400> SEQUENCE: 149

Pro Ile Lys Lys Thr Gly His Leu Gln Ile Leu
1               5                   10

<210> SEQ ID NO 150
<211> LENGTH: 11
<212> TYPE: PRT
<213> ORGANISM: Arabidopsis thaliana

<400> SEQUENCE: 150

Pro Ile Lys Glu Thr Gly His Ile Gln Ile Leu
1 5 10

<210> SEQ ID NO 151
<211> LENGTH: 1647
<212> TYPE: DNA
<213> ORGANISM: Artificial Sequence
<220> FEATURE:
<223> OTHER INFORMATION: L. lactis kivD codon-optimized for expression
in S. cerevisiae

<400> SEQUENCE: 151
atgtatacag tgggtgatta cttgctagac cgtttacatg aattaggcat agaagagatt 60
tttggagtac caggtgatta caatttgcaa ttcttggatc agattatctc acataaggat 120

```
atgaaatggg tcgggaatgc gaacgagtta aacgcttcct atatggcaga tggttatgcg      180
agaaccaaaa aggccgctgc tttcttaca actttcggtg taggtgaact ttcagccgtt       240
aatggattag ccggatctta cgctgaaaac ttaccagtcg ttgaaattgt tggttctcct      300
acttctaagg tacaaaacga gggaaagttt gttcaccata ctttagcgga tggtgatttc      360
aaacatttca tgaagatgca tgaacctgtc acagcagcga aacacttttt gaccgcagag      420
aacgctactg ttgaaatcga tagagtatta agtgctttgt taaaagagag aaagccagtg      480
tatatcaact tgcctgttga tgtcgctgcc gcaaaagcag aaaaaccatc tttaccattg      540
aaaaaggaaa actcaaccag taacacatct gatcaagaga ttctaaacaa aatccaagag      600
tcattgaaaa acgccaaaaa gccaatcgtt ataacaggcc atgaaatcat ctcctttggt      660
ttagaaaaga ccgttacaca attcatctct aagacaaaat tgccaatcac tactttaaac      720
tttggcaaat cttctgtaga tgaagcttta ccatcttttc taggtatcta caatggtact      780 cttctgaac caaacctaaa agagtttgtc gaatccgctg atttcatact tatgtgggt      840 gttaagctaa ctgatagttc aactggtgca ttcactcacc acttgaacga aaacaagatg      900
atatcattga atatcgatga gggcaagata ttcaacgaac gtattcaaaa cttcgatttt      960
gaatcactaa tttcttctct acttgatttg tcagaaatag aatacaaagg aaaatacatc     1020
gacaaaaagc aagaggattt cgtgccatca aacgcattgt tgtcacaaga tagactttgg     1080
caagctgtgg aaaacctaac tcaatctaac gaaacaattg tggctgagca aggcacatca     1140
ttcttcggcg catctagtat tttcttgaag agtaagtccc acttcatcgg tcaacctctt     1200
tggggatcta ttgggtacac cttccctgcc gcattgggat cacagatcgc agacaaggag     1260
tccagacatc tactattcat tggggacgga tcattgcaac ttaccgttca ggaattaggg     1320
ttggctataa gagaaaagat caatcctatt tgttttatca tcaacaatga tggctataca     1380
gtagaacgtg agattcacgg tccaaatcaa agttacaatg acatcccaat gtggaattac     1440
tctaagttgc ctgaatcttt cggtgcaaca gaagatagag ttgttccaa aatagtcaga     1500 acagaaaatg agtttgtttc tgtcatgaag gaagctcaag ccgatcctaa tagaatgtac     1560
tggattgaac taatcttggc caaggaagga gccccaaaag tattgaaaaa gatgggaaaa     1620
cttttcgctg aacagaataa gtcctga                                        1647
```

<210> SEQ ID NO 152
<211> LENGTH: 1023
<212> TYPE: DNA
<213> ORGANISM: Artificial Sequence
<220> FEATURE:
<223> OTHER INFORMATION: L. lactis alcohol dehydrogenase (adhA) RE1

<400> SEQUENCE: 152

```
atgaaagcag cagtagtaag acacaatcca gatggttatg cggaccttgt tgaaaaggaa       60
cttcgagcaa tcaaacctaa tgaagctttg cttgacatgg agtattgtgg agtctgtcat      120
accgatttgc acgttgcagc aggtgatttt ggcaacaaag cagggactgt tcttggtcat      180
gaaggaattg gaattgtcaa agaaattgga gctgatgtaa gctcgcttca agttggtgat      240
cgggtttcag tggcttggtt cttttgaagga tgtggtcact gtgaatactg tgtatctggt      300
aatgaaactt ttgtcgagaa agttaaaaat gcaggatatt cagttgatgg cggaatggct      360
gaagaagcaa ttgttgttgc cgattatgct gtcaaagttc ctgacggact tgacccaatt      420
gaagctagct caattacttg tgctggagta acaacttaca aagcaatcaa agtatcagga      480
gtaaaacctg gtgattggca gtaattttt ggtgctggag gacttggaaa tttagcaatt      540
```

| | |
|---|---|
| caatatgcta aaaatgtttt tggagcaaaa gtaattgctg ttgatattaa tcaagataaa | 600 |
| ttaaatttag ctaaaaaaat tggagctgat gtgactatca attctggtga tgtaaatcca | 660 |
| gttgatgaaa ttaaaaaaat aactggcggc ttaggggtgc aaagtgcaat agtttgtgct | 720 |
| gttgcaagga ttgcttttga acaagcggtt gcttctttga aacctatggg caaaatggtt | 780 |
| gctgtggcag ttcccaatac tgagatgact ttatcagttc aacagttgt ttttgacgga | 840 |
| gtggaggttg caggttcact tgtcggaaca agacttgact tggcagaagc ttttcaattt | 900 |
| ggagcagaag gtaaggtaaa accaattgtt gcgacacgca aactggaaga aatcaatgat | 960 |
| attattgatg aaatgaaggc aggaaaaatt gaaggccgaa tggtcattga ttttactaaa | 1020 |
| taa | 1023 |

<210> SEQ ID NO 153
<211> LENGTH: 2073
<212> TYPE: DNA
<213> ORGANISM: Saccharomyces cerevisiae

<400> SEQUENCE: 153

| | |
|---|---|
| atggaaggct tcaatccggc tgacatagaa catgcgtcac cgattaattc atctgacagc | 60 |
| cattcatcct cctttgtata tgctctaccc aaaagtgcta gtgaatatgt agtcaaccat | 120 |
| aatgagggtc gtgcaagtgc aagtggaaat ccagccgcag tgccgtctcc cataatgaca | 180 |
| ctgaatctca aaagcacaca ttccctcaat attgatcagc atgttcatac ctcaacatcg | 240 |
| ccgacggaaa ctattgggca tattcatcat gtggaaaagc tgaatcaaaa caatttgatt | 300 |
| catctggatc cagtacccaa cttttgaagat aagtccgata ttaagccttg gttgcaaaag | 360 |
| attttttatc ctcaaggaat agaacttgtg atagaaaggt cggacgcatt taagttgtc | 420 |
| ttcaagtgta aagctgctaa aaggggaagg aacgcgagaa ggaaaagaaa agataagccc | 480 |
| aaaggacagg accacgaaga cgagaaatcc aagatcaatg atgacgaatt agaatatgcg | 540 |
| agtccttcta atgccacagt aaccaatggg cctcaaacat cgcccgatca acatcctcc | 600 |
| ataaagccaa agaaaaaaag atgtgtatcg aggtttaata actgtccgtt tagagtacga | 660 |
| gctacttatt cgttaaagag gaaagatgg agcattgttg taatggacaa taaccattca | 720 |
| catcagctaa agtttaaccc tgattccgaa gagtacaaaa aattcaaaga aaaattaaga | 780 |
| aaggataatg acgtagatgc aatcaagaaa ttcgacgaat tggaatacag aactttggcc | 840 |
| aatttgccca ttccaacagc tacaatcccc tgtgattgtg gtttaacaaa tgaaatacaa | 900 |
| agtttcaatg tcgtattgcc cactaacagt aatgttactt catcagcatc ctcttcaact | 960 |
| gtatcgtcca tatcccttga ttcatcgaat gcatctaaaa ggccatgctt accctctgta | 1020 |
| aataacaccg gtagtatcaa taccaataac gtaaggaaac cgaaaagcca gtgtaagaat | 1080 |
| aaagacacac tcttaaaaag aaccaccatg cagaactttc tcacaactaa atcaaggctg | 1140 |
| cgtaagaccg gtacgccaac atcttcgcaa cactcatcta cagcattttc aggatatatt | 1200 |
| gatgatcctt tcaatttgaa tgaaatcttg ccactgccgg catccgattt caagctaaac | 1260 |
| actgtaacaa atttgaacga aattgacttt acgaacattt ttaccaaatc gccgcatcca | 1320 |
| catagcgggt ctacccatcc aagacaagtc ttcgaccaat tggacgattg ttcctctata | 1380 |
| ctcttctctc cattaactac aaacacgaat aatgaatttg aaggagagtc agatgatttt | 1440 |
| gttcattctc catatttgaa ctcagaggca gatttcagcc aaaattctag tagtgctccc | 1500 |
| ccagtccatc atgacccaaa tgaaacacat caggaaaacc aggatatatt tgatagattt | 1560 |
| gctaatagtt cccaagaaca taatgagtat attctacaat atttgacgca ctccgatgct | 1620 |

```
gctaaccaca ataacatcgg cgttccaaac aacaattcac attcgctaaa tactcagcat    1680
aacgtttctg atctgggcaa ctcactttta agacaagaag ctttagttgg cagctcttca    1740
acaaaaatct tcgacgaatt gaaatttgta caaaatggcc cacacggttc tcaacatcct    1800
atagattttc aacatgttga ccatcgtcat ctcagctcta atgaacctca agtacgatca    1860
catcaatatg gtccgcaaca gcagccaccg cagcaattgc aatatcacca aaatcagccc    1920
cacgacggcc ataaccacga acagcaccaa acagtacaaa aggatatgca aacgcatgaa    1980
tcgctagaaa taatgggaaa cacattattg gaagagttca aagacattaa aatggtgaac    2040
ggcgagttga agtatgtgaa gccagaagat tag                                 2073
```

<210> SEQ ID NO 154
<211> LENGTH: 1494
<212> TYPE: DNA
<213> ORGANISM: Artificial Sequence
<220> FEATURE:
<223> OTHER INFORMATION: E. coli ketolacid reductoisomerase P2D1-A1

<400> SEQUENCE: 154

```
atggccaact attttaacac attaaatttg agacaacaat ggctcaact gggtaagtgc       60 agatttatgg gaagggacga gtttgctgat ggtgcttctt atctgcaagg aaagaaagta    120
gtaattgttg gctgcggtgc tcagggtcta aaccaaggtt taaacatgag agattcaggt    180
ctggatattt cgtatgcatt gaggaaagag tctattgcag aaaaggatgc cgattggcgt    240
aaagcgacgg aaaatgggtt caaagttggt acttacgaag aactgatccc tcaggcagat    300
ttagtgatta acctaacacc agataaggtt cactcagacg tagtaagaac agttcaaccg    360
ctgatgaagg atggggcagc tttaggttac tctcatggct ttaatatcgt tgaagtgggc    420
gagcagatca gaaaaggtat aacagtcgta atggttgcgc caaagtgccc aggtacggaa    480
gtcagagagg agtacaagag gggttttggt gtacctacat tgatcgccgt acatcctgaa    540
aatgacccca acgtgaagg tatggcaata gcgaaggcat gggcagccgc aaccggaggt    600
catagagcgg gtgtgttaga gagttctttc gtagctgagg tcaagagtga cttaatgggt    660
gaacaaacca ttctgtgcgg aatgttcag gcagggtctt tactatgctt tgataaattg    720
gtcgaagagg gtacagatcc tgcctatgct gaaaagttga tacaatttgg ttgggagaca    780
atcaccgagg cacttaaaca aggtggcata acattgatga tggatagact ttcaaatccg    840
gccaagctaa gagcctacgc cttatctgag caactaaaag agatcatggc accattattc    900
caaaagcaca tggacgatat tatctccggt gagtttttcct caggaatgat ggcagattgg    960
gcaaacgatg ataaaaagtt attgacgtgg agagaagaaa ccggcaagac ggcattcgag   1020
acagccccac aatacgaagg taaaattggt gaacaagaat acttgataa gggagtattg    1080 atgatagcta tggtgaaggc aggggtagaa cttgcattcg aaactatggt tgactccggt   1140
atcattgaag aatctgcata ctatgagtct ttgcatgaat tgcctttgat agcaaatact   1200
attgcaagaa aaagacttta cgagatgaat gttgtcatat cagacactgc agaatatggt   1260
aattacttat ttagctacgc gtgtgtcccg ttgttagagc ccttcatggc cgagttacaa   1320
cctggtgatt tggggaaggc tattccggaa ggagcggttg acaatggcca actgagagac   1380
gtaaatgaag ctattcgttc gcatgctata aacaggtgg gtaaaaagct gagaggatat   1440
atgaccgata tgaaaagaat tgcagtggca ggacaccacc accaccacca ctaa         1494
```

<210> SEQ ID NO 155
<211> LENGTH: 1713
<212> TYPE: DNA

<213> ORGANISM: Artificial Sequence
<220> FEATURE:
<223> OTHER INFORMATION: L. lactis ilvD codon-optimized for expression in S. cerevisiae

<400> SEQUENCE: 155

```
atggagttta agtataacgg caaagttgaa tctgttgaac tgaataagta cagcaaaacg      60
ttgacacaag atcccacaca acccgccaca caggcaatgt attacggcat cgggtttaaa     120
gacgaagatt tcaagaaagc tcaagtgggt atagtgtcga tggactggga tggaaatcca     180
tgcaacatgc atttaggaac ccttggatca aagattaaaa gctcagtaaa tcagacagat     240
ggtctgatcg gcttacaatt tcatacgata ggagtttctg atgggatagc aaatggaaag     300
ttgggaatga atactccct tgtttccaga gaagttatag ctgactctat tgaaaccaac      360
gctggcgctg aatactatga tgcaattgta gccatcccag ttgtgacaa aaatatgcca     420
ggttctatta ttggtatggc aagacttaat aggccaagca ttatggtgta tggaggaaca     480
atagaacacg tgaatataa aggtgagaaa ttgaacatcg tatcggcttt tgaatctcta     540
ggccagaaaa ttaccggcaa tatctctgat gaagattatc acggtgttat ttgtaatgct     600
attcctggtc aaggggcatg tgggggggatg tacacagcta ataccttagc tgccgctatc     660
gaaacactag gtatgtcatt gccgtattct tcttcgaacc ctgcagtatc tcaagaaaaa      720
caagaagaat gtgatgagat tggattagcc attaagaatc ttttggaaaa agacatcaag     780
cctagtgata taatgactaa ggaggcgttc gagaacgcta ttaccattgt gatggtcttg     840
gggggtagta ctaatgctgt cttgcatatt attgcaatgg ctaacgcgat aggtgtcgaa     900
ataactcagg atgacttcca aagaattagt gacattactc cagtactagg tgattttaaa     960
ccttcaggta aatatatgat ggaagatttg cataaaattg gaggcttgcc agcagtgctt    1020
aagtaccttc taaaggaagg aaaattgcat ggtgactgcc ttactgtgac gggtaaaaca    1080
ttagccgaga atgtcgagac tgccctagac ttggatttcg actcacaaga tatcatgagg    1140
ccactaaaga atcctatcaa ggccaccggc cacttgcaga ttctgtacgg taatttagct    1200
caagggggtt ccgtagcaaa aattagcggt aaagaaggag agttcttcaa aggcactgcc    1260
agagtctttg atggtgaaca acatttatc gacggcatag aatctggtcg tttgcatgct     1320
ggagatgtag cggtaattag gaatataggt cccgtcggcg gacctggtat gcccgaaatg    1380
ctgaagccta catcagcatt aattggtgcg ggtttaggga aaagttgcgc gttaattacg    1440
gatggtagat ctccggtgg cactcacggt tttgttgtcg gccatattgt gcctgaagcc    1500
gttgagggtg gactaatcgg cttagttgaa gatgacgata ataaggagat agatgcagtc    1560
aacaactcta tatccctgaa agtttccgat gaagaaatcg caaagagaag agctaattat    1620
cagaagccaa ctccgaaagc caccaggggga gttttggcaa aattcgctaa attaacccgt    1680
cctgcatcgg aagggtgtgt tactgatctg taa                                  1713
```

<210> SEQ ID NO 156
<211> LENGTH: 1683
<212> TYPE: DNA
<213> ORGANISM: Artificial Sequence
<220> FEATURE:
<223> OTHER INFORMATION: F. tularensis ilvD codon-optimized for expression in S. cerevisiae

<400> SEQUENCE: 156

```
atgaaaaagg tgctgaataa gtactcaaga cgtcttaccg aagataagtc tcaaggtgct      60
tctcaggcta tgctatacgg aacagagatg aatgatgcag atatgcacaa gcctcaaatc     120
```

```
ggtatcggtt ccgtttggta tgaaggaaat acttgtaata tgcatttgaa tcaattagca    180
caatttgtca aggattctgt tgaaaaggaa aacttgaaag gcatgagatt caacacaatt    240
ggagtttctg atggtatctc catgggtact gatggcatgt cctactctct acaatcacgt    300
gatctaatcg ctgattcaat cgaaacagtt atgagtgcac actggtatga tggcctagtt    360
tcaatcccag ttgtgacaa aacatgcca ggttgcatga tggcccttgg tagattaaac      420
agaccaggtt tcgtgatcta cggtggaacc atacaagctg gcgttatgag aggcaaacct    480
attgatattg tcacagcttt ccaatcatat ggagcatgct atctgggca ataactgaa      540 caggaaagac aagagactat caaaaaggct tgtccaggtg caggagcctg tggcggcatg    600
tacacagcta acacaatggc ctgtgccatt gaggcccttg aatgagtttt gccttttcc     660 tcttctactt ctgcaacttc agttgaaaag gtacaagagt gtgataaggc aggcgaaaca    720
atcaaaaact tgttagaatt ggacattaaa ccaagagaca tcatgactag aaaagctttc    780
gaaaacgcta tggtactaat tacagtaatg ggaggttcaa caaatgccgt gttacatctg    840
ttagcaatgg cttcatccgt cgatgtagat ttgagtatcg atgactttca ggaaatagct    900
aacaaaactc cagtgctggc tgatttcaag ccatccggga aatatgtcat ggcaaacttg    960
catgcaattg gcgggactcc tgcagttatg aaaatgttgc tgaaggccgg aatgcttcat    1020
ggcgattgtt tgactgtaac tgggaaaacc ttagccgaaa acttggaaaa tgtgccgac    1080 ctgccagaag ataacacaat catacacaaa ctagataacc aatcaaaaa gactggtcat    1140 ttgcaaatct tgaaggggaa tgttgcccca gaaggttctg ttgctaagat aacagggaag   1200
gaaggtgaga tattcgaggg cgtagccaat gtctttgatt cagaggaaga gatggttgcc   1260
gcagtcgaaa ctggaaaagt caaaaagggc gatgttattg ttattagata cgaaggtcct   1320
aaaggtggcc ctggcatgcc tgaaatgctt aagccaacct ctttgataat gggtgctgga   1380
ctaggccagg atgttgcatt aatcacagat ggcagatttt caggtggtag tcatggtttc   1440
attgtaggtc acattacacc agaagcatac gaaggcggta tgatcgcctt attagaaaac   1500
ggtgataaga taacaatcga tgctatcaac aatgtgataa atgtagactt aagtgatcaa   1560
gagattgctc aacgtaaatc taagtggaga gcatcaaagc aaaaagcttc cagaggtaca   1620
ctgaaaaagt acattaagac cgtctcttct gcttctaccg ggtgcgtgac tgatttggat   1680
tga                                                                  1683

<210> SEQ ID NO 157
<211> LENGTH: 1704
<212> TYPE: DNA
<213> ORGANISM: Saccharomyces cerevisiae

<400> SEQUENCE: 157
atggcaaaga agctcaacaa gtactcgtat atcatcactg aacctaaggg ccaaggtgcg    60
tcccaggcca tgctttatgc caccggtttc aagaaggaag atttcaagaa gcctcaagtc    120
ggggttggtt cctgttggtg gtccggtaac ccatgtaaca tgcatctatt ggacttgaat    180
aacagatgtt ctcaatccat tgaaaaagcg gtttgaaag ctatgcagtt caacaccatc     240
ggtgtttcag acggtatctc tatgggtact aaaggtatga gatactcgtt acaaagtaga    300
gaaatcattg cagactccctt tgaaaccatc atgatggcac aacactacga tgctaacatc    360
gccatcccat catgtgacaa aaacatgccc ggtgtcatga tggccatggg tagacataac    420
agaccttcca tcatggtata tggtggtact atcttgcccg tcatccaac atgtggttct     480 tcgaagatct ctaaaaacat cgatatcgtc tctgcgttcc aatcctacgg tgaatatatt    540
```

-continued

| | |
|---|---|
| tccaagcaat tcactgaaga agaaagagaa gatgttgtgg aacatgcatg cccaggtcct | 600 |
| ggttcttgtg gtggtatgta tactgccaac acaatggctt ctgccgctga agtgctaggt | 660 |
| ttgaccattc caaactcctc ttccttccca gccgtttcca aggagaagtt agctgagtgt | 720 |
| gacaacattg gtgaatacat caagaagaca atggaattgg gtattttacc tcgtgatatc | 780 |
| ctcacaaaag aggcttttga aaacgccatt acttatgtcg ttgcaaccgg tgggtccact | 840 |
| aatgctgttt tgcatttggt ggctgttgct cactctgcgg gtgtcaagtt gtcaccagat | 900 |
| gatttccaaa gaatcagtga tactacacca ttgatcggtg acttcaaacc ttctggtaaa | 960 |
| tacgtcatgg ccgatttgat taacgttggt ggtacccaat ctgtgattaa gtatctatat | 1020 |
| gaaaacaaca tgttgcacgg taacacaatg actgttaccg gtgacacttt ggcagaacgt | 1080 |
| gcaaagaaag caccaagcct acctgaagga caagagatta ttaagccact ctcccaccca | 1140 |
| atcaaggcca acggtcactt gcaaattctg tacggttcat tggcaccagg tggagctgtg | 1200 |
| ggtaaaatta ccggtaagga aggtacttac ttcaagggta gagcacgtgt gttcgaagag | 1260 |
| gaaggtgcct ttattgaagc cttggaaaga ggtgaaatca agaagggtga aaaaaccgtt | 1320 |
| gttgttatca gatatgaagg tccaagaggt gcaccaggta tgcctgaaat gctaaagcct | 1380 |
| tcctctgctc tgatgggtta cggtttgggt aaagatgttg cattgttgac tgatggtaga | 1440 |
| ttctctggtg gttctcacgg gttcttaatc ggccacattg ttcccgaagc cgctgaaggt | 1500 |
| ggtcctatcg ggttggtcag agacggcgat gagattatca ttgatgctga taataacaag | 1560 |
| attgacctat tagtctctga taaggaaatg gctcaacgta aacaaagttg ggttgcacct | 1620 |
| ccacctcgtt acacaagagg tactctatcc aagtatgcta agttggtttc caacgcttcc | 1680 |
| aacggttgtg ttttagatgc ttga | 1704 |

<210> SEQ ID NO 158
<211> LENGTH: 1692
<212> TYPE: DNA
<213> ORGANISM: Saccharomyces cerevisiae

<400> SEQUENCE: 158

| | |
|---|---|
| atgaacaagt actcgtatat catcactgaa cctaagggcc aaggtgcgtc ccaggccatg | 60 |
| ctttatgcca ccggttttcaa gaaggaagat ttcaagaagc ctcaagtcgg ggttggttcc | 120 |
| tgttggtggt ccggtaaccc atgtaacatg catctattgg acttgaataa cagatgttct | 180 |
| caatccattg aaaaagcggg tttgaaagct atgcagttca acaccatcgg tgtttcagac | 240 |
| ggtatctcta tgggtactaa aggtatgaga tactcgttac aaagtagaga atcattgca | 300 |
| gactcctttg aaaccatcat gatggcacaa cactacgatg ctaacatcgc catcccatca | 360 |
| tgtgacaaaa acatgcccgg tgtcatgatg gccatgggta gacataacag accttccatc | 420 |
| atggtatatg gtggtactat cttgcccggt catccaacat gtggttcttc gaagatctct | 480 |
| aaaaacatcg atatcgtctc tgcgttccaa tcctacggtg aatatatttc caagcaattc | 540 |
| actgaagaag aaagagaaga tgttgtggaa catgcatgcc aggtcctgg ttcttgtggt | 600 |
| ggtatgtata ctgccaacac aatggcttct gccgctgaag tgctaggttt gaccattcca | 660 |
| aactcctctt ccttcccagc cgtttccaag gagaagttag ctgagtgtga caacattggt | 720 |
| gaatacatca agaagacaat ggaattgggt attttacctc gtgatatcct cacaaaagag | 780 |
| gcttttgaaa acgccattac ttatgtcgtt gcaaccggtg gtccactaa tgctgttttg | 840 |
| catttggtgg ctgttgctca ctctgcgggt gtcaagttgt caccagatga tttccaaaga | 900 |
| atcagtgata ctacaccatt gatcggtgac ttcaaacctt ctggtaaata cgtcatggcc | 960 |

```
gatttgatta acgttggtgg tacccaatct gtgattaagt atctatatga aaacaacatg      1020
ttgcacggta acacaatgac tgttaccggt gacactttgg cagaacgtgc aaagaaagca      1080
ccaagcctac ctgaaggaca agagattatt aagccactct cccacccaat caaggccaac      1140
ggtcacttgc aaattctgta cggttcattg caccaggtg gagctgtggg taaaattacc       1200
ggtaaggaag gtacttactt caagggtaga gcacgtgtgt tcgaagagga aggtgccttt      1260
attgaagcct tggaaagagg tgaaatcaag aagggtgaaa aaccgttgt tgttatcaga       1320 tatgaaggtc caagaggtgc accaggtatg cctgaaatgc taaagccttc ctctgctctg      1380
atgggttacg gtttgggtaa agatgttgca ttgttgactg atggtagatt ctctggtggt      1440
tctcacgggt tcttaatcgg ccacattgtt cccgaagccg ctgaaggtgg tcctatcggg      1500
ttggtcagag acggcgatga gattatcatt gatgctgata taacaagat tgacctatta       1560 gtctctgata aggaaatggc tcaacgtaaa caaagttggg ttgcacctcc acctcgttac      1620
acaagaggta ctctatccaa gtatgctaag ttggtttcca acgcttccaa cggttgtgtt      1680
ttagatgctt ga                                                           1692
```

```
<210> SEQ ID NO 159
<211> LENGTH: 1923
<212> TYPE: DNA
<213> ORGANISM: Neurospora crassa

<400> SEQUENCE: 159
atggcttcta atcaagataa caaggcagtt gctccagacg ctgctgcacc agcgggtcag       60
tcaacaacca ccacaactac aaatgataac agtgaaagga atctaccaaa ggaaggcgaa      120
tacattcaat ggaggacact tccagcgggc aatccagatc agttgaacag atggagtcat      180
ttcctgactc gtgagcatga gtttccaggc gctcaggcaa tgttgtacgg tgcgggtgta      240
cctaacaaag atatgatgaa aaaggctcct catgttggga tcgctactgt ttggtgggaa      300
ggtaacccat gtaatactca tctgcttgat ctaggtcaaa aagtcaaaaa ggctgttgaa      360
agagagaaga tgttagcttg gcaattcaac acaattggcg ttagtgacgg aataacaatg      420
ggtggtgaag gcatgaggta ctcttttgcag agcagagaga tcatagcaga ttctatagag      480
actgtgacat gtgcacaaca ccatgatgcc aatatctcaa ttccagggtg cgacaaaaac      540
atgccaggcg tcatcatggc agctgcaaga cacaacagac cattcgttat gatctacgga      600
ggtacaatga gaggcggtca ttccgaatta cttgatagac ctatcaatat cgtaacttgt      660
tacgaggcct caggggccta tacttatggt agacttaagc cagcctgtcc aaaactccact    720 gctaccccat ctgacgtgat ggacgatata gaacaacacg cctgtccagg ggctggagct     780 tgtgaggga tgtacaccgc gaatactatg gcaaccgcca tagaagctat gggtctgaca       840
gcaccagggt catcctcctt tccagccagc tcaccagaaa agttcagaga gtgcgaaaaa      900
gccgcggaat acattaagat atgcatggaa aaagatattc gtccaagaga cttactaaca      960
aaggcttcct tcgagaatgc tctcgtcttg acaatgattc taggtggttc aaccaacggt     1020
gttttacatt acttagccat ggccaactcc gccgatgtcg atctaactct tgatgatatc     1080
aatagagtca gtgctaagac tccttttcctc gctgatatgg ctccatctgg tagatactat     1140
atggaggatt tgtacaaggt aggtggtact ccagccgtac tcaagatgtt gatagctgcc     1200
ggctatatcg atgaacaat tccaacaata acaggaaaat cttttggctga aacgtgtca     1260 gattggccat ctttagaccc tgatcaaaag attatccgtc ctttggataa tcctatcaaa     1320
tcacaaggtc acattgagtt gctgtatggt aacttctctc ctggtgggcc tgttgccaag     1380
```

```
atcacgggta aggaaggtct tagttttact ggtaaggcaa gatgctttaa caaagagttt    1440
gaattggatg ctgcgctgaa aaactctgaa atcacgctcg aacaaggaaa tcaagttcta    1500
attgtaaggt atgaaggccc taagggcgga ccaggcatgc cagaacaatt gaaagcatct    1560
gccgctatca tgggcgctgg tttgacgaac gtagctttag tcacggatgg gcgatactct    1620
ggcgcttctc acggtttcat cgtcggtcac gtcgtgcctg aggcggcaac tggcggacct    1680
attgctttag taaggatgg agatttgatc acaattgatg cagtcagaaa tagaattgat    1740
gttgtcaaaa ccgtagaagg agtggagggc gaggaggaaa ttgcaaaggt tttagaagag    1800
aggaaaaagg gatggaaagc acctaagatg aagccaacaa gaggagccct ggccaaatac    1860
gcaagacttg ttggtgacgc atcacatgga gcagttacag acttaggagg agatgcttac    1920
taa                                                                  1923

<210> SEQ ID NO 160
<211> LENGTH: 1686
<212> TYPE: DNA
<213> ORGANISM: Acaryochloris marina

<400> SEQUENCE: 160
atgtcagata atcgtaattc tcaagtagtc acacaaggtg ttcaaagagc acctaataga     60
gctatgttaa gagctgtagg attcggagat gatgatttca cgaaaccaat agttggattg    120
gctaatggtt tctctactat tactccttgt aacatgggaa ttgatagttt ggccacaaga    180
gctgaagcat ctattaggac ggctggtgca atgccacaaa agtttggaac cattacaata    240
agcgatggga tatcaatggg tacagaaggt atgaagtatt ctctcgtttc aagagaagtg    300
attgccgatt ccattgaaac agcttgcatg ggccagagta tggatggcgt attagcaatt    360
ggtggctgcg acaaaaacat gcctggcgcg atgttagcaa tggctcgtat gaacatacca    420
gccatcttcg tatatggtgg cactatcaag ccaggccacc tcaatggtga agatttgact    480
gtcgtatcag ctttcgaagc tgtggggcaa cattccgccg gtagaatatc cgaagccgaa    540
cttacagcag tcgaaaagca tgcatgtcca ggcgctggat catgtggtgg catgtacacg    600
gccaacacaa tgtctagtgc ttttgaggct atgggcatgt ccttgatgta ctcatccact    660
atggctgcag aagatgagga gaaggctgtt tctgccgaac aatctgcggc tgtgctagtt    720
gaggcaatcc acaaacagat tctaccaaga gatattctaa ccagaaaggc gtttgagaac    780
gcaatagcag tcataatggc tgttgggggt tccacaaatg cagttctcca cttgttagcg    840
atttcaagag cagcaggaga ctctttaact ttagatgatt tcgaaactat cagggctcaa    900
gttccagtga tttgtgattt gaagccttct ggtcgatatg tcgctacaga ccttcataaa    960
gctggcggaa tcccattagt tatgaaaatg ctattagagc atgggctatt acatgggat    1020
gcattgacta ttaccggcaa gacaattgca gagcaattgg ccgatgtgcc atctgaacct    1080
tctcctgatc aagacgtaat ccgtccttgg gataatccaa tgtacaagca aggtcacctt    1140
gccatcttga gaggtaactt ggccacagaa ggtgcagtag ccaagatcac agggatcaaa    1200
aaccctcaaa tcactggacc agctagagtt ttcgagtcag aggaagcctg tttagaagcg    1260
atcctggccg gaaagatcca accaaatgac gtgatagtcg ttcgatacga aggtccaaaa    1320
ggaggaccag gtatgaggga aatgctggct cctacttccg caatcatagg tgcgggtcta    1380
ggagactcag ttggccttat cactgatggg agattttccg gtgggacata cggtatggtt    1440
gttggacatg tagcaccaga agcagctgtt ggtgggacca ttgctctggt tcaagagggt    1500
gaccaaatca ctatcgatgc tcacgctaga aagttggagc tgcatgtctc tgaccaagag    1560
```

```
cttaaagagc gtaaggaaaa gtgggagcag ccaaaaccac tgtacaataa gggtgtgctt    1620
gcgaagtacg ccaaactcgt aagctctagt tcagtaggag cggttacaga tttggatttg    1680
ttctaa                                                                1686
```

<210> SEQ ID NO 161
<211> LENGTH: 1683
<212> TYPE: DNA
<213> ORGANISM: Lyngbya spp.

<400> SEQUENCE: 161

```
atgtccgata acttccgttc tcaagccatt acacagggca aaaagagaac tcctaataga      60
gctatgctga gagcagttgg atttggagat gaagatttca acaaaccaat tgttggtatt     120
gccaatggct actccaccat aactccttgc aacatcggtc ttaacgatct tgcacatagg     180
gccgaaacag ctctaaagca agcagacgcc atgccacaaa tgttcggaac tattactgta     240
agtgatggaa ttgcaatggg aaccgaaggt atgaagtact ctcttgttag cagagaagtt     300
atagccgatg ctattgaaac tgcttgtaac ggacagtcta tggatggggt cttagcaata     360
ggaggttgtg acaaaaacat gcctggtgct atgatcgcca tagcgcgtat gaatatccct     420
gctatctttg tatacggcgg tacaatcaag ccaggtaatc taaacggttg tgatctaaca     480
gttgtctccg cattcgaagc cgttggagag tattctgctg gcaaactaga tgacgataga     540
ttactggaca tcgagagatt agcatgccct ggttctggct catgtggggg aatgttcact     600
gctaatacaa tgtctagtgc atttgaagca atgggtatga gtctgatgta cagcagtaca     660
atggcatccg aagatgctga aaaggctgat tccaccgaaa agtccgcttt tgttttgaga     720
gaggcaattt ctcagagaat cctacctaag caaatcctga cgaggaaagc cttcgaaaac     780
gcaattgcag tcatcatggc ggtaggcggc tccacaaact ctgtattgca tctattggct     840
attgcctatg ctgccgatgt agaattgacc atagatgatt tcgaaacaat tcgtgggaga     900
gtaccagttt tgtgtgatct taagccatca ggacgatttg tcactaccga tttccataag     960
gctggtggag tcccattgat catgaagatg ttactcgaac aaggtttgat ccatggggat    1020
gcccttacta taacgggtaa aacagtcgca gagcaattag ctgatatccc atctcaacca    1080
tctgccgacc aagaggtgat aagaccatgg aataacccaa tgtacaagca aggtcacttg    1140
gcgatcctta aggggaatct tgcaacagaa ggttcagtcg ccaagataac aggtgtgaaa    1200
aagcctcaga tgacaggtcc agcgcgagtt tttgaatcag aagagcaatg cttagaagct    1260
atactagccg gcaaaatcca agctggggac gttttagtgg ttagatacga aggtccaaaa    1320
gggggaccag gtatgagaga aatgctggct ccaacatctg caatcattgg tgccggcttg    1380
ggtgattctg ttggactcat tacgatggc agattctctg gcggaacata tggtttggta    1440
gtcggacacg ttgctccaga ggctgcagtg ggtggtaaca tcgctttagt gcaagagggc    1500
gattcaatta ctattgatgc ttcacagcgt ttgttacaag taaacatctc tgaccaggtg    1560
ttggagcaaa gacgacaaaa ctggcaacca ccacaaccta gatacactaa aggcgtatta    1620
gcgaagtacg caaagttggt ttcaagtagt tcagttggcg cagttactga tctcgattgt    1680
taa                                                                  1683
```

<210> SEQ ID NO 162
<211> LENGTH: 1851
<212> TYPE: DNA
<213> ORGANISM: Artificial Sequence
<220> FEATURE:
<223> OTHER INFORMATION: E. coli ilvD codon-optimized for expression in K. lactis

<400> SEQUENCE: 162

```
atgccgaaat acagatcagc aacaacaacc catggtagaa atatggctgg tgcaagggct      60
ctatggagag ctactggcat gactgatgca gatttcggaa agccaatcat tgccgtcgtc     120
aactctttta cacaattcgt tccgggtcat gtccatttgc gtgatctagg taagcttgtt     180
gccgaacaaa ttgaagctgc aggtggtgtc gcaaaagagt ttaatactat tgctgtggac     240
gacggtatag ctatggggca tggcggtatg ttatactctt taccatcgag agaattaatt     300
gcagactcag tcgaatatat ggttaatgct cattgtgccg atgcaatggt ttgtatctct     360
aattgtgata agataacgcc tggtatgttg atggcgtcct tgagattgaa catcccagta     420
atcttcgtat ctggcggccc aatggaggct ggtaaaacta gttaagtga tcagatcatc     480
aaacttgatc ttgtggatgc aatgattcaa ggtgcagatc caaaagtttc agactcgcag     540
tcagaccaag ttgaaagaag tgcatgtcca acttgtggtt cttgcagtgg aatgttcacg     600
gctaactcta tgaattgctt gactgaagct ctaggtttat ctcaaccagg aaatggttca     660
ttattagcga cccatgcaga cagaaagcaa ttgttcttaa atgccggaaa aagaattgtg     720
gaactaacga aaaggtatta cgaacaaaat gatgaatcag cattaccgag aatatagct      780
tcaaaggctg cattcgaaaa tgccatgaca ttggatattg caatgggtgg tagtacaaac     840
acggtcttac atcttctagc tgcagcccaa gaagctgaga tagatttcac catgtctgat     900
atcgacaagc tttcacgtaa ggttccacag ttatgtaagg ttgcaccatc aactcaaaag     960
tatcacatgg aagacgttca tcgtgcagga ggggttattg gtattttagg ggagttggac    1020
agagccggtc ttttaaacag ggatgtgaag aatgtattgg gtttaacact tccacagaca    1080
ttagagcaat acgatgtcat gttaactcaa gatgatgccg tgaaaaacat gttcagggca    1140
ggtccagcag ggatcagaac cacccaagca ttctcgcaag actgtaggtg ggacactttg    1200
gacgatgata gagcaaatgg atgtataaga tcgcttgagc atgcttatag taaggatggt    1260
ggtttagcag tattatatgg aaacttcgct gaaaatggtt gcattgtgaa aactgctggt    1320
gtagatgata gtattttgaa atttactgga cccgctaaag tttacgaaag tcaagacgat    1380
gctgttgagg ctatacttgg cggaaaggtg gtagcaggag acgtggtagt gataagatat    1440
gagggaccaa agggaggacc aggtatgcag gaaatgcttt acccaacttc attttttgaag    1500
tccatgggac taggaaaagc ttgtgcctt atcactgacg tagattctc tggtggcact     1560
tcgggttta gtatcggtca cgtatcacca gaggcagctt ctggtggttc gattggattg    1620
attgaagatg gagatttgat cgccatagat atcccaaata gaggtatcca attacaagtc    1680
tcagacgctg aattggctgc aagaagagaa gcacaagatg ccagaggaga taaggcttgg    1740
actcctaaaa atagagaacg tcaagtaagt ttcgcccta gggcttatgc ttcattggct    1800
acttcagccg ataaggggc agtaagagac aaatcgaagt tgggtggatg a             1851
```

<210> SEQ ID NO 163
<211> LENGTH: 567
<212> TYPE: PRT
<213> ORGANISM: Saccharomyces cerevisiae

<400> SEQUENCE: 163

```
Met Ala Lys Lys Leu Asn Lys Tyr Ser Tyr Ile Ile Thr Glu Pro Lys
1               5                   10                  15

Gly Gln Gly Ala Ser Gln Ala Met Leu Tyr Ala Thr Gly Phe Lys Lys
            20                  25                  30

Glu Asp Phe Lys Lys Pro Gln Val Gly Val Gly Ser Cys Trp Trp Ser
```

-continued

```
                35                  40                  45
Gly Asn Pro Cys Asn Met His Leu Leu Asp Leu Asn Arg Cys Ser
 50                  55                  60
Gln Ser Ile Glu Lys Ala Gly Leu Lys Ala Met Gln Phe Asn Thr Ile
65                  70                  75                  80
Gly Val Ser Asp Gly Ile Ser Met Gly Thr Lys Gly Met Arg Tyr Ser
                 85                  90                  95
Leu Gln Ser Arg Glu Ile Ile Ala Asp Ser Phe Glu Thr Ile Met Met
            100                 105                 110
Ala Gln His Tyr Asp Ala Asn Ile Ala Ile Pro Ser Cys Asp Lys Asn
            115                 120                 125
Met Pro Gly Val Met Met Ala Met Gly Arg His Asn Arg Pro Ser Ile
       130                 135                 140
Met Val Tyr Gly Gly Thr Ile Leu Pro Gly His Pro Thr Cys Gly Ser
145                 150                 155                 160
Ser Lys Ile Ser Lys Asn Ile Asp Ile Val Ser Ala Phe Gln Ser Tyr
                165                 170                 175
Gly Glu Tyr Ile Ser Lys Gln Phe Thr Glu Glu Arg Glu Asp Val
            180                 185                 190
Val Glu His Ala Cys Pro Gly Pro Gly Ser Cys Gly Gly Met Tyr Thr
            195                 200                 205
Ala Asn Thr Met Ala Ser Ala Ala Glu Val Leu Gly Leu Thr Ile Pro
       210                 215                 220
Asn Ser Ser Ser Phe Pro Ala Val Ser Lys Glu Lys Leu Ala Glu Cys
225                 230                 235                 240
Asp Asn Ile Gly Glu Tyr Ile Lys Lys Thr Met Glu Leu Gly Ile Leu
                245                 250                 255
Pro Arg Asp Ile Leu Thr Lys Glu Ala Phe Glu Asn Ala Ile Thr Tyr
            260                 265                 270
Val Val Ala Thr Gly Gly Ser Thr Asn Ala Val Leu His Leu Val Ala
       275                 280                 285
Val Ala His Ser Ala Gly Val Lys Leu Ser Pro Asp Asp Phe Gln Arg
       290                 295                 300
Ile Ser Asp Thr Thr Pro Leu Ile Gly Asp Phe Lys Pro Ser Gly Lys
305                 310                 315                 320
Tyr Val Met Ala Asp Leu Ile Asn Val Gly Gly Thr Gln Ser Val Ile
                325                 330                 335
Lys Tyr Leu Tyr Glu Asn Asn Met Leu His Gly Asn Thr Met Thr Val
            340                 345                 350
Thr Gly Asp Thr Leu Ala Glu Arg Ala Lys Lys Ala Pro Ser Leu Pro
            355                 360                 365
Glu Gly Gln Glu Ile Ile Lys Pro Leu Ser His Pro Ile Lys Ala Asn
       370                 375                 380
Gly His Leu Gln Ile Leu Tyr Gly Ser Leu Ala Pro Gly Gly Ala Val
385                 390                 395                 400
Gly Lys Ile Thr Gly Lys Glu Gly Thr Tyr Phe Lys Gly Arg Ala Arg
                405                 410                 415
Val Phe Glu Glu Glu Gly Ala Phe Ile Glu Ala Leu Glu Arg Gly Glu
            420                 425                 430
Ile Lys Lys Gly Glu Lys Thr Val Val Ile Arg Tyr Glu Gly Pro
       435                 440                 445
Arg Gly Ala Pro Gly Met Pro Glu Met Leu Lys Pro Ser Ser Ala Leu
   450                 455                 460
```

```
Met Gly Tyr Gly Leu Gly Lys Asp Val Ala Leu Leu Thr Asp Gly Arg
465                 470                 475                 480

Phe Ser Gly Gly Ser His Gly Phe Leu Gly His Ile Val Pro Glu
                485                 490                 495

Ala Ala Glu Gly Gly Pro Ile Gly Leu Val Arg Asp Gly Asp Glu Ile
                500                 505                 510

Ile Ile Asp Ala Asp Asn Asn Lys Ile Asp Leu Leu Val Ser Asp Lys
                515                 520                 525

Glu Met Ala Gln Arg Lys Gln Ser Trp Val Ala Pro Pro Arg Tyr
530                 535                 540

Thr Arg Gly Thr Leu Ser Lys Tyr Ala Lys Leu Val Ser Asn Ala Ser
545                 550                 555                 560

Asn Gly Cys Val Leu Asp Ala
                565

<210> SEQ ID NO 164
<211> LENGTH: 563
<212> TYPE: PRT
<213> ORGANISM: Saccharomyces cerevisiae

<400> SEQUENCE: 164

Met Asn Lys Tyr Ser Tyr Ile Ile Thr Glu Pro Lys Gly Gln Gly Ala
1               5                   10                  15

Ser Gln Ala Met Leu Tyr Ala Thr Gly Phe Lys Lys Glu Asp Phe Lys
                20                  25                  30

Lys Pro Gln Val Gly Val Gly Ser Cys Trp Trp Ser Gly Asn Pro Cys
                35                  40                  45

Asn Met His Leu Leu Asp Leu Asn Asn Arg Cys Ser Gln Ser Ile Glu
                50                  55                  60

Lys Ala Gly Leu Lys Ala Met Gln Phe Asn Thr Ile Gly Val Ser Asp
65                  70                  75                  80

Gly Ile Ser Met Gly Thr Lys Gly Met Arg Tyr Ser Leu Gln Ser Arg
                85                  90                  95

Glu Ile Ile Ala Asp Ser Phe Glu Thr Ile Met Met Ala Gln His Tyr
                100                 105                 110

Asp Ala Asn Ile Ala Ile Pro Ser Cys Asp Lys Asn Met Pro Gly Val
                115                 120                 125

Met Met Ala Met Gly Arg His Asn Arg Pro Ser Ile Met Val Tyr Gly
                130                 135                 140

Gly Thr Ile Leu Pro Gly His Pro Thr Cys Gly Ser Ser Lys Ile Ser
145                 150                 155                 160

Lys Asn Ile Asp Ile Val Ser Ala Phe Gln Ser Tyr Gly Glu Tyr Ile
                165                 170                 175

Ser Lys Gln Phe Thr Glu Glu Arg Glu Asp Val Val Glu His Ala
                180                 185                 190

Cys Pro Gly Pro Gly Ser Cys Gly Gly Met Tyr Thr Ala Asn Thr Met
                195                 200                 205

Ala Ser Ala Ala Glu Val Leu Gly Leu Thr Ile Pro Asn Ser Ser Ser
                210                 215                 220

Phe Pro Ala Val Ser Lys Glu Lys Leu Ala Glu Cys Asp Asn Ile Gly
225                 230                 235                 240

Glu Tyr Ile Lys Lys Thr Met Glu Leu Gly Ile Leu Pro Arg Asp Ile
                245                 250                 255

Leu Thr Lys Glu Ala Phe Glu Asn Ala Ile Thr Tyr Val Val Ala Thr
                260                 265                 270
```

Gly Gly Ser Thr Asn Ala Val Leu His Leu Val Ala Val Ala His Ser
            275                 280                 285

Ala Gly Val Lys Leu Ser Pro Asp Asp Phe Gln Arg Ile Ser Asp Thr
290                 295                 300

Thr Pro Leu Ile Gly Asp Phe Lys Pro Ser Gly Lys Tyr Val Met Ala
305                 310                 315                 320

Asp Leu Ile Asn Val Gly Gly Thr Gln Ser Val Ile Lys Tyr Leu Tyr
                325                 330                 335

Glu Asn Asn Met Leu His Gly Asn Thr Met Thr Val Thr Gly Asp Thr
            340                 345                 350

Leu Ala Glu Arg Ala Lys Lys Ala Pro Ser Leu Pro Glu Gly Gln Glu
355                 360                 365

Ile Ile Lys Pro Leu Ser His Pro Ile Lys Ala Asn Gly His Leu Gln
370                 375                 380

Ile Leu Tyr Gly Ser Leu Ala Pro Gly Gly Ala Val Gly Lys Ile Thr
385                 390                 395                 400

Gly Lys Glu Gly Thr Tyr Phe Lys Gly Arg Ala Arg Val Phe Glu Glu
                405                 410                 415

Glu Gly Ala Phe Ile Glu Ala Leu Glu Arg Gly Glu Ile Lys Lys Gly
            420                 425                 430

Glu Lys Thr Val Val Val Ile Arg Tyr Glu Gly Pro Arg Gly Ala Pro
435                 440                 445

Gly Met Pro Glu Met Leu Lys Pro Ser Ser Ala Leu Met Gly Tyr Gly
450                 455                 460

Leu Gly Lys Asp Val Ala Leu Leu Thr Asp Gly Arg Phe Ser Gly Gly
465                 470                 475                 480

Ser His Gly Phe Leu Ile Gly His Ile Val Pro Glu Ala Ala Glu Gly
                485                 490                 495

Gly Pro Ile Gly Leu Val Arg Asp Gly Asp Glu Ile Ile Ile Asp Ala
            500                 505                 510

Asp Asn Asn Lys Ile Asp Leu Leu Val Ser Asp Lys Glu Met Ala Gln
515                 520                 525

Arg Lys Gln Ser Trp Val Ala Pro Pro Arg Tyr Thr Arg Gly Thr
530                 535                 540

Leu Ser Lys Tyr Ala Lys Leu Val Ser Asn Ala Ser Asn Gly Cys Val
545                 550                 555                 560

Leu Asp Ala

<210> SEQ ID NO 165
<211> LENGTH: 640
<212> TYPE: PRT
<213> ORGANISM: Neurospora crassa

<400> SEQUENCE: 165

Met Ala Ser Asn Gln Asp Asn Lys Ala Val Ala Pro Asp Ala Ala Ala
1               5                   10                  15

Pro Ala Gly Gln Ser Thr Thr Thr Thr Thr Asn Asp Asn Ser Glu
            20                  25                  30

Arg Asn Leu Pro Lys Glu Gly Glu Tyr Ile Gln Trp Arg Thr Leu Pro
        35                  40                  45

Ala Gly Asn Pro Asp Gln Leu Asn Arg Trp Ser His Phe Leu Thr Arg
    50                  55                  60

Glu His Glu Phe Pro Gly Ala Gln Ala Met Leu Tyr Gly Ala Gly Val
65                  70                  75                  80

Pro Asn Lys Asp Met Met Lys Lys Ala Pro His Val Gly Ile Ala Thr

```
                    85                  90                  95
Val Trp Trp Glu Gly Asn Pro Cys Asn Thr His Leu Leu Asp Leu Gly
            100                 105                 110

Gln Lys Val Lys Lys Ala Val Glu Arg Glu Lys Met Leu Ala Trp Gln
            115                 120                 125

Phe Asn Thr Ile Gly Val Ser Asp Gly Ile Thr Met Gly Gly Glu Gly
            130                 135                 140

Met Arg Tyr Ser Leu Gln Ser Arg Glu Ile Ile Ala Asp Ser Ile Glu
145                 150                 155                 160

Thr Val Thr Cys Ala Gln His His Asp Ala Asn Ile Ser Ile Pro Gly
                165                 170                 175

Cys Asp Lys Asn Met Pro Gly Val Ile Met Ala Ala Arg His Asn
            180                 185                 190

Arg Pro Phe Val Met Ile Tyr Gly Gly Thr Met Arg Gly Gly His Ser
            195                 200                 205

Glu Leu Leu Asp Arg Pro Ile Asn Ile Val Thr Cys Tyr Glu Ala Ser
            210                 215                 220

Gly Ala Tyr Thr Tyr Gly Arg Leu Lys Pro Ala Cys Pro Asn Ser Thr
225                 230                 235                 240

Ala Thr Pro Ser Asp Val Met Asp Asp Ile Glu Gln His Ala Cys Pro
                245                 250                 255

Gly Ala Gly Ala Cys Gly Gly Met Tyr Thr Ala Asn Thr Met Ala Thr
            260                 265                 270

Ala Ile Glu Ala Met Gly Leu Thr Ala Pro Gly Ser Ser Ser Phe Pro
            275                 280                 285

Ala Ser Ser Pro Glu Lys Phe Arg Glu Cys Glu Lys Ala Ala Glu Tyr
            290                 295                 300

Ile Lys Ile Cys Met Glu Lys Asp Ile Arg Pro Arg Asp Leu Leu Thr
305                 310                 315                 320

Lys Ala Ser Phe Glu Asn Ala Leu Val Leu Thr Met Ile Leu Gly Gly
                325                 330                 335

Ser Thr Asn Gly Val Leu His Tyr Leu Ala Met Ala Asn Ser Ala Asp
            340                 345                 350

Val Asp Leu Thr Leu Asp Asp Ile Asn Arg Val Ser Ala Lys Thr Pro
            355                 360                 365

Phe Leu Ala Asp Met Ala Pro Ser Gly Arg Tyr Tyr Met Glu Asp Leu
            370                 375                 380

Tyr Lys Val Gly Gly Thr Pro Ala Val Leu Lys Met Leu Ile Ala Ala
385                 390                 395                 400

Gly Tyr Ile Asp Gly Thr Ile Pro Thr Ile Thr Gly Lys Ser Leu Ala
                405                 410                 415

Glu Asn Val Ser Asp Trp Pro Ser Leu Asp Pro Asp Gln Lys Ile Ile
            420                 425                 430

Arg Pro Leu Asp Asn Pro Ile Lys Ser Gln Gly His Ile Arg Val Leu
            435                 440                 445

Tyr Gly Asn Phe Ser Pro Gly Gly Ala Val Ala Lys Ile Thr Gly Lys
            450                 455                 460

Glu Gly Leu Ser Phe Thr Gly Lys Ala Arg Cys Phe Asn Lys Glu Phe
465                 470                 475                 480

Glu Leu Asp Ala Ala Leu Lys Asn Ser Glu Ile Thr Leu Glu Gln Gly
                485                 490                 495

Asn Gln Val Leu Ile Val Arg Tyr Glu Gly Pro Lys Gly Gly Pro Gly
            500                 505                 510
```

```
Met Pro Glu Gln Leu Lys Ala Ser Ala Ala Ile Met Gly Ala Gly Leu
        515                 520                 525

Thr Asn Val Ala Leu Val Thr Asp Gly Arg Tyr Ser Gly Ala Ser His
        530                 535                 540

Gly Phe Ile Val Gly His Val Val Pro Glu Ala Ala Thr Gly Gly Pro
545                 550                 555                 560

Ile Ala Leu Val Lys Asp Gly Asp Leu Ile Thr Ile Asp Ala Val Arg
                565                 570                 575

Asn Arg Ile Asp Val Val Lys Thr Val Glu Gly Val Glu Gly Glu
                580                 585                 590

Glu Ile Ala Lys Val Leu Glu Glu Arg Lys Lys Gly Trp Lys Ala Pro
        595                 600                 605

Lys Met Lys Pro Thr Arg Gly Ala Leu Ala Lys Tyr Ala Arg Leu Val
        610                 615                 620

Gly Asp Ala Ser His Gly Ala Val Thr Asp Leu Gly Gly Asp Ala Tyr
625                 630                 635                 640

<210> SEQ ID NO 166
<211> LENGTH: 561
<212> TYPE: PRT
<213> ORGANISM: Acaryochloris marina

<400> SEQUENCE: 166

Met Ser Asp Asn Arg Asn Ser Gln Val Val Thr Gln Gly Val Gln Arg
1               5                   10                  15

Ala Pro Asn Arg Ala Met Leu Arg Ala Val Gly Phe Gly Asp Asp Asp
                20                  25                  30

Phe Thr Lys Pro Ile Val Gly Leu Ala Asn Gly Phe Ser Thr Ile Thr
        35                  40                  45

Pro Cys Asn Met Gly Ile Asp Ser Leu Ala Thr Arg Ala Glu Ala Ser
    50                  55                  60

Ile Arg Thr Ala Gly Ala Met Pro Gln Lys Phe Gly Thr Ile Thr Ile
65                  70                  75                  80

Ser Asp Gly Ile Ser Met Gly Thr Glu Gly Met Lys Tyr Ser Leu Val
                85                  90                  95

Ser Arg Glu Val Ile Ala Asp Ser Ile Glu Thr Ala Cys Met Gly Gln
                100                 105                 110

Ser Met Asp Gly Val Leu Ala Ile Gly Gly Cys Asp Lys Asn Met Pro
        115                 120                 125

Gly Ala Met Leu Ala Met Ala Arg Met Asn Ile Pro Ala Ile Phe Val
    130                 135                 140

Tyr Gly Gly Thr Ile Lys Pro Gly His Leu Asn Gly Glu Asp Leu Thr
145                 150                 155                 160

Val Val Ser Ala Phe Glu Ala Val Gly Gln His Ser Ala Gly Arg Ile
                165                 170                 175

Ser Glu Ala Glu Leu Thr Ala Val Glu Lys His Ala Cys Pro Gly Ala
        180                 185                 190

Gly Ser Cys Gly Gly Met Tyr Thr Ala Asn Thr Met Ser Ser Ala Phe
    195                 200                 205

Glu Ala Met Gly Met Ser Leu Met Tyr Ser Ser Thr Met Ala Ala Glu
    210                 215                 220

Asp Glu Glu Lys Ala Val Ser Ala Glu Gln Ser Ala Ala Val Leu Val
225                 230                 235                 240

Glu Ala Ile His Lys Gln Ile Leu Pro Arg Asp Ile Leu Thr Arg Lys
                245                 250                 255
```

```
Ala Phe Glu Asn Ala Ile Ala Val Ile Met Ala Val Gly Gly Ser Thr
            260                 265                 270

Asn Ala Val Leu His Leu Leu Ala Ile Ser Arg Ala Ala Gly Asp Ser
            275                 280                 285

Leu Thr Leu Asp Asp Phe Glu Thr Ile Arg Ala Gln Val Pro Val Ile
            290                 295                 300

Cys Asp Leu Lys Pro Ser Gly Arg Tyr Val Ala Thr Asp Leu His Lys
305                 310                 315                 320

Ala Gly Gly Ile Pro Leu Val Met Lys Met Leu Glu His Gly Leu
                325                 330                 335

Leu His Gly Asp Ala Leu Thr Ile Thr Gly Lys Thr Ile Ala Glu Gln
            340                 345                 350

Leu Ala Asp Val Pro Ser Glu Pro Ser Pro Asp Gln Asp Val Ile Arg
            355                 360                 365

Pro Trp Asp Asn Pro Met Tyr Lys Gln Gly His Leu Ala Ile Leu Arg
            370                 375                 380

Gly Asn Leu Ala Thr Glu Gly Ala Val Ala Lys Ile Thr Gly Ile Lys
385                 390                 395                 400

Asn Pro Gln Ile Thr Gly Pro Ala Arg Val Phe Glu Ser Glu Ala
            405                 410                 415

Cys Leu Glu Ala Ile Leu Ala Gly Lys Ile Gln Pro Asn Asp Val Ile
            420                 425                 430

Val Val Arg Tyr Glu Gly Pro Lys Gly Gly Pro Gly Met Arg Glu Met
            435                 440                 445

Leu Ala Pro Thr Ser Ala Ile Ile Gly Ala Gly Leu Gly Asp Ser Val
            450                 455                 460

Gly Leu Ile Thr Asp Gly Arg Phe Ser Gly Thr Tyr Gly Met Val
465                 470                 475                 480

Val Gly His Val Ala Pro Glu Ala Ala Val Gly Gly Thr Ile Ala Leu
                485                 490                 495

Val Gln Glu Gly Asp Gln Ile Thr Ile Asp Ala His Ala Arg Lys Leu
            500                 505                 510

Glu Leu His Val Ser Asp Gln Glu Leu Lys Arg Lys Glu Lys Trp
            515                 520                 525

Glu Gln Pro Lys Pro Leu Tyr Asn Lys Gly Val Leu Ala Lys Tyr Ala
            530                 535                 540

Lys Leu Val Ser Ser Ser Ser Val Gly Ala Val Thr Asp Leu Asp Leu
545                 550                 555                 560

Phe

<210> SEQ ID NO 167
<211> LENGTH: 559
<212> TYPE: PRT
<213> ORGANISM: Lyngbya spp.

<400> SEQUENCE: 167

Met Ser Asp Asn Phe Arg Ser Gln Ala Ile Thr Gln Gly Lys Lys Arg
1               5                   10                  15

Thr Pro Asn Arg Ala Met Leu Arg Ala Val Gly Phe Gly Asp Glu Asp
            20                  25                  30

Phe Asn Lys Pro Ile Val Gly Ile Ala Asn Gly Tyr Ser Thr Ile Thr
            35                  40                  45

Pro Cys Asn Ile Gly Leu Asn Asp Leu Ala His Arg Ala Glu Thr Ala
50                  55                  60

Leu Lys Gln Ala Asp Ala Met Pro Gln Met Phe Gly Thr Ile Thr Val
```

```
                65                  70                  75                  80
Ser Asp Gly Ile Ala Met Gly Thr Glu Gly Met Lys Tyr Ser Leu Val
                    85                  90                  95

Ser Arg Glu Val Ile Ala Asp Ala Ile Glu Thr Ala Cys Asn Gly Gln
                    100                 105                 110

Ser Met Asp Gly Val Leu Ala Ile Gly Gly Cys Asp Lys Asn Met Pro
                    115                 120                 125

Gly Ala Met Ile Ala Ile Ala Arg Met Asn Ile Pro Ala Ile Phe Val
                    130                 135                 140

Tyr Gly Gly Thr Ile Lys Pro Gly Asn Leu Asn Gly Cys Asp Leu Thr
145                 150                 155                 160

Val Val Ser Ala Phe Glu Ala Val Gly Glu Tyr Ser Ala Gly Lys Leu
                    165                 170                 175

Asp Asp Asp Arg Leu Leu Asp Ile Glu Arg Leu Ala Cys Pro Gly Ser
                    180                 185                 190

Gly Ser Cys Gly Gly Met Phe Thr Ala Asn Thr Met Ser Ser Ala Phe
                    195                 200                 205

Glu Ala Met Gly Met Ser Leu Met Tyr Ser Ser Thr Met Ala Ser Glu
                    210                 215                 220

Asp Ala Glu Lys Ala Asp Ser Thr Glu Lys Ser Ala Phe Val Leu Arg
225                 230                 235                 240

Glu Ala Ile Ser Gln Arg Ile Leu Pro Lys Gln Ile Leu Thr Arg Lys
                    245                 250                 255

Ala Phe Glu Asn Ala Ile Ala Val Ile Met Ala Val Gly Gly Ser Thr
                    260                 265                 270

Asn Ser Val Leu His Leu Leu Ala Ile Ala Tyr Ala Ala Asp Val Glu
                    275                 280                 285

Leu Thr Ile Asp Asp Phe Glu Thr Ile Arg Gly Arg Val Pro Val Leu
                    290                 295                 300

Cys Asp Leu Lys Pro Ser Gly Arg Phe Val Thr Thr Asp Phe His Lys
305                 310                 315                 320

Ala Gly Gly Val Pro Leu Ile Met Lys Met Leu Leu Glu Gln Gly Leu
                    325                 330                 335

Ile His Gly Asp Ala Leu Thr Ile Thr Gly Lys Thr Val Ala Glu Gln
                    340                 345                 350

Leu Ala Asp Ile Pro Ser Gln Pro Ser Ala Asp Gln Glu Val Ile Arg
                    355                 360                 365

Pro Trp Asn Asn Pro Met Tyr Lys Gln Gly His Leu Ala Ile Leu Lys
                    370                 375                 380

Gly Asn Leu Ala Thr Glu Gly Ser Val Ala Lys Ile Thr Gly Val Lys
385                 390                 395                 400

Lys Pro Gln Met Thr Gly Pro Ala Arg Val Phe Glu Ser Glu Glu Gln
                    405                 410                 415

Cys Leu Glu Ala Ile Leu Ala Gly Lys Ile Gln Ala Gly Asp Val Leu
                    420                 425                 430

Val Val Arg Tyr Glu Gly Pro Lys Gly Gly Pro Gly Met Arg Glu Met
                    435                 440                 445

Leu Ala Pro Thr Ser Ala Ile Ile Gly Ala Gly Leu Gly Asp Ser Val
                    450                 455                 460

Gly Leu Ile Thr Asp Gly Arg Phe Ser Gly Gly Thr Tyr Gly Leu Val
465                 470                 475                 480

Val Gly His Val Ala Pro Glu Ala Ala Val Gly Gly Asn Ile Ala Leu
                    485                 490                 495
```

```
Val Gln Glu Gly Asp Ser Ile Thr Ile Asp Ala Ser Gln Arg Leu Leu
            500                 505                 510

Gln Val Asn Ile Ser Asp Gln Val Leu Glu Gln Arg Gln Asn Trp
        515                 520                 525

Gln Pro Pro Gln Pro Arg Tyr Thr Lys Gly Val Leu Ala Lys Tyr Ala
    530                 535                 540

Lys Leu Val Ser Ser Ser Val Gly Ala Val Thr Asp Leu Asp
545                 550                 555

<210> SEQ ID NO 168
<211> LENGTH: 616
<212> TYPE: PRT
<213> ORGANISM: Escherichia coli

<400> SEQUENCE: 168

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320
```

```
Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615

<210> SEQ ID NO 169
<211> LENGTH: 571
<212> TYPE: PRT
<213> ORGANISM: Bacillus subtilis

<400> SEQUENCE: 169

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80
```

```
Val Leu Val Thr Ser Gly Pro Gly Ala Ser Asn Leu Ala Thr Gly Leu
                 85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510
```

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570

<210> SEQ ID NO 170
<211> LENGTH: 491
<212> TYPE: PRT
<213> ORGANISM: Artificial Sequence
<220> FEATURE:
<223> OTHER INFORMATION: E. coli ilvC Q110V

<400> SEQUENCE: 170

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

```
Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
            325                 330                 335

Thr Ala Phe Glu Thr Ala Pro Gln Tyr Glu Gly Lys Ile Gly Glu Gln
        340                 345                 350

Glu Tyr Phe Asp Lys Gly Val Leu Met Ile Ala Met Val Lys Ala Gly
    355                 360                 365

Val Glu Leu Ala Phe Glu Thr Met Val Asp Ser Gly Ile Ile Glu Glu
370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
            405                 410                 415

Ala Glu Tyr Gly Asn Tyr Leu Phe Ser Tyr Ala Cys Val Pro Leu Leu
        420                 425                 430

Lys Pro Phe Met Ala Glu Leu Gln Pro Gly Asp Leu Gly Lys Ala Ile
    435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
            485                 490

<210> SEQ ID NO 171
<211> LENGTH: 1476
<212> TYPE: DNA
<213> ORGANISM: Artificial Sequence
<220> FEATURE:
<223> OTHER INFORMATION: E. coli ilvC codon-optimized for expression in
      S. cerevisiae (P2D1-A1)

<400> SEQUENCE: 171
atggccaact attttaacac attaaatttg agacaacaat ggctcaact gggtaagtgc       60 agatttatgg aagggacga gtttgctgat ggtgcttctt atctgcaagg aaagaaagta     120
gtaattgttg gctgcggtgc tcagggtcta aaccaaggtt taaacatgag agattcaggt     180
ctggatattt cgtatgcatt gaggaaagag tctattgcag aaaaggatgc cgattggcgt     240
aaagcgacgg aaaatgggtt caaagttggt acttacgaag aactgatccc tcaggcagat     300
ttagtgatta acctaacacc agataaggtt cactcagacg tagtaagaac agttcaaccg     360
ctgatgaagg atggggcagc tttaggttac tctcatggct ttaatatcgt tgaagtgggc     420
gagcagatca gaaaaggtat aacagtcgta atggttgcgc caaagtgccc aggtacggaa     480
gtcagagagg agtacaagag gggttttggt gtacctacat tgatcgccgt acatcctgaa     540
aatgacccca acgtgaagg tatggcaata gcgaaggcat gggcagccgc aaccggaggt     600
catagagcgg gtgtgttaga gagttctttc gtagctgagg tcaagagtga cttaatgggt     660
gaacaaacca ttctgtgcgg aatgttgcag gcagggtctt tactatgctt tgataaattg     720
gtcgaagagg gtacagatcc tgcctatgct gaaaagttga caatttgg ttgggagaca     780 atcaccgagg cacttaaaca aggtggcata acattgatga tggatagact ttcaaatccg     840
gccaagctaa agcctacgc cttatctgag caactaaaag agatcatggc accattattc     900
caaaagcaca tggacgatat tatctccggt gagttttcct caggaatgat ggcagattgg     960
gcaaacgatg ataaaaagtt attgacgtgg agagaagaaa ccggcaagac ggcattcgag    1020
```

```
acagccccac aatacgaagg taaaattggt gaacaagaat actttgataa gggagtattg    1080
atgatagcta tggtgaaggc aggggtagaa cttgcattcg aaactatggt tgactccggt    1140
atcattgaag aatctgcata ctatgagtct ttgcatgaat tgcctttgat agcaaatact    1200
attgcaagaa aaagacttta cgagatgaat gttgtcatat cagacactgc agaatatggt    1260
aattacttat ttagctacgc gtgtgtcccg ttgttagagc ccttcatggc cgagttacaa    1320
cctggtgatt tggggaaggc tattccggaa ggagcggttg acaatggcca actgagagac    1380
gtaaatgaag ctattcgttc acatgctata gaacaggtgg gtaaaaagct gagaggatat    1440
atgaccgata tgaaaagaat tgcagtggca ggatga                             1476

<210> SEQ ID NO 172
<211> LENGTH: 491
<212> TYPE: PRT
<213> ORGANISM: Artificial Sequence
<220> FEATURE:
<223> OTHER INFORMATION: E. coli ilvC codon-optimized for expression in
      S. cerevisiae (P2D1-A1)

<400> SEQUENCE: 172

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Ile Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Gly Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Arg Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
```

```
                    275                 280                 285
Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Thr Gly Lys
                325                 330                 335

Thr Ala Phe Glu Thr Ala Pro Gln Tyr Glu Gly Lys Ile Gly Glu Gln
                340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Glu Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 173
<211> LENGTH: 548
<212> TYPE: PRT
<213> ORGANISM: Lactococcus lactis

<400> SEQUENCE: 173

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
```

```
                165                 170                 175
Ser Leu Pro Leu Lys Lys Glu Asn Ser Thr Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Leu Asn
225                 230                 235                 240

Phe Gly Lys Ser Val Asp Glu Ala Leu Pro Ser Phe Leu Gly Ile
            245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
            325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 174
<211> LENGTH: 1023
<212> TYPE: DNA
<213> ORGANISM: Lactococcus lactis
```

```
<400> SEQUENCE: 174
atgaaagcag cagtagtaag acacaatcca gatggttatg cggaccttgt tgaaaaggaa    60
cttcgagcaa tcaaacctaa tgaagctttg cttgacatgg agtattgtgg agtctgtcat   120
accgatttgc acgttgcagc aggtgattat ggcaacaaag cagggactgt tcttggtcat   180
gaaggaattg gaattgtcaa agaaattgga gctgatgtaa gctcgcttca agttggtgat   240
cgggtttcag tggcttggtt ctttgaagga tgtggtcact gtgaatactg tgtatctggt   300
aatgaaactt tttgtcgaga agttaaaaat gcaggatatt cagttgatgg cggaatggct   360
gaagaagcaa ttgttgttgc cgattatgct gtcaaagttc ctgacggact tgacccaatt   420
gaagctagct caattacttg tgctggagta acaacttaca aagcaatcaa agtatcagga   480
gtaaaacctg gtgattggca agtaattttt ggtgctggag gacttggaaa tttagcaatt   540
caatatgcta aaaatgtttt tggagcaaaa gtaattgctg ttgatattaa tcaagataaa   600
ttaaatttag ctaaaaaaat tggagctgat gtgattatca attctggtga tgtaaatcca   660
gttgatgaaa ttaaaaaaat aactggcggc ttaggggtgc aaagtgcaat agtttgtgct   720
gttgcaagga ttgcttttga acaagcggtt gcttctttga aacctatggg caaaatggtt   780
gctgtggcac ttcccaatac tgagatgact ttatcagttc aacagttgt ttttgacgga   840
gtggaggttg caggttcact tgtcggaaca agacttgact tggcagaagc ttttcaattt   900
ggagcagaag gtaaggtaaa accaattgtt gcgacacgca aactggaaga atcaatgat   960
attattgatg aaatgaaggc aggaaaaatt gaaggccgaa tggtcattga tttactaaa  1020
taa                                                                1023

<210> SEQ ID NO 175
<211> LENGTH: 340
<212> TYPE: PRT
<213> ORGANISM: Lactococcus lactis

<400> SEQUENCE: 175

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
                20                  25                  30

Met Glu Tyr Cys Gly Val Cys His Thr Asp Leu His Val Ala Ala Gly
            35                  40                  45

Asp Tyr Gly Asn Lys Ala Gly Thr Val Leu Gly His Glu Gly Ile Gly
        50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
```

-continued

```
                180                 185                 190
Ala Val Asp Ile Asn Gln Asp Lys Leu Asn Leu Ala Lys Lys Ile Gly
            195                 200                 205

Ala Asp Val Ile Ile Asn Ser Gly Asp Val Asn Pro Val Asp Glu Ile
        210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
            260                 265                 270

Val Pro Thr Val Val Phe Asp Gly Val Glu Val Ala Gly Ser Leu Val
        275                 280                 285

Gly Thr Arg Leu Asp Leu Ala Glu Ala Phe Gln Phe Gly Ala Glu Gly
                290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340

<210> SEQ ID NO 176
<211> LENGTH: 256
<212> TYPE: PRT
<213> ORGANISM: Drosophila melanogaster

<400> SEQUENCE: 176

Met Ser Phe Thr Leu Thr Asn Lys Asn Val Ile Phe Val Ala Gly Leu
1               5                   10                  15

Gly Gly Ile Gly Leu Asp Thr Ser Lys Glu Leu Leu Lys Arg Asp Leu
            20                  25                  30

Lys Asn Leu Val Ile Leu Asp Arg Ile Glu Asn Pro Ala Ala Ile Ala
        35                  40                  45

Glu Leu Lys Ala Ile Asn Pro Lys Val Thr Val Thr Phe Tyr Pro Tyr
    50                  55                  60

Asp Val Thr Val Pro Ile Ala Glu Thr Thr Lys Leu Leu Lys Thr Ile
65                  70                  75                  80

Phe Ala Gln Leu Lys Thr Val Asp Val Leu Ile Asn Gly Ala Gly Ile
                85                  90                  95

Leu Asp Asp His Gln Ile Glu Arg Thr Ile Ala Val Asn Tyr Thr Gly
            100                 105                 110

Leu Val Asn Thr Thr Ala Ile Leu Asp Phe Trp Asp Lys Arg Lys
        115                 120                 125

Gly Gly Pro Gly Gly Ile Ile Cys Asn Ile Gly Ser Val Thr Gly Phe
    130                 135                 140

Asn Ala Ile Tyr Gln Val Pro Val Tyr Ser Gly Thr Lys Ala Ala Val
145                 150                 155                 160

Val Asn Phe Thr Ser Ser Leu Ala Lys Leu Ala Pro Ile Thr Gly Val
                165                 170                 175

Thr Ala Tyr Thr Val Asn Pro Gly Ile Thr Arg Thr Thr Leu Val His
            180                 185                 190

Thr Phe Asn Ser Trp Leu Asp Val Glu Pro Gln Val Ala Glu Lys Leu
        195                 200                 205

Leu Ala His Pro Thr Gln Pro Ser Leu Ala Cys Ala Glu Asn Phe Val
```

```
              210                 215                 220
Lys Ala Ile Glu Leu Asn Gln Asn Gly Ala Ile Trp Lys Leu Asp Leu
225                 230                 235                 240

Gly Thr Leu Glu Ala Ile Gln Trp Thr Lys His Trp Asp Ser Gly Ile
                245                 250                 255

<210> SEQ ID NO 177
<211> LENGTH: 340
<212> TYPE: PRT
<213> ORGANISM: Artificial Sequence
<220> FEATURE:
<223> OTHER INFORMATION: L. lactis AdhA RE1

<400> SEQUENCE: 177

Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
                20                  25                  30

Met Glu Tyr Cys Gly Val Cys His Thr Asp Leu His Val Ala Ala Gly
            35                  40                  45

Asp Phe Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
    115                 120                 125

Tyr Ala Val Lys Val Pro Asp Gly Leu Asp Pro Ile Glu Ala Ser Ser
130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
    195                 200                 205

Ala Asp Val Thr Ile Asn Ser Gly Asp Val Asn Pro Val Asp Glu Ile
210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Val Pro Asn Thr Glu Met Thr Leu Ser
            260                 265                 270

Val Pro Thr Val Val Phe Asp Gly Val Glu Val Ala Gly Ser Leu Val
    275                 280                 285

Gly Thr Arg Leu Asp Leu Ala Glu Ala Phe Gln Phe Gly Ala Glu Gly
290                 295                 300

Lys Val Lys Pro Ile Val Ala Thr Arg Lys Leu Glu Glu Ile Asn Asp
305                 310                 315                 320
```

```
Ile Ile Asp Glu Met Lys Ala Gly Lys Ile Glu Gly Arg Met Val Ile
                325                 330                 335
Asp Phe Thr Lys
        340
```